(12) United States Patent
Dunten et al.

(10) Patent No.: US 7,135,475 B2
(45) Date of Patent: Nov. 14, 2006

(54) AMIDE SUBSTITUTED XANTHINE DERIVATIVES

(75) Inventors: Peter W. Dunten, Mountain View, CA (US); Louise H. Foley, Old Forge, NY (US); Nicholas J. S. Huby, Scotch Plains, NJ (US); Sherrie L. Pietranico-Cole, Montclair, NJ (US); Weiya Yun, Warren, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 127 days.

(21) Appl. No.: 10/459,944

(22) Filed: Jun. 12, 2003

(65) Prior Publication Data

US 2004/0014766 A1 Jan. 22, 2004

Related U.S. Application Data

(60) Provisional application No. 60/461,010, filed on Apr. 7, 2003, provisional application No. 60/388,164, filed on Jun. 12, 2002.

(51) Int. Cl.
| | |
|---|---|
| C07D 473/06 | (2006.01) |
| C07D 239/545 | (2006.01) |
| C07D 249/08 | (2006.01) |
| A61K 31/522 | (2006.01) |
| A61P 3/10 | (2006.01) |

(52) U.S. Cl. ............... 514/263.2; 514/263.21; 514/263.22; 514/263.23; 514/263.34; 514/263.36; 544/269; 544/270; 544/271; 544/272; 544/310; 544/312; 544/229; 548/268.2; 548/266.8; 548/334.5; 548/374.1

(58) Field of Classification Search ............ 514/263.2, 514/263.21, 263.22, 263.23, 263.34, 263.36; 544/269, 270, 271, 272

See application file for complete search history.

(56) References Cited

U.S. PATENT DOCUMENTS

2004/0192708 A1* 9/2004 Dunten et al. ......... 514/263.22

2005/0119258 A1* 6/2005 Wilson et al. ........... 514/227.8
2005/0187226 A1* 8/2005 Wilson et al. ........... 514/263.2

FOREIGN PATENT DOCUMENTS

WO  WO 01 77110  10/2001

OTHER PUBLICATIONS

Definition for "carbamoyl" Stedman's Online Medical Dictionary, 27th Edition <http://216.251.232.159/semdweb/internetsomd/ASP/1499429.asp> download from the Internet Oct. 3, 2005.*
DeFronzo et al., Diabetes Reviews, 6, pp. 89-131 (1998).
Shulman, G. I., Am. J. Card., 84 (Suppl.1A), pp. 3J-10J (1999).
Consoli et al., J. Diabetes, 38, pp. 550-557 (1989).
Gastaldelli et al., Diabetes, 49, pp. 1367-1373 (2000).
Cimbala et al., J. Biol. Chem., 257, pp. 7629-7636 (1982).
DeFronzo et al., Diabetes Care, 15, pp. 318-368 (1992).
Müller et al., J. Med. Chem., 36, pp. 3341-3349 (1993).
Papesch et al., J. Org. Chem., 16, pp. 1879-1890 (1951).

* cited by examiner

*Primary Examiner*—Mark L. Berch
(74) *Attorney, Agent, or Firm*—George W. Johnston; Dennis P. Tramaloni; Samuel H. Megerditchian

(57) ABSTRACT

The present invention is a 1,3,8 substituted xanthine derivative of formula I

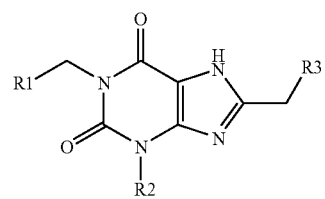

or a pharmaceutically acceptable salt thereof, wherein $R^1$, $R^2$ and $R^3$ are as defined in the specification.

Compounds of formula I and pharmaceutically acceptable salts or prodrugs thereof show activity as modulators of gluconeogenesis.

76 Claims, No Drawings

AMIDE SUBSTITUTED XANTHINE DERIVATIVES

PRIORITY TO PROVISIONAL APPLICATION(S) UNDER 35 U.S.C. § 119(e)

This application claims priority under 35 U.S.C. § 119(e) of provisional application(s) Ser. No. 60/388,164, filed Jun. 12, 2002 and Ser. No. 60/461,010, filed Apr. 7, 2003.

FIELD OF INVENTION

The present invention is directed to 1,3,8 substituted xanthine derivatives of formula I

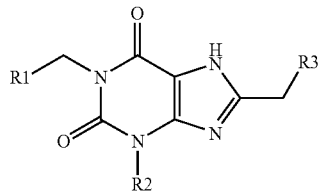

Compounds of formula I and pharmaceutically acceptable salts thereof are modulators of gluoneogenesis and are useful in the treatment of type 2 diabetes.

BACKGROUND

The control of glucose production is one of the key aspects of anti-diabetic therapy. Type 2 diabetics have elevated levels of postprandial and fasting blood glucose (Consoli, A., Nurjhan, N., Capani, F. and Gerich, J. Diabetes 38, 550–7, 1989; Shulman, G I Am. J. Card. 84(Suppl.1A): 3J-10J, 1999). Excessive hepatic glucose production (HGP) contributes to the fasting hyperglycemia observed in patients with Type 2 diabetes (T2D) (Gastadelli, A., Baldi S., Pettiti M., Toschi, E., Camastra, S., Natali, A., Landau, B. R. & Ferranini, E., Diabetes 49:1367–1373, 2000. Gluconeogenesis is believed to be the major pathway for this increased glucose production (Defronzo, R. A., Bonadonna, R. C. and Ferrannini, E., Diabetes Care 15:318–367, 1992).

Phosphoenolpyruvate carboxykinase (PEPCK) is a key regulatory enzyme in the gluconeogenic pathway. PEPCK is believed to be the flux controlling, rate limiting enzyme for this pathway (Cimbala, A. N., Lamers, W. H., Nelson, J. E., Monahan, J. E., Yoo-Warren, H., and Hanson R. W., J. Biol. Chem. 257:7629–7636, 1982), hence inhibition of this enzyme represents a novel way to improve glucose homeostasis. Previously, attempts to control hepatic glucose production through inhibition of gluconeogeneis were limited to biguanides such as metformin (Defronzo, R. A., Diabetes Reviews 6:89–131, 1998). Metformin inhibits HGP, but by an unknown mechanism. In addition, it has side effects such as gastrointestinal (GI) disturbances and lactic acidosis. Inhibition of PEPCK provides superior efficacy and, coupled with reduced side effects, represents a novel treatment for type 2 diabetes.

SUMMARY OF THE INVENTION

The present invention is directed to a compound of formula

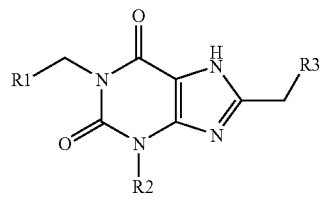

wherein $R^1$ is selected from the group consisting of
  lower alkenyl,
  lower alkynyl,
  lower alkenyl substituted by halogen,
  phenyl, and
  phenyl substituted by one or two substituents independently selected from the group consisting of halogen, hydroxy, lower alkoxy, nitro, amino and a 5- or 6-membered aromatic heterocyclic ring having 1, 2, 3 or 4 nitrogen atoms, the heterocyclic ring attached to the phenyl by a ring carbon atom;

$R^2$ is selected from the group consisting of
  unsubstituted lower alkyl,
  lower alkyl substituted by lower alkoxy or hydroxy,
  lower alkenyl,
  phenyl,
  —$(CH_2)_n$-unsubstituted lower cycloalkyl,
  —$(CH_2)_n$-lower cycloalkyl substituted by at least one substitutent selected from the group consisting of carboxy, lower alkyl, carboxy-lower alkyl and lower alkyl substituted by hydroxy,
  —$(CH_2)_n$—$C(O)R^b$, wherein $R^b$ is selected from the group consisting of hydroxyl, lower alkoxy, —$NHR^c$ wherein $R^c$ is selected from the group consisting of hydrogen, benzyl, lower alkyl and —$NHR^d$ wherein $R^d$ is hydrogen or carboxy-lower alkyl;
  —$(CH_2)_n$-unsubstituted aromatic five-member heterocyclic ring with oxygen or sulfur,
  —$(CH_2)_n$-aromatic five-member heterocyclic ring with one heteroatom being oxygen or sulfur, the ring substituted by a carboxylic acid moiety,
  —$(CH_2)_n$-unsubstituted aromatic five-member heterocyclic ring with 1, 2 or 3 nitrogen atoms,
  —$(CH_2)_n$-non-aromatic five or six member heterocyclic ring with at least one oxygen atom and no or two nitrogen atoms, the non-aromatic heterocyclic ring having no substituents or having one ring carbon in the form of a carbonyl; and wherein $R^3$ is

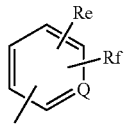

wherein Q is N or CH, with the proviso that
when Q is N, R$^e$ is —NH—C(O)—CH$_3$ and R$^f$ is H,
when Q is CH, R$^e$ is —NR$^g$—C(O)—R$^h$ or

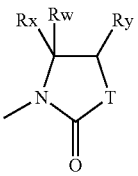

and R$^f$ is selected from the group consisting of H,
—NH$_2$ and —NH—C(O)—CH$_3$,
R$^g$ is selected from the group consisting of
  H,
  lower alkyl and
  —(CH$_2$)$_n$-unsubstituted lower cycloalkyl,
R$^h$ is selected from the group consisting of
  —(CH$_2$)$_n$-5- or 6-member aromatic heterocyclic ring
    having one, two or three hetero atoms independently
    selected from the group consisting of N, O and S, the
    aromatic heterocyclic ring being unsubstituted or
    having at least one substituent independently
    selected from the group consisting of lower alkyl,
    lower alkoxy, hydroxy, halogen, —NH$_2$, —NH—C
    (O)-lower alkyl, —CN, —C(O)—NH$_2$ and —SO$_2$-
    lower alkyl,
  lower alkyl,
  lower alkyl substituted by at least one substituent
    independently selected from the group consisting of
    halogen, phenyl and —(CH$_2$)$_n$NR$^i$R$^i$ wherein R$^i$ is
    independently selected from the group consisting of
    H, lower alkyl and carbonyloxybenzyl (CBZ),
  —NHR$^j$, wherein R$^j$ is selected from the group con-
    sisting of a 5- or 6-membered aromatic heterocyclic
    ring having one, two or three heteroatoms indepen-
    dently selected from the group consisting of N, O
    and S, the heterocyclic ring being substituted by at
    least one substituent selected from the group con-
    sisting of halogen, lower alkyl and phenyl,
  —C(O)—R$^k$, wherein R$^k$ is a 5- or 6-member aromatic
    heterocyclic ring having one, two or three hetero
    atoms independently selected from the group con-
    sisting of N, O and S, the aromatic heterocyclic ring
    being unsubstituted or substituted by at least one
    lower alkyl,
  unsubstituted phenyl,
  phenyl substituted by at least one substitutent indepen-
    dently selected from the group consisting of lower
    alkyl, lower alkoxy, —(CH$_2$)$_m$—NH R$^1$, wherein R$^1$
    is selected from the group consisting of H, lower
    alkyl and carbonyloxybenzyl (CBZ), and
wherein T is NH or CH$_2$, and
when T is NH, R$^w$ and R$^x$ are, taken together with the
  carbon to which they are attached, to form —C(O)—
  and R$^y$ is —(CH$_2$)OR$^z$, wherein R$^z$ is selected from the
  group consisting of hydrogen and lower alkyl, and
when T is CH$_2$, R$^w$ and R$^x$ are both hydrogen or are, taken
  together with the carbon to which they are attached, to
  form —C(O)—; and
n is 0, 1 or 2;
m is 0 or 1;
or a pharmaceutically acceptable salt thereof.

Phosphoenolpyruvate carboxykinase (PEPCK) is a key regulatory enzyme in the gluconeogenic pathway. As stated above, PEPCK is believed to be the flux controlling, rate limiting enzyme for this pathway, hence inhibition of this enzyme represents a novel way to improve glucose homeostasis. Previous attempts to control hepatic glucose production (HGP) through inhibition of gluconeogenes were limited to biguanides such as metformin which inhibits HGP, but by an unknown mechanism. Inhibition of HGP by specifically targeting an enzyme, PEPCK, known to be in the gluconeogenic pathway, by administration of a therapeutically effective amount of a compound of formula I or a pharmaceutically effective salt thereof is an alternative therapy. In addition, inhibition of PEPCK by administration of a therapeutically effective amount of a compound of formula I provides superior efficacy and, coupled with reduced side effects, represents a novel treatment for type 2 (non-insulin dependent) diabetes.

The present invention is also directed to pharmaceutical compositions comprising a therapeutically effective amount of one or more compounds of formula I and a pharmaceutically acceptable carrier or excipient.

The present invention is further directed to a method of treatment of type 2 diabetes comprising administering a therapeutically effective amount of a compound of formula I or a pharmaceutically acceptable salt thereof to a patient in need of such treatment.

DETAILED DESCRIPTION OF THE INVENTION

The following definitions of the general terms used in the present description apply irrespective of whether the terms in question appear alone or in combination.

"Lower alkyl" includes both straight chain and branched chain hydrocarbon groups having from one to seven carbon atoms, such as methyl, ethyl, propyl, butyl, isopropyl, isobutyl and the like. Preferred alkyl groups are methyl, ethyl, butyl and isopropyl.

The term "lower alkoxy" denotes a group wherein the alkyl residues are as defined above and which is attached via an oxygen atom.

The term "alkenyl" refers to a hydrocarbon chain as defined for alkyl having at least one olefinic double bond, e.g., vinyl, allyl, butenyl and the like.

The term "alkynyl" refers to a hydrocarbon chain as defined for alkyl having at least one acetylenic triple bond, e.g., propinyl and the like.

"Lower cycloalkyl" refers to cyclic saturated hydrocarbons having between three and seven carbon atoms, such as cyclopropyl, cyclobutyl, cyclopentyl and the like. Cyclopropyl, cyclobutyl and cyclopentyl are preferred, with cyclopropyl being more preferred. These cycloalkyl groups may be unsubstituted or substituted with one or more substituents.

The term "unsubstituted" denotes that there are no other atoms attached to a chain or ring other than hydrogen. The term "substituted" as in substituted alkyl or subsituted aromatic heterocycle, means that the substitution can occur at one or more positions and, unless otherwise indicated, that the substitutents at each substitution site are independently selected from the specified options. The term "at least one" substituted means, one, two or three substituents.

As used herein, the terms "halogen" or "halogen" means fluorine, chlorine, bromine and iodine. Preferred halogens are fluorine and chlorine.

Other chemical and structural terms used in the description are to be interpreted with their normal meaning in the art of organic chemistry. The terms "amino" and formula "—NH$_2$" may be used interchangably.

The term "five or six membered heterocyclic ring" means a non-aromatic ring with one, two or three heteroatoms independently selected from the group consisting of nitrogen, sulfur and oxygen. Exemplary of the five or six membered heterocyclic rings are tetrahydrofuranyl (THF), tetrahydropyranyl (THP), tetrahydrothiophenyl and the like. The term "five or six membered heteroaromatic ring" means an aromatic ring with one, two or three heteroatoms independently selected from the group consisting of nitrogen, sulfur and oxygen. Exemplary of five or six member heteroaromatic ring moieties are pyrazole, imidazole, thiazole, isoxazole, pyridine, pyrazine, pyrimidine, triazole, thiophene and the like.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Prodrug" means a compound that may be converted, under physiological conditions or by solvolysis, to a pharmaceutically active compound. A prodrug may be inactive when administered to a subject but is converted in vivo to an active compound. That is, a prodrug may be an inactive species in in vitro cell based assays, but converted to an active species in vivo in the subject.

"Therapeutically effective amount" means an amount that is effective to prevent, alleviate or ameliorate symptoms of disease or prolong the survival of the subject being treated. Determination of a therapeutically effective amount is within the skill in the art.

In one embodiment, the invention is directed to a compound of formula

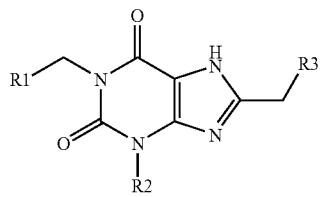

I wherein
$R^1$ is selected from the group consisting of
lower alkenyl,
lower alkynyl,
lower alkenyl substituted by halogen,
phenyl and
phenyl substituted by one or two substituents independently selected from the group consisting of halogen, hydroxy, lower alkoxy, nitro, amino and a 5- or 6-membered aromatic heterocyclic ring having 1, 2, 3 or 4 nitrogen atoms, the heterocyclic ring attached to the phenyl by a ring carbon atom;

$R^2$ is selected from the group consisting of
lower alkyl,
lower alkyl substituted by lower alkoxy or hydroxy,
lower alkenyl,
phenyl,
—(CH$_2$)$_n$-unsubstituted lower cycloalkyl and
—(CH$_2$)$_n$-lower cycloalkyl substituted by at least one substitutent selected from the group consisting of carboxy, lower alkyl carboxy-lower alkyl and lower alkyl substituted by hydroxy,
—(CH$_2$)$_n$—C(O)R$^b$, wherein R$^b$ is selected from the group consisting of hydroxyl, lower alkoxy, —NHR$^c$ wherein R$^c$ is selected from the group consisting of hydrogen, benzyl, lower alkyl, and —NHR$^d$ wherein R$^d$ is hydrogen or carboxy-lower alkyl;
—(CH$_2$)$_n$-unsubstituted aromatic five-member heterocyclic ring with one heteroatom being oxygen or sulfur,
—(CH$_2$)$_n$-aromatic five-member heterocyclic ring with one heteroatom being oxygen or sulfur, the ring substituted by a carboxylic acid moiety,
—(CH$_2$)$_n$-unsubstituted aromatic five-member heterocyclic ring with 1, 2 or 3 nitrogen atoms,
—(CH$_2$)$_n$-non-aromatic five or six member heterocylic ring with at least one oxygen atom and no or two nitrogen atoms, the non-aromatic heterocyclic ring having no substituents or having one ring carbon in the form of a carbonyl; and wherein
$R^3$ is

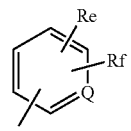

wherein Q is N or CH,
when Q is N, R$^e$ is —NH—C(O)—CH$_3$ and R$^f$ is H,
when Q is CH, R$^e$ is —NR$^g$—C(O)—R$^h$ or

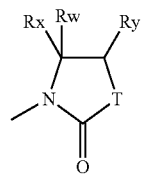

where
R$^f$ is selected from the group consisting of
H,
—NH$_2$, and
—NH—C(O)—CH$_3$,
R$^g$ is selected from the group consisting of
H,
lower alkyl, and
—(CH$_2$)$_n$-unsubstituted lower cycloalkyl, R$^h$ is selected from the group consisting of
- —(CH$_2$)$_n$-5- or 6-member aromatic heterocyclic ring having one, two or three hetero atoms independently selected from the group consisting of N, O and S, the aromatic heterocyclic ring being unsubstituted or having at least one substituent independently selected from the group consisting of
  - lower alkyl,
  - lower alkoxy,
  - hydroxy,
  - halogen,
  - —NH$_2$,
  - —NH—C(O)-lower alkyl,
  - —CN,
  - —C(O)—NH$_2$ and
  - —SO$_2$-lower alkyl,
- lower alkyl substituted by at least one substituent independently selected from the group consisting of halogen, phenyl and —(CH$_2$)$_n$NR$^i$R$^i$, wherein R$^i$ is independently selected from the group consisting of H, lower alkyl and carbonyloxybenzyl (CBZ),
- —NHR$^j$, wherein R$^j$ is selected from the group consisting of a 5- or 6-membered aromatic heterocyclic ring having one, two or three heteroatoms independently selected from the group consisting of N, O and S, the heterocyclic ring being substituted by at least one substituent selected from the group consisting of halogen, lower alkyl and phenyl,
- —C(O)—R$^k$, wherein R$^k$ is a 5- or 6-member aromatic heterocyclic ring having one, two or three hetero atoms independently selected from the group consisting of N, O and S, the aromatic heterocyclic ring being unsubstituted or substituted by at least one lower alkyl,
- unsubstituted phenyl,
- phenyl substituted by at least one substituent independently selected from the group consisting of lower alkyl, lower alkoxy, and —(CH$_2$)$_m$—NH R$^1$, wherein R$^1$ is selected from the group consisting of H, lower alkyl and carbonyloxybenzyl (CBZ), and wherein T is NH or CH$_2$, with the proviso that
when T is NH, R$^w$ and R$^x$ are, taken together with the carbon to which they are attached, to form —C(O)— and R$^y$ is H or —(CH$_2$)OR$^z$, wherein R$^z$ is selected from the group consisting of hydrogen and lower alkyl, and
when T is CH$_2$, R$^w$ and R$^x$ are both hydrogen or are, taken together with the carbon to which they are attached, to form —C(O)—; and
n is 0, 1 or 2;
m is 0 or 1;
or a pharmaceutically acceptable salt thereof.

In one preferred embodiment of the compound of formula I, R$^1$ is selected from the group consisting of lower alkenyl, lower alkenyl substituted by halogen, and lower alkynyl. Compounds representative of this preferred embodiment of formula I are selected from the group consisting of
- N-{4-[1-allyl-3-(2-methoxy-ethyl)-2,6-dioxo-2,3,6,7-tetrahydro-1H-purin-8-ylmethyl]-phenyl}-acetamide,
- N-{4-[3-butyl-1-(3-methyl-but-2-enyl)-2,6-dioxo-2,3,6,7-tetrahydro-1H-purin-8-ylmethyl]-phenyl}-acetamide,
- N-[4-(1-but-2-enyl-3-butyl-2,6-dioxo-2,3,6,7-tetrahydro-1H-purin-8-ylmethyl)-phenyl]-acetamide,
- N-[4-(1-allyl-3-butyl-2,6-dioxo-2,3,6,7-tetrahydro-1H-purin-8-ylmethyl)-phenyl]-acetamide,
- N-{4-[1-(3-bromo-allyl)-3-butyl-2,6-dioxo-2,3,6,7-tetrahydro-1H-purin-8-ylmethyl]-phenyl}-acetamide and
- N-[4-(3-butyl-2,6-dioxo-1-prop-2-ynyl-2,3,6,7-tetrahydro-1H-purin-8-ylmethyl)-phenyl]-acetamide.

In another preferred embodiment of the compound of formula I, R$^1$ is selected from the group consisting of phenyl and phenyl substituted by a substituent selected from the group consisting of
- halogen,
- amino
- lower alkoxy
- hydroxy,
- nitro and
- a 5- or 6-membered heterocyclic ring having 1, 2, 3 or 4 nitrogen atoms, the heterocyclic ring attached to the phenyl by a ring carbon atom.

A further preferred compound of formula 1 is when R$^1$ is selected from the group consisting of

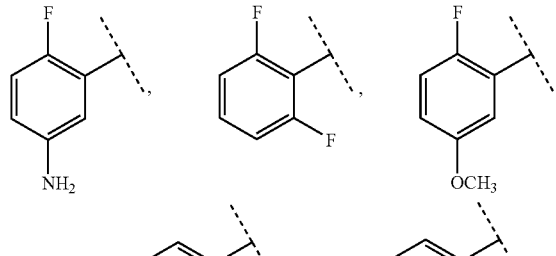
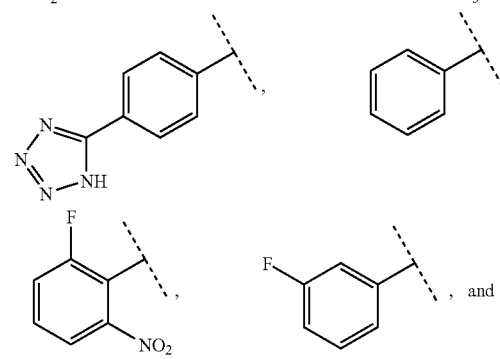
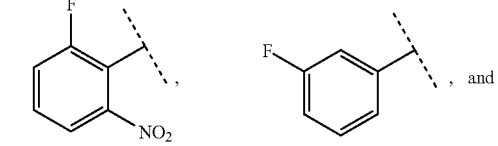
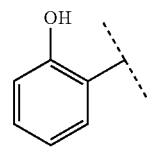

Exemplary of these further preferred compounds of formula I, are compounds selected from the group consisting of
- N-[4-(1-benzyl-3-methoxymethyl-2,6-dioxo-2,3,6,7-tetrahydro-1H-purin-8-ylmethyl)-phenyl]-acetamide,
- [4-(1-benzyl-3-butyl-2,6-dioxo-2,3,6,7-tetrahydro-1H-purin-8-ylmethyl)-phenyl]-carbamic acid tert-butyl ester,
- N-[4-(1-benzyl-3-methyl-2,6-dioxo-2,3,6,7-tetrahydro-1H-purin-8-ylmethyl)-phenyl]-acetamide,
- N-[3-(1-benzyl-3-furan-3-ylmethyl-2,6-dioxo-2,3,6,7-tetrahydro-1H-purin-8-ylmethyl)-phenyl]-acetamide,
- N-(4-{3-butyl-1-[4-(1-methyl-1H-tetrazol-5-yl)-benzyl]-2,6-dioxo-2,3,6,7-tetrahydro-1H-purin-8-ylmethyl}-phenyl)-acetamide, N-[4-(1-benzyl-3-butyl-2,6-dioxo-2,3,6,7-tetrahydro-1H-purin-8-ylmethyl)-phenyl]-acetamide,
N-[5-(1-benzyl-3-butyl-2,6-dioxo-2,3,6,7-tetrahydro-1H-purin-8-ylmethyl)-pyridin-2-yl]-acetamide,
N-{4-[3-butyl-1-(3-fluoro-benzyl)-2,6-dioxo-2,3,6,7-tetrahydro-1H-purin-8-ylmethyl]-phenyl}-acetamide,
N-{4-[3-butyl-1-(2,6-difluoro-benzyl)-2,6-dioxo-2,3,6,7-tetrahydro-1H-purin-8-ylmethyl]-phenyl}-acetamide,
5-[8-(4-acetylamino-benzyl)-1-benzyl-2,6-dioxo-1,2,6,7-tetrahydro-purin-3-ylmethyl]-furan-2-carboxylic acid; compound with trifluoro-acetic acid,
N-[4-(1-benzyl-2,6-dioxo-3-thiophen-2-ylmethyl-2,3,6,7-tetrahydro-1H-purin-8-ylmethyl)-phenyl]-acetamide,
N-[6-(1-benzyl-3-butyl-2,6-dioxo-2,3,6,7-tetrahydro-1H-purin-8-ylmethyl)-pyridin-3-yl]-acetamide,
N-[4-(1-benzyl-3-furan-3-ylmethyl-2,6-dioxo-2,3,6,7-tetrahydro-1H-purin-8-ylmethyl)-phenyl]-acetamide,
1-benzyl-3-butyl-8-[4-(2,5-dioxo-pyrrolidin-1-yl)-benzyl]-3,7-dihydro-purine-2,6-dione,
N-{4-[1-(5-amino-2-fluorobenzyl)-3-butyl-2,6-dioxo-2,3,6,7-tetrahydro-1H-purin-8-ylmethyl]-phenyl}-acetamide; compound with trifluoro-acetic acid,
N-{4-[3-butyl-1-(2-hydroxy-benzyl)-2,6-dioxo-2,3,6,7-tetrahydro-1H-purin-8-ylmethyl]-phenyl }-acetamide,
1-benzyl-3-butyl-8-[4-(2-oxo-pyrrolidin-1-yl)-benzyl]-3,7-dihydro-purine-2,6-dione, and
N-{4-[1-(5-methoxy-2-fluorobenzyl)-3-butyl-2,6-dioxo-2,3,6,7-tetrahydro-1H-purin-8-ylmethyl]-phenyl}-acetamide; compound with trifluoro-acetic acid.

Another preferred compound of formula I has the formula

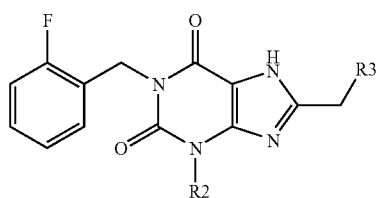

Ia wherein R2 and R3 are defined above.

Particularly preferred among the compounds of formula Ia is a compound wherein $R^2$ is selected from the group consisting of phenyl,
—$(CH_2)_n$-unsubstituted aromatic 5-member heterocyclic ring with one heteroatom selected from the group consisting of O and S,
—$(CH_2)_n$-aromatic 5-member heterocyclic ring with one heteroatom selected from the group consisting of O and S, the 5-member heterocyclic ring being substituted by a carboxylic acid,
—$(CH_2)_n$-unsubstituted aromatic heterocyclic ring having one, two or three N-atoms and
—$(CH_2)_n$-non-aromatic five or six member heterocyclic ring with at least one oxygen atom and no or two nitrogen atoms, the non-aromatic heterocyclic ring having no substituents or having one ring carbon in the form of a carbonyl.

Exemplary of these particularly preferred compounds of formula Ia are selected from the group consisting of N-{4-[1-(2-fluorobenzyl)-2,6-dioxo-3-(1H-[1,2,4]triazol-3-ylmethyl)-2,3,6,7-tetrahydro-1H-purin-8-ylmethyl]-phenyl}-acetamide; compound with trifluoro-acetic acid,
N-{4-[1-(2-fluorobenzyl)-2,6-dioxo-3-(tetrahydro-pyran-2-ylmethyl)-2,3,6,7-tetrahydro-1H-purin-8-ylmethyl]-phenyl}-acetamide,
N-(4-{1-(2-fluorobenzyl)-2,6-dioxo-3-[2-(5-oxo-4,5-dihydro-[1,3,4]oxadiazol-2-yl)-ethyl]-2,3,6,7-tetrahydro-1H-purin-8-ylmethyl}-phenyl)-acetamide,
N-(4-{1-(2-fluorobenzyl)-2,6-dioxo-3-[3-(5-oxo-4,5-dihydro-[1,3,4]oxadiazol-2-yl)-propyl]-2,3,6,7-tetrahydro-1H-purin-8-ylmethyl}-phenyl)-acetamide,
N-{4-[1-(2-fluorobenzyl)-3-phenyl-2,6-dioxo-2,3,6,7-tetrahydro-1H-purin-8-ylmethyl]-phenyl}-acetamide,
N-{4-[1-(2-fluorobenzyl)-3-furan-3-ylmethyl-2,6-dioxo-2,3,6,7-tetrahydro-1H-purin-8-ylmethyl]-phenyl}-acetamide,
N-{4-[1-(2-fluorobenzyl)-3-(tetrahydrofuran-2-ylmethyl)-2,6-dioxo-2,3,6,7-tetrahydro-1H-purin-8-ylmethyl]-phenyl}-acetamide, and
N-{4-[1-(2-fluorobenzyl)-2,6-dioxo-3-thiophen-2-ylmethyl-2,3,6,7-tetrahydro-1H-purin-8-ylmethyl]-phenyl}-acetamide.

Particularly preferred are compounds of formula Ia wherein $R^2$ is selected from the group consisting of lower alkyl, lower alkyl substituted by lower alkoxy or hydroxy, and lower alkenyl, more particularly, unsubstituted lower alkyl and lower alkenyl. Exemplary of these particularly preferred compounds are selected from the group consisting of N-{4-[1-(2-fluorobenzyl)-3-hexyl-2,6-dioxo-2,3,6,7-tetrahydro-1H-purin-8-ylmethyl]-phenyl}-acetamide,
N-{3-acetylamino-4-[3-butyl-1-(2-fluorobenzyl)-2,6-dioxo-2,3,6,7-tetrahydro-1H-purin-8-ylmethyl]-phenyl}-acetamide,
3-chloro-4-(propane-2-sulfonyl)-thiophene-2-carboxylic acid {4-[3-butyl-1-(2-fluorobenzyl)-2,6-dioxo-2,3,6,7-tetrahydro-1H-purin-8-ylmethyl]-phenyl}-amide,
N-{5-amino-2-[3-butyl-1-(2-fluorobenzyl)-2,6-dioxo-2,3,6,7-tetrahydro-1H-purin-8-ylmethyl]-phenyl}-acetamide,
N-{6-[3-butyl-1-(2-fluorobenzyl)-2,6-dioxo-2,3,6,7-tetrahydro-1H-purin-8-ylmethyl]-pyridin-3-yl }-acetamide,
N-{4-[1-(2-fluorobenzyl)-3-(3,3-dimethylbutyl)-2,6-dioxo-2,3,6,7-tetrahydro-1H-purin-8-ylmethyl]-phenyl}-acetamide,
N-{5-[3-butyl-1-(2-fluorobenzyl)-2,6-dioxo-2,3,6,7-tetrahydro-1H-purin-8-ylmethyl]-pyridin-2-yl}-acetamide,
N-{4-[3-butyl-1-(2-fluorobenzyl)-2,6-dioxo-2,3,6,7-tetrahydro-1H-purin-8-ylmethyl]-phenyl}-3,4-dimethoxy-benzamide,
N-{4-[1-(2-fluorobenzyl)-3-(3-methylbutyl)-2,6-dioxo-2,3,6,7-tetrahydro-1H-purin-8-ylmethyl]-phenyl}-acetamide,
N-{4-[1-(2-fluorobenzyl)-3-butyl-2,6-dioxo-2,3,6,7-tetrahydro-1H-purin-8-ylmethyl]-phenyl}-acetamide,
N-{4-[1-(2-fluorobenzyl)-3-butyl-2,6-dioxo-2,3,6,7-tetrahydro-1H-purin-8-ylmethyl]-phenyl}-2,2,2-trifuoro-acetamide,
N-{4-[1-(2-fluorobenzyl)-3-isobutyl-2,6-dioxo-2,3,6,7-tetrahydro-1H-purin-8-ylmethyl]-phenyl}-acetamide,
{4-[3-butyl-1-(2-fluorobenzyl)-2,6-dioxo-2,3,6,7-tetrahydro-1H-purin-8-ylmethyl]-phenyl}-urea,
1H-imidazole-4-carboxylic acid {4-[3-butyl-1-(2-fluorobenzyl)-2,6-dioxo-2,3,6,7-tetrahydro-1H-purin-8-ylmethyl]-phenyl}-amide; compound with trifluoro-acetic acid, 1H-[1,2,4]triazole-3-carboxylic acid {4-[3-butyl-1-(2-fluorobenzyl)-2,6-dioxo-2,3,6,7-tetrahydro-1H-purin-8-ylmethyl]-phenyl}-amide; compound with trifluoroacetic acid, N-{4-[1-(2-fluorobenzyl)-3-propyl-2,6-dioxo-2,3,6,7-tetrahydro-1H-purin-8-ylmethyl]-phenyl}-acetamide, N-{4-[3-butyl-1-(2-fluorobenzyl)-2,6-dioxo-2,3,6,7-tetrahydro-1H-purin-8-ylmethyl]-phenyl}-6,N-dimethyl-nicotinamide, N-butyl-N-{4-[3-butyl-1-(2-fluorobenzyl)-2,6-dioxo-2,3,6,7-tetrahydro-1H-purin-8-ylmethyl]-phenyl}-6-methyl-nicotinamide, and N-{4-[1-(2-fluorobenzyl)-3-(3-methyl-but-2-enyl)-2,6-dioxo-2,3,6,7-tetrahydro-1H-purin-8-ylmethyl]-phenyl}-acetamide.

Further preferred compounds of formula Ia are those when $R^2$ is lower alkyl substituted by hydroxy or lower alkoxy. Representative compounds are selected from the group consisting of N-{4-[1-(2-fluorobenzyl)-3-(2-hydroxymethyl-butyl)-2,6-dioxo-2,3,6,7-tetrahydro-1H-purin-8-ylmethyl]-phenyl}-acetamide, N-{4-[1-(2-fluorobenzyl)-3-(4-hydroxy-propyl)-2,6-dioxo-2,3,6,7-tetrahydro-1H-purin-8-ylmethyl]-phenyl}-acetamide and N-{4-[1-(2-fluorobenzyl)-3-(4-hydroxy-butyl)-2,6-dioxo-2,3,6,7-tetrahydro-1H-purin-8-ylmethyl]-phenyl}-acetamide.

Further preferred compounds of formula Ia are those wherein $R^2$ is —$(CH_2)_n$—$C(O)R^b$, wherein $R^b$ is selected from the group consisting of hydroxyl, lower alkoxy, —$NHR^c$, wherein $R^c$ is selected from the group consisting of hydrogen, benzyl, lower alkyl and —$NHR^d$, wherein $R^d$ is hydrogen or carboxy-lower alkyl.

Exemplary of these compounds of formula Ia are compounds selected from the group consisting of N-{4-[1-(2-fluorobenzyl)-3-(2-hydrazinocarbonyl-ethyl)-2,6-dioxo-2,3,6,7-tetrahydro-1H-purin-8-ylmethyl]-phenyl}-acetamide, 3-[8-(4-acetylamino-benzyl)-1-(2-fluorobenzyl)-2,6-dioxo-1,2,6,7-tetrahydro-purin-3-yl]-propionic acid methyl ester, 4-[8-(4-acetylamino-benzyl)-1-(2-fluorobenzyl)-2,6-dioxo-1,2,6,7-tetrahydro-purin-3-yl]-N-butyl-butyramide, 4-[8-(4-acetylamino-benzyl)-1-(2-fluorobenzyl)-2,6-dioxo-1,2,6,7-tetrahydro-purin-3-yl]-butyric acid methyl ester, 4-[8-(4-acetylamino-benzyl)-1-(2-fluorobenzyl)-2,6-dioxo-1,2,6,7-tetrahydro-purin-3-yl]-butyramide, N'-{4-[8-(4-acetylamino-benzyl)-1-(2-fluorobenzyl)-2,6-dioxo-1,2,6,7-tetrahydro-purin-3-yl]-butyryl}-hydrazinecarboxylic acid ethyl ester, 4-[8-(4-acetylamino-benzyl)-1-(2-fluorobenzyl)-2,6-dioxo-1,2,6,7-tetrahydro-purin-3-yl]-N-benzyl-butyramide, 4-[8-(4-acetylamino-benzyl)-1-(2-fluorobenzyl)-2,6-dioxo-1,2,6,7-tetrahydro-purin-3-yl]-propionic acid, N-{4-[1-(2-fluorobenzyl)-3-(3-hydrazinocarbonyl-propyl)-2,6-dioxo-2,3,6,7-tetrahydro-1H-purin-8-ylmethyl]-phenyl}-acetamide, and 4-[8-(4-acetylamino-benzyl)-1-(2-fluorobenzyl)-2,6-dioxo-1,2,6,7-tetrahydro-purin-3-yl]-butyric acid.

Another preferred compound of formula Ia is when $R^2$ is substituted cycloalkyl. Exemplary of these preferred compounds of formula Ia are selected from the group consisting of 2-[8-(4-acetylamino-benzyl)-1-(2-fluorobenzyl)-2,6-dioxo-1,2,6,7-tetrahydro-purin-3-ylmethyl]-cyclopropanecarboxylic acid, N-{4-[1-(2-fluorobenzyl)-3-(2-methyl-cyclopropylmethyl)-2,6-dioxo-2,3,6,7-tetrahydro-1H-purin-8-ylmethyl]-phenyl}-acetamide, N-{4-[3-(2,2-bis-hydroxymethyl-cyclopropylmethyl)-1-(2-fluorobenzyl)-2,6-dioxo-2,3,6,7-tetrahydro-1H-purin-8-ylmethyl]-phenyl}-acetamide, N-{4-[1-(2-fluorobenzyl)-3-(2-hydroxymethyl-cyclopropylmethyl)-2,6-dioxo-2,3,6,7-tetrahydro-1H-purin-8-ylmethyl]-phenyl}-acetamide and 2-[8-(4-acetylamino-benzyl)-1-(2-fluorobenzyl)-2,6-dioxo-1,2,6,7-tetrahydro-purin-3-ylmethyl]-cyclopropanecarboxylic acid methyl ester.

Further preferred compounds of formula Ia are found when $R^2$ is unsubstituted cycloalkyl. Further preferred compounds of Formula I are found where $R^2$ is unsubstituted cycloalkyl. Preferred among the unsubstituted cycloalkyl compounds of formula I are wherein $R^2$ is —$CH_2$-cyclopentyl. Preferred among the unsubstituted cycloalkyl compounds of formula Ia are wherein $R^2$ is cyclopentyl, exemplified by N-{4-[3-cyclopentylmethyl-1-(2-fluorobenzyl)-2,6-dioxo-2,3,6,7-tetrahydro-1H-purin-8-ylmethyl]-phenyl}-acetamide.

A further preferred compound of Ia wherein $R^2$ is cycloalkyl is wherein $R^2$ is —$(CH_2)_n$-cycloalkyl is wherein $R^2$ is —(CH2)-cyclobutyl. A further preferred compound of formula Ia wherein $R^2$ is cycloalkyl is wherein $R^2$ is cyclobutyl. Representative examples of these compounds are selected from the group consisting of N-{4-[3-cyclobutylmethyl-1-(2-fluorobenzyl)-2,6-dioxo-2,3,6,7-tetrahydro-1H-purin-8-ylmethyl]-phenyl}-6,N-dimethyl-nicotinamide, N-cyclobutylmethyl-N-{4-[3-cyclobutylmethyl-1-(2-fluorobenzyl)-2,6-dioxo-2,3,6,7-tetrahydro-1H-purin-8-ylmethyl]-phenyl}-6-methyl-nicotinamide and N-{4-[3-cyclobutylmethyl-1-(2-fluorobenzyl)-2,6-dioxo-2,3,6,7-tetrahydro-1H-purin-8-ylmethyl]-phenyl}-acetamide.

A further preferred compound of formula Ia wherein $R^2$ is —$(CH_2)_n$-cycloalkyl is wherein $R^2$ is —$(CH_2)$-cyclopropyl. A particularly preferred compound derived from a compound of formula Ia wherein $R^2$ is unsubsituted cycloalkyl has the formula

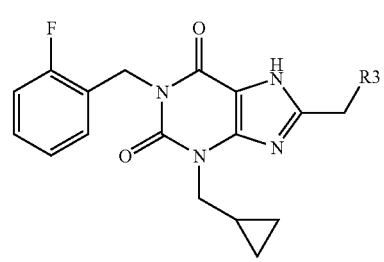

Ib

-continued wherein $R^3$ is 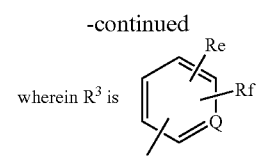

wherein Q is N or CH, with the proviso that
when Q is N, $R^e$ is —NH—C(O)—CH$_3$ and $R^f$ is H,
when Q is CH, $R^e$ is —NR$^g$—C(O)—R$^h$ or

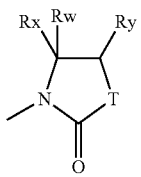

and $R^f$ is selected from the group consisting of H, —NH$_2$ and —NH—C(O)—CH$_3$,
$R^g$ is selected from the group consisting of
  H,
  lower alkyl and
  —(CH$_2$)$_n$-unsubstituted lower cycloalkyl,
$R^h$ is selected from the group consisting of
  —(CH$_2$)$_n$-5- or 6-member aromatic heterocyclic ring having one, two or three hetero atoms independently selected from the group consisting of N, O and S, the aromatic heterocyclic ring being unsubstituted or having at least one substituent independently selected from the group consisting of lower alkyl, lower alkoxy, hydroxy, halogen, —NH$_2$, —NH—C(O)-lower alkyl, —CN, —C(O)—NH$_2$ and —SO$_2$-lower alkyl,
  lower alkyl,
  lower alkyl substituted by at least one substituent independently selected from the group consisting of halogen, phenyl and —(CH$_2$)$_n$NHR$^i$R$^i$, wherein R$^i$ is independently selected from the group consisting of H, lower alkyl, and carbonyloxybenzyl (CBZ),
  —NHR$^j$, wherein R$^j$ is selected from the group consisting of a 5- or 6-membered aromatic heterocyclic ring having one, two or three heteroatoms independently selected from the group consisting of N, O and S, the heterocyclic ring being substituted at least one substituent selected from the group consisting of halogen, lower alkyl and phenyl,
  —C(O)—R$^k$, wherein R$^k$ is a 5- or 6-member aromatic heterocyclic ring having one, two or three hetero atoms independently selected from the group consisting of N, O and S, the aromatic heterocyclic ring being unsubstituted or substituted by at least one lower alkyl, unsubstituted phenyl, the phenyl ring substituted by a substitutent independently selected from the group consisting of lower alkyl, lower alkoxy, and —(CH$_2$)$_m$—NH R$^1$, wherein R$^1$ is selected from the group consisting of H, lower alkyl and carbonyloxybenzyl (CBZ), and
wherein T is NH or CH$_2$, with the proviso that
when T is NH, R$^w$ and R$^x$ are, taken together with the carbon to which they are attached, form —C(O)— and R$^y$ is —(CH$_2$)OR$^z$ wherein R$^z$ is selected from the group consisting of hydrogen and lower alkyl, and when T is CH$_2$, R$^w$ and R$^x$ are both hydrogen or are, taken together with the carbon to which they are attached, form —C(O)—; and
n is 0, 1 or 2;
m is 0 or 1;
or a pharmaceutically acceptable salt or prodrug thereof.
A preferred compound of formula 1b has the formula

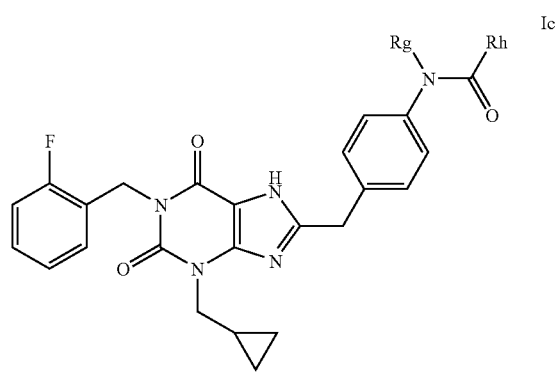

wherein
$R^g$ is selected from the group consisting of H, lower alkyl and —(CH$_2$)$_n$-unsubstituted lower cycloalkyl; and
$R^h$ is selected from the group consisting of
  a —(CH$_2$)$_n$-5- or 6-member aromatic heterocyclic ring having one, two or three hetero atoms independently selected from the group consisting of N, O and S, the aromatic heterocyclic ring being unsubstituted or having at least one substituent independently selected from the group consisting of lower alkyl, lower alkoxy, hydroxy, halogen, —NH$_2$, —NH—C(O)-lower alkyl, —CN, —C(O)—NH$_2$ and —SO$_2$-lower alkyl,
  lower alkyl,
  lower alkyl substituted by at least one substituent independently selected from the group consisting of halogen, phenyl and —(CH$_2$)$_n$NHR$^i$R$^i$, wherein R$^i$ is independently selected from the group consisting of H, lower alkyl, lower alkyl substituted by halogen and carbonyloxybenzyl (CBZ),
  —NHR$^j$, wherein R$^j$ is selected from the group consisting of a 5- or 6-membered aromatic heterocyclic ring having one, two or three heteroatoms independently selected from the group consisting of N, O and S, the heterocyclic ring being substituted at least one substituent selected from the group consisting of halogen, lower alkyl and an unsubstituted 6 membered aromatic ring,
  —C(O)—R$^k$, wherein R$^k$ is a 5- or 6-member aromatic heterocyclic ring having one, two or three hetero atoms independently selected from the group consisting of N, O and S, the aromatic heterocyclic ring being unsubstituted or substituted by at least one lower alkyl, unsubstituted phenyl, or phenyl substituted by a substitutent independently selected from the group consisting of lower alkyl, lower alkoxy, and —(CH$_2$)$_m$—NH R$^1$, wherein R$^1$ is selected from the group consisting of H, lower alkyl and carbonyloxybenzyl (CBZ); and
n is 0, 1 or 2; and
m is 0 or 1;
or a pharmaceutically acceptable salt or prodrug thereof.

A particularly preferred compound of formula Ic is wherein $R^g$ is lower alkyl.

A more preferred compound of formula Ic with $R^g$ as lower alkyl has the formula

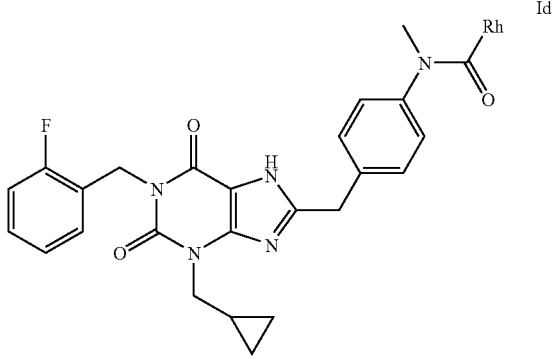

Id wherein $R^h$ is selected from the group consisting of
- a —(CH$_2$)$_n$-5- or 6-member aromatic heterocyclic ring having one, two or three hetero atoms independently selected from the group consisting of N, O and S, the aromatic heterocyclic ring being unsubstituted or having at least one substituent independently selected from the group consisting of lower alkyl, lower alkoxy, hydroxy, halogen, —NH$_2$, —NH—C(O)-lower alkyl, —CN, —C(O)—NH$_2$ and —SO$_2$-lower alkyl,
- lower alkyl,
- lower alkyl substituted by at least one substituent independently selected from the group consisting of halogen, phenyl and —(CH$_2$)$_n$NR$^i$R$^i$, wherein R$^i$ is independently selected from the group consisting of H, lower alkyl, and carbonyloxybenzyl (CBZ),
- —NHR$^j$, wherein R$^j$ is selected from the group consisting of a 5- or 6-membered aromatic heterocyclic ring having one, two or three heteroatoms independently selected from the group consisting of N, O and S, the heterocyclic ring being substituted at least one substituent selected from the group consisting of halogen, lower alkyl and phenyl,
- —C(O)—R$^k$, wherein R$^k$ is a 5- or 6-member aromatic heterocyclic ring having one, two or three hetero atoms independently selected from the group consisting of N, O and S, the aromatic heterocyclic ring being unsubstituted or substituted by at least one lower alkyl, unsubstituted phenyl, phenyl substituted by a substitutent independently selected from the group consisting of lower alkyl, lower alkoxy, and —(CH$_2$)$_n$—NH R$^1$, wherein R$^1$ is selected from the group consisting of H, lower alkyl and carbonyloxybenzyl (CBZ); and n is 0, 1 or 2;
m is 0 or 1;
or a pharmaceutically acceptable salt or prodrug thereof.

A preferred compound of formula 1d is wherein $R^h$ is a —(CH$_2$)$_n$-5- or 6-membered aromatic heterocyclic ring with 1, 2 or 3 heteroatoms independently selected from the group consisting of N, O and S, the aromatic heterocyclic ring being unsubstituted or having at least one substituent selected from the group consisting of
lower alkyl,
lower alkoxy,
hydroxy,
halogen,
amino,
—NH—C(O)-lower alkyl,
—CN,
—C(O)—NH$_2$ and
—SO$_2$-lower alkyl.

A more preferred compound of formula Id is wherein $R^h$ is an unsubstituted —(CH$_2$)$_n$-5- or 6-membered aromatic heterocyclic ring having 1, 2 or 3 heteroatoms independently selected from the group consisting of N, O and S. Representative of the more preferred compound of formula Id is a compound selected from the group consisting of
- pyrimidine-5-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide,
- N-{4-[3-cyclopropylmethyl-1-(2-fluorobenzyl)-2,6-dioxo-2,3,6,7-tetrahydro-1H-purin-8-ylmethyl]-phenyl}-N-methyl-2-pyridin-3-yl-acetamide,
- N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide,
- pyrazine-2-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide and
- [1,2,3]thiadiazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide.

Another preferred compound of formula Id is wherein $R^h$ is a —(CH$_2$)$_n$-5- or 6-membered aromatic heterocyclic ring having 1, 2 or 3 heteroatoms independently selected from the group consisting of N, O and S, the aromatic heterocyclic ring being substituted by lower alkyl. Exemplary of these preferred compounds is a compound selected from the group consisting of
- 1,3,5-trimethyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide,
- 2,4-dimethyl-thiazole-5-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide,
- 4-amino-1-methyl-1H-pyrazole-3-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide,
- 3-methyl-isoxazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide,
- 2,4-dimethyl-thiazole-5-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide,
- 3,5-dimethyl-isoxazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide,
- N-{4-[3-cyclopropylmethyl-1-(2-fluorobenzyl)-2,6-dioxo-2,3,6,7-tetrahydro-1H-purin-8-ylmethyl]-phenyl}-5,N-dimethyl-nicotinamide,
- N-{4-[3-cyclopropylmethyl-1-(2-fluorobenzyl)-2,6-dioxo-2,3,6,7-tetrahydro-1H-purin-8-ylmethyl]-phenyl}-6,N-dimethyl-nicotinamide,
- 4-methyl-[1,2,3]thiadiazole-5-carboxylic acid {4-[3-cyclopropyl-methyl-1-(2-fluorobenzyl)-2,6-dioxo-2,3,6,7-tetrahydro-1H-purin-8-ylmethyl]-phenyl}-methyl-amide, 1,3-dimethyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide, 1-methyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide, and 5-methyl-isoxazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide.

Another preferred compound of formula Id is wherein the $-(CH_2)_n$-5- or 6-membered aromatic heterocyclic ring is substituted by halogen and lower alkyl. Exemplary of these preferred compound is 3-chloro-1,5-dimethyl-1H-pyrazole-4-carboxylic acid {4-[3-cyclopropyl-methyl-1-(2-fluorobenzyl)-2,6-dioxo-2,3,6,7-tetrahydro-1H-purin-8-ylmethyl]-phenyl}-methyl-amide.

Another preferred compound of formula Id is wherein the $-(CH_2)_n$-5- or 6-membered aromatic heterocyclic ring is substituted by hydroxy. Exemplary of this preferred compound is a compound selected from the group consisting of N-{4-[3-cyclopropylmethyl-1-(2-fluorobenzyl)-2,6-dioxo-2,3,6,7-tetrahydro-1H-purin-8-ylmethyl]-phenyl}-6-hydroxy-N-methyl-nicotinamide and 4-[3-cyclopropylmethyl-1-(2-fluorobenzyl)-2,6-dioxo-2,3,6,7-tetrahydro-1H-purin-8-ylmethyl]-phenyl}-2-hydroxy-N-methyl-nicotinamide.

More preferred compounds of formula Id are found when the $-(CH_2)_n$-5- or 6-membered aromatic heterocyclic ring is substituted by $-NH_2$. Representive of these more preferred compounds of formula Id are selected from the group consisting of 2-amino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide and 6-amino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide.

Another preferred compound of formula Id is wherein the $-(CH_2)_n$-5- or 6-membered aromatic heterocyclic ring is substituted by amino and alkyl. An exemplary compound of this preferred compound of formula Id is selected from the group consisting of 2-amino-4-methyl-thiazole-5-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide and 4-amino-1-methyl-1H-pyrazole-3-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide.

Another preferred compound of formula Id is wherein the $-(CH_2)_n$-5- or 6-membered aromatic heterocyclic ring is substituted by lower alkoxy. Representative of this compound is N-{4-[3-cyclopropylmethyl-1-(2-fluorobenzyl)-2,6-dioxo-2,3,6,7-tetrahydro-1H-purin-8-ylmethyl]-phenyl}-2,6-dimethoxy-N-methyl-nicotinamide.

In a further preferred embodiment of formula Id the $-(CH_2)_n$-5- or 6-membered aromatic heterocyclic ring is substituted by $-CN$. Representative of this further preferred embodiment is 6-cyano-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide.

An additional preferred compound of formula Id is wherein the $-(CH_2)_n$-5- or 6-membered heteroaromatic ring is substituted by $-NH-C(O)$-lower alkyl. An exemplary compound of the additional preferred compound is selected from the group consisting of 6-acetylamino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide, 6-acetylamino-pyridine-2-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide and 4-acetylamino-2-methyl-thiophene-3-carboxylic acid {4-[3-cyclopropyl-methyl-1-(2-fluorobenzyl)-2,6-dioxo-2,3,6,7-tetrahydro-1H-purin-8-ylmethyl]-phenyl}-methyl-amide.

Another additional preferred compound of formula Id is wherein the $-(CH_2)_n$-5- or 6-membered heteroaromatic ring is substituted by lower alkyl and $-NH-C(O)$-lower alkyl. Representative of this additional preferred compound is 2-acetamino-N-{4-[3-cyclopropylmethyl-1-(2-fluorobenzyl)-2,6-dioxo-2,3,6,7-tetrahydro-1H-purin-8-ylmethyl]-phenyl}-4,6,N-trimethyl-nicotinamide.

A further additional preferred compound of formula Id is wherein the $-(CH_2)_n$-5- or 6-membered heteroaromatic ring is substituted by $-C(O)-NH_2$. Exemplary of this preferred compound of formula Id is thiophene-2,3-dicarboxylic acid 3-amide 2-({4-[3-cyclopropylmethyl-1-(2-fluorobenzyl)-2,6-dioxo-2,3,6,7-tetrahydro-1H-purin-8-ylmethyl]-phenyl}-methyl-amide).

An additional preferred compound of formula Id is wherein $R^h$ is $-C(O)-R^k$, wherein $R^k$ is a 5- or 6-member aromatic heterocyclic ring having one, two or three hetero atoms independently selected from the group consisting of N, O and S, the aromatic heterocyclic ring being unsubstituted or substituted by at least one lower alkyl. Exemplary of the additional preferred compound is N-{4-[3-cyclopropyl-methyl-1-(2-fluorobenzyl)-2,6-dioxo-2,3,6,7-tetrahydro-1H-purin-8-ylmethyl]-phenyl}-N-methyl-2-oxo-2-(1,3,5-trimethyl-1H-pyrazol-4-yl)-acetamide.

Another preferred compound of formula 1d is wherein $R^h$ is phenyl, the phenyl substituted by a substituent independently selected from the group consisting of lower alkyl, lower alkoxy, and $-(CH_2)_n-NHR^1$, wherein $R^1$ is selected from the group consisting of H, lower alkyl and carbonyloxybenzyl (CBZ). Exemplary of this preferred compound of formula Id is selected from the group consisting of

[4-({4-[3-cyclopropyl-1-(2-fluorobenzyl)-2,6-dioxo-2,3,6,7-tetrahydro-1H-purin-8-ylmethyl]-phenyl}-methyl-carbamoyl)-benzyl]-carbamic acid benzyl ester, 4-aminomethyl-N-{4-[3-cyclopropylmethyl-1-(2-fluorobenzyl)-2,6-dioxo-2,3,6,7-tetrahydro-1H-purin-8-ylmethyl]phenyl-4-ethylaminomethyl-N-methylbenzamide; compound with trifluoro-acetic acid and 4-aminomethyl-N-{4-[3-cyclopropylmethyl-1-(2-fluorobenzyl)-2,6-dioxo-2,3,6,7-tetrahydro-1H-purin-8-ylmethyl]-phenyl}-N-methyl-benzamide;

compound with trifluoro-acetic acid.

A further preferred compound of formula Id is wherein $R^h$ is lower alkyl substituted by $-(CH_2)_n-NHR^j$ wherein $R^j$ is independently selected from the group consisting of H, lower alkyl and carbonyloxybenzyl (CBZ). Exemplary of the further preferred compound is selected from the group consisting of 2-amino-N-{4-[3-cyclopropylmethyl-1-(2-fluorobenzyl)-2,6-dioxo-2,3,6,7-tetrahydro-1H-purin-8-ylmethyl]-phenyl}-N-methyl-2-phenyl-acetamide and

[({4-[3-cyclopropylmethyl-1-(2-fluorobenzyl)-2,6-dioxo-2,3,6,7-tetrahydro-1H-purin-8-ylmethyl]phenyl}-methyl-carbamoyl)-phenyl-methyl]-carbamic acid benzyl ester.

An additional preferred compound of formula Ic is wherein $R_g$ is ethyl. An example of this compound is 1,3,5-trimethyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-ethyl-amide.

Another additional preferred compound of formula Ic is wherein Rg is isopropyl. A compound of exemplary of this additional preferred compound is selected from the group consisting of N-{4-[3-cyclopropylmethyl-1-(2-fluorobenzyl)-2,6-dioxo-2,3,6,7-tetrahydro-1H-purin-8-ylmethyl]-phenyl}-N-isopropyl-6-methyl-nicotinamide and N-{4-[3-cyclopropylmethyl-1-(2-fluorobenzyl)-2,6-dioxo-2,3,6,7-tetrahydro-1H-purin-8-ylmethyl]-phenyl}-N-isopropyl-2-pyridin-3-yl-acetamide.

N-{4-[3-Cyclopropylmethyl-1-(2-fluorobenzyl)-2,6-dioxo-2,3,6,7-tetrahydro-1H-purin-8-ylmethyl]-phenyl}-N-isopropyl-6-methyl-nicotinamide is a particularly preferred embodiment of formula Ic.

Another particularly preferred compound of formula Ic is N-{4-[3-cyclopropylmethyl-1-(2-fluorobenzyl)-2,6-dioxo-2,3,6,7-tetrahydro-1H-purin-8-ylmethyl]-phenyl}-N-isopropyl-2-pyridin-3-yl-acetamide.

Another preferred compound of formula Ic is wherein $R^g$ is H and $R^h$ is lower alkyl substituted by halogen. Exemplary of this preferred compound is N-{4-[3-cyclopentylmethyl-1-(2-fluorobenzyl)-2,6-dioxo-2,3,6,7-tetrahydro-1H-purin-8-ylmethyl]-phenyl}-2,2,2-trifluoroacetamide.

A further additional preferred compound of formula Ic is wherein $R^g$ is H and $R^h$ is a —$(CH_2)_n$-5- or 6-membered aromatic heterocyclic ring having 1, 2 or 3 heteroatoms independently selected from the group consisting of N, O and S, the aromatic heterocyclic ring being substituted by lower alkyl. Exemplary of the additional preferred compound is 1-methyl-1H-pyrazole-4-carboxylic acid {4-[3-cyclopropyl-methyl-1-(2-fluorobenzyl)-2,6-dioxo-2,3,6,7-tetrahydro-1H-purin-8-ylmethyl]-phenyl}-amide.

Another preferred compound of formula Ic is wherein $R^g$ is H and $R^h$ is —NHR$^j$, wherein R$^j$ is selected from the group consisting of a 5- or 6-membered aromatic heterocyclic ring having one, two or three heteroatoms independently selected from the group consisting of N, O and S, the heterocyclic ring being substituted at least one substituent selected from the group consisting of halogen, lower alkyl and phenyl.

Exemplary of these preferred compounds are compounds selected from the group consisting of 1-{4-[3-cyclopropylmethyl-1-(2-fluorobenzyl)-2,6-dioxo-2,3,6,7-tetrahydro-1H-purin-8-ylmethyl]-phenyl}-3-(2,6-dichloro-pyridin-4-yl)-urea and 1-{4-[3-cyclopropylmethyl-1-(2-fluorobenzyl)-2,6-dioxo-2,3,6,7-tetrahydro-1H-purin-8-ylmethyl]-phenyl}-3-(3,5-dimethyl-1-phenyl-1H-pyrazol-4-yl)-urea.

A further preferred compound of formula Ic is wherein $R^g$ is H and $R^h$ is —NH—C(O)-lower alkyl. Exemplary of this preferred compound is N-{4-[3-cyclopropylmethyl-1-(2-fluorobenzyl)-2,6-dioxo-2,3,6,7-tetrahydro-1H-purin-8-ylmethyl]-phenyl}-acetamide.

An additional preferred compound of formula I c is wherein $R^g$ is H and $R^h$ is lower alkyl substituted by least one substituent independently selected from the group consisting of halogen, phenyl and —$(CH_2)_n$NR$^i$R$^i$, wherein R$^i$ is independently selected from the group consisting of H, lower alkyl, and carbonyloxybenzyl (CBZ). This preferred compound is exemplified by N-{4-[3-cyclopropylmethyl-1-(2-fluorobenzyl)-2,6-dioxo-2,3,6,7-tetrahydro-1H-purin-8-ylmethyl]-phenyl}-2-dimethylamino-acetamide; compound with trifluoro-acetic acid.

A further preferred compound of formula Ib is wherein $R^3$ is

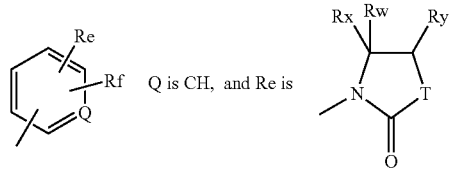

and R$^f$ is selected from the group consisting of H, —$NH_2$ and —NH—C(O)—$CH_3$, wherein T is NH or $CH_2$, with the proviso that when T is NH, R$^w$ and R$^x$ are, taken together with the carbon to which they are attached, form —C(O)— and R$^y$ is —$(CH_2)OR^z$ wherein R$^z$ is selected from the group consisting of hydrogen and lower alkyl. This preferred compound is exemplified by a compound selected from the group consisting of 8-[4-(4-tert-butoxymethyl-2,5-dioxo-imidazolidin-1-yl)-benzyl]-3-cyclopropylmethyl-1-(2-fluorobenzyl)-3,7-dihydro-purine-2,6-dione and 3-cyclopropylmethyl-1-(2-fluorobenzyl)-8-[4-(4-(S)-hydroxymethyl-2,5-dioxo-imidazolidin-1-yl)-benzyl]-3,7-dihydro-purine-2,6-dione.

The prodrugs of the compounds of this invention are preferred embodiments of this invention. As defined above, a prodrug is a compound that may be converted, under physiological conditions or by solvolysis, to a pharmaceutically active compound. Prodrugs are generally known in the art. See, for example, Design of Prodrugs, Bundgaard, Hans, ed., Neth (1985), 360 pp., Elsevier, Amsterdam, Neth. In accordance therefor, the compounds of this invention further includes its prodrug form.

A further embodiment of the present invention relates to a process for the preparation of a compound of formula I as defined before, which process comprises cyclisation of a compound of formula II

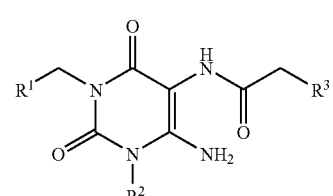

wherein $R^1$, $R^2$ and $R^3$ are as defined before, to yield the compound of formula I. Appropriate reaction conditions for such cyclisations are known in the art, e.g. as described below, in the examples or in analogy. Compounds as defined above, when manufactured by a process as defined above also constitute an embodiment of the present invention.

Purification of GST-PEPCK

E. coli cells expressing GST-PEPCK were suspended in 5 volumes of lysis buffer (50 mM Tris-hydroxymethyl aminomethyl (TRIS), 150 mM sodium chloride (NaCl), 10 mM ethylene-diametetraacetic acid (EDTA), 5 mM dithiothreitol (DTT), 1% Nonidet P-40, pH 7.4) in the presence of protease inhibitors, incubated with lysozyme at 200 micrograms/ml for 30 min. at room temperature, and sonicated 4×30 seconds at 4 degrees C. After centrifugation at 12,000×g for 20 min. to remove insoluble material, the supernatant was loaded onto glutathione Sepharose (Pharmacia), washed with lysis buffer followed by washing with lysis buffer in the absence of NP-40. GST-PEPCK was eluted with the same buffer containing 20 mM glutathione. The eluted protein was concentrated and dialyzed against 25 mM Hepes(N-[2-hydroxyethyl]piperazine-N'[2-ethanesulfonic acid), 150 mM NaCl, 2.5 mM EDTA, 5 mM DTT, 30% glycerol, pH 7.4, and stored at −20 °C.

PEPCK Enzyme Assay

The inhibitory effect of the compounds of the present invention on PEPCK enzymatic activity was determined using recombinant human cytosolic PEPCK, expressed and purified from *E.coli* as a GST-fusion. Guanosine triphosphate (GTP) and manganese dependent PEPCK enzyme activity catalyzed the decarboxylation of oxalacetate leading to the formation of guanosine diphosphate (GDP) and phosphoenol pyruvate (PEP). This reaction is coupled to pyruvate kinase and lactate dehydrogenase catalyzed reactions and the overall reaction rate determined by measuring the change in absorbance at 340 nM (Chang, H. C. and Lane M. D., J. Biol.Chem. 241:2413–2420, 1966). The following modifications were made to the protocol: 2.5 µg of recombinant, human cytosolic glutathione-S-transferase (GST)-PEPCK was added to a reaction mixture at room temperature which contained 0.3 mM GTP, 0.3 mM oxaloacetate (OAA), 3 mM magnesium chloride ($MgCl_2$), 0.075 mM manganese chloride ($MnCl_2$), 30 mM potassium phosphates ($KPO_4$), pH 7.6, 1 mM dithiothreitol (DTT), 0.2 mM adenosine diphosphate (ADP), 1 mM nicotinamide adenine dinucleotide, reduced form (NADH), 0.9 Units/ml each of pyruvate kinase and lactate dehydrogenase and 1 mg/ml bovine serum albumin (BSA). Test compounds were added such that final concentration of DMSO was 10%. Reactions were run for twenty minutes.

$K_m$ values for GTP and OAA were determined according to Michelis-Menton conditions as described in Cornish-Bowden (Fundamentals of Enzyme Kinetics, 1995) in essentially the coupled assay conditions described above. To determine the concentrations at which test compounds inhibited the enzyme 50% ($IC_{50}$), reaction mixtures containing 3 fold and 10 fold the calculated $K_m$ values for GTP and OAA, respectively, were employed. Test compounds were added to reactions over a range of concentrations and $IC_{50}$'s were calculated from plots of inhibitor concentration versus enzyme rate. This method of determination of $IC_{50}$ values is equally applicable to calculations based on PEPCK cellular assay.

The in vitro biological activity of several representative preferred compounds of the present invention in the foregoing PEPCK enzymatic assay is presented in Table 1.

TABLE 1

| Compound of Example No. | In vitro $IC_{50}$ (µM) |
|---|---|
| 42 | 0.93 |
| 47 | 0.56 |
| 79 | 0.56 |
| 85 | 0.40 |
| 86 | 0.42 |

TABLE 1-continued

| Compound of Example No. | In vitro $IC_{50}$ (µM) |
|---|---|
| 88 | 0.34 |
| 90 | 0.34 |
| 91 | 0.41 |
| 92 | 0.44 |
| 93 | 0.28 |
| 94 | 0.34 |
| 95 | 0.37 |
| 96 | 0.38 |
| 97 | 0.42 |
| 98 | 0.44 |
| 99 | 0.46 |
| 100 | 0.55 |
| 101 | 0.63 |
| 102 | 0.23 |
| 103 | 0.25 |
| 104 | 0.28 |
| 105 | 0.32 |
| 106 | 0.37 |
| 107 | 0.50 |
| 108 | 0.55 |
| 109 | 0.57 |
| 110 | 0.66 |
| 111 | 0.66 |
| 112 | 0.69 |
| 113 | 0.74 |
| 114 | 0.74 |
| 115 | 0.93 |
| 117 | 0.19 |
| 118 | 0.56 |
| 119 | 0.31 |
| 120 | 0.40 |
| 121 | 0.39 |

All reagents purchased were from one of: Fisher Scientific, Sigma, Pharamacia, Molecular Probes and Roche Mannheim Biochemicals and were of the highest quality available.

PEPCK Amide Derivatives—General Description of Synthetic Schemes

One route which was used for the preparation of some of the 1,3,8-trisubstituted xanthine derivatives of the present invention is shown in scheme 1. Commercially available ethyl cyanoacetate and the appropriately substituted commercially available mono-substituted urea were condensed in the presence of sodium ethoxide in refluxing ethanol according to the procedure of Papesch and Schroeder as described in *J. Org. Chem.* 1951, 16, 1879 to give a 1-substituted-6-amino-1H-pyrimidine-2,4-dione (compounds of general formula Ie in scheme 1).

Scheme 1

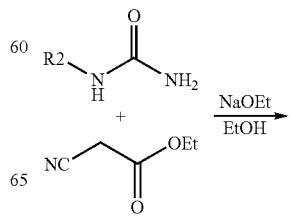

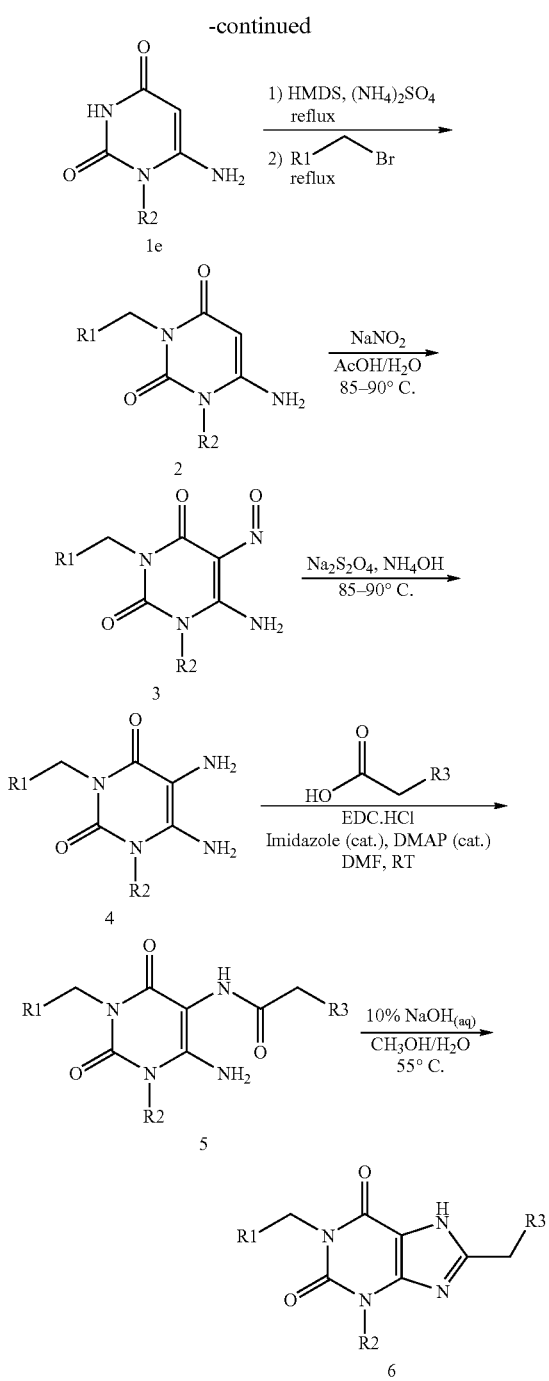

bromide) and a catalytic amount of commercially available elemental iodine at reflux. The reaction was judged complete when a good level of conversion to the 3-substituted derivatives of general formula 2 was achieved (as judged by thin layer chromatography (TLC) (EM Science TLC plates, catalog number 5719-2)) and prior to the formation of significant amounts of undesired by-products. Remaining silyl groups were removed by treatment with methanol prior to isolation and purification.

Nitrosylation of 1,3-disubstituted-6-amino-1H-pyrimidine-2,4-diones of general formula 2 were performed according to the procedure of Müller et al. as described in *J. Med. Chem.* 1993, 36, 3341. Compounds of general formula 2 were heated in aqueous acetic acid and treated with commercially available sodium nitrite to form the orange to red colored 6-amino-5-nitroso-1H-pyrimidine-2,4-diones of general formula 3 which were isolated as solids after cooling to 0° C.

The 6-amino-5-nitroso-1H-pyrimidine-2,4-diones 3 were reduced to the 5,6-diamino-1H-pyrimidine-2,4-diones of general formula 4. Chemical reduction of the nitroso group in compounds of general structure 3 was performed according to the procedure of Müller et al. as described in *J. Med. Chem.* 1993, 36, 3341. Commercially available sodium dihydrosulfite was added portionwise to a solution of the nitroso derivatives 3 in 10% aqueous ammonium hydroxide at 90° C. The reaction was judged complete when the color of the nitroso compounds had been fully discharged. The 5,6-diamino-1H-pyrimidine-2,4-diones of general formula 4 are relatively unstable and were used immediately in the next step in the synthetic pathway without additional purification.

Acylation of the 5,6-diamino-1H-pyrimidine-2,4-diones of general formula 4 was performed according to the procedure of Jacobson et al. as described in *J. Med. Chem.* 1993, 36(10), 1333. Treatment of a mixture of a diamine of general formula 4 with the appropriately substituted acetic acid derivative with commercially available 1-(3-dimethylaminopropyl)-3-ethylcarbodiimide hydrochloride (EDC) resulted in amide formation selectively at the 5-position of the 1H-pyrimidine-2,4-dione ring. Amide derivatives of general formula 5 were stable products which were typically not purified following isolation of the crude reaction product.

5-Acetamido-6-amino derivatives of general formula 5 were cyclized to form the 1,3,8-trisubstituted xanthines of general formula 6 by heating to approximately 50° C. in methanol containing 10% aqueous sodium hydroxide solution in a manner similar to that described by Müller et al. in *Synthesis* 1995, 1295. The reactions were monitored by TLC until all of the starting 5-acetamido-6-amino derivative 5 had been consumed. Pure products were obtained using standard chemical purification techniques such as chromatography or crystallization.

1-Substituted-6-amino-1H-pyrimidine-2,4-diones were alkylated at the 3-position by use of the method of Müller et al. as described in *J. Med. Chem.* 1993, 36, 3341. Compounds of general formula 1 were heated to reflux in commercially available 1,1,1,3,3,3-hexamethyldisilazane (HMDS) in the presence of a catalytic amount of commercially available ammonium sulfate and under an inert atmosphere for 4 hours to form the per-silylated derivative. The per-silylated derivatives of compounds of general formula 1 were isolated by concentration under high vacuum and reacted immediately with the desired commercially available alkylating agent (typically an alkyl, allyl or benzylic In cases where $R^3$ in structure 5 is a substituted phenyl acetic acid wherein the substituent is not stable to the conditions used to effect cyclization, the xanthine derivatives formed contained substituents on the phenyl ring which were the products of alkaline hydrolysis. As is shown in scheme 2 for compounds of general formula 7 where the phenyl substituent is 2,2,2-trifluoroacetamide, the amide group is hydrolyzed under the conditions used to effect cyclization and primary anilines of general formula 8 were obtained after cyclization. The anilines thus formed were derivatised further by application of one or more of the procedures outlined in schemes 8 to 13.

Scheme 2

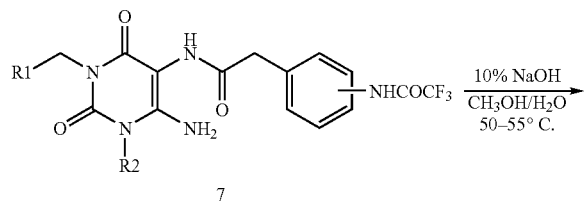

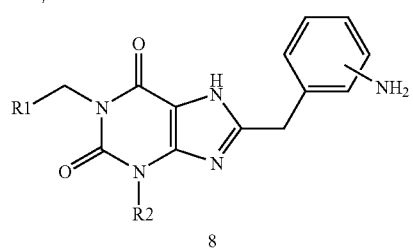

A second route which was used to prepare some of the 1,3,8-trisubstituted xanthine derivatives of the present invention is shown in scheme 3. Starting from commercially available 6-amino-1H-pyrimidine-2,4-dione 9, alkylation of the nitrogen at position 3 to give compounds of general structure 10 was achieved by using the procedure of Müller as described in *Tetrahedron Lett.* 1991, 32(45), 6539. Nitrosylation at position 5 to give compounds of general structure 11, reduction to the 5,6-diamino derivatives of general structure 12 and selective acylation of the 5-amino group to give compounds of general structure 13 was performed using the same conditions described in scheme 1, and with reference to the procedures of Müller et al. as described in *Synthesis* 1995, 1295 where these transformations were performed on similarly substituted uracil derivatives. An alternative method for the reduction of the nitroso derivatives of general formula 11 was catalytic reduction using platinum oxide catalyst in ethanol with 50 psi pressure of hydrogen by a procedure similar to that of Wells et al. as described in *J. Med. Chem.* 1981, 24(8), 954. Hydrogenation of the nitroso group was not a feasible alternative when there are functional groups present in the $R^1$ and $R^2$ substituents of compounds of general formula 11 which were sensitive to these conditions.

Scheme 3

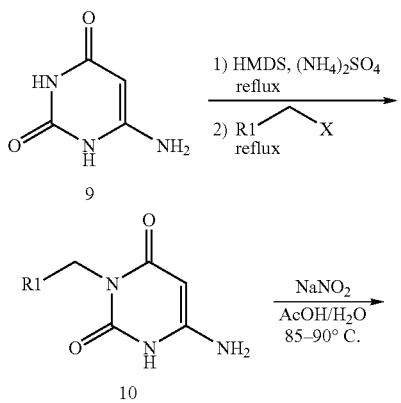

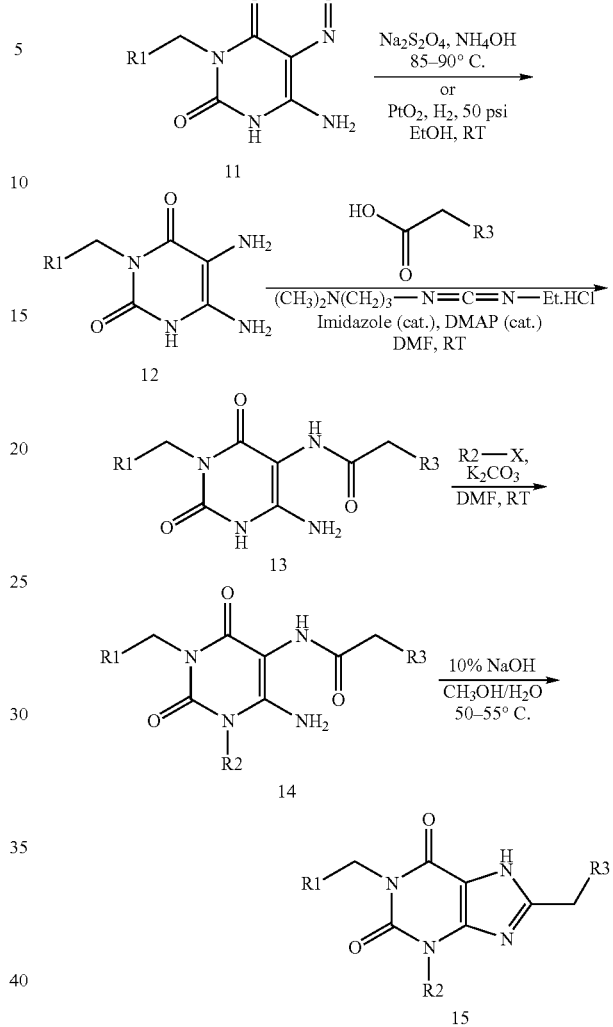

5-Acetamido-6-amino uracil derivatives of general formula 13 were selectively alkylated at the 1 position of the 1H-pyrimidine-2,4-dione to give compounds of general structure 14 by use of the appropriate alkylating agent (typically alkyl, allyl or benzylic bromides or iodides) with anhydrous potassium carbonate in DMF by analogy with the procedure of Müller et al. as described in *Synthesis* 1995, 1295. The 1-alkylated-5-acetamido-6-amino uracil derivatives of general formula 14 were cyclized to form the 1,3,8-trisubstituted xanthines of general formula 15 by the same method used for the conversion of compounds of general formula 5 to compounds of general formula 6 as shown in scheme 1.

Compounds of general formula 14 and 15 shown in scheme 3 are equivalent with the compounds of general formula 5 and 6 respectively shown in scheme 1. However the route shown in scheme 3 allows for variation of the $R^2$ at the penultimate step of the synthesis. In scheme 1 the $R^2$ substituent was introduced at the first step of the synthesis. Also, if the $R^2$ substituent in compounds of general formula 14 could not be introduced by alkylation (i.e., unreactive towards nucleophilic substitution) it was be possible to form such a compound when the requisite urea was available for use in the first step of scheme 1.

As is shown in scheme 4, when the R³ substituent was a phenyl ring bearing a 2,2,2-trifluoroacetamide group, alkylation occured on the acetanilide nitrogen. Thus, alkylation of compounds of general formula 16 using the conditions described in scheme 3 resulted in a mixture of the monoalkylated compounds of general formula 17 and dialkylated compounds of general formula 18. During cyclization the trifluoroacetamide group was hydrolyzed under the conditions used to effect cyclization and the resulting aniline derivatives 19 and alkylated analogs 20 were isolated, separated and subsequently derivatized separately by application of the procedures outlined in schemes 8 to 13.

Scheme 4

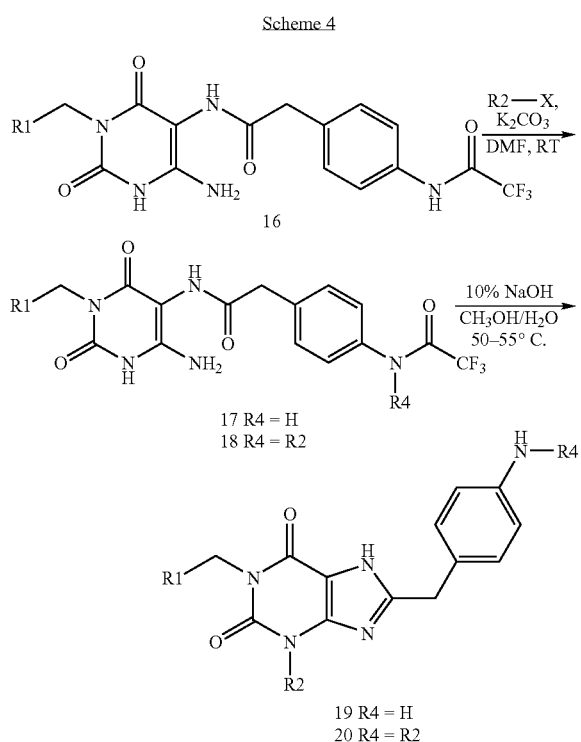

A third route which was used to prepare some of the 1,3,8-trisubstituted xanthine derivatives of the present invention is shown in scheme 5. Starting from commercially available 6-chloro-1H-pyrimidine-2,4-dione selective alkylation of the nitrogen at the 1-position of the pyrimidine ring was achieved with the appropriate alkylating agent to give compounds of general formula 21 by use of a method similar to that of Ishikawa et al. as described in *Heterocycles* 1990, 31(9), 1641. Using the same reaction conditions and a second alkylating agent (or a second equivalent of the first alkylating agent) a substituent can be introduced at the 3-position of the pyrimidine ring to furnish compounds of general formula 22.

Scheme 5

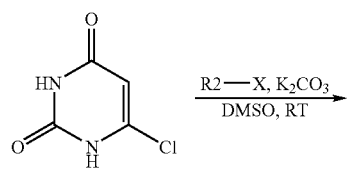

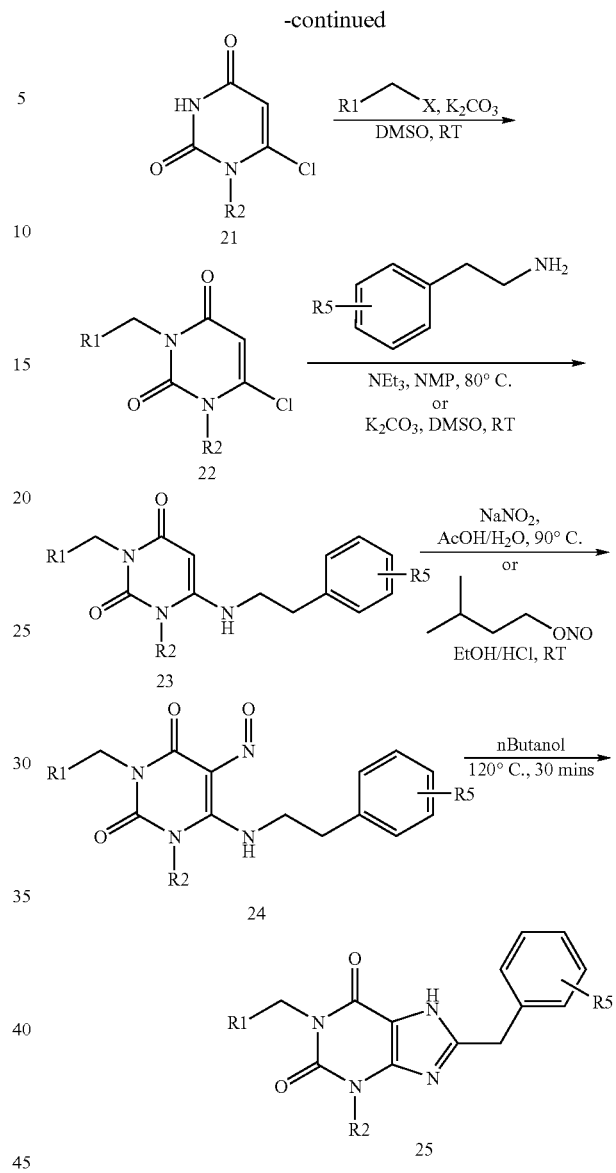

Displacement of chloride from compounds of general formula 22 with an appropriately substituted phenethylamine with potassium carbonate in dimethyl sulfoxide (DMSO) at ambient temperature or with triethylamine in N-methylpyrrolidinone (NMP) at 80° C. resulted in formation of compounds of general formula 23. These procedures are similar in nature to those previously described by Müller et al. in *J. Med. Chem.* 1993, 36,3341 and by Shamin et al. in *J. Med. Chem.* 1989, 32(6), 1231 wherein similar transformations are performed on N1-unsubstituted uracils. Where the required phenethylamines were not commercially available they were prepared readily from the corresponding benzylic halide in 2 steps by displacement with cyanide followed by reduction with Raney nickel and hydrazine.

Treatment of compounds of general formula 23 with sodium nitrite in aqueous acetic acid (as previously discussed for scheme 1) or by treatment with commercially available isoamyl nitrite results in introduction of a nitroso group at the 5-position of the uracil ring as in compounds of general formula 24.

Cyclization of the 5-nitroso-6-amino substituted uracil derivatives of general formula 24 to the trisubstituted xanthines of general formula 25 is effected in refluxing n-butanol as shown in scheme 5. Compounds of general formula 25 are equivalent to the trisubstituted xanthines 6 and 15 shown in schemes 1 and 3 respectively. However, because of the different reaction conditions used in scheme 5 and the different components used in assembling the 1,3,8-trisubstituted xanthines of general formula 25 the range of possible structural variations readily accessible complements that from the synthetic routes shown in schemes 1 and 3.

In the case where $R^5$ in scheme 5 was a 4-nitro-substituent, the final product of scheme 5 are compounds of general formula 26 as shown in scheme 6. Compounds of general formula 26 were reduced to the corresponding anilines of general formula 27 with zinc powder and ammonium chloride in aqueous methanol. The anilines thus formed were derivatized further by application of the procedures outlined in schemes 8 to 13.

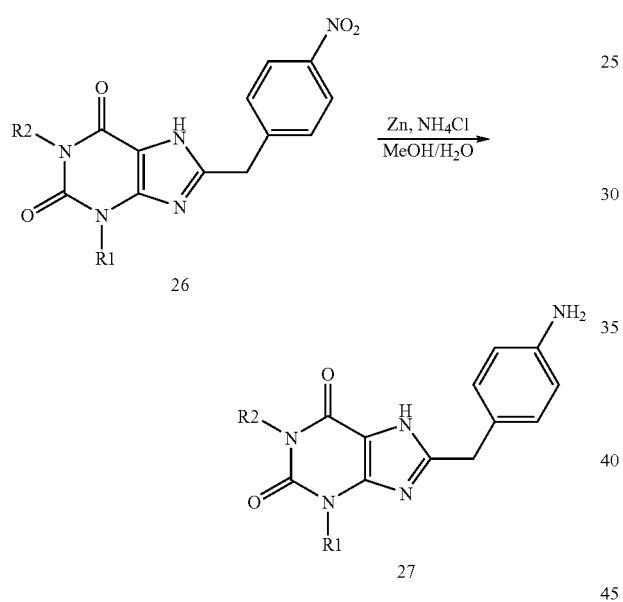

A fourth route which was also used in the preparation of some of the 1,3,8-trisubstituted xanthine derivatives of the present invention is shown in scheme 7. The first, second, third and fourth steps of scheme 7 were performed analogously to the third, fourth, fifth and sixth steps of scheme 1. In compounds of general formula 28, 29, 30 and 31 shown in scheme 7 there were no $R^1$—$(CH_2)$— substituents present as shown for the analogous compounds in scheme 1.

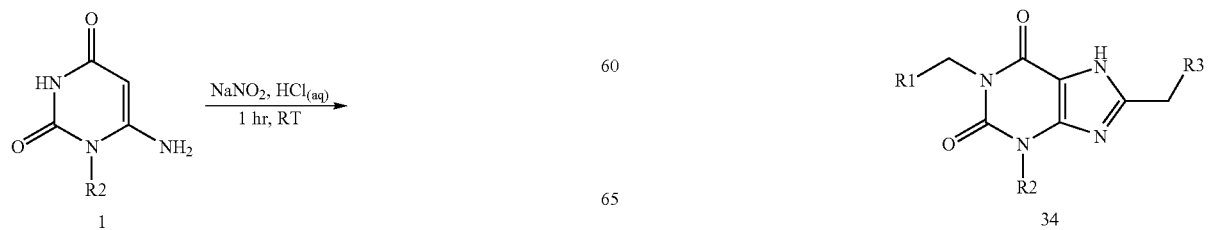

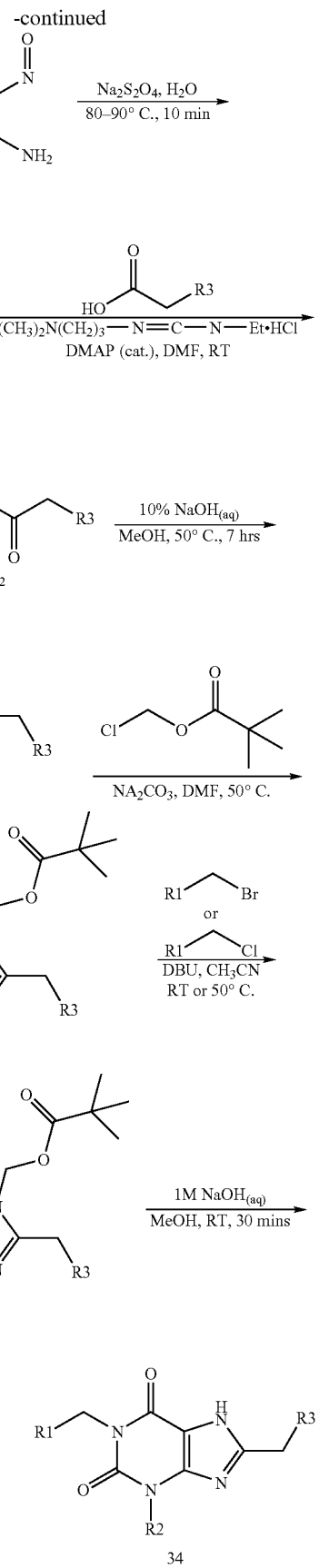

Compounds of general formula 31 were selectively protected at the N7-position with 2,2-dimethyl-propionic acid chloromethyl ester (pivaloyloxymethyl chloride, POM-Cl) and sodium carbonate using the protocol of M. W. Hu et al. as described in *J. Org. Chem.* 1980, 45(9), 1711. With the POM-protecting group attached at the N7-position it was possible to selectively alkylate compounds of general formula 32 at the N1-position with an appropriate alkylating agent in the presence of a strong organic base such as 1,8-diazabicyclo[5.4.0]undec-7-ene (DBU) to form compounds of general formula 33. Following N1-alkylation, the pivaloyloxymethyl protecting group were removed from the N7-position by treatment with aqueous sodium hydroxide in methanol by a procedure similar to that reported by Dhanak et al. as described in *J. Chem. Soc., Perkin Trans.* 1, 1986, 2181 to liberate the trisubstituted xanthine of general formula 34. Compounds of general formula 34 are equivalent to the trisubstituted xanthines of general formula 6, 15 and 25 shown in schemes 1, 3 and 5 respectively. Using the sequence of steps shown in scheme 7 it was possible to introduce the N1-substituent, R1-(CH₂)— in compounds of general formula 34, at the penultimate step of the synthetic route rather than at the beginning of the synthesis.

In the cases where the R³ substituent in compounds of general formula 6, 15, or 34 from schemes 1, 3, or 7 respectively was a phenyl ring bearing a protected amine, further chemical modification of the products from these three schemes was possible.

In the case where R³ is a tertbutylcarbonyloxy (Boc) protected aniline of general formula 35, the corresponding primary aniline of general formula 36 can be liberated under acidic conditions as shown in scheme 8. Primary anilines of general formula 36 are identical with the primary anilines of general formula 8, 19 and 27 shown in schemes 2, 4 and 6 respectively. Primary anilines of general formula 36 were derivatized in a number of ways. Primary anilines of general formula 36 were converted into the corresponding γ-lactam derivatives of general formula 37 by application of the procedure outlined in scheme 8. When compounds of general formula 36 were treated with 6,6-dimethyl-5,7-dioxaspiro[2.5]octane-4,8-dione in DMF at 100° C. according to the procedure of Danishefsky et al. as described in *J. Am. Chem. Soc.* 1975, 97(11), 3239 the reported initially formed γ-carboxylic acid derivatives are not isolated. Instead a decarboxylation occured at the elevated temperature under which the reaction was performed and γ-lactams of general formula 37 were isolated after prolonged heating.

Scheme 8

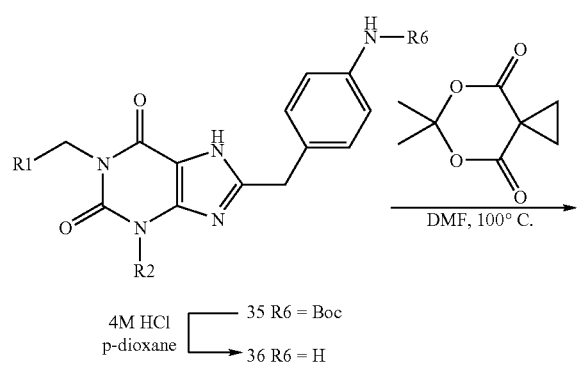

-continued

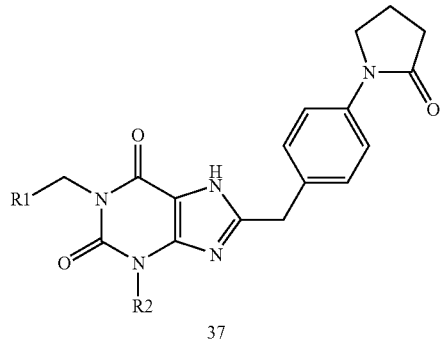

37

Primary anilines of general formula 36 were converted into the corresponding succinimide derivatives 38 by the 2 step process shown in scheme 9. Treatment of primary anilines of general formula 36 with commercially available succinic anhydride resulted in formation of intermediate succinic acid mono-amides. Reaction of the crude monoamides with commercially available acetyl chloride caused in situ anhydride formation and subsequent cyclization to the succinimide derivatives of general formula 38.

Scheme 9

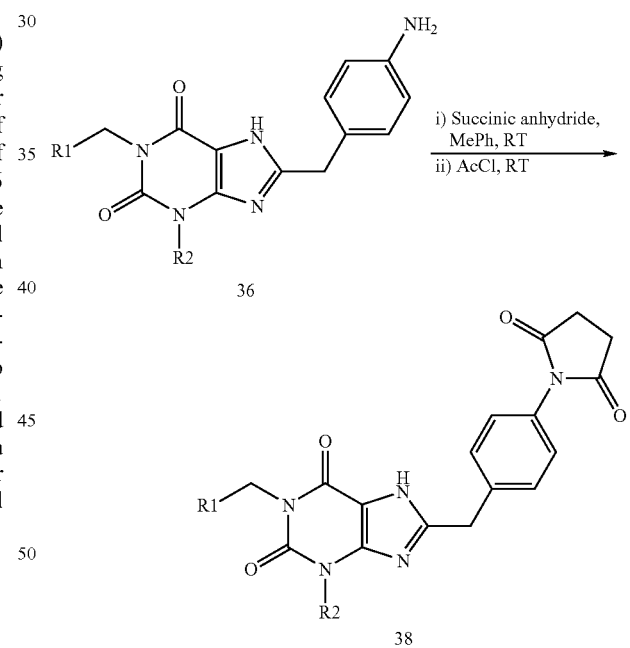

Primary anilines of general formula 36 were converted to the acetanilide derivatives of general formula 39 in one of two ways as outlined in scheme 10. Methods which were effective at performing this transformation were in situ formation of the acid chloride derivatives of aliphatic, substituted aliphatic, heterocyclic or substituted heterocyclic carboxylic acids by pre-treatment of the acid with commercially available triphenylphosphine and N-chlorosuccinimide (NCS) prior to addition of the anilines of general formula 36, or by reaction of the aniline with the pre-formed acid chloride in pyridine. In this way acylated anilines of general formula 39 were prepared.

Scheme 10

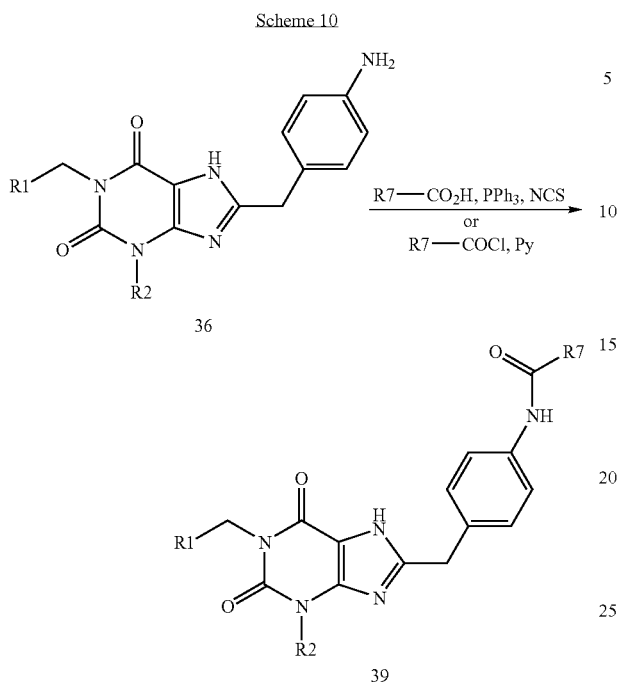

Primary anilines of general formula 36 were converted into the corresponding urea derivatives of general formula 40 by condensation with the appropriate isocyanate derivative as outlined in scheme 11.

Scheme 11

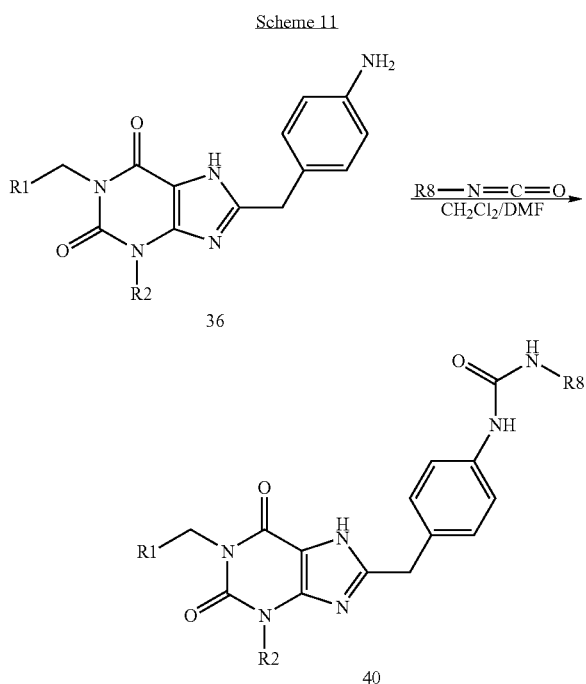

Primary anilines of general formula 36 were converted into the corresponding hydantoin derivatives of general formula 41 by application of the procedure outlined in scheme 12. Coupling of primary anilines of general formula 36 with a suitably protected amino acid using standard peptide chemistry protocols resulted in amide formation. Deprotection followed by urea formation and cyclization with commercially available carbonyl diimidazole (CDI) resulted in formation of the substituted hydantoins of general formula 41. If the substituent R9 in hydantoins of general formula 41 were chemically reactive, further modifications of this substituent were possible by application of standard chemical techniques.

Scheme 12

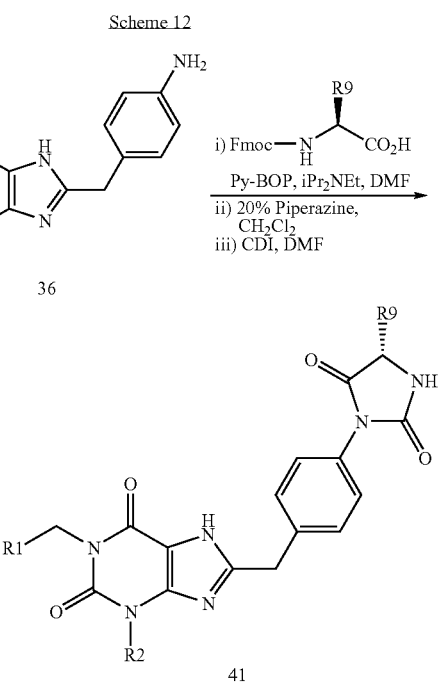

Primary anilines of general formula 36 were converted into the corresponding N-alkylated anilines and N-alkylated anilides of general formula 42 and 43 respectively by application of the synthetic route outlined in scheme 13. Reduction of the intermediate imine formed from primary anilines of general formula 36 and simple alkyl aldehydes was performed by catalytic hydrogenation using 10% palladium on carbon at atmospheric pressure to give alkyl substituted aniline derivatives of general formula 42 where $R^{11}$ is hydrogen or alkyl and $R^{10}$ is hydrogen. Reduction of the intermediate imine formed from primary anilines of general formula 36 and simple alkyl ketones was performed using sodium cyanoborohydride as reducing agent in the presence of acetic acid to give alkyl substituted aniline derivatives of general formula 42 where $R^{10}$ and $R^{11}$ are both alkyl. Use of sodium cyanoborohydride to reduce simple alkyl aldehyde imine derivatives of compounds of general formula 36 resulted in significant amounts of dialkylated aniline being formed. With imine derivatives of 36 derived from simple alkyl ketones catalytic hydrogenation was impracticably slow. N-alkylated anilines of general formula 42 were converted into the corresponding N-alkylated anilides of general formula 43 by acylation with a range of aliphatic, substituted aliphatic, heterocyclic or substituted heterocyclic carboxylic acids by application of the conditions previously outlined in scheme 10 for acylation of the primary anilines of general formula 36. In compounds of general formula 43 if the substituent R12 contained chemically reactive functionality, further modifications of this substituent were possible by application of the appropriate standard chemical transformation techniques.

Scheme 13

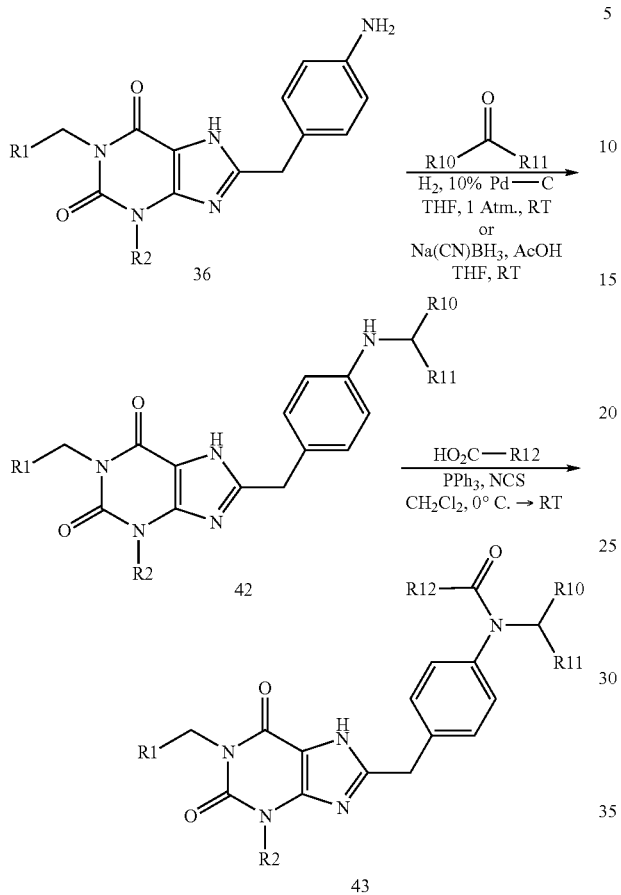

The following examples illustrate preferred methods for synthesizing the compounds and formulations of the present invention. All of the compounds listed below were prepared and characterized as reported using standard chemical techniques.

EXAMPLES

Example 1

N-[4-(1-Allyl-3-butyl-2,6-dioxo-2,3,6,7-tetrahydro-1H-purin-8-ylmethyl)-phenyl]-acetamide

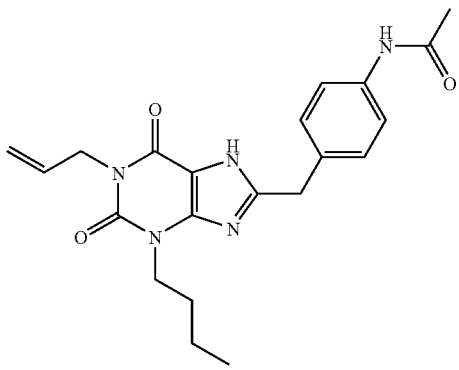

This compound was prepared by the route outlined in scheme 1.

Step 1: Preparation of 6-Amino-1-butyl-1H-pyrimidine-2,4-dione.

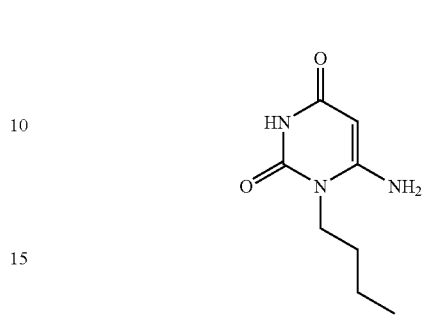

This compound was prepared by a method similar to method B as described by V. Papesch, E. F. Schroeder in *J. Org. Chem.* 1951, 16, 1879 except that the filtration step was replaced by concentration.

In a 1 L flask was placed 330 mL of absolute ethanol and sodium metal (11.5 g, 0.5 mol) was added in small pieces. When all the sodium had reacted commercial N-butyl urea (34.9 g, 0.3 mol) and commercial ethyl cyanoacetate (33 mL, 35 g, 0.31 mol) were added. The resulting mixture was stirred at room temperature for ½ h and then heated at reflux for 25 h. After cooling to room temperature the resulting mixture was concentrated under vacuum to give an oily-solid residue. This residue was taken up in water, acidified by addition of a 6N aqueous hydrochloric acid solution (at which time a solid formed), and this mixture was cooled in a 0° C. refrigerator overnight. The solids were filtered off and washed with ice water and then dried under high vacuum to afford the product as an off white solid. $^1$H NMR (DMSO-d6) 0.85 (t, 3H), 1.22 & 1.45 (2 m, 4H), 3.7 (m, 2H), 4.5 (s, 1H), 6.79 (br s, 2H), 10.25 (s, 1H).

Step 2: Preparation of 3-allyl-6-amino-1-butyl-1H-pyrimidine-2,4-dione.

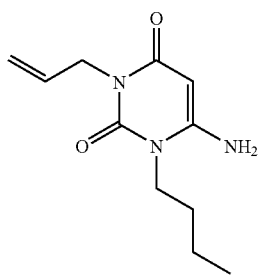

This compound was prepared by a method similar to that described by C. Müller et al. as described in *J. Med. Chem.* 1993, 36, 3341.

In a 250 mL flask under nitrogen was placed 6-amino-1-butyl-1H-pyrimidine-2,4-dione (5.0 g, 0.0273 mol) and commercial 1,1,1,3,3,3-hexamethyldisilazane (70 mL) with a catalytic amount of commercial ammonium sulfate (0.1 g). The resulting mixture was heated under nitrogen to reflux for 4 h. The 1,1,1,3,3,3-hexamethyldisilazane was then removed under high vacuum to give the disilylated intermediate as a white solid. To this solid was added commerical allylbromide (5 mL, 7 g, 0.058 mol) and a few crystals of iodine and the warm solution heated at reflux for 16 h. The reaction mixture was cooled in an ice bath and methanol cautiously added and the resulting solution stirred at room temperature for 1 h, and then concentrated to a brown oil which was diluted with 150 mL of chloroform and placed in the freezer. The product was isolated by filtration to give 4.2 g of 2 as a light yellow solid following chromatography on silica gel eluted with 95:5 chloroform/methanol. $^1$H NMR (CDCl$_3$) 0.97 (t, 3H), 1.42 & 1.65 (2m, 4H), 3.94 (t, 2H), 4.40 (br s, 2H), 4.52 (d, 2H), 5.0 (s, 1H), 5.2 (m, 2H), 5.9 (m, 1H).

Step 3: Preparation of 3-Allyl-6-amino-1-butyl-5-nitroso-1H-pyrimidine-2,4-dione.

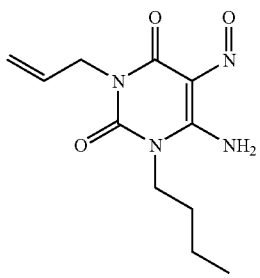

This compound was prepared by a method similar to that described by C. Müller et al. as described in *J. Med. Chem.* 1993, 36, 3341.

3-Allyl-6-amino-1-butyl-1H-pyrimidine-2,4-dione (1.2 g, 5.37 mmol) was dissolved in a 1:1 mixture of acetic acid and water (40 mL total volume). The resulting yellow solution was heated in a 95° C. oil bath and commercial sodium nitrite (0.76 g, 11 mmol) was added in portions over 40 min. Once the addition was complete cooling of the reaction solution at 0° C. and filtration afforded the nitroso derivative as a red colored solid. $^1$H NMR (DMSO-d6) 1.85 (t, 3H), 1.25 & 1.45 (2m, 4H), 3.8 (t, 2H), 4.5 (m, 2H), 5.15 (m, 2H), 5.85 (m, 1H), 9.18 (br s, 2H).

Step 4: Preparation of 3-allyl-5,6-diamino-1-butyl-1H-pyrimidine-2,4-dione.

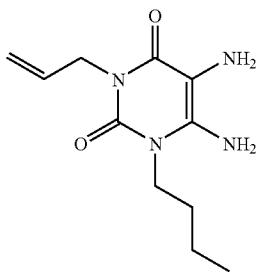

This compound was prepared by a method similar to that of C. Müller et al. as described in *J. Med. Chem.* 1993, 36, 3341.

3-Allyl-6-amino-1-butyl-5-nitroso-1H-pyrimidine-2,4-dione (410 mg, 1.63 mmol) was dissolved in 10% aqueous ammonium hydroxide solution and the resulting red colored solution was heated in a 95° C. oil bath while commercial sodium dihydrosulfite (1.2 g, 7.0 mmol) was added in portions until the rose color disappeared. After the solution had cooled it was extracted with chloroform, the extracts dried and concentrated to give the diamine (390 mg) as an light yellow solid (which darkened rapidly on exposure to air). 3-Allyl-5,6-diamino-1-butyl-1H-pyrimidine-2,4-dione was used immediately in the next step of the synthetic pathway without further purification.

Step 5: Preparation of 2-(4-Acetylamino-phenyl)-N-(3-allyl-6-amino-1-butyl-2,4-dioxo-1,2,3,4-tetrahydro-pyrimidin-5-yl)-acetamide.

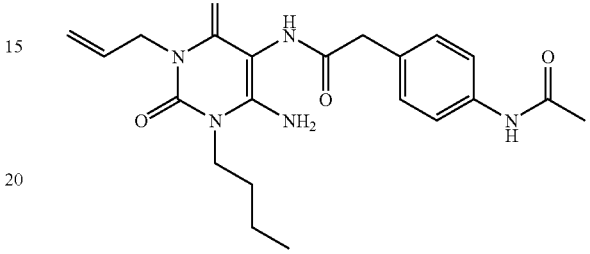

This compound was prepared using a method similar to that of K. A. Jacobson et al. as described in *J. Med. Chem.* 1993, 36, 1333.

Under nitrogen 3-allyl-5,6-diamino-1-butyl-1H-pyrimidine-2,4-dione (360 mg, 1.51 mmol) and N-acetyl-4-aminophenylacetic acid [prepared by a method analogous to that of K. D. Janda et al. described in *J. Amer. Chem. Soc.* 1991, 113, 291 for the preparation of [[4-(2,2,2-trifluoro-acetylamino)-phenyl]-acetic acid] (0.29 g, 1.5 mmol) were dissolved in dry N,N-dimethylformamide (12 mL) and then commercially available 1-(3-dimethylaminopropyl)-3-ethylcarbodiimide hydrochloride (0.3 g, 1.58 mmol) was added followed by commercially available 4-dimethylaminopyridine (70 mg) and commercially available imidazole (40 mg). The resulting solution was stirred at room temperature for 12 hours. Saturated aqueous sodium chloride solution was then added and mixture partitioned between chloroform and water. The chloroform extracts were combined, dried and concentrated to give a yellow oil (460 mg) which was cyclized to N-[4-(1-allyl-3-butyl-2,6-dioxo-2,3,6,7-tetrahydro-1H-purin-8-ylmethyl)-phenyl]-acetamide without further purification. LRMS, m/z(M+H)=414.5.

Step 6: N-[4-(1-Allyl-3-butyl-2,6-dioxo-2,3,6,7-tetrahydro-1H-purin-8-ylmethyl)-phenyl]-acetamide.

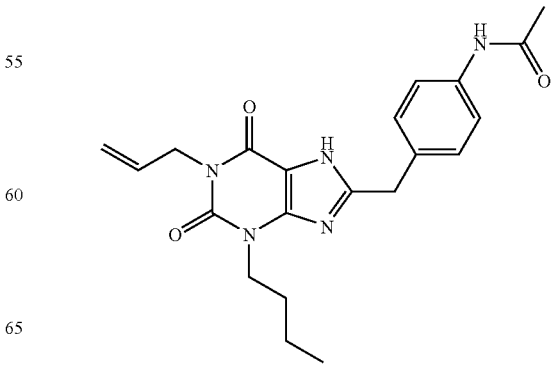

This compound was prepared by a method similar to that reported by Müller et al. in *Synthesis* 1995, 1295.

2-(4-Acetylamino-phenyl)-N-(3-allyl-6-amino-1-butyl-2,4-dioxo-1,2,3,4-tetrahydro-pyrimidin-5-yl)-acetamide (310 mg) was taken up in 3N aqueous sodium hydroxide (11 mL) and methanol (11 mL) added until the solid had dissolved. The resulting solution was heated in a 50° C. oil bath until TLC indicated the reaction to be complete. The solution was cooled and acidified with 6N aqueous hydrochloric acid until acidic to pH paper, a precipitate formed at pH 6. The resulting mixture was extracted with chloroform. Extracts were dried and concentrated to give a yellow solid (190 mg). $^1$H NMR (DMSO-d6) 0.87 (t, 3H), 1.26 (m, 2H), 1.61 (m, 2H), 2.00 (s, 3H), 3.94 (t, 2H), 3.97 (s, 2H), 4.44 (br d, 2H), 5.06 (m, 2H), 5.82 (m, 1H), 7.17 (d, 2H), 7.47 (d, 2H), 9.89 (s, 1H) and 13.4 (s, 1H). MS, m/z(M+)=395.1947.

Example 2

N-[4-(1-Benzyl-3-butyl-2,6-dioxo-2,3,6,7-tetrahydro-1H-purin-8-ylmethyl)-phenyl]-acetamide

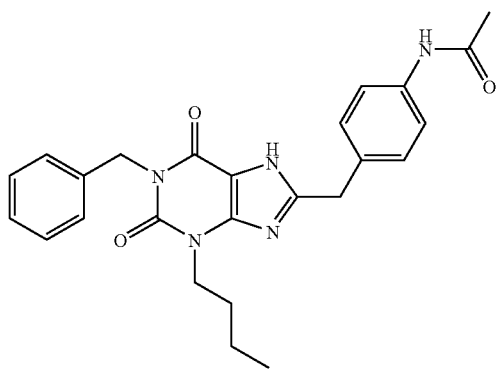

This compound was prepared by a route similar to that used for the preparation of compound in example 1 and as outlined in scheme 1.

Step 1: Preparation of 6-amino-3-benzyl-1-butyl-1H-pyrimidine-2,4-dione.

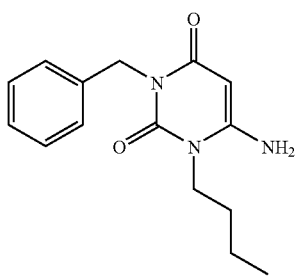

6-Amino-1-butyl-1H-pyrimidine-2,4-dione (1.72 g, 9.4 mmol), 1,1,1,3,3,3-hexamethyldisilazane (30 mL), and ammonium sulfate (0.03 g, 0.2 mmol) were heated under nitrogen at reflux for 24 h. After cooling to room temperature the 1,1,1,3,3,3-hexamethyldisilazane was removed under vacuum to give a light brown oil to which was added benzylbromide (1.1 mL, 1.58 g, 9.2 mmol) and a crystal of iodine. The resulting mixture was heated in a 110° C. oil bath for 1 h. The mixture was cooled in as ice bath while methanol was cautiously added. After concentration and trituration with chloroform and cooling to −20° C. freezer, the solid product was isolated by filtration. This material was passed through a pad of silica gel 60 (35–70 mesh) eluted with 9:1 chloroform/methanol to give 1.0 g of pure 6-amino-3-benzyl-1-butyl-1H-pyrimidine-2,4-dione. LRMS, m/z (M+H)=274.4.

Step 2: Preparation of 3-benzyl-6-amino-1-butyl-5-nitroso-1H-pyrimidine-2,4-dione.

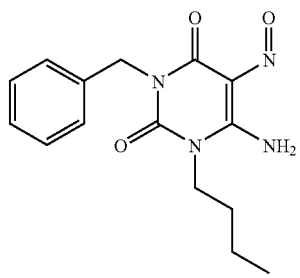

This compound was prepared by a method similar to that described for step 3 of example 1 except that 6-amino-3-benzyl-1-butyl-1H-pyrimidine-2,4-dione was used in place of 3-allyl-6-amino-1-butyl-1H-pyrimidine-2,4-dione. 3-Benzyl-6-amino-1-butyl-5-nitroso-1H-pyrimidine-2,4-dione was obtained as a red colored solid. This material was immediately subjected to the conditions of the next step in the synthetic pathway without further purification. LRMS, m/z(M+H)=303.4.

Step 3: Preparation of 3-benzyl-5,6-diamino-1-butyl-1H-pyrimidine-2,4-dione.

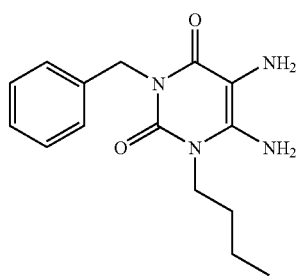

This compound was prepared by a method similar to that described for step 4 of example 1 except that 3-benzyl-6-amino-1-butyl-5-nitroso-1H-pyrimidine-2,4-dione was used in place of 3-allyl-6-amino-1-butyl-5-nitroso-1H-pyrimidine-2,4-dione. 3-Benzyl-5,6-diamino-1-butyl-1H-pyrimidine-2,4-dione was used immediately in the next step of the synthetic pathway without further purification.

Step 4: Preparation of 2-(4-acetylamino-phenyl)-N-(6-amino-3-benzyl-1-butyl-2,4-dioxo-1,2,3,4-tetrahydro-pyrimidin-5-yl)-acetamide.

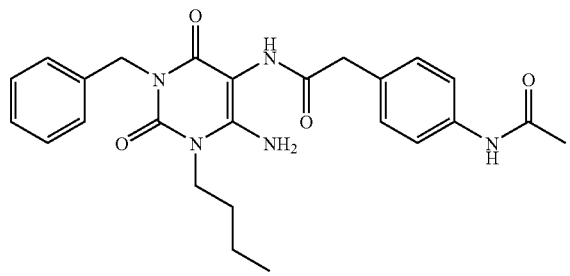

This compound was prepared by a method similar to that described for step 5 of example 1 except that 3-benzyl-5,6-diamino-1-butyl-1H-pyrimidine-2,4-dione was used in place of 3-allyl-5,6-diamino-1-butyl-1H-pyrimidine-2,4-dione and the reaction was allowed to proceed for 24 h at room temperature prior to work up. After the addition of aqueous sodium chloride solution the resultant mixture was cooled to 0° C. for ½ h and then the solid product was isolated by filtration and dried. The crude product was used without purification. $^1$H NMR (DMSO-d6) 0.86 (t, 3H), 1.28 (m, 2H), 1.45 (m, 2H), 2.01 (s, 3H), 3.49 (s, 2H), 3.83 (t, 2H), 4.90 (s, 2H), 6.66 (brs, 2H), 7.23 (m, 7H), 7.47 (d, 2H), 8.60 (s, 1H), 9.92 (s, 1H).

Step 5: Preparation of N-[4-(1-benzyl-3-butyl-2,6-dioxo-2,3,6,7-tetrahydro-1H-purin-8-ylmethyl)-phenyl]-acetamide.

This compound was prepared by a method similar to that described for step 6 of example 1 except that 2-(4-acetylamino-phenyl)-N-(6-amino-3-benzyl-1-butyl-2,4-dioxo-1,2,3,4-tetrahydro-pyrimidin-5-yl)-acetamide was used in place of 2-(4-acetylamino-phenyl)-N-(3-allyl-6-amino-1-butyl-2,4-dioxo-1,2,3,4-tetrahydro-pyrimidin-5-yl)-acetamide. The product was purified by crystallization from methanol/water. MS, m/z(M+)=446.2199.

Example 3

N-[5-(1-Benzyl-3-butyl-2,6-dioxo-2,3,6,7-tetrahydro-1H-purin-8-ylmethyl)-pyridin-2-yl]-acetamide

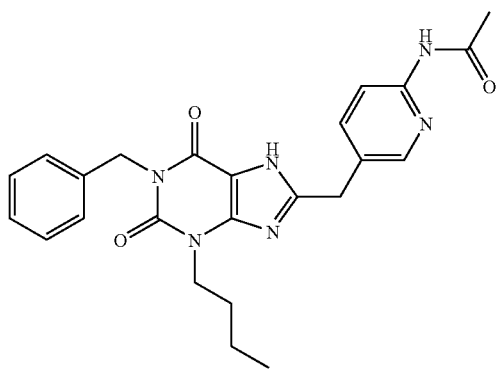

This compound was prepared by a method similar to that described in example 2 except that the hydrochloride salt of (6-acetylamino-pyridin-3-yl)-acetic acid was used in place of N-acetyl-4-aminophenylacetic acid in step 4 and the coupling was performed with O-benzotriazol-1-yl-N,N,N',N'-tetramethyluronium hexafluorophosphate and diisopropylethyl amine in N,N-dimethylformamide. MS, m/z(M+)=446.2067.

[(6-Acetylamino-pyridin-3-yl)-acetic acid was prepared from 2-amino-5-bromo-pyridine (Aldrich) by the following 5 step procedure: (i) oxidation with 30% hydrogen peroxide in concentrated sulfuric acid according to the procedure of G. J. Fox et al. as described in *J. Chem. Soc. Perkin Trans I* 1973, 68 to form 5-bromo-2-nitropyridine as a pale yellow solid (63%); (ii) malonate displacement of bromide was performed by the procedure of M. A. E. Bowman et al. as described in *Org. Prep. Proc. Int.* 1990, 22(5), 636 to give 2-(6-nitro-pyridin-3-yl)-malonic acid diethyl ester as a yellow oil (67%); (iii) nitro group reduction with 10 equivalents of zinc dust (<10 micron particle size) and 25 equivalents of ammonium chloride in 2:1 methanol/water (quantitative); (iv) acetylation with acetic anhydride and triethylamine in dichloromethane; and (v) hydrolysis and decarboxylation of the diethylmalonate with 3M aqueous lithium hydroxide in tetrahydrofuran followed by acidification with c. aqueous hydrochloric acid (quantitative).]

Example 4

N-[6-(1-Benzyl-3-butyl-2,6-dioxo-2,3,6,7-tetrahydro-1H-purin-8-ylmethyl)-pyridin-3-yl]-acetamide

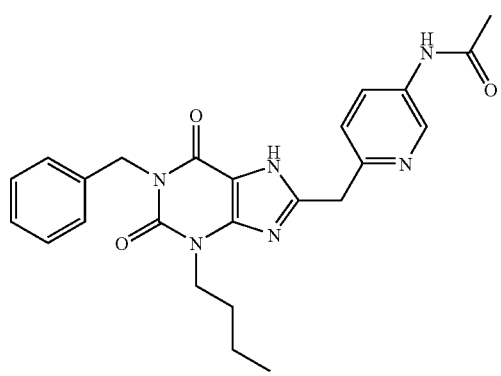

This compound was prepared by the method similar to that described in example 3 except that the hydrochloride salt of (5-acetylamino-pyridin-2-yl)-acetic acid was used in place of hydrochloride salt of (6-acetylamino-pyridin-3-yl)-acetic acid. MS, m/z(M+)=446.2063.

[(5-Acetylamino-pyridin-2-yl)-acetic acid was prepared from 2-chloro-5-nitro-pyridine (Aldrich) by a method analogous to that used for the preparation of (6-acetylamino-pyridin-3-yl)-acetic acid with the exception that the chloride displacement with diethyl malonate anion was performed according to the procedure of M. C. Liu et al. as described in *Synth. Commun.* 1990, 20(19), 2965.]

Example 5

N-[4-(1-Benzyl-3-furan-3-ylmethyl-2,6-dioxo-2,3,6,7-tetrahydro-1H-purin-8-ylmethyl)-phenyl]-acetamide

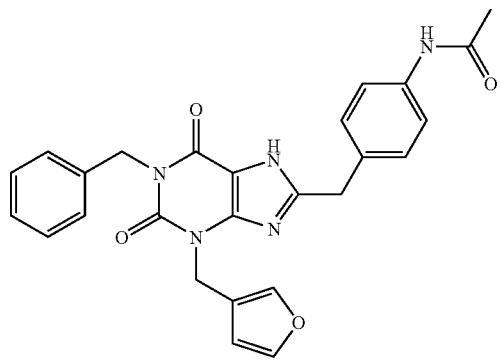

This compound was prepared by the route outlined in scheme 3.

Step 1: Preparation of 6-amino-3-benzyl-1H-pyrimidine-2,4-dione.

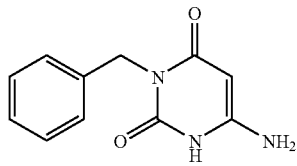

This compound was prepared by a method similar to that of Müller et al. as described in *Tetrahedron Lett.* 1991, 36(45), 6539.

In a 250 mL flask was placed commercial 6-amino-1H-pyrimidine-2,4-dione 9 (10 g, 0.08 mol), 1,1,1,3,3,3-hexamethyldisilazane (50 mL), and ammonium sulfate (80 mg). The resulting mixture was heated to reflux under nitrogen for 2.5 h and then concentrated under high vacuum to give the trisilylated derivative as a white solid. To this solid were immediately added benzyl bromide (17 g, 11.8 mL, 0.1 mol) and a few crystals of $I_2$ and the resulting mixture heated to reflux for 2 h. Methanol (120 mL) was cautiously added to the reaction mixture cooled in an ice bath and it was then allowed to warm to room temperature and stirred for a further 2 h. To this was added a saturated aqueous solution of sodium carbonate and the solids present filtered off and washed with ice cold water and dried under vacuum to give 7.8 g of crude product. This was further purified by crystallization from acetone-water to give 6.5 g of 6-amino-3-benzyl-1H-pyrimidine-2,4-dione as a white solid. $^1$H NMR (DMSO-d6) 4.59 (s, 1H), 4.82 (s, 2H), 6.30 (brs, 2H), 7.23 (m, 5H), 10.59 (brs, 1H).

Step 2: Preparation of 6-amino-3-benzyl-5-nitroso-1H-pyrimidine-2,4-dione.

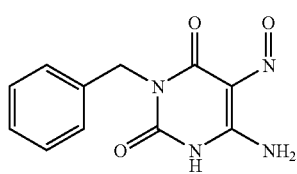

This compound was prepared by a method similar to that of Müller et al. as described in *Synthesis* 1995, 1295.

6-Amino-3-benzyl-1H-pyrimidine-2,4-dione (1.0 g, 4.6 mmol) was dissolved in glacial acetic acid (11 mL) and water (11 mL) and then heated in a 98° C. oil bath while sodium nitrite (0.68 g, 9.9 mmol) was added in small portions over 40 min. Once the addition was complete, stirring in the oil bath was continued for 15 min and then the mixture was cooled to 0° C. overnight and then the solids isolated by filtration, washed with water and dried under high vacuum to give of 6-amino-3-benzyl-5-nitroso-1H-pyrimidine-2,4-dione as an orange solid (0.92 g). $^1$H NMR (DMSO-d6-$D_2O$) 5.0 (s, 2H), 7.23 (m, 5H).

Step 3: Preparation of 3-benzyl-5,6-diamino-1H-pyrimidine-2,4-dione.

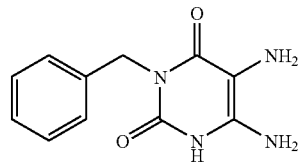

Method 1: This compound was prepared by a method similar to that of Müller et al. as described in *Synthesis* 1995, 1295. The method used was similar to that used in scheme 1 for the preparation of 3-allyl-5,6-diamino-1-butyl-1H-pyrimidine-2,4-dione except that 6-amino-3-benzyl-5-nitroso-1H-pyrimidine-2,4-dione was used as the substrate for the reaction in place of 3-allyl-6-amino-1-butyl-5-nitroso-1H-pyrimidine-2,4-dione and concentration was continued only until a solid precipitate was observed. This mixture was then cooled overnight at 0° C. and the solids isolated by filtration under an atmosphere of nitrogen to give 3-benzyl-5,6-diamino-1H-pyrimidine-2,4-dione.

Method 2: This compound can also be prepared by a method similar to that of Wells et al. as described in *J. Med. Chem.* 1981, 24(8), 954. Catalytic reduction of 6-amino-3-benzyl-5-nitroso-1H-pyrimidine-2,4-dione using $PtO_2$ in ethanol at 50 psi of hydrogen at room temperature. Once the reduction is complete the catalyst is filtered off through a pad of Celite and the filtrate concentrated to give 3-benzyl-5,6-diamino-1H-pyrimidine-2,4-dione as a tan solid.

3-Benzyl-5,6-diamino-1H-pyrimidine-2,4-dione prepared by either of these 2 methods was used immediately in the next step of the synthetic pathway without further purification.

Step 4: Preparation of 2-(4-acetylamino-phenyl)-N-(6-amino-3-benzyl-2,4-dioxo-1,2,3,4-tetrahydro-pyrimidin-5-yl)-acetamide.

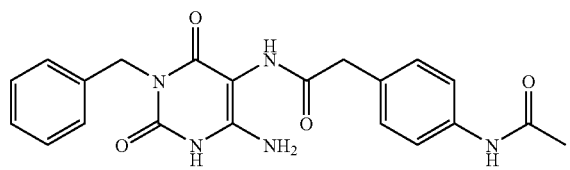

In a 50 mL flask was placed the crude product from step 3 (0.252 g, 1.09 mmol) and N-acetyl-4-aminophenylacetic acid (prepared as described in example 1) (0.235 g, 1.22 mmol) dissolved in dry N,N-dimethylformamide (10 mL) and then commercial 1-(3-dimethylaminopropyl)-3-ethyl-carbodiimide hydrochloride (0.24 g, 1.24 mmol) was added followed by 4-dimethylaminopyridine (28 mg) and imidazole (18 mg). The resulting solution was stirred at room temperature for 29 hours. Water (10 mL) was then added and mixture stirred at room temperature for ½ h to give a cloudy mixture. Addition of chloroform gave an insoluble solid which was filtered off to give the crude product which was used without further purification (0.26 g). MS m/z(M–H)= 406.3.

Step 5: Preparation of 2-(4-acetylamino-phenyl)-N-(6-amino-3-benzyl-1-furan-3-ylmethyl-2,4-dioxo-1,2,3,4-tetrahydro-pyrimidin-5-yl)-acetamide.

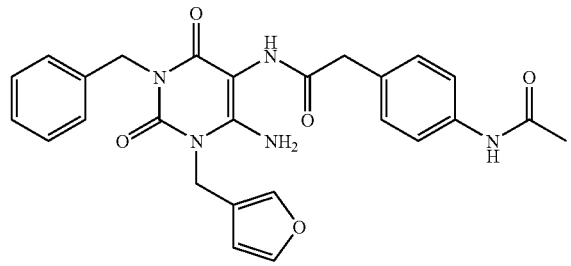

In a 10 mL flask was placed the crude product from step 4 (75 mg, 0.18 mmol) dissolved in reagent grade N,N-dimethylformamide (2 mL) and to this was added powdered potassium carbonate (90 mg) and commercially available 3-bromomethylfuran (41 mg, 0.26 mmol) and this mixture was capped and stirred at room temperature for 18 h. Saturated aqueous sodium chloride solution (5 mL) was added and stirring at room temperature continued for ½ h. The resulting cloudy, yellow solution was extracted with chloroform. The extracts were combined, dried, and concentrated to give the crude product which was used without further purification (110 mg).

Step 6: Preparation of N-[4-(1-benzyl-3-furan-3-ylmethyl-2,6-dioxo-2,3,6,7-tetrahydro-1H-purin-8-ylmethyl)-phenyl]-acetamide.

The crude product from step 5 (110 mg) was dissolved in methanol (6 mL) and 10% aqueous sodium hydroxide (3 mL) was added and then the resulting solution was heated in a 55° C. oil bath for 2 ½ h. The reaction solution was extracted with chloroform and the combined extracts dried and concentrated to give 78 mg of an oily solid. This was purified by chromatography using silica gel eluted with 9:1 chloroform/methanol to give N-[4-(1-benzyl-3-furan-3-ylmethyl-2,6-dioxo-2,3,6,7-tetrahydro-1H-purin-8-ylmethyl)-phenyl]-acetamide as an off white solid (40 mg). MS, m/z(M+)=469.1748.

Example 6

N-[4-(1-Benzyl-3-methoxymethyl-3-ylmethyl-2,6-dioxo-2,3,6,7-tetrahydro-1H-purin-8-ylmethyl)-phenyl]-acetamide

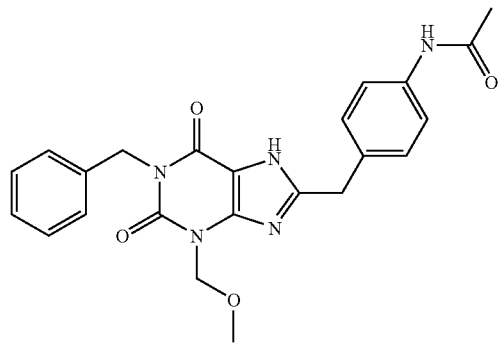

This compound was prepared by a method similar to that described example 5 except that bromomethyl methyl ether was used in place of 3-bromomethylfuran. Crystallized from methanol. MS, m/z(M+Na)=456.1656.

Example 7

N-[4-(1-Benzyl-2,6-dioxo-3-thiophen-2-ylmethyl-2,3,6,7-tetrahydro-1H-purin-8-ylmethyl)-phenyl]-acetamide

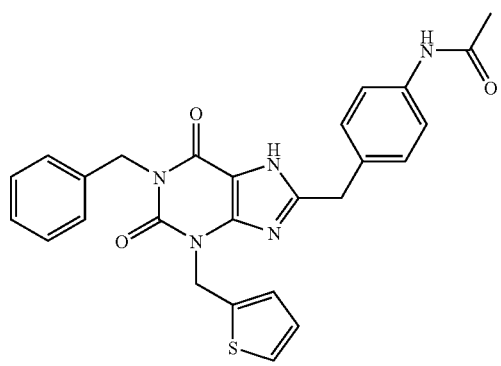

This compound was prepared by a method similar to that described in example 5 except that 2-thiophenylmethylbromide was used in place of 3-bromomethylfuran. MS, m/z (M+H)=486.1593.

[2-Thiophenylmethylbromide was prepared from thiophene-2-methanol (Fluka) with carbontetrabromide and triphenylphosphine using the general procedure of Hulin et al. as described in *J. Med. Chem.* 1992, 35(10), 1853.]

Example 8

5-[8-(4-Acetylamino-benzyl)-1-benzyl-2,6-dioxo-1,2,6,7-tetrahydro-purin-3-ylmethyl]-furan-2-carboxylic acid; compound with trifluoro-acetic acid

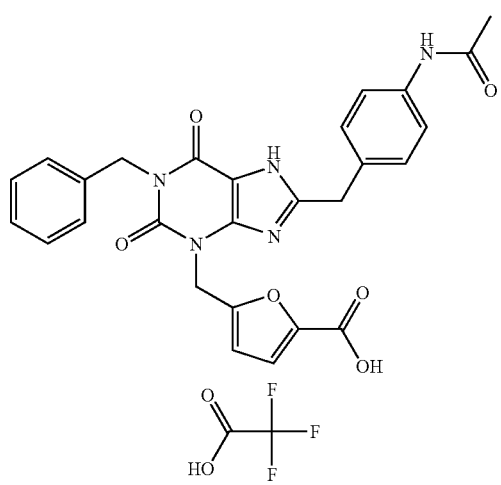

This compound was prepared by a method similar to that described in example 5 except that 5-chloromethyl-furan-2- carboxylic acid methyl ester was used in place of 3-bromomethylfuran. The methyl ester was hydrolyzed to the carboxylic acid during cyclization to form the xanthine. MS, m/z(M+)=513.1654.

Example 9

N-[3-(1-Benzyl-3-furan-3-ylmethyl-2,6-dioxo-2,3,6,7-tetrahydro-1H-purin-8-ylmethyl)-phenyl]-acetamide

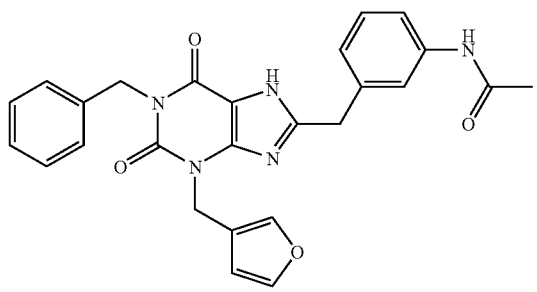

This compound was prepared by a method similar to that described in example 5 except that N-acetyl-3-aminophenylacetic acid was used in place of N-acetyl-4-aminophenylacetic acid. MS, m/z(M+H)=470.1832.

[N-Acetyl-3-aminophenylacetic acid was prepared by a method similar to that described for the preparation of N-acetyl-4-aminophenylacetic acid as described in example 1, step 5.]

Example 10

N-{4-[1-(2-fluorobenzyl)-3-furan-3-ylmethyl-2,6-dioxo-2,3,6,7-tetrahydro-1H-purin-8-ylmethyl]-phenyl}-acetamide

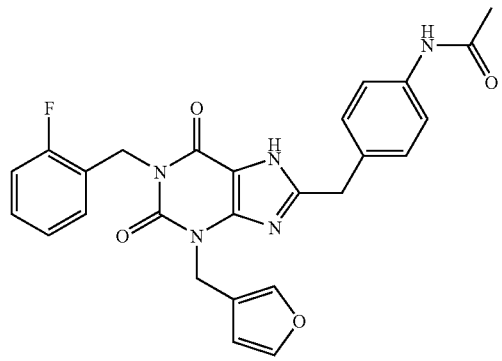

This compound was prepared by a method similar to that described in example 5 except that 2-fluorobenzyl bromide (Aldrich) was used in place of benzyl bromide in step 1. MS, m/z(M+)=488.1748.

Example 11

N-{4-[1-(2-fluorobenzyl)-3-butyl-2,6-dioxo-2,3,6,7-tetrahydro-1H-purin-8-ylmethyl]-phenyl}-acetamide

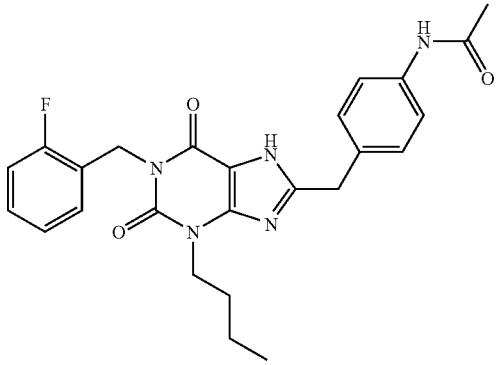

This compound was prepared by either of the 2 following methods.

Method 1: The method used was as outlined in scheme 3. This compound was prepared by a method similar to that described in example 5 except that n-butyl bromide (Aldrich) was used in place of 3-bromomethylfuran. MS, m/z (M+)=464.2086.

Method 2: The method used was as outlined in scheme 5.

Step 1: Preparation of 1-butyl-6-chloro-1H-pyrimidine-2,4-dione.

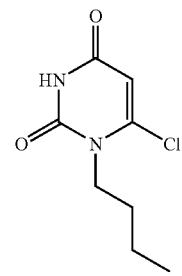

This compound was prepared by the method of Ishikawa et al. as described in *Heterocycles* 1990, 3](9), 1641.

4-Chloro-uracil (Lancaster) (23.36 g, 0.16 mol) was dissolved in dimethyl sulfoxide (100 mL) and treated with potassium carbonate (11.2 g, 0.08 mol) and 1-iodobutane (Aldrich) (52.8 mL, 0.48 mol). After stirring at 23° C. for 18 h, the reaction was then mixed with water and extracted with ethyl acetate (3×). The combined ethyl acetate layers were then washed with diluted aqueous sodium chloride solution and brine, dried (sodium sulfate) and concentrated to dryness to afford the crude product as an off-white solid (27.34 g, 85%). $^1$H NMR (CDCl$_3$, 200 MHz) $\delta_H$ 0.95 (t, 3H), 1.40 (m, 2H), 1.58 (m, 2H), 4.02 (t, 2H), 5.80 (s, 1H), 8.93 (br s, 1H).

Step 2: Preparation of 1-butyl-6-chloro-3-(2-fluorobenzyl)-1H-pyrimidine-2,4-dione.

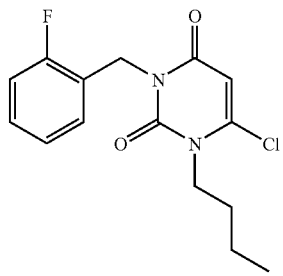

The crude product from step 1 (3.0 g, 14.8 mmol) was dissolved in N,N-dimethylformamide (30 mL) and treated with potassium carbonate (4.08 g, 29.6 mmol) and 2-fluorobenzyl bromide (Aldrich) (1.8 ml, 14.8 mmol). The reaction was stirred at 23° C. for 2 hours and then at 48° C. for 3 hours. The reaction was mixed with diluted brine and extracted with ethyl acetate (3×). The combined ethyl acetate extracts were then washed with diluted aqueous sodium chloride solution and brine, dried (sodium sulfate) and concentrated to dryness to afford 1-butyl-6-chloro-3-(2-fluorobenzyl)-1H-pyrimidine-2,4-dione as a yellow oil (4.07 g, 89%). $^1$H NMR (CDCl$_3$, 200 MHz) $\delta_H$ 0.96 (t, 3H), 1.25–1.48 (m, 2H), 1.58–1.76 (m, 2H), 4.03 (t, 2H), 5.20 (s, 2H), 5.97 (s, 1H), 6.97–7.10 (m, 2H), 7.17–7.30 (m, 2H).

Step 3: Preparation of N-(4-{2-[3-butyl-1-(2-fluorobenzyl)-2,6-dioxo-1,2,3,6-tetrahydro-pyrimidin-4-ylamino]-ethyl}-phenyl)-acetamide.

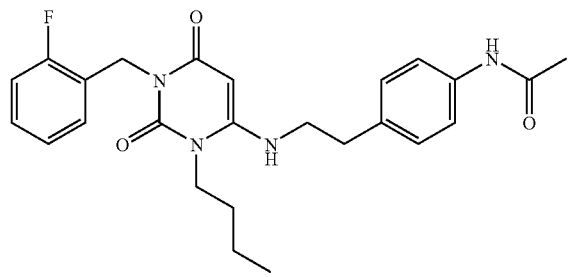

A mixture of N-[4-(2-amino-ethyl)-phenyl]-acetamide (53 mg, 0.3 mmol), the crude product from step 2 (77 mg, 0.25 mmol) and triethylamine (90 µL; 0.5 mmol) in N-methyl-pyrrolidin-2-one (2.5 mL) was stirred at 75° C. for 4 hours. The reaction was then loaded onto an ion-exchange column (CUBCX12M6 from United Chemical Technologies, Inc., Bristol, Pa.) and eluted with methanol to remove the excess amine. Concentration of the methanolic eluant under reduced pressure afforded the crude product which was used directly in the next step. [N-[4-(2-Amino-ethyl)-phenyl]-acetamide was prepared from N-(4-cyanomethyl-phenyl)-acetamide (Transworld) by the procedure of Kornet et al. as described in *J. Med. Chem.* 1977, 20(3), 405.]

Step 4: Preparation of N-{4-[1-(2-fluorobenzyl)-3-butyl-2,6-dioxo-2,3,6,7-tetrahydro-1H-purin-8-ylmethyl]-phenyl}-acetamide.

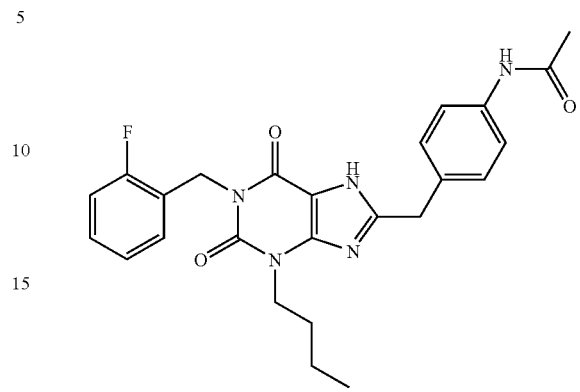

The crude product from step 3 was dissolved in ethanol (2 mL) and treated with isoamyl nitrite (170 µl, 1.25 mmol). Concentrated aqueous hydrochloric acid (2 drops) was added to the reaction mixture and the reaction was stirred at 23° C. for 40 minutes. The ethanol was removed under reduced pressure and the residue was washed with Et$_2$O. The solid residue was then dissolved in n-butanol (2 mL), and the mixture was refluxed for 30 minutes. After cooling to the room temperature the solvent was removed under the reduced pressure. The residue was then purified by reverse phase HPLC to afford the stated product. LCMS, m/z(M+H)=464.17.

Example 12

N-{4-[1-(2-fluorobenzyl)-3-butyl-2,6-dioxo-2,3,6,7-tetrahydro-1H-purin-8-ylmethyl]-phenyl}-2,2,2-trifuoroacetamide

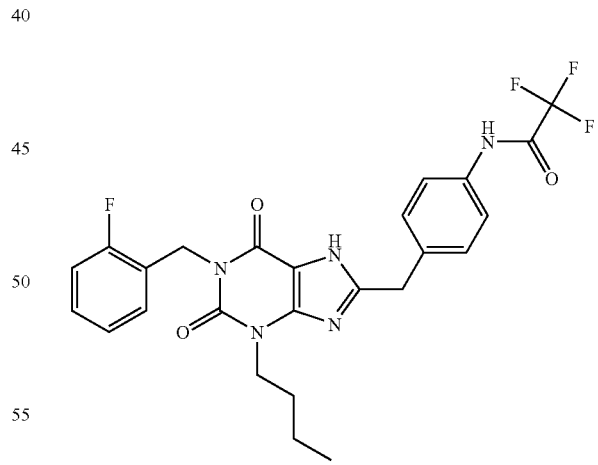

This compound was prepared by a method similar to that described in example 11 (method 1) except that [4-(2,2,2-trifluoro-acetylamino)-phenyl]-acetic acid (prepared by the method of K. D. Janda et al, as described in *J. Amer. Chem. Soc.* 1991, 113, 291) was used in place of (4-acetylamino-phenyl)-acetic acid. The trifluoroacetyl group is hydrolyzed under the conditions used to effect cyclization to the xanthine. Therefore the trifluoroacetyl group is reintroduced with N-(trifluoroacetoxy)succinimide according to the general procedure of Bergeron et al. as described in *J. Org. Chem.* 1988, 53, 3108. MS, m/z(M+)=517.1737.

Example 13

N-{5-[3-Butyl-1-(2-fluorobenzyl)-2,6-dioxo-2,3,6,7-tetrahydro-1H-purin-8-ylmethyl]-pyridin-2-yl}-acetamide

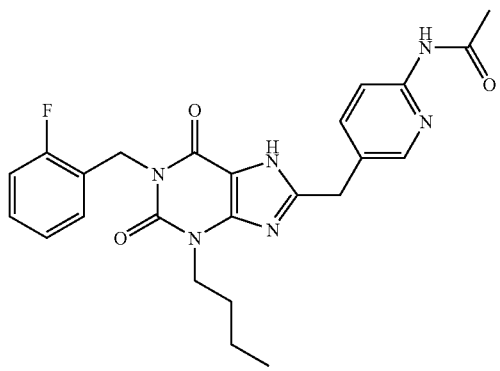

This compound was prepared by the method similar to that described in example 11 (method 1) except that the hydrochloride salt of (6-acetylamino-pyridin-3-yl)-acetic acid was used in place of N-acetyl-4-aminophenylacetic acid and the coupling to 5,6-diamino-1-butyl-3-(2-fluorobenzyl)-1H-pyrimidine-2,4-dione was performed with O-benzotriazol-1-yl-N,N,N',N'-tetramethyluronium hexafluorophosphate and diisopropylethyl amine in N,N-dimethylformamide. MS, m/z(M+)=464.1971.

[(6-Acetylamino-pyridin-3-yl)-acetic acid was prepared as described in example 3.]

Example 14

N-{6-[3-Butyl-1-(2-fluorobenzyl)-2,6-dioxo-2,3,6,7-tetrahydro-1H-purin-8-ylmethyl]-pyridin-3-yl}-acetamide

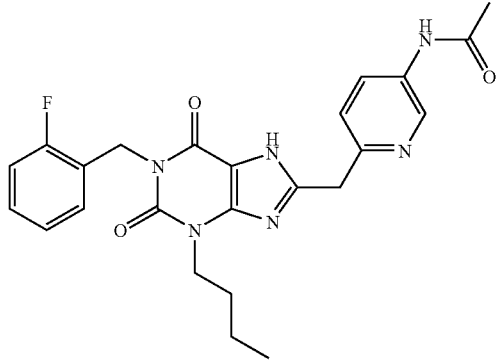

This compound was prepared by the method similar to that described in example 11 (method 1) except that the hydrochloride salt of (5-acetylamino-pyridin-2-yl)-acetic acid was used in place of hydrochloride salt of (6-acetylamino-pyridin-3-yl)-acetic acid. MS, m/z(M+)=464.1975.

[(5-Acetylamino-pyridin-2-yl)-acetic acid was prepared as described in example 4.]

Example 15

N-{4-[1-(2-fluorobenzyl)-2,6-dioxo-3-(tetrahydro-pyran-2-ylmethyl)-2,3,6,7-tetrahydro-1H-purin-8-ylmethyl]-phenyl}-acetamide

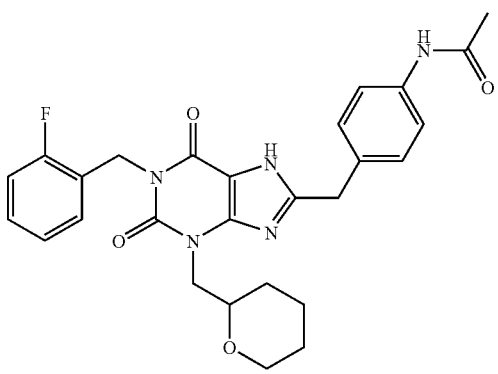

This compound was prepared by a method similar to that described in example 10 except that 2-(bromomethyl)tetrahydro-2H-pyran (Aldrich) was used in place of 3-bromomethylfuran. MS, m/z(M+)=506.2211.

Example 16

N-{4-[1-(2-fluorobenzyl)-2,6-dioxo-3-thiophen-2-ylmethyl-2,3,6,7-tetrahydro-1H-purin-8-ylmethyl]-phenyl}-acetamide

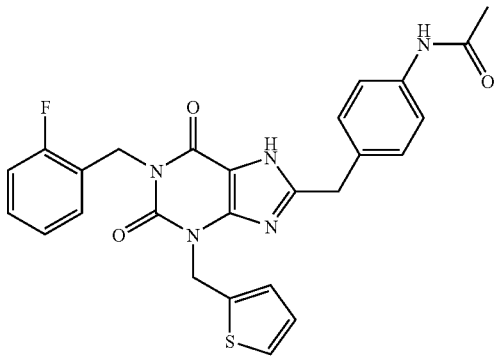

This compound was prepared by a method similar to that described in example 10 except that 2-bromomethylthiophene was used in place of 3-bromomethylfuran. MS, m/z(M+)=503.1436.

[2-Bromomethylthiophene was prepared as described in example 7.]

Example 17

N-{4-[1-(2-fluorobenzyl)-3-(tetrahydrofuran-2-ylmethyl)-2,6-dioxo-2,3,6,7-tetrahydro-1H-purin-8-ylmethyl]-phenyl}-acetamide

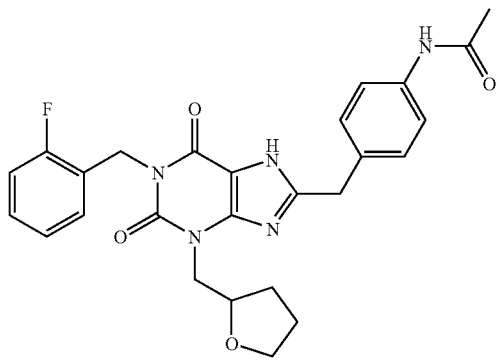

This compound was prepared by a method similar to that described in example 10 except that tetrahydrofurfuryl bromide (Lancaster) was used in place of 3-bromomethylfuran. MS, m/z(M+)=492.2054.

Example 18

N-{4-[1-(2-fluorobenzyl)-2,6-dioxo-3-(1H-[1,2,4]triazol-3-ylmethyl)-2,3,6,7-tetrahydro-1H-purin-8-ylmethyl]-phenyl}-acetamide; compound with trifluoro-acetic acid

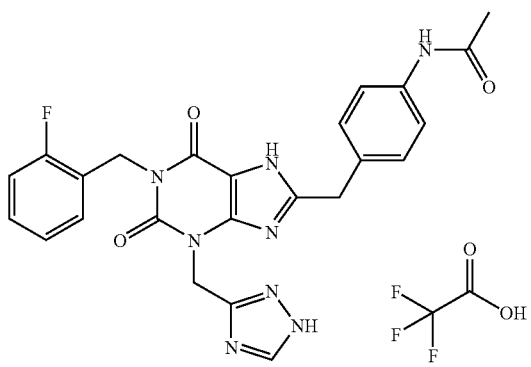

Step 1: Preparation of 1-trityl-1H-[1,2,4]triazole-3-carboxylic acid methyl ester

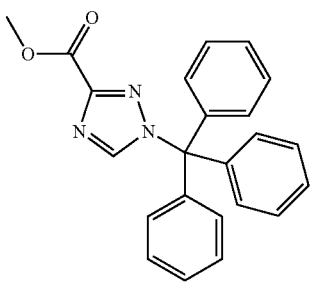

A solution of 1H-[1,2,4]triazole-3-carboxylic acid methyl ester (3.0 g, 0.23 mol) in N,N-dimethylformamide (76 mL) at 25° C. was treated with triphenylmethylchloride (7.2 g, 0.23 mol) and triethylamine (6.41 mL, 0.23 mol). The reaction mixture was stirred at 25° C. for 4 days and then diluted with ethyl acetate. The mixture was then washed with a dilute aqueous hydrochloric acid solution. At this time, methanol was added to the organic layer. A precipitate formed and was removed by filtration. The organics were further washed with a saturated aqueous sodium chloride solution, dried over magnesium sulfate, filtered, and concentrated in vacuo. The resulting solid was triturated with diethyl ether. The solid was collected by filtration and washed again with diethyl ether to afford 1-trityl-1H-[1,2,4]triazole-3-carboxylic acid methyl ester as a white solid (2.45 g, 84%) which was used without further purification: LR-FAB for $C_{23}H_{19}N_3O_2$ (M+) at m/z=369.

Step 2: Preparation of (1-trityl-1H-[1,2,4]triazol-3-yl)-methanol.

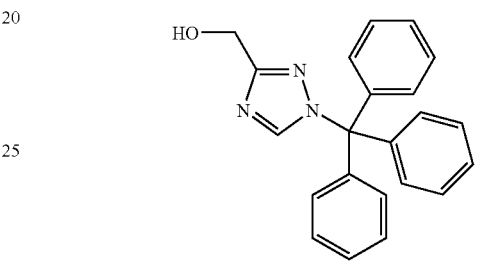

A solution of 1-trityl-1H-[1,2,4]triazole-3-carboxylic acid methyl ester (4.7 g, 0.12 mol) in tetrahydrofuran was added dropwise to a suspension of lithium aluminum hydride (724 mg, 0.12 mol) in tetrahydrofuran (63 mL) cooled to 0° C. The reaction mixture was allowed to gradually warm to 25° C. The reaction was then stirred at 25° C. for 48 h. At this time, the reaction was cooled to 0° C. and diluted with ethyl acetate (140 mL). The reaction mixture was then consecutively treated with water (0.925 mL), a 15% aqueous sodium hydroxide solution (0.925 mL), and water (2.8 mL). This mixture was stirred at 0° C. for 15 min. At this time, magnesium sulfate was added. The resulting mixture was filtered to remove the solids. The solids were washed with tetrahydrofuran and dichloromethane. The filtrate was concentrated in vacuo to afford (1-trityl-1H-[1,2,4]triazol-3-yl)-methanol (2.2 g, 51%) as a white solid: $^1$H NMR (DMSO-$d_6$, 300 MHz) δ 8.02 (s, 1H), 7.37 (m, 9H), 7.04 (m, 6H), 5.30 (broad s, 1H), 4.41 (s, 2H).

Step 3: Preparation of 2-(4-acetylamino-phenyl)-N-[6-amino-3-(2-fluoro-benzyl)-2,4-dioxo-1-(1-trityl-1H-[1,2,4]triazol-3-ylmethyl)-1,2,3,4-tetrahydro-pyrimidin-5-yl]-acetamide

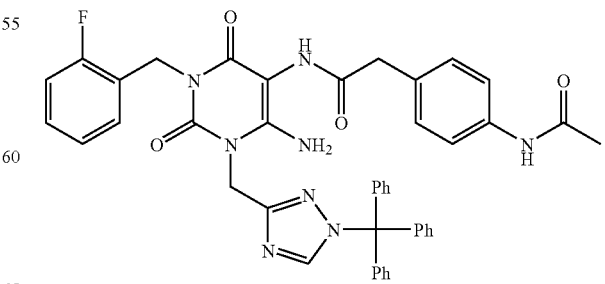

A mixture of (1-trityl-1H-[1,2,4]triazol-3-yl)-methanol (320 mg, 0.47 mmol) and triphenylphosphine (136 mg, 0.47 mmol) in tetrahydrofuran (9.4 mL) cooled to 0° C. was treated with diethylazodicarboxylate (0.82 mL, 0.47 mmol). This solution was warmed to 25° C. for 5 min and then was re-cooled to 0° C. where it was stirred for an additional 10 min. At this time, the reaction was treated with 2-(4-acetylamino-phenyl)-N-[6-amino-3-(2-fluoro-benzyl)-2,4-dioxo-1,2,3,4-tetrahydro-pyrimidin-5-yl]-acetamide (200 mg, 0.47 mmol). The reaction was then allowed to slowly warm to 25° C. The resulting solids were removed by filtration. The filtrate was diluted with ethyl acetate, washed with water and a saturated aqueous sodium chloride solution, dried over magnesium sulfate, filtered, and concentrated in vacuo. Flash chromatography (Merck Silica gel 60, 230–400 mesh) afforded 2-(4-acetylamino-phenyl)-N-[6-amino-3-(2-fluoro-benzyl)-2,4-dioxo-1-(1-trityl-1H-[1,2,4]triazol-3-ylmethyl)-1,2,3,4-tetrahydro-pyrimidin-5-yl]-acetamide (55 mg, 15.6%) as a yellow foam: LR-APCI for $C_{43}H_{37}FN_8O_4$ (M+H)$^+$ at m/z=749.

Step 4: Preparation of N-{4-[1-(2-fluoro-benzyl)-2,6-dioxo-3-(1-trityl-1H-[1,2,4]triazol-3-ylmethyl)-2,3,6,7-tetrahydro-1H-purin-8-ylmethyl]-phenyl}-acetamide

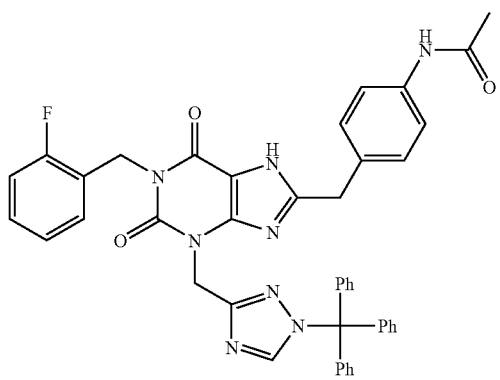

A solution of 2-(4-acetylamino-phenyl)-N-[6-amino-3-(2-fluoro-benzyl)-2,4-dioxo-1-(1-trityl-1H-[1,2,4]triazol-3-ylmethyl)-1,2,3,4-tetrahydro-pyrimidin-5-yl]-acetamide (50 mg, 0.06 mmol) in methanol (2.0 mL) was treated with a 10% aqueous sodium hydroxide solution (0.8 mL). The reaction was heated to 50° C. for 8 h. At this time, the reaction was cooled to 0° C., acidified with a 3N aqueous hydrochloric acid solution, filtered, and washed with water to afford N-{4-[1-(2-fluoro-benzyl)-2,6-dioxo-3-(1-trityl-1H-[1,2,4]triazol-3-ylmethyl)-2,3,6,7-tetrahydro-1H-purin-8-ylmethyl]-phenyl}-acetamide (36 mg, 75%) as an off-white solid: $^1$H NMR (DMSO-d$_6$, 300 MHz) δ13.45 (broad s, 1H), 9.87 (s, 1H), 7.94 (s, 1H), 7.47–6.89 (m, 23H), 5.21 (s, 2H), 5.07 (s, 2H), 3.95 (s, 2H), 2.48 (s, 3H).

Step 5: Preparation of N-{4-[1-(2-fluoro-benzyl)-2,6-dioxo-3-(1H-[1,2,4]triazol-3-ylmethyl)-2,3,6,7-tetrahydro-1H-purin-8-ylmethyl]-phenyl}-acetamide A suspension of N-{4-[1-(2-fluoro-benzyl)-2,6-dioxo-3-(1-trityl-1H-[1,2,4]triazol-3-ylmethyl)-2,3,6,7-tetrahydro-1H-purin-8-ylmethyl]-phenyl}-acetamide (47 mg, 0.06 mmol) in dichloromethane (1.0 mL) at 25° C. was treated with trifluoroacetic acid (1.0 mL). The reaction was stirred at 25° C. for 1 h. At this time, the reaction was treated with triethylsilane (0.01 mL, 0.06 mmol) and then was concentrated in vacuo. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (100 mL) and was washed with a saturated aqueous sodium bicarbonate solution (25 mL). The aqueous layer was re-extracted with dichloromethane (1×50 mL). The combined organics were dried over magnesium sulfate, filtered, and concentrated in vacuo. The resulting solid was dried in vacuo for 24 h to afford N-{4-[1-(2-fluoro-benzyl)-2,6-dioxo-3-(1H-[1,2,4]triazol-3-ylmethyl)-2,3,6,7-tetrahydro-1H-purin-8-ylmethyl]-phenyl}-acetamide (12 mg, 26%) as a white solid: LR-MS for $C_{24}H_{21}FN_8O_3$ (M+H)$^+$ at m/z=489. S, m/z(ion)=503.1436.

Example 19

4-[8-(4-Acetylamino-benzyl)-1-(2-fluorobenzyl)-2,6-dioxo-1,2,6,7-tetrahydro-purin-3-yl]-propionic acid

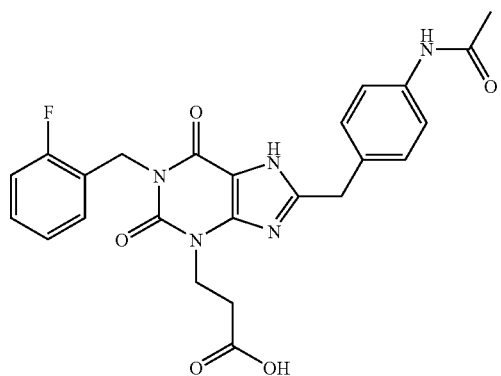

This compound was prepared by a method similar to that described in example 10 except that ethyl 3-bromopropionate (Aldrich) was used in place of 3-bromomethylfuran. Under the conditions used to effect cyclization to the xanthine (step 6) the ethyl ester is hydrolysed to the carboxylic acid. MS, m/z(M+H)=480.1684.

Example 20

4-[8-(4-Acetylamino-benzyl)-1-(2-fluorobenzyl)-2,6-dioxo-1,2,6,7-tetrahydro-purin-3-yl]-butyric acid

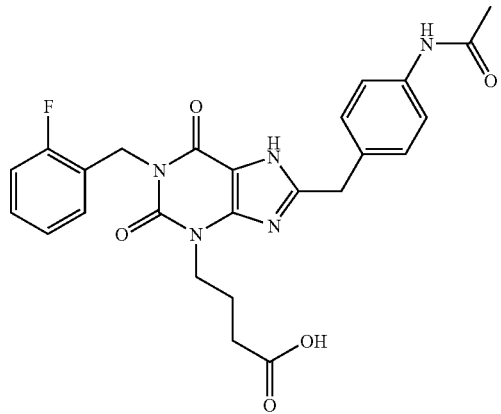

This compound was prepared by a method similar to that described in example 10 except that ethyl 4-bromobutyrate (Aldrich) was used in place of 3-bromomethylfuran. Under the conditions used to effect hydrolysis to the xanthine (step 6) the ethyl ester is hydrolysed to the carboxylic acid. MS, m/z(M+)=494.1823.

Example 21

3-[8-(4-Acetylamino-benzyl)-1-(2-fluorobenzyl)-2,6-dioxo-1,2,6,7-tetrahydro-purin-3-yl]-propionic acid methyl ester

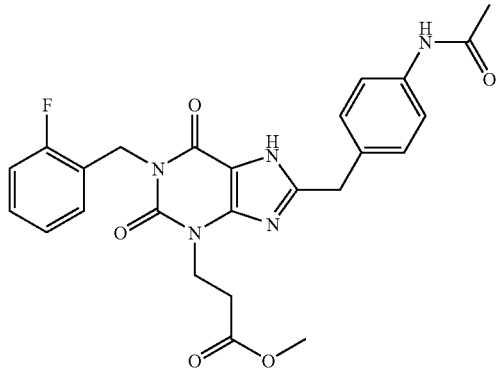

This compound was prepared by a method similar to that described in example 10 except that ethyl 3-bromopropionate (Aldrich) was used in place of 3-bromomethylfuran. Following step 6 (cyclization to the xanthine) the crude product was refluxed in methanol with catalytic amount of aqueous hydrochloric acid to form the methyl ester. MS, m/z(M+)=493.

Example 22

4-[8-(4-Acetylamino-benzyl)-1-(2-fluorobenzyl)-2,6-dioxo-1,2,6,7-tetrahydro-purin-3-yl]-butyric acid methyl ester

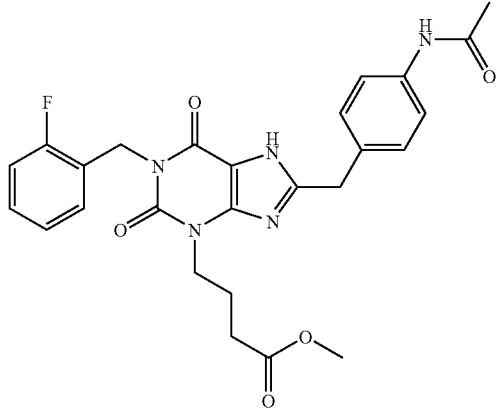

Prepared by reaction of 4-[8-(4-acetylamino-benzyl)-1-(2-fluorobenzyl)-2,6-dioxo-1,2,6,7-tetrahydro-purin-3-yl]-butyric acid with thionyl chloride in dichloromethane/tetrahydrofuran at room temperature and then reaction with excess methanol. Crystallization from methanol gave the product as a colorless solid. MS, m/z(M+H)=508.1986.

Example 23

N-{4-[1-(2-fluorobenzyl)-3-(4-hydroxy-butyl)-2,6-dioxo-2,3,6,7-tetrahydro-1H-purin-8-ylmethyl]-phenyl}-acetamide

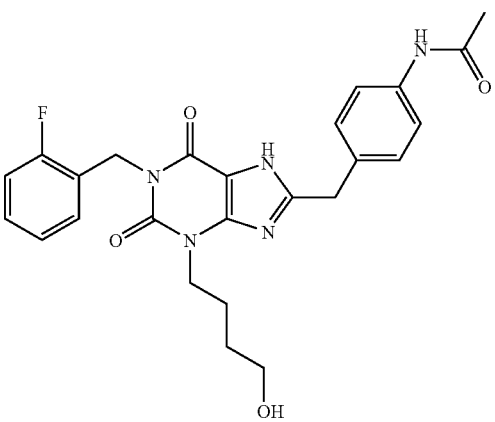

Prepared by the reduction of 4-[8-(4-acetylamino-benzyl)-1-(2-fluorobenzyl)-2,6-dioxo-1,2,6,7-tetrahydro-purin-3-yl]-butyric acid methyl ester with lithium borohydride in tetrahydrofuran. The product was purified by chromatography on silica gel eluted with 9:1 chloroform/methanol. MS, m/z(M+)=479.1967.

Example 24

N-{4-[1-(2-fluorobenzyl)-3-(4-hydroxy-propyl)-2,6-dioxo-2,3,6,7-tetrahydro-1H-purin-8-ylmethyl]-phenyl}-acetamide

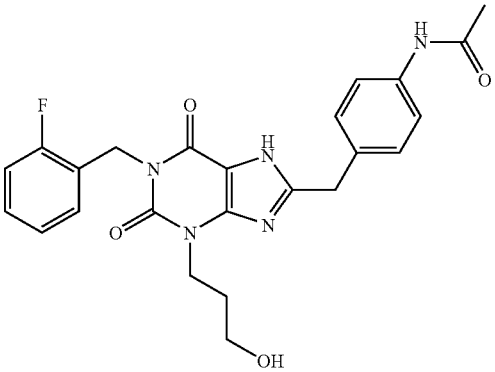

This compound was prepared by a method similar to that described in example 23 except that 3-[8-(4-acetylamino-benzyl)-1-(2-fluorobenzyl)-2,6-dioxo-1,2,6,7-tetrahydro-purin-3-yl]-propionic acid methyl ester was used in place of 4-[8-(4-acetylamino-benzyl)-1-(2-fluorobenzyl)-2,6-dioxo-1,2,6,7-tetrahydro-purin-3-yl]-butyric acid methyl ester. The product was purified by crystallization from methanol/diethyl ether. MS, m/z(M+)=465.1813.

Example 25

4-[8-(4-Acetylamino-benzyl)-1-(2-fluorobenzyl)-2,6-dioxo-1,2,6,7-tetrahydro-purin-3-yl]-N-benzyl-butyramide

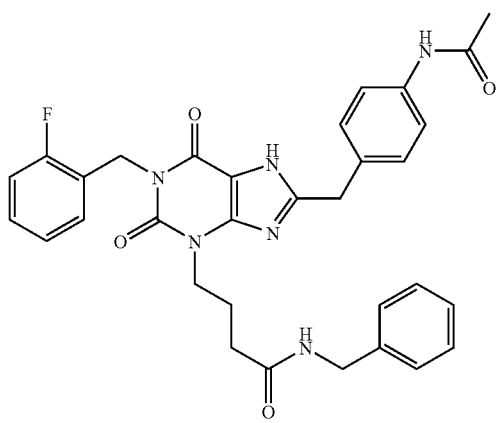

4-[8-(4-Acetylamino-benzyl)-1-(2-fluorobenzyl)-2,6-dioxo-1,2,6,7-tetrahydro-purin-3-yl]-butyric acid was converted to the N-benzyl amide using the procedure of Back et al. as described in *Synthesis* 1995, 162. Specifically, the starting butyric acid was treated with 4 equivalents of thionyl chloride in tetrahydrofuran at room temperature for 2 hrs and the acid chloride so formed was then reacted with 4 equivalents of benzylamine (Aldrich). After stirring at room temperature for 2 hrs the product was isolated and purified by chromatography using silica gel eluted 9:1 with chloroform/methanol. MS, m/z(M+H)=583.2480.

Example 26

4-[8-(4-Acetylamino-benzyl)-1-(2-fluorobenzyl)-2,6-dioxo-1,2,6,7-tetrahydro-purin-3-yl]-N-butyl-butyramide

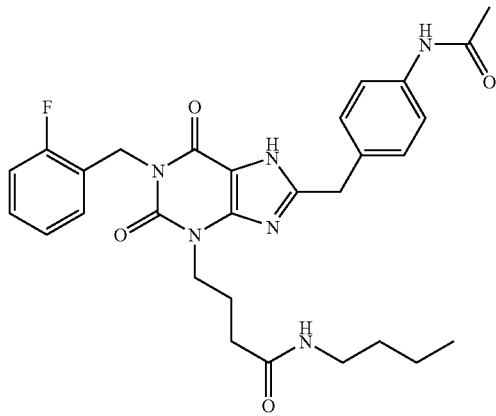

This compound was prepared by a method similar to that described in example 25 except that butylamine (Aldrich) was used in place of benzylamine. MS, m/z(M+H)=549.2628.

Example 27

4-[8-(4-Acetylamino-benzyl)-1-(2-fluorobenzyl)-2,6-dioxo-1,2,6,7-tetrahydro-purin-3-yl]-butyramide

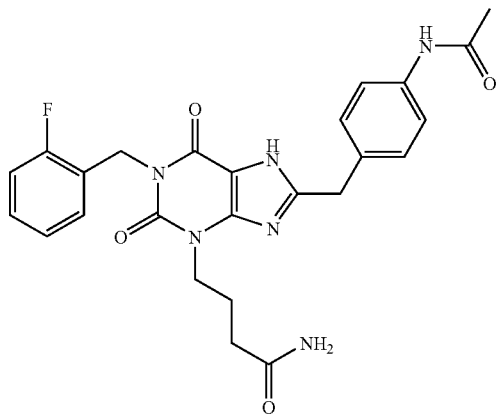

This compound was prepared by a method similar to that described in example 25 except that concentrated aqueous ammonium hydroxide was used in place of benzylamine. MS, m/z(M+H)=493.1979.

Example 28

N'-{4-[8-(4-Acetylamino-benzyl)-1-(2-fluorobenzyl)-2,6-dioxo-1,2,6,7-tetrahydro-purin-3-yl]-butyryl}-hydrazinecarboxylic acid ethyl ester

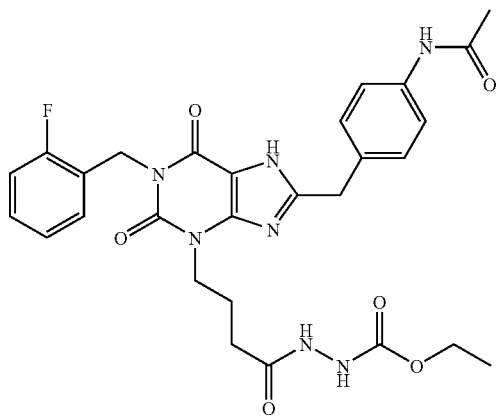

This compound was prepared by a method similar to that described in example 25 except that excess thionyl chloride was removed prior to the addition of hydrazinecarboxylic acid ethyl ester in tetrahydrofuran. MS, m/z(M+H)=580.2293.

Example 29

N-{4-[1-(2-fluorobenzyl)-3-(3-hydrazinocarbonyl-propyl)-2,6-dioxo-2,3,6,7-tetrahydro-1H-purin-8-ylmethyl]-phenyl}-acetamide

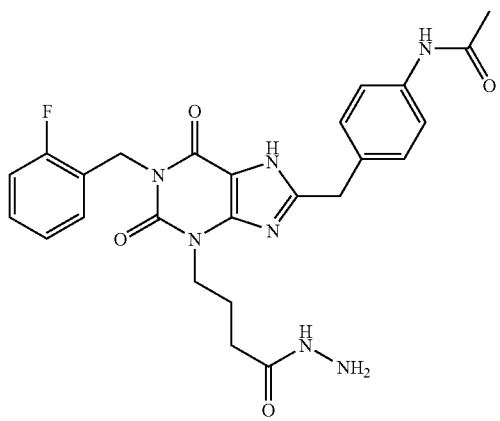

Prepared by the reaction of 4-[8-(4-acetylamino-benzyl)-1-(2-fluorobenzyl)-2,6-dioxo-1,2,6,7-tetrahydro-purin-3-yl]-butyric acid methyl ester with hydrazine (10 equivalents) in methanol/tetrahydrofuran according to the general procedure of Kramer et al. as described in *J. Heterocyclic Chem.* 1994, 31, 1439. MS, m/z(M+H)=508.2111.

Example 30

N-(4-{1-(2-fluorobenzyl)-2,6-dioxo-3-[3-(5-oxo-4,5-dihydro-[1,3,4]oxadiazol-2-yl)-propyl]-2,3,6,7-tetrahydro-1H-purin-8-ylmethyl}-phenyl)-acetamide

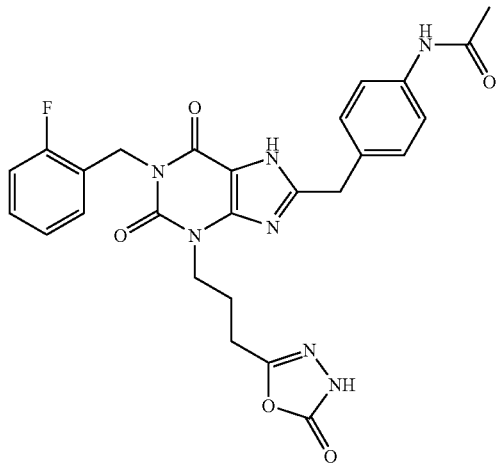

Prepared by reacting N-{4-[1-(2-fluorobenzyl)-3-(3-hydrazinocarbonyl-propyl)-2,6-dioxo-2,3,6,7-tetrahydro-1H-purin-8-ylmethyl]-phenyl}-acetamide with phosgene according to the general procedure of Kramer et al. as described in *J. Heterocyclic Chem.* 1994,31, 1439. MS, m/z(M+H)=533.1821.

Example 31

N-{4-[1-(2-fluorobenzyl)-3-(2-hydrazinocarbonyl-ethyl)-2,6-dioxo-2,3,6,7-tetrahydro-1H-purin-8-ylmethyl]-phenyl}-acetamide

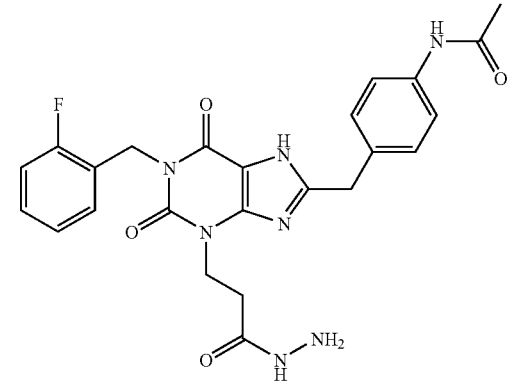

This compound was prepared by a method similar to that described in example 29 except that 3-[8-(4-acetylamino-benzyl)-1-(2-fluorobenzyl)-2,6-dioxo-1,2,6,7-tetrahydro-purin-3-yl]-propionic acid methyl ester was used in place of 4-[8-(4-acetylamino-benzyl)-1-(2-fluorobenzyl)-2,6-dioxo-1,2,6,7-tetrahydro-purin-3-yl]-butyric acid methyl ester. MS, m/z(M+H)=494.1975.

Example 32

N-(4-{1-(2-fluorobenzyl)-2,6-dioxo-3-[2-(5-oxo-4,5-dihydro-[1,3,4]oxadiazol-2-yl)-ethyl]-2,3,6,7-tetrahydro-1H-purin-8-ylmethyl}-phenyl)-acetamide

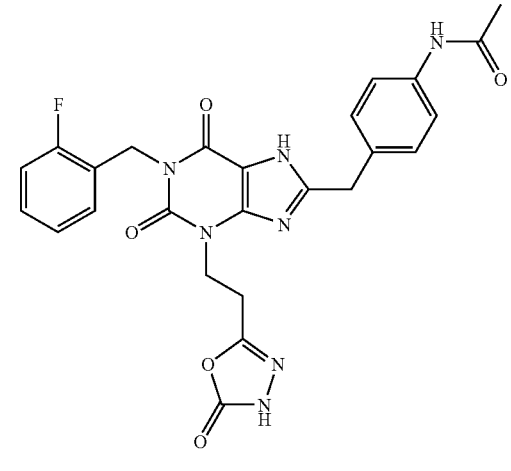

This compound was prepared by a method similar to that described in example 31 except that N-{4-[1-(2-fluorobenzyl)-3-(2-hydrazinocarbonyl-ethyl)-2,6-dioxo-2,3,6,7-tetrahydro-1H-purin-8-ylmethyl]-phenyl}-acetamide was used in place of N-{4-[1-(2-fluorobenzyl)-3-(3-hydrazinocarbonyl-propyl)-2,6-dioxo-2,3,6,7-tetrahydro-1H-purin-8-ylmethyl]-phenyl}-acetamide. MS, m/z(M+H)=519.1668.

Example 33

N-[4-(1-Benzyl-3-methyl-2,6-dioxo-2,3,6,7-tetrahydro-1H-purin-8-ylmethyl)-phenyl]-acetamide

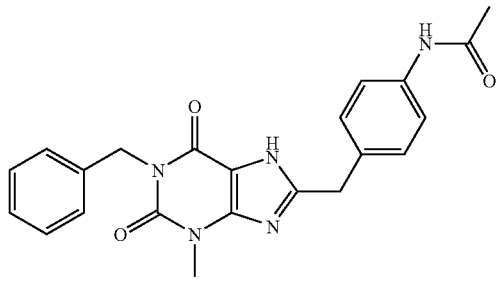

This compound was prepared by a method similar to that described in example 5 except that commercially available methyl iodide was used in place of 3-bromomethylfuran. The product was purified by chromatography using silica gel eluted with 95:5 chloroform/methanol. MS, m/z(M+H)= 404.

Example 34

N-{4-[1-(2-fluorobenzyl)-3-propyl-2,6-dioxo-2,3,6,7-tetrahydro-1H-purin-8-ylmethyl]-phenyl}-acetamide

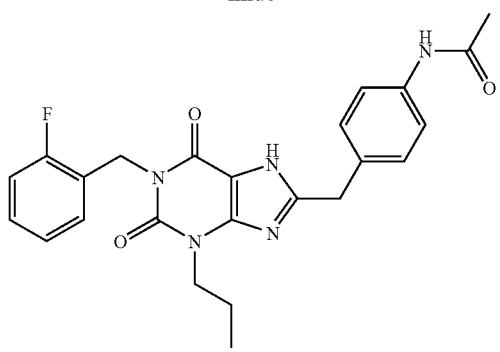

This compound was prepared by a method similar to that described in example 10 except that propyl bromide (Aldrich) was used in place of 3-bromomethylfuran. MS, m/z (M+)=449.1868.

Example 35

N-{4-[1-(2-fluorobenzyl)-3-hexyl-2,6-dioxo-2,3,6,7-tetrahydro-1H-purin-8-ylmethyl]-phenyl}-acetamide

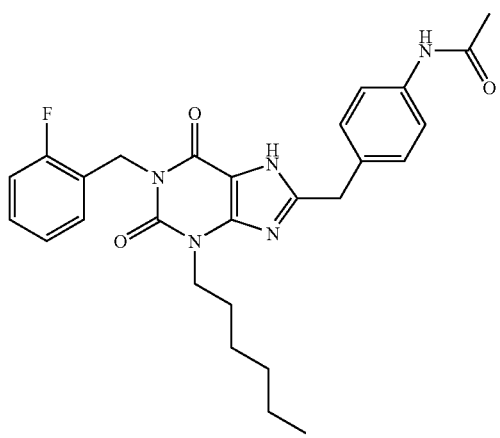

This compound was prepared by a method similar to that described in example 10 except that 1-iodohexane (Aldrich) was used in place of 3-bromomethylfuran. MS, m/z(M+)= 491.2332.

Example 36

N-{4-[1-(2-fluorobenzyl)-3-isobutyl-2,6-dioxo-2,3,6,7-tetrahydro-1H-purin-8-ylmethyl]-phenyl}-acetamide

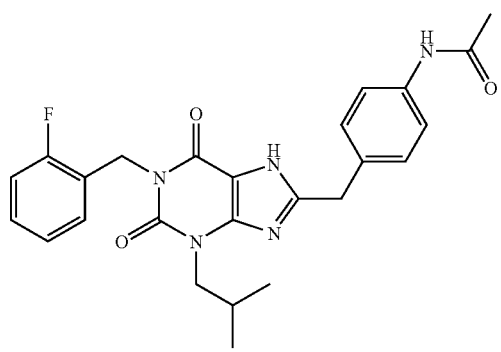

This compound was prepared by a method similar to that described in example 10 except that isobutyl bromide (Aldrich) was used in place of 3-bromomethylfuran. MS, m/z (M+)=463.2029.

Example 37

N4-[1-(2-fluorobenzyl)-3-(3-methylbutyl)-2,6-dioxo-2,3,6,7-tetrahydro-1H-purin-8-ylmethyl]-phenyl}-acetamide

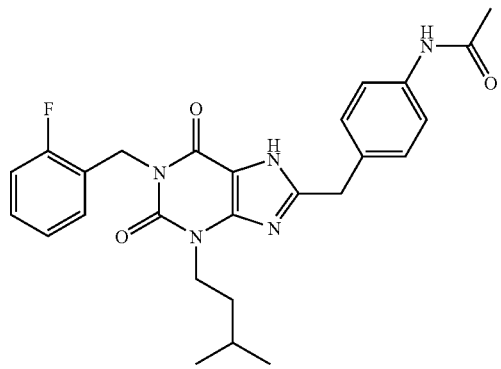

This compound was prepared by a method similar to that described in example 10 except that 1-iodo-3-methylbutane (Lancaster) was used in place of 3-bromomethylfuran. MS, m/z(M+)=477.2179.

Example 38

N-{4-[1-(2-fluorobenzyl)-3-(3,3-dimethylbutyl)-2,6-dioxo-2,3,6,7-tetrahydro-1H-purin-8-ylmethyl]-phenyl}-acetamide

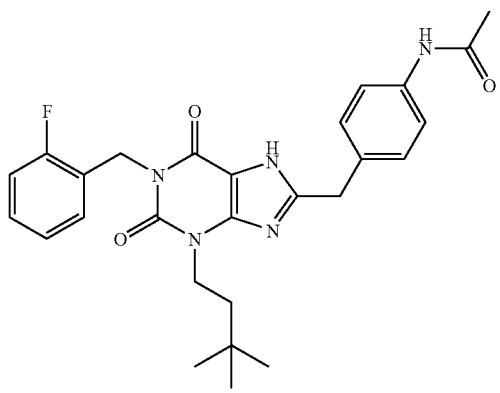

This compound was prepared by a method similar to that described in example 10 except that 1-bromo-3,3-dimethylbutane (Wiley) was used in place of 3-bromomethylfuran. MS, m/z(M+)=491.2335.

Example 39

N-{4-[1-(2-fluorobenzyl)-3-(2-hydroxymethyl-butyl)-2,6-dioxo-2,3,6,7-tetrahydro-1H-purin-8-ylmethyl]-phenyl}-acetamide

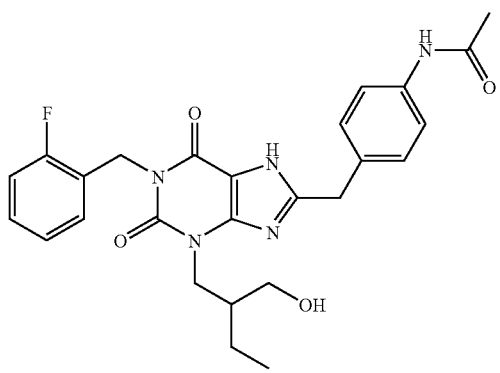

This compound was prepared by a method similar to that described in example 10 except that (2-bromomethyl-butoxy)-tert-butyl-dimethyl-silane was used in place of 3-bromomethylfuran. MS, m/z(M+)=493.2133.

[(2-Bromomethyl-butoxy)-tert-butyl-dimethyl-silane was prepared according to the procedure of Ihara et al. as reported in *J. Org. Chem.* 1994, 59, 5317.]

Example 40

N-{4-[1-(2-fluorobenzyl)-3-(3-methyl-but-2-enyl)-2,6-dioxo-2,3,6,7-tetrahydro-1H-purin-8-ylmethyl]-phenyl}-acetamide

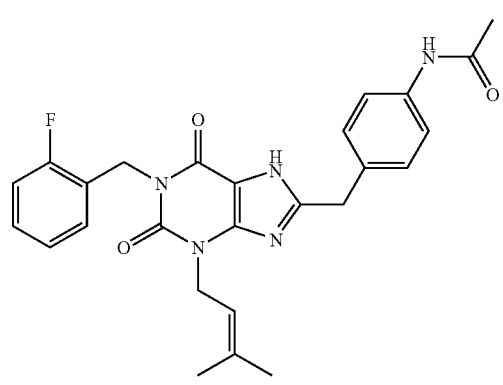

This compound was prepared by a method similar to that described in example 10 except that 1-bromo-3-methyl-2-butene (Aldrich) was used in place of 3-bromomethylfuran. MS, m/z(M+)=475.2021.

Example 41

N-{4-[1-(2-fluorobenzyl)-3-phenyl-2,6-dioxo-2,3,6,7-tetrahydro-1H-purin-8-ylmethyl]-phenyl}-acetamide

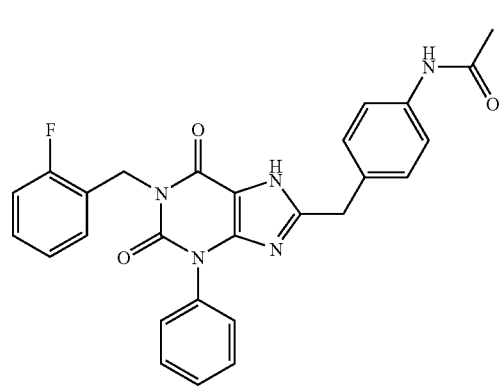

This compound was prepared by a method similar to that described in example 1 except that commercially available phenyl urea was used in place of n-butyl urea and 2-fluorobenzyl bromide (Aldrich) was used in place of allyl bromide. MS, m/z(M+)=484.

Example 42

N-{4-[3-Cyclopropylmethyl-1-(2-fluorobenzyl)-2,6-dioxo-2,3,6,7-tetrahydro-1H-purin-8-ylmethyl]-phenyl}-acetamide

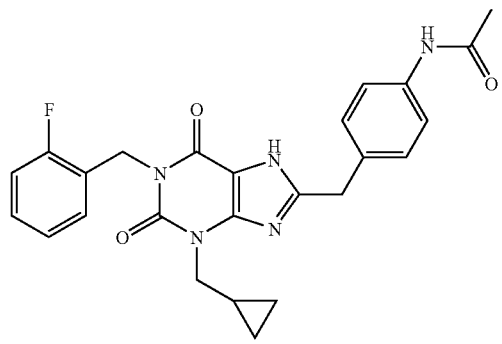

This compound was prepared by a method similar to that described in example 10 except that cyclopropylmethyl bromide (Lancaster) was used in place of 3-bromomethylfuran. MS, m/z(M+)=461.1863.

Example 43

N-{4-[3-Cyclopentylmethyl-1-(2-fluorobenzyl)-2,6-dioxo-2,3,6,7-tetrahydro-1H-purin-8-ylmethyl]-phenyl}-2,2,2-trifluoroacetamide

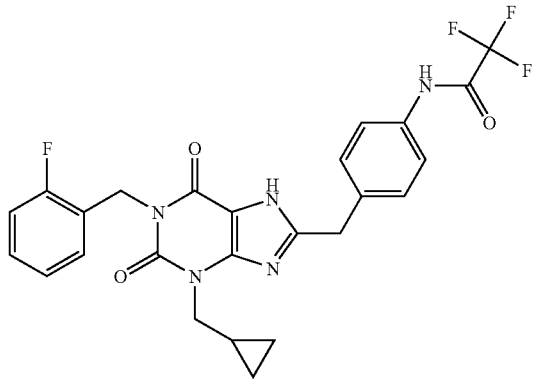

This compound was prepared by a method similar to that described in example 42 except that [4-(2,2,2-trifluoro-acetylamino)-phenyl]-acetic acid was used in place of (4-acetylamino-phenyl)-acetic acid. The trifluoroacetyl group is hydrolyzed under the conditions used to effect cyclization to the xanthine. Therefore the trifluoroacetyl group is reintroduced with N-(trifluoroacetoxy)succinimide according to the general procedure of Bergeron et al. as described in *J. Org. Chem.* 1988, 53, 3108. MS, m/z(M+)=516.1656.

[[4-(2,2,2-Trifluoro-acetylamino)-phenyl]-acetic acid was prepared by the method of K. D. Janda et al. as described in *J. Amer. Chem. Soc.* 1991, 113, 291.]

Example 44

N-{4-[3-Cyclobutylmethyl-1-(2-fluorobenzyl)-2,6-dioxo-2,3,6,7-tetrahydro-1H-purin-8-ylmethyl]-phenyl}-acetamide

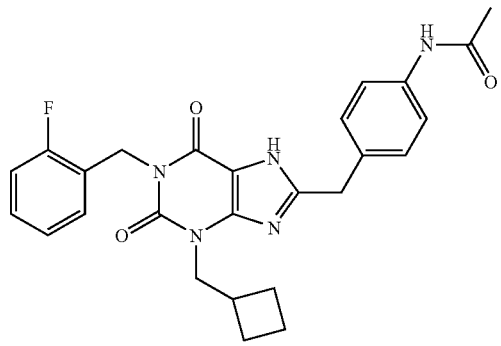

This compound was prepared by a method similar to that described in example 10 except that cyclobutylmethyl bromide (Aldrich) was used in place of 3-bromomethylfuran. MS, m/z(M+)=475.2028.

Example 45

N-{4-[3-Cyclopentylmethyl-1-(2-fluorobenzyl)-2,6-dioxo-2,3,6,7-tetrahydro-1H-purin-8-ylmethyl]-phenyl}-acetamide

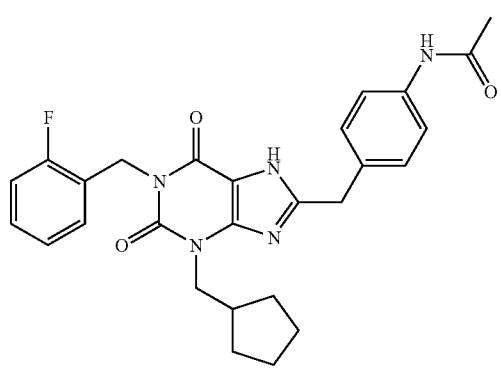

This compound was prepared by a method similar to that described in example 10 except that cyclopentylmethyl iodide was used in place of 3-bromomethylfuran. MS, m/z(M+)=489.2170.

[Cyclopentylmethyl iodide prepared according to the procedure of Bizzarro et al. as reported in WO0058293 (A2).]

Example 46

N-{4-[1-(2-fluorobenzyl)-3-(2-methyl-cyclopropyl-methyl)-2,6-dioxo-2,3,6,7-tetrahydro-1H-purin-8-ylmethyl]-phenyl}-acetamide

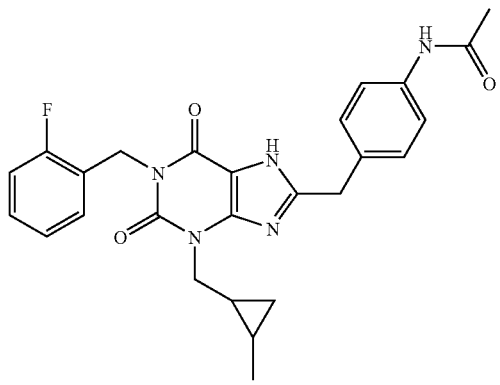

This compound was prepared by a method similar to that described in example 10 except that 2-methylcyclopropyl-methyl bromide was used in place of 3-bromomethylfuran. MS, m/z(M+)=475.2025.

[2-Methylcyclopropylmethyl bromide was prepared from 2-methylcyclopropylmethanol (Aldrich) with carbon-tetrabromide and triphenylphosphine using the method of Gurjar et al. as described in *Tetrahedron Lett.* 1997, 38(39), 6885].

Example 47

2-[8-(4-Acetylamino-benzyl)-1-(2-fluorobenzyl)-2,6-dioxo-1,2,6,7-tetrahydro-purin-3-ylmethyl]-cyclopropanecarboxylic acid

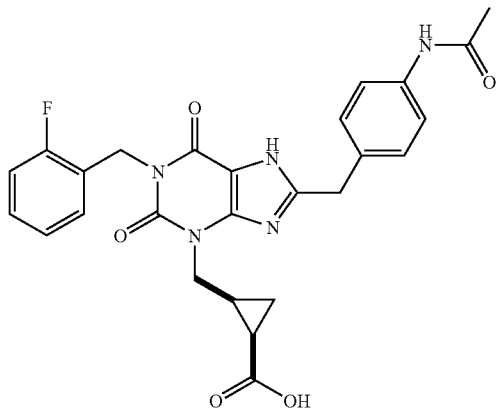

This compound was prepared by a method similar to that described in example 10 except that 2-carboxymethylcyclo-propylmethyl bromide was used in place of 3-bromometh-ylfuran. The methyl ester was hydrolysed to the carboxylic acid under the conditions used to effect cyclization to the xanthine (step 6). MS, m/z(M+)=506.1826.

2-Carboxymethylcyclopropylmethyl bromide was prepared from 3-oxabicyclo[3.1.0]hexane-2,4-dione (Ald-rich) by ring opening of the anhydride with methanol followed by reduction of the carboxylic acid with borane-tetrahydrofuran according to the procedure of Schroff et al. *J. Org. Chem.* 1971, 36(22), 1971. The alcohol was then converted to the bromide using the method of B. Hulin et al. as described in *J. Med. Chem.* 1992, 35, 1853.]

Example 48

2-[8-(4-Acetylamino-benzyl)-1-(2-fluorobenzyl)-2,6-dioxo-1,2,6,7-tetrahydro-purin-3-ylmethyl]-cyclo-propanecarboxylic acid methyl ester

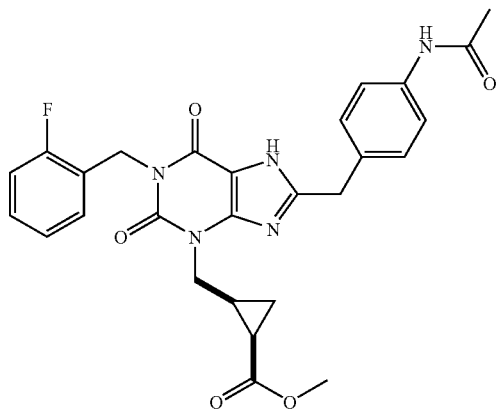

This compound was prepared by the reaction of 2-[8-(4-acetylamino-benzyl)-1-(2-fluorobenzyl)-2,6-dioxo-1,2,6,7-tetrahydro-purin-3-ylmethyl]-cyclopropanecarboxylic acid with thionyl chloride to form the acid chloride which was then reacted with methanol. MS, m/z(M+)=519.1916.

Example 49

N-{4-[1-(2-fluorobenzyl)-3-(2-hydroxymethyl-cy-clopropylmethyl)-2,6-dioxo-2,3,6,7-tetrahydro-1H-purin-8-ylmethyl]-phenyl}-acetamide

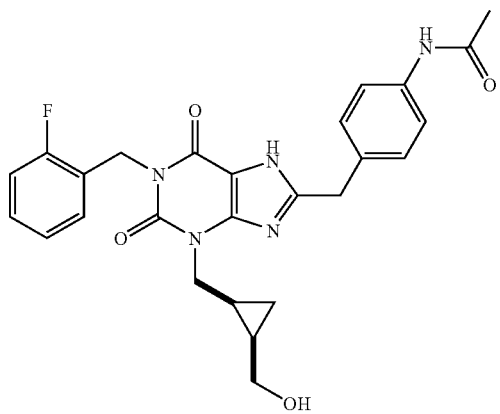

This compound was prepared by the reduction of 2-[8-(4-acetylamino-benzyl)-1-(2-fluorobenzyl)-2,6-dioxo-1,2,6,7-tetrahydro-purin-3-ylmethyl]-cyclopropanecarboxylic acid methyl ester with lithium borohydride in tetrahydrofuran. MS, m/z(M+)=491.1966.

Example 50

N-{4-[3-(2,2-Bis-hydroxymethyl-cyclopropylmethyl)-1-(2-fluorobenzyl)-2,6-dioxo-2,3,6,7-tetrahydro-1H-purin-8-ylmethyl]-phenyl}-acetamide

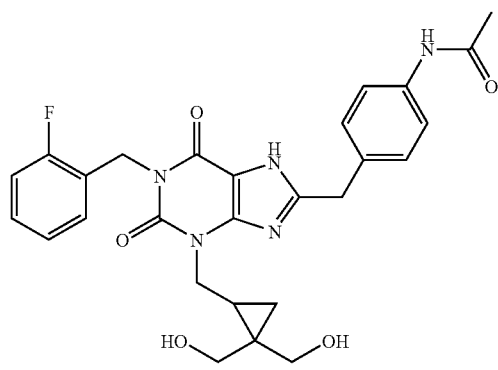

This compound was prepared by a method similar to that described in example 10 except that the dibenzoic acid ester of 2,2-bis-hydroxymethyl-cyclopropylmethyl bromide was used in place of 3-bromomethylfuran. MS, m/z(M+)=543.1973.

[The dibenzoic acid ester of 2,2-bis-hydroxymethyl-cyclopropylmethyl bromide was prepared from 1-allyl-2,2-dicarboethoxycyclopropane (prepared by the procedure of Kierstead et al. as described in *J. Chem. Soc.* 1952, 3610) by reduction to the diol, protection as the dibenzoate, ozonolysis and reduction according to the procedures of Ashton et al. as described in *J. Med. Chem.* 1988, 31, 2304. Conversion of the alcohol to the bromide was achieved using the method of B. Hulin et al. as described in *J. Med Chem.* 1992, 35, 1853.]

Example 51

N-{4-[1-Allyl-3-(2-methoxy-ethyl)-2,6-dioxo-2,3,6,7-tetrahydro-1H-purin-8-ylmethyl]-phenyl}-acetamide

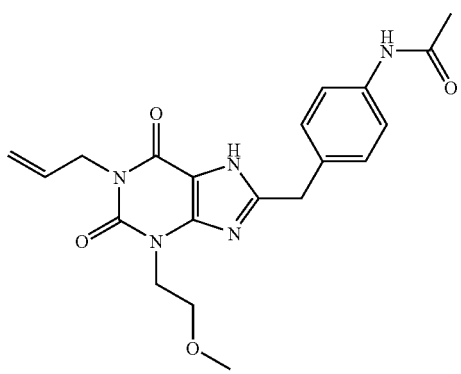

This compound was prepared by a method similar to that described in example 5 except that allyl bromide (Aldrich) was used in place of benzyl bromide and methoxyethyl bromide (Aldrich) was used in place of 3-bromomethylfuran. MS, m/z(M+H)=398.1834.

Example 52

N-[4-(1-But-2-enyl-3-butyl-2,6-dioxo-2-2,3,6,7-tetrahydro-1H-purin-8-ylmethyl)-phenyl]-acetamide

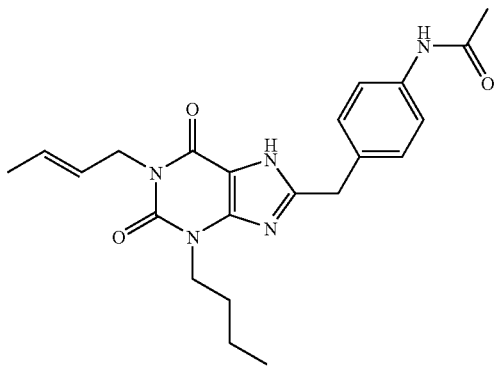

This compound was prepared by a method similar to that in described example 11 (method 2) except that 1-bromobut-2-ene (Aldrich) was used in place of 2-fluorobenzyl bromide. LCMS, m/z(M+H)=410.23.

Example 53

N-{4-[1-(3-Bromo-allyl)-3-butyl-2,6-dioxo-2,3,6,7-tetrahydro-1H-purin-8-ylmethyl]-phenyl}-acetamide

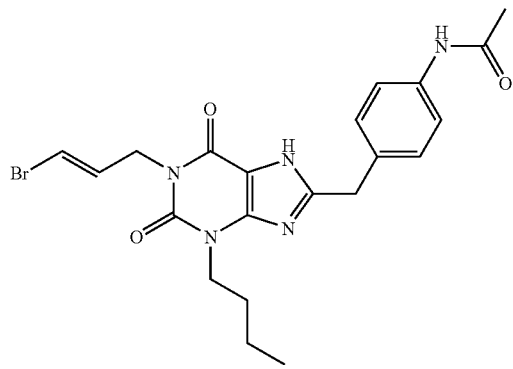

This compound was prepared by a method similar to that described in example 11 (method 2) except that 1,3-dibromo-1-propene (Aldrich) was used in place of 2-fluorobenzyl bromide. LCMS, m/z(M+H)=474.09.

Example 54

N-{4-[3-Butyl-1-(3-methyl-but-2-enyl)-2,6-dioxo-2,3,6,7-tetrahydro-1H-purin-8-ylmethyl]-phenyl}-acetamide

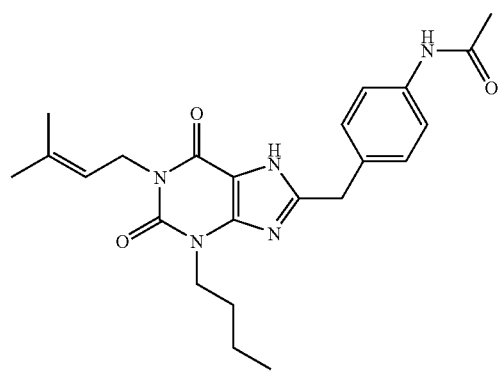

This compound was prepared by a method similar to that described in example 11 (method 2) except that 1-bromo-3-methyl-2-butene (Aldrich) was used in place of 2-fluorobenzyl bromide. LCMS, m/z(M+H)=424.17.

Example 55

N-[4-(3-Butyl-2,6-dioxo-1-prop-2-ynyl-2,3,6,7-tetrahydro-1H-purin-8-ylmethyl)-phenyl]-acetamide

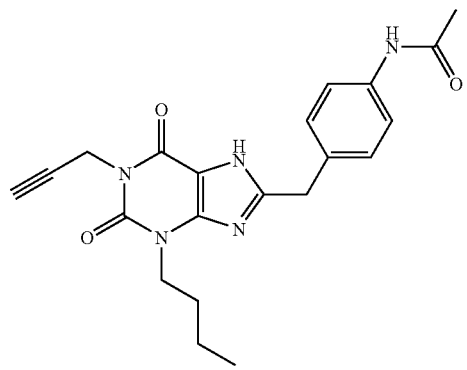

This compound was prepared by a method similar to that described in example 11 (method 2) except that propargyl bromide (Aldrich) was used in place of 2-fluorobenzyl bromide. LCMS, m/z(M+H)=394.20.

Example 56

N-{4-[3-Butyl-1-(3-fluoro-benzyl)-2,6-dioxo-2,3,6,7-tetrahydro-1H-purin-8-ylmethyl]-phenyl}-acetamide

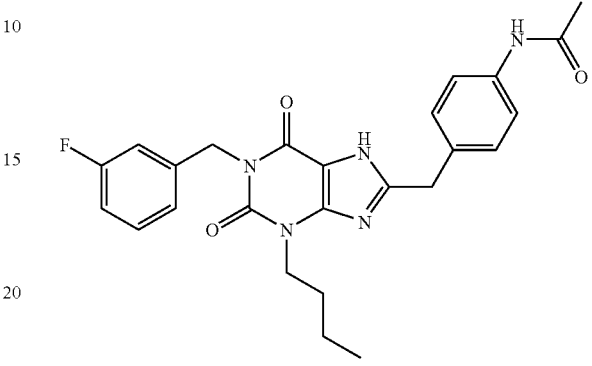

This compound was prepared by a method similar to that described in example 1 except that 3-fluorobenzyl bromide was used in place of allyl bromide. MS, m/z(M+)=463.2018.

Example 57

N-{4-[3-Butyl-1-(2,6-difluoro-benzyl)-2,6-dioxo-2,3,6,7-tetrahydro-1H-purin-8-ylmethyl]-phenyl}-acetamide

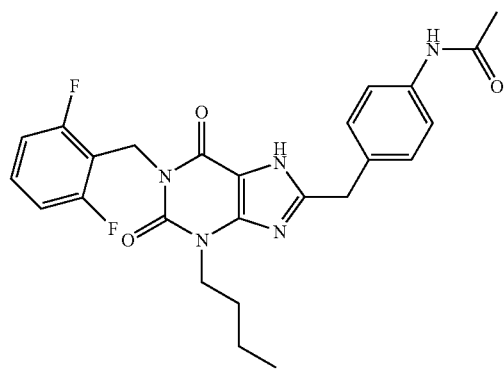

This compound was prepared by a method similar to that described in example 11 (method 2) except that 2,6-difluorobenzyl bromide (Aldrich) was used in place of 2-fluorobenzyl bromide. LCMS, m/z(M+H)=482.14.

Example 58

N-{4-[3-Butyl-1-(2-fluoro-6-nitro-benzyl)-2,6-dioxo-2,3,6,7-tetrahydro-1H-purin-8-ylmethyl]-phenyl}-acetamide

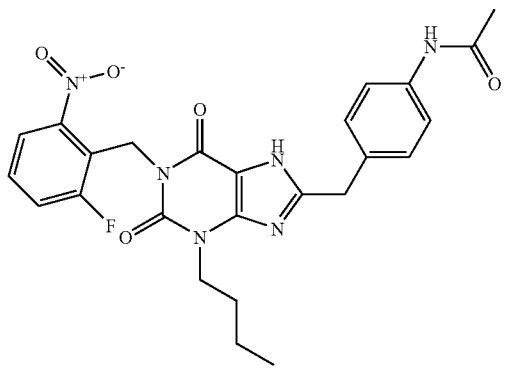

This compound was prepared by a method similar to that described in example 11 (method 2) except that 2-fluoro-6-nitrobenzyl bromide (Lancaster) was used in place of 2-fluorobenzyl bromide. LCMS, m/z(M+H)=509.15.

Example 59

N-(4-{3-Butyl-1-[4-(1-methyl-1H-tetrazol-5-yl)-benzyl]-2,6-dioxo-2,3,6,7-tetrahydro-1H-purin-8-ylmethyl}-phenyl)-acetamide

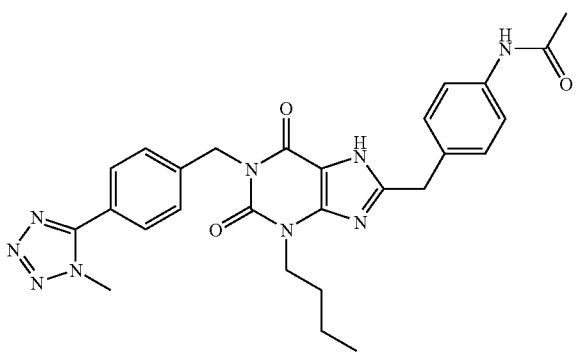

This compound was prepared by a method similar to that described in example 11 (method 2) except that 5-(4-chloromethyl-phenyl)-1-methyl-1H-tetrazole was used in place of 2-fluorobenzyl bromide. LCMS, m/z(M+H)= 528.13.

Example 60

N-{4-[1-5-Amino-2-fluorobenzyl-3-butyl-2,6-dioxo-2,3,6,7-tetrahydro-1H-purin-8-ylmethyl]-phenyl}-acetamide; compound with trifluoro-acetic acid

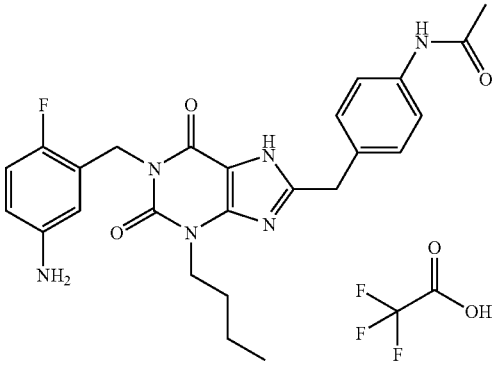

This compound was prepared by the route outlined in scheme 7.

Step 1: Preparation of 6-amino-1-butyl-5-nitroso-1H-pyrimidine-2,4-dione

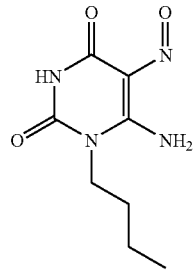

A suspension of 6-amino-1-butyl-1H-pyrimidine-2,4-dione (3.0 g, 16.4 mmol) in a 1N aqueous hydrochloric acid solution (33 mL) at 25° C. was treated with sodium nitrite (1.47 g, 21.32 mmol) in portions. The pH was adjusted to pH=5 by the addition of ammonium hydroxide (22 mL). The reaction was stirred at 25° C. for 10 min. At this time, the resulting solid was collected by filtration, washed with a pH=5 aqueous buffer, and then dried in vacuo to afford 6-amino-1-butyl-5-nitroso-1H-pyrimidine-2,4-dione (2.89 g, 83%) as a purple solid: LR-MS for $C_8H_{12}N_4O_3$ $(M+H)^+$ at m/z=213.

Step 2: Preparation of 5,6-diamino-1-butyl-1H-pyrimidine-2,4-dione

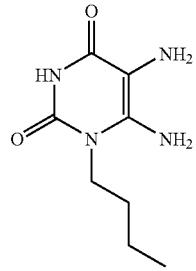

A suspension of 6-amino-1-butyl-5-nitroso-1H-pyrimidine-2,4-dione (500 mg, 2.36 mmol) in water (8.3 mL) at 85° C. was treated with sodium hydrosulfate (1.23 g, 7.08 mmol). The reaction was stirred at 85° C. for 20 min. At this time, the reaction was cooled to 0° C. The resulting green solid was collected by filtration, washed with water, and air dried for 30 min to afford 5,6-diamino-1-butyl-1H-pyrimidine-2,4-dione (304 mg, 65%) as a pale green solid: LR-MS for $C_8H_{14}N_4O_2$ (M+H)$^+$ at m/z=199.

Step 3: Preparation of 2-(4-acetylamino-phenyl)-N-(6-amino-1-butyl-2,4-dioxo-1,2,3,4-tetrahydro-pyrimidin-5-yl)-acetamide

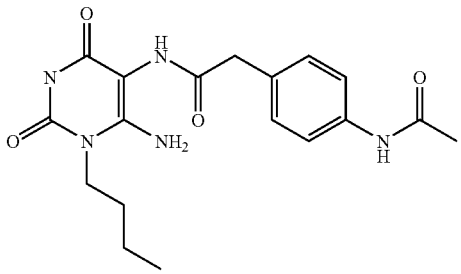

A solution of (4-acetylamino-phenyl)-acetic acid (348 mg, 1.65 mmol) in N,N-dimethylformamide (2.5 mL) was treated with 1-(3-dimethylaminopropyl)-3-ethylcarbodiimide hydrochloride (316 mg, 1.80 mmol). The resulting mixture was stirred at 25° C. for 20 min. At this time, the reaction was treated with 5,6-diamino-1-butyl-1H-pyrimidine-2,4-dione (300 mg, 1.5 mmol) followed by 4-dimethylaminopyridine (37 mg, 0.3 mmol). The reaction was stirred at 25° C. for 18 h. At this time, the reaction was concentrated in vacuo. The residue was diluted with water (5.0 mL) and was brought to pH=5 with a 1N aqueous hydrochloric acid solution. The resulting solid was collected by filtration, washed with water, and dried in vacuo to afford 2-(4-acetylamino-phenyl)-N-(6-amino-1-butyl-2,4-dioxo-1,2,3,4-tetrahydro-pyrimidin-5-yl)-acetamide (330 mg, 59%) as a light tan solid: LR-MS for $C_{18}H_{23}N_5O_4$ (M+H)+ at m/z=374

Step 4: Preparation of N-[4-(3-butyl-2,6-dioxo-2,3,6,7-tetrahydro-1H-purin-8-ylmethyl)-phenyl]-acetamide

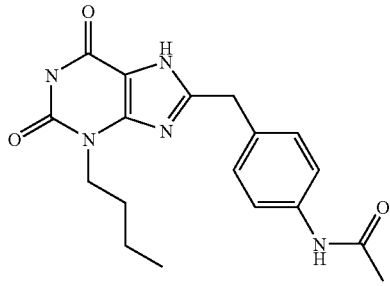

A solution of 2-(4-acetylamino-phenyl)-N-(6-amino-1-butyl-2,4-dioxo-1,2,3,4-tetrahydro-pyrimidin-5-yl)-acetamide (330 mg, 0.88 mmol) in methanol (7.0 mL) was treated with a 10% aqueous sodium hydroxide solution (3.54 mL). The resulting solution was stirred at 25° C. for 5 min and then was heated to 50° C. for 3 h. At this time, another portion of a 10% aqueous sodium hydroxide solution (3.54 mL) was added. The reaction was heated to 50° C. for an additional 4 h. At this time, the reaction was concentrated in vacuo. The residue was cooled to 0° C. and then treated with a 1N aqueous hydrochloric acid solution. The resulting precipitate was collected by filtration, washed with water, and dried in vacuo to afford N-[4-(3-butyl-2,6-dioxo-2,3,6,7-tetrahydro-1H-purin-8-ylmethyl)-phenyl]-acetamide (196 mg, 62%) as an orange-yellow solid: $^1$H NMR (DMSO-d$_6$, 300 MHz) δ 13.32 (broad s, 1H), 10.96 (broad s, 1H), 9.94 (broad s, 1H), 7.48 (d, J=8.42 Hz, 2H), 7.17 (d, J=8.42 Hz, 1H), 3.95 (s, 2H), 3.86 (m, 2H), 1.99 (s, 3H), 1.59 (m, 2H), 1.27 (m, 2H), 0.87 (t, J=7.32 Hz, 3H).

Step 5: Preparation of 2,2-dimethyl-propionic acid 8-(4-acetylamino-benzyl)-3-butyl-2,6-dioxo-1,2,3,6-tetrahydro-purin-7-ylmethyl ester

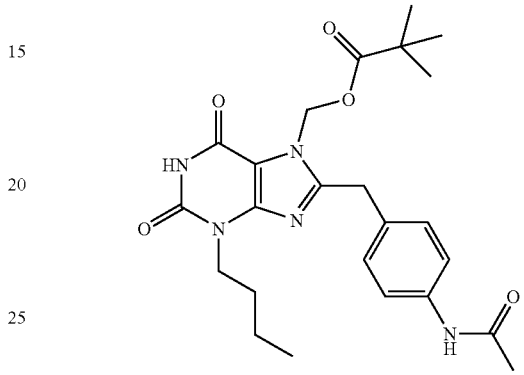

A mixture of N-[4-(3-butyl-2,6-dioxo-2,3,6,7-tetrahydro-1H-purin-8-ylmethyl)-phenyl]-acetamide (196 mg, 0.55 mmol) in N,N-dimethylformamide (5.0 mL) at 25° C. was treated with sodium carbonate (117 mg, 0.55 mmol) and 2,2-dimethyl-propionic acid chloromethyl ester (0.10 mL, 0.55 mmol). The resulting mixture was warmed to 50° C. for 8 h. At this time, the reaction mixture was poured into a solution of water (2.5 mL) containing a 1N aqueous hydrochloric acid solution (1.65 mL). This solution was extracted with ethyl acetate. The organics were washed with water (1×100 mL) and a saturated aqueous sodium chloride solution (1×100 mL), dried over magnesium sulfate, filtered, and concentrated in vacuo. Flash chromatography (Merck Silica gel 60, 230–400 mesh, 3:2 ethyl acetate/petroleum ether) afforded 2,2-dimethyl-propionic acid 8-(4-acetylamino-benzyl)-3-butyl-2,6-dioxo-1,2,3,6-tetrahydro-purin-7-ylmethyl ester (107 mg, 41.4%) as a yellow foam: FAB-HRMS m/e calcd for $C_{24}H_{31}N_5O_5$ (M+H)$^+$ 470.2403, found 470.2408.

Step 6: Preparation of 2,2-dimethyl-propionic acid 8-(4-acetylamino-benzyl)-3-butyl-1-(2-fluoro-5-nitro-benzyl)-2,6-dioxo-1,2,3,6-tetrahydro-purin-7-ylmethyl ester

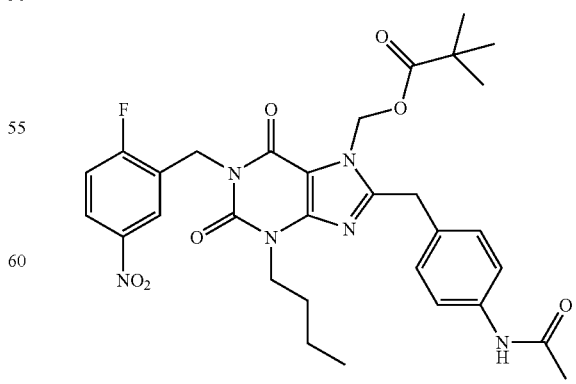

A solution of 2,2-dimethyl-propionic acid 8-(4-acetylamino-benzyl)-3-butyl-2,6-dioxo-1,2,3,6-tetrahydro-purin- 7-ylmethyl ester (104 mg, 0.22 mmol) in acetonitrile (2.0 mL) was treated with 1,8-diazabicyclo[5.4.0]undec-7-ene (0.03 mL, 0.24 mmol) and 2-bromomethyl-1-fluoro-4-nitrobenzene (56.6 mg, 0.24 mmol). The resulting solution was heated to 50° C. for 6 h. At this time, another portion of 1,8-diazabicyclo[5.4.0]undec-7-ene (0.03 mL, 0.24 mmol) was added. The reaction was stirred at 25° C. for 18 h. At this time, the reaction was poured into ethyl acetate (200 mL) and was washed with a 1N aqueous hydrochloric acid solution (1×50 mL) and a saturated aqueous sodium chloride solution (1×50 mL). The organics were dried over magnesium sulfate, filtered, and concentrated in vacuo. Flash chromatography (Merck Silica gel 60, 230–400 mesh, 1:1 ethyl acetate/petroleum ether) afforded 2,2-dimethyl-propionic acid 8-(4-acetylamino-benzyl)-3-butyl-1-(2-fluoro-5-nitro-benzyl)-2,6-dioxo-1,2,3,6-tetrahydro-purin-7-ylmethyl ester (45.3 mg, 33%) as a tan solid: FAB-HRMS m/e calcd for $C_{31}H_{35}N_6O_7F$ (M+H)$^+$ 623.2630, found 623.2631.

Step 8: Preparation of 2,2-dimethyl-propionic acid 8-(4-acetylamino-benzyl)-1-(5-amino-2-fluoro-benzyl)-3-butyl-2,6-dioxo-1,2,3,6-tetrahydro-purin-7-ylmethyl ester

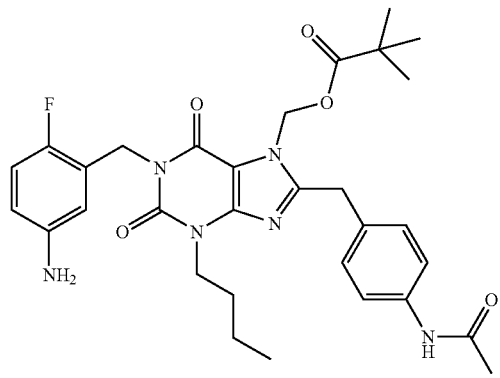

A mixture of 2,2-dimethyl-propionic acid 8-(4-acetylamino-benzyl)-3-butyl-1-(2-fluoro-5-nitro-benzyl)-2,6-dioxo-1,2,3,6-tetrahydro-purin-7-ylmethyl ester (45 mg, 0.07 mmol) in methanol (30 mL) was treated with 10% palladium on carbon (45 mg). The reaction mixture was subjected to 48 psi pressure of hydrogen gas in a Parr apparatus for 2 h. At this time, the reaction mixture was filtered through a pad of celite and washed with methanol. The filtrate was concentrated in vacuo to afford 2,2-dimethyl-propionic acid 8-(4-acetylamino-benzyl)-1-(5-amino-2-fluoro-benzyl)-3-butyl-2,6-dioxo-1,2,3,6-tetrahydro-purin-7-ylmethyl ester (39.8 mg, 92.9%) as an off-white solid: LR-MS for $C_{31}H_{37}FN_6O_5$ (M–H)$^+$ at m/z=591.

Step 9: Preparation of N-{4-[1-(5-amino-2-fluorobenzyl)-3-butyl-2,6-dioxo-2,3,6,7-tetrahydro-1H-purin-8-ylmethyl]-phenyl}-acetamide; compound with trifluoro-acetic acid A solution of 2,2-dimethyl-propionic acid 8-(4-acetylamino-benzyl)-1-(5-amino-2-fluoro-benzyl)-3-butyl-2,6-dioxo-1,2,3,6-tetrahydro-purin-7-ylmethyl ester (39.7 mg, 0.06 mmol) in methanol (1.5 mL) at 25° C. was treated with a 1N aqueous sodium hydroxide solution (0.33 mL). The reaction was stirred at 25° C. for 30 min. At this time, the reaction was concentrated in vacuo. The resulting residue was purified by HPLC (20–70% acetonitrile/water (0.075% trifluoroacetic acid in both solvents) over 20 min). Fractions with the desired product were combined and concentrated in vacuo. The resulting residue was diluted with acetonitrile and water and freeze dried to afford N-{4-[1-(5-amino-2-fluoro-benzyl)-3-butyl-2,6-dioxo-2,3,6,7-tetrahydro-1H-purin-8-ylmethyl]-phenyl}-acetamide trifluoro-acetic acid (25 mg, 78%) as a white solid: EI-HRMS m/e calcd for $C_{25}H_{27}N_6O_3F$ (M$^+$) 478.2129, found 478.2139.

Example 61

N-{4-[1-(5-Methoxy-2-fluorobenzyl)-3-butyl-2,6-dioxo-2,3,6,7-tetrahydro-1H-purin-8-ylmethyl]-phenyl}-acetamide; compound with trifluoro-acetic acid

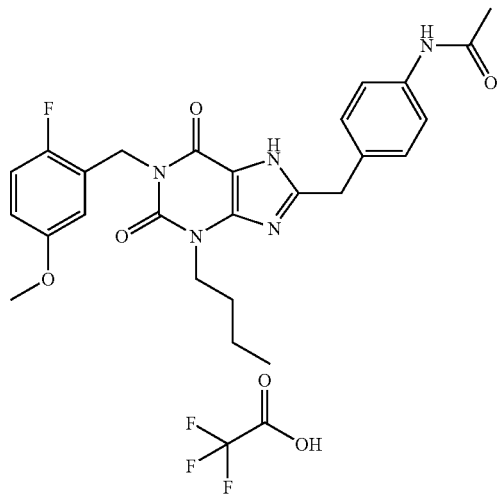

Step 1: Preparation of 2,2-dimethyl-propionic acid 8-(4-acetylamino-benzyl)-3-butyl-1-(2-fluoro-5-methoxy-benzyl)-2,6-dioxo-1,2,3,6-tetrahydro-purin-7-ylmethyl ester

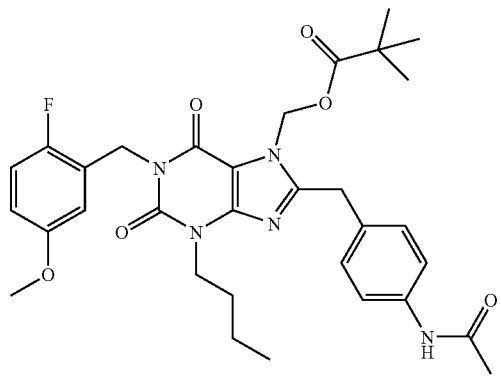

A solution of 2,2-dimethyl-propionic acid 8-(4-acetylamino-benzyl)-3-butyl-2,6-dioxo-1,2,3,6-tetrahydro-purin-7-ylmethyl ester (100 mg, 0.21 mmol) and 2-bromomethyl-1-fluoro-4-methoxy-benzene (56 mg, 0.25 mmol) in acetonitrile (2.0 mL) was treated with 1,8-diazabicyclo[5.4.0]undec-7-ene (0.06 mL, 0.45 mmol). The reaction was stirred at 25° C. The reaction was diluted with ethyl acetate and was washed with a 1N aqueous hydrochloric acid solution and a saturated aqueous sodium chloride solution. The organics were dried over magnesium sulfate, filtered, and concentrated in vacuo. Flash chromatography (Merck Silica gel 60, 230–400 mesh, 1:1 ethyl acetate/petroleum ether) afforded 2,2-dimethyl-propionic acid 8-(4-acetylamino-benzyl)-3-butyl-1-(2-fluoro-5-methoxy-benzyl)-2,6-dioxo-1,2,3,6-tetrahydro-purin-7-ylmethyl ester (26 mg, 20%) as a yellow solid. This material was taken on without further purification or characterization.

Step 2: Preparation of N-{4-[3-butyl-1-(2-fluoro-5-methoxy-benzyl)-2,6-dioxo-2,3,6,7-tetrahydro-1H-purin-8-ylmethyl]-phenyl}-acetamide trifluoro-acetic acid A solution of 2,2-dimethyl-propionic acid 8-(4-acetylamino-benzyl)-3-butyl-1-(2-fluoro-5-methoxy-benzyl)-2,6-dioxo-1,2,3,6-tetrahydro-purin-7-ylmethyl ester (25 mg, 0.04 mmol) in methanol (1.0 mL) was treated with a 1N aqueous sodium hydroxide solution (0.12 mL, 0.12 mmol). The reaction was stirred at 25° C. for 3 h. At this time, the reaction was concentrated in vacuo. The residue was diluted with acetonitrile and water and then acidified with trifluoroacetic acid. The resulting residue was purified by HPLC (20–70% acetonitrile/water (0.075% trifluoroacetic acid in both solvents) over 30 min). Fractions with the desired product were combined and concentrated in vacuo. The resulting residue was diluted with acetonitrile and water and was freeze dried to afford N-{4-[3-butyl-1-(2-fluoro-5-methoxy-benzyl)-2,6-dioxo-2,3,6,7-tetrahydro-1H-purin-8-ylmethyl]-phenyl}-acetamide trifluoro-acetic acid (9.0 mg, 36%) as a light purple solid: EI-HRMS m/e calcd for $C_{26}H_{28}N_5O_4F$ (M$^+$) 493.2125, found 493.2121.

Example 62

N-{4-[3-Butyl-1-(2-hydroxy-benzyl)-2,6-dioxo-2,3,6,7-tetrahydro-1H-purin-8-ylmethyl]-phenyl}-acetamide

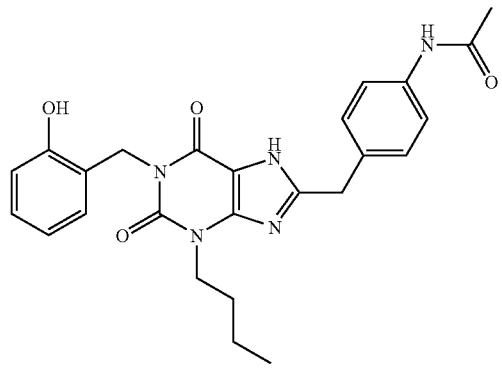

Step 1: Preparation of 2,2-dimethyl-propionic acid 8-(4-acetylamino-benzyl)-3-butyl-1-[2-(tert-butyl-dimethyl-silanyloxy)-benzyl]-2,6-dioxo-1,2,3,6-tetrahydro-purin-7-ylmethyl ester

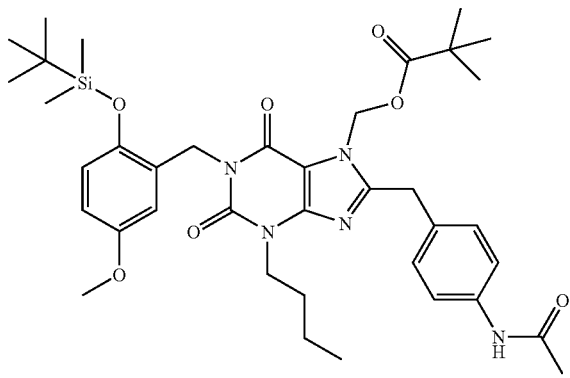

A solution of 2,2-dimethyl-propionic acid 8-(4-acetylamino-benzyl)-3-butyl-2,6-dioxo-1,2,3,6-tetrahydro-purin-7-ylmethyl ester (100 mg, 0.21 mmol) in N,N-dimethylformamide (2.0 mL) was treated with sodium carbonate (68 mg, 0.64 mmol), (2-bromomethyl-phenoxy)-tert-butyl-dimethyl-silane (70.6 mg, 0.23 mmol) in N,N-dimethylformamide (0.5 mL), and tetrabutylammonium iodide (24 mg, 0.06 mmol). The reaction was heated at 50° C. for 4 h. At this time, the reaction was poured onto a solution of water (125 mL) and a 1N aqueous hydrochloric acid solution (1.28 mL). The product was extracted into ethyl acetate. The organics were washed with water (1×100 mL) and a saturated aqueous sodium chloride solution (1×100 mL), dried over magnesium sulfate, filtered, and concentrated in vacuo. Flash chromatography (Merck Silica gel 60, 230–400 mesh, 1:4 ethyl acetate/petroleum ether) afforded 2,2-dimethyl-propionic acid 8-(4-acetylamino-benzyl)-3-butyl-1-[2-(tert-butyl-dimethyl-silanyloxy)-benzyl]-2,6-dioxo-1,2,3,6-tetrahydro-purin-7-ylmethyl ester (91.9 mg, 63%) as an off-white foam: FAB-HRMS m/e calcd for $C_{37}H_{51}N_5O_6Si$ (M+H)$^+$ 690.3687, found 690.3685.

Step 2: Preparation of N-(4-{3-butyl-1-[2-(tert-butyl-dimethyl-silanyloxy)-benzyl]-2,6-dioxo-2,3,6,7-tetrahydro-1H-purin-8-ylmethyl}-phenyl)-acetamide sodium salt

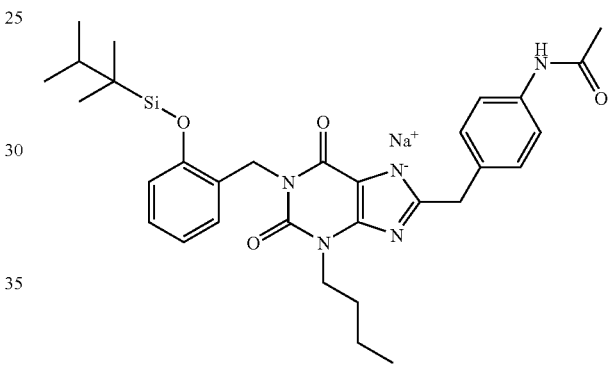

A solution of 2,2-dimethyl-propionic acid 8-(4-acetylamino-benzyl)-3-butyl-1-[2-(tert-butyl-dimethyl-silanyloxy)-benzyl]-2,6-dioxo-1,2,3,6-tetrahydro-purin-7-ylmethyl ester (91 mg, 0.13 mmol) in methanol (5.0 mL) at 25° C. was treated with a 1N aqueous sodium hydroxide solution (0.39 mL, 0.39 mmol). The reaction was stirred at 25° C. for 45 min. At this time, the reaction was concentrated in vacuo to afford N-(4-{3-butyl-1-[2-(tert-butyl-dimethyl-silanyloxy)-benzyl]-2,6-dioxo-2,3,6,7-tetrahydro-1H-purin-8-ylmethyl}-phenyl)-acetamide sodium salt (75 mg, 95%). This material was taken on without further purification or characterization.

Step 3: Preparation of N-{4-[3-butyl-1-(2-hydroxy-benzyl)-2,6-dioxo-2,3,6,7-tetrahydro-1H-purin-8-ylmethyl]-phenyl}-acetamide A suspension of N-(4-{3-butyl-1-[2-(tert-butyl-dimethyl-silanyloxy)-benzyl]-2,6-dioxo-2,3,6,7-tetrahydro-1H-purin-8-ylmethyl}-phenyl)-acetamide sodium salt (75 mg, 0.12 mmol) in tetrahydrofuran cooled to 0° C. was treated with tetrabutylammonium fluoride. The reaction was stirred at 0° C. for 1.5 h. At this time, the reaction mixture was treated with a saturated aqueous ammonium chloride solution (1.0 mL) and then diluted with ethyl acetate (50 mL). This solution was washed with water and brine. The organics were dried over magnesium sulfate, filtered, and concentrated in vacuo. The resulting residue was diluted with acetonitrile. The insolubles were collected, washed with acetonitrile, and dried in vacuo for 24 hrs to afford N-{4-[3-butyl-1-(2-hydroxy-benzyl)-2,6-dioxo-2,3,6,7-tetrahydro-1H-purin-8-ylmethyl]-phenyl}-acetamide (11.4 mg, 19%) as a white solid: EI-HRMS m/e calcd for $C_{25}H_{27}N_5O_4$ ($M^+$) 461.2063, found 461.2073.

Example 63

[4-(1-Benzyl-3-butyl-2,6-dioxo-2,3,6,7-tetrahydro-1H-purin-8-ylmethyl)-phenyl]-carbamic acid tert-butyl ester

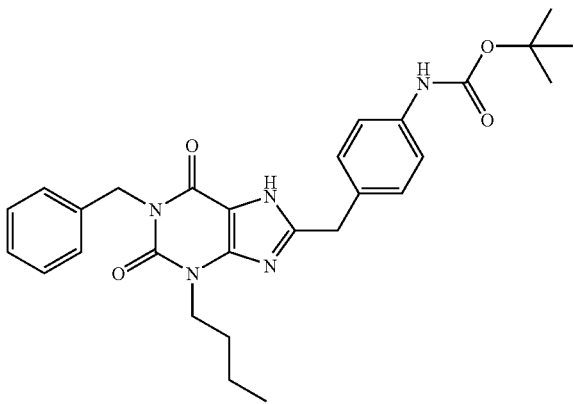

This compound was prepared by a method similar to that described in example 2 except (4-tert-butoxycarbonylamino-phenyl)-acetic acid was used in place of N-acetyl-4-aminophenylacetic acid. MS, m/z(M+H)=504.2599.

[(4-Tert-butoxycarbonylamino-phenyl)-acetic acid was prepared according to the method of Rai et al. as reported in *J. Med. Chem.* 1992, 35, 4150.]

Example 64

1-3-butyl-8-[4-(2-oxo-pyrrolidin-1-yl)-benzyl]-3,7-dihydro-purine-2,6-dione

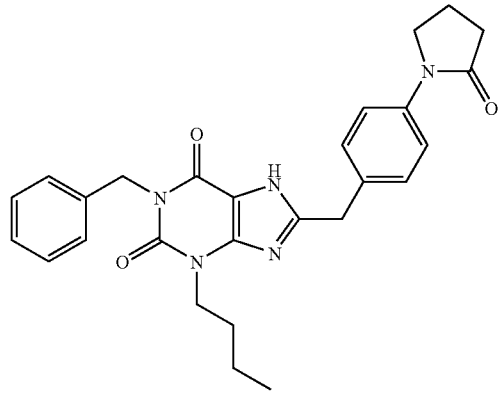

This compound was prepared as outlined in scheme 8.

Step 1: Preparation of 8-(4-amino-benzyl)-1-benzyl-3-butyl-3,7-dihydro-purine-2,6-dione

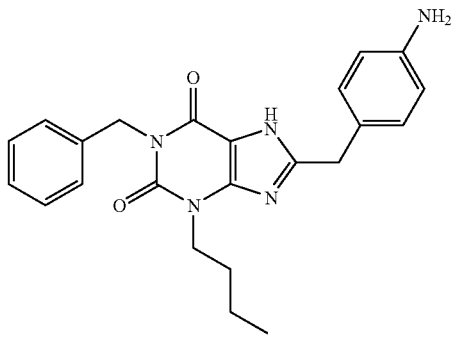

[4-(1-Benzyl-3-butyl-2,6-dioxo-2,3,6,7-tetrahydro-1H-purin-8-ylmethyl)-phenyl]-carbamic acid tert-butyl ester (303 mg) was suspended in p-dioxane (3 mL) and 4M HCl in p-dioxane (Aldrich, 5 mL) added. After 17 h the reaction mixture was poured into water and the mixture cautiously neutralized with saturated aqueous sodium bicarbonate. Brine was added to the mixture which was then thoroughly extracted with dichloromethane. The combined organic extracts were dried (sodium sulfate) and concentrated in vacuo to give the desired product as an orange solid (241 mg).

Step 2: Preparation of 1-benzyl-3-butyl-8-[4-(2-oxo-pyrrolidin-1-yl)-benzyl]-3,7-dihydro-purine-2,6-dione To a solution of 8-(4-amino-benzyl)-1-benzyl-3-butyl-3,7-dihydro-purine-2,6-dione (60 mg) in N,N-dimethylformamide (2 mL) was added 6,6-dimethyl-5,7-dioxa-spiro[2.5]octane-4,8-dione (Lancaster) (34 mg) and the mixture heated to 100° C. under argon for 16 hrs. The reaction mixture was cooled to RT and poured into saturated aqueous ammonium chloride, diluted with water and extracted with ethyl acetate. The combined organic extracts were washed with brine, dried (sodium sulfate) and concentrated in vacuo. Purification by chromatotron using a 2 mm silica plate eluted with 95:5 chloroform/methanol gave the desired product as a pale yellow solid (36 mg). MS, m/z(M+)= 471.2272.

Example 65

1-Benzyl-3-butyl-8-[4-(2,5-dioxo-pyrrolidin-1-yl)-benzyl]-3,7-dihydro-purine-2,6-dione

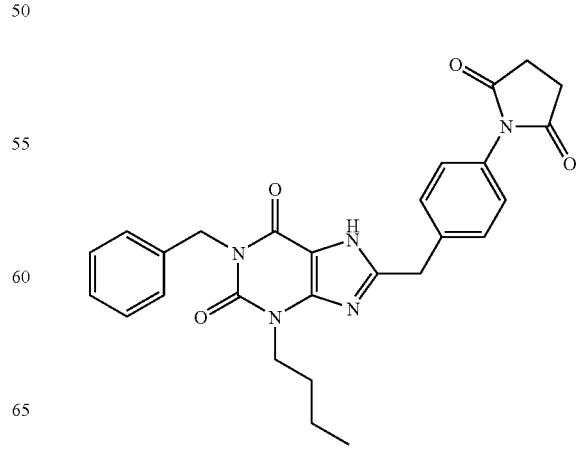

To a solution of 8-(4-amino-benzyl)-1-benzyl-3-butyl-3,7-dihydro-purine-2,6-dione (60 mg) (prepared as described in example 64) in N,N-dimethylformamide (2 mL) was added succinic anhydride (Aldrich) (20 mg) and the mixture stirred at RT under argon for 48 h. The reaction mixture was concentrated in vacuo and acetyl chloride (Aldrich) (2 mL) added to the residue. After stirring at RT for an additional 70 h saturated aqueous sodium bicarbonate (5 mL) was added cautiously to the reaction mixture. The mixture was poured into water and extracted with ethyl acetate. The combined organic extracts were washed with brine, dried (sodium sulfate) and concentrated in vacuo. Purified by crystallization from methanol/water to give the desired product as a pale yellow solid (36%). Mp=208–212° C. MS, m/z(M+)= 485.2064.

Example 66

1H-[1,2,4]Triazole-3-carboxylic acid {4-[3-butyl-1-(2-fluorobenzyl)-2,6-dioxo-2,3,6,7-tetrahydro-1H-purin-8-ylmethyl]-phenyl}-amide; compound with trifluoro-acetic acid

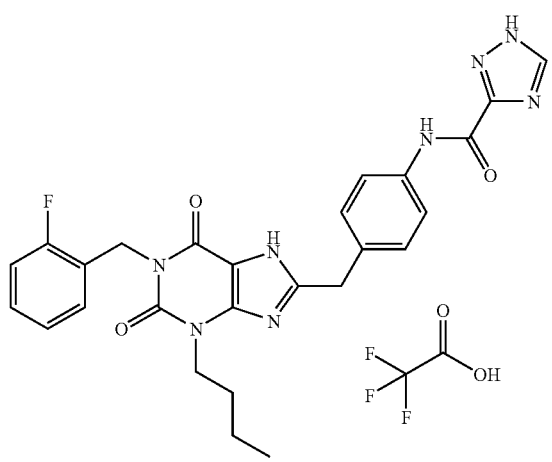

Step 1: Preparation of 1-trityl-1H-[1,2,4]triazole-3-carboxylic acid methyl ester

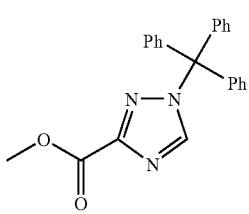

A solution of 1H-[1,2,4]triazole-3-carboxylic acid methyl ester (3.0 g, 0.023 mol) in N,N-dimethylformamide at 25° C. was treated with triphenylmethylchloride (7.2 g, 0.025 mol) and triethylamine (6.41 mL, 0.046 mol). The reaction was stirred at 25° C. for 4 days. At this time, the reaction was concentrated in vacuo. The residue was diluted with ethyl acetate and then washed with a dilute 1N aqueous hydrochloric acid solution and a saturated aqueous sodium chloride solution. The organics were dried over magnesium sulfate, filtered, and concentrated in vacuo. The resulting solids were diluted with ether, collected by filtration, washed with ether, and dried in vacuo to afford 1-trityl-1H-[1,2,4]triazole-3-carboxylic acid methyl ester (2.45 g, 84%) as a white solid: LR-FAB for $C_{23}H_{19}N_3O_2$ (M+H)$^+$ at m/z=370.

Step 2: Preparation of 1-trityl-1H-[1,2,4]triazole-3-carboxylic acid

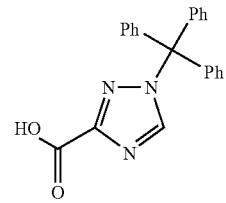

A mixture of 1-trityl-1H-[1,2,4]triazole-3-carboxylic acid methyl ester (500 mg, 1.35 mmol) in methanol at 25° C. was treated with a 1N aqueous sodium hydroxide solution (4.0 mL). The reaction was stirred at 25° C. for 24 h. At this time, the reaction mixture was poured into water (100 mL) and acidified with a 1N aqueous hydrochloric acid solution. This solution was extracted with ethyl acetate (2×150 mL). The organics were washed with a saturated aqueous sodium chloride solution (1×150 mL), dried over magnesium sulfate, filtered, and concentrated in vacuo to afford 1-trityl-1H-[1,2,4]triazole-3-carboxylic acid (326 mg, 67%) as a white solid: $^1$H NMR (DMSO-$d_6$, 300 MHz) δ 8.37 (s, 1H), 7.39 (m, 9H), 7.05 (m, 6H), 3.82 (s, 3H).

Step 3: Preparation of 1-trityl-1H-[1,2,4]triazole-3-carboxylic acid (4-{[6-amino-1-butyl-3-(2-fluoro-benzyl)-2,4-dioxo-1,2,3,4-tetrahydro-pyrimidin-5-ylcarbamoyl]-methyl}-phenyl)-amide

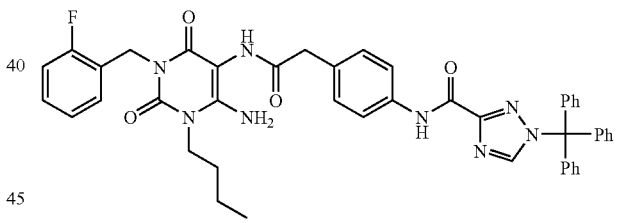

A solution of 1-trityl-1H-[1,2,4]triazole-3-carboxylic acid (51 mg, 0.65 mmol) in N,N-dimethylformamide (0.8 mL) at 25° C. was treated with 1-hydroxybenzotriazole hydrate (19.3 mg, 0.14 mmol) and O-benzotriazol-1-yl-N,N,N'N'-tetramethyluronium hexafluorophosphate (54 mg, 0.14 mmol). The resulting mixture was cooled to 0° C. and then treated with the hydrochloric acid salt of N-[6-amino-1-butyl-3-(2-fluoro-benzyl)-2,4-dioxo-1,2,3,4-tetrahydro-pyrimidin-5-yl]-2-(4-amino-phenyl)-acetamide (62 mg, 0.13 mmol) and N,N-diisopropylethylamine (0.11 mL, 0.65 mmol). The reaction was stirred at 0° C. for 1 h and then at 25° C. for 4.5 h. At this time, the reaction was concentrated in vacuo. The residue was dissolved in dichloromethane (50 mL) and washed with a saturated aqueous sodium bicarbonate solution (1×15 mL) and a saturated aqueous sodium chloride solution (1×20 mL). The organics were dried over magnesium sulfate, filtered, and concentrated in vacuo. Flash chromatography (Merck Silica gel 60, 230–00 mesh, 93:7 dichloromethane/methanol) afforded 1-trityl-1H-[1,2,4]triazole-3-carboxylic acid (4-{[6-amino-1-butyl-3-(2- fluoro-benzyl)-2,4-dioxo-1,2,3,4-tetrahydro-pyrimidin-5-ylcarbamoyl]-methyl}-phenyl)-amide (67.9 mg, 68%) as a pale yellow solid: FAB-HRMS m/e calcd for $C_{45}H_{41}N_8O_4F$ (M+Na)$^+$ 799.3133, found 799.3113.

Step 4: Preparation of 1-trityl-1H-[1,2,4]triazole-3-carboxylic acid {4-[3-butyl-1-(2-fluoro-benzyl)-2,6-dioxo-2,3,6,7-tetrahydro-1H-purin-8-ylmethyl]-phenyl}-amide

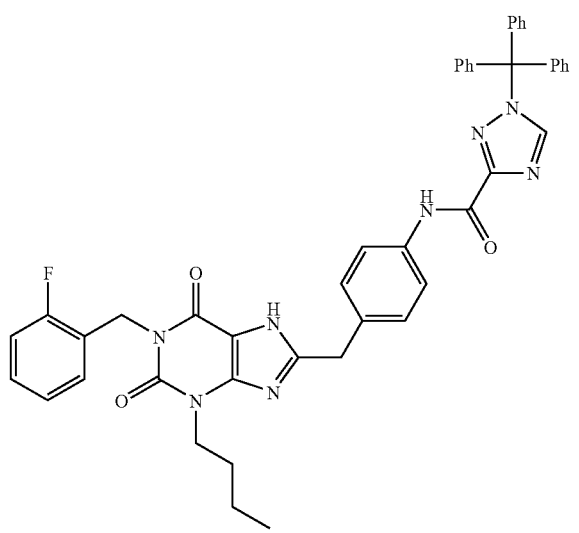

A solution of 1-trityl-1H-[1,2,4]triazole-3-carboxylic acid (4-{[6-amino-1-butyl-3-(2-fluoro-benzyl)-2,4-dioxo-1,2,3,4-tetrahydro-pyrimidin-5-ylcarbamoyl]-methyl}-phenyl)-amide (70 mg, 0.09 mmol) in methanol (3.0 mL) heated to 50° C. was treated with a 10% aqueous sodium hydroxide solution (1.08 mL). The reaction was heated at 50° C. for 4 h. At this time, the reaction was treated with a 3N aqueous hydrochloric acid solution (0.9 mL). This solution was stirred at 25° C. for 30 min. The resulting solids were collected by filtration, washed with water, and dried in vacuo to afford 1-trityl-1H-[1,2,4]triazole-3-carboxylic acid {4-[3-butyl-1-(2-fluoro-benzyl)-2,6-dioxo-2,3,6,7-tetrahydro-1H-purin-8-ylmethyl]-phenyl}-amide (41.3 mg, 60.5%) as a pale yellow solid: EI-HRMS m/e calcd for $C_{45}H_{39}N_8O_3F$ (M+Na)$^+$ 781.3027, found 781.3039.

Step 5: Preparation of 1H-[1,2,4]triazole-3-carboxylic acid {4-[3-butyl-1-(2-fluorobenzyl)-2,6-dioxo-2,3,6,7-tetrahydro-1H-purin-8-ylmethyl]-phenyl}-amide; compound with trifluoro-acetic acid A solution of 1-trityl-1H-[1,2,4]triazole-3-carboxylic acid {4-[3-butyl-1-(2-fluoro-benzyl)-2,6-dioxo-2,3,6,7-tetrahydro-1H-purin-8-ylmethyl]-phenyl}-amide (15 mg, 0.02 mmol) in dichloromethane (1.0 mL) at 25° C. was treated with trifluoroacetic acid (1.0 mL). The resulting solution was stirred at 25° C. for 45 min. At this time, the reaction was treated with triethylsilane (0.003 mL, 0.02 mmol). This solution was stirred at 25° C. for 5 min and then was concentrated in vacuo. The resulting residue was purified by HPLC (20–90% acetonitrile/water (0.075% trifluoroacetic acid in both solvents) over 30 min). Fractions with the desired product were freeze dried to afford 1H-[1,2,4]triazole-3-carboxylic acid {4-[3-butyl-1-(2-fluoro-benzyl)-2,6-dioxo-2,3,6,7-tetrahydro-1H-purin-8-ylmethyl]-phenyl}-amide; compound with trifluoro-acetic acid (4.5 mg, 40%) as a white, fluffy solid: EI-HRMS m/e calcd for $C_{26}H_{25}N_8O_3F$ (M$^+$) 516.2033, found 516.2027.

Example 67

1H-Imidazole-4-carboxylic acid {4-[3-butyl-1-(2-fluorobenzyl)-2,6-dioxo-2,3,6,7-tetrahydro-1H-purin-8-ylmethyl]-phenyl}-amide; compound with trifluoro-acetic acid

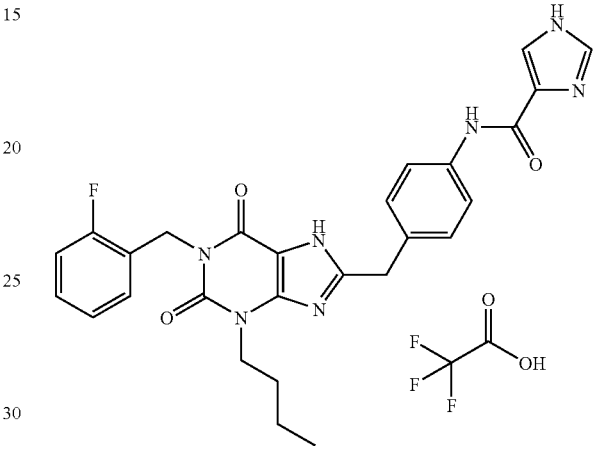

Step 1: Preparation of 1-trityl-1H-imidazole-4-carboxylic acid methyl ester

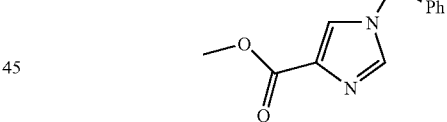

A solution of 1H-Imidazole-4-carboxylic acid methyl ester (1.0 g, 7.93 mmol) in N,N-dimethylformamide at 25° C. was treated with triethylamine (2.2 mL, 15.86 mmol) and triphenylmethylchloride (2.43 g, 8.72 mmol). The reaction was stirred at 25° C. for 8 h and then concentrated in vacuo. The residue was diluted with ethyl acetate and then washed with water, a 1N aqueous hydrochloric acid solution, water, and a saturated aqueous sodium chloride solution. The organics were dried over magnesium sulfate, filtered, and concentrated in vacuo. Flash chromatography (Merck Silica gel 60, 230–400 mesh, 50:50 ethyl acetate/petroleum ether) afforded 1-trityl-1H-imidazole-4-carboxylic acid methyl ester (2.88 g, 98.6%) as a white foam: $^1$H NMR (DMSO-d$_6$, 300 MHz) δ7.56 (s, 1H), 7.47 (m, 10H), 7.09 (m, 6H), 3.69 (s, 3H).

Step 2: Preparation of 1-trityl-1H-imidazole-4-carboxylic acid

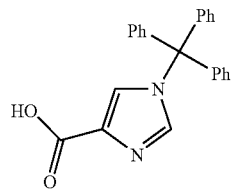

A solution of 1-trityl-1H-imidazole-4-carboxylic acid methyl ester (1.75 g, 4.60 mmol) in methanol (50 mL) at 25° C. was treated with a 1N aqueous sodium hydroxide solution (13.8 mL, 13.8 mmol). The reaction was stirred at 25° C. for 18 h and then heated to 50° C. for 1.5 h. At this time, the reaction was cooled to 25° C. and diluted with water (150 mL). The aqueous layer was brought to pH=1 by treatment with a 1N aqueous hydrochloric acid solution and then diluted with ethyl acetate (250 mL). The resulting precipitated product was collected by filtration. The filtrate was extracted with ethyl acetate (1×150 mL). The combined organics were then washed with a saturated aqueous sodium chloride solution (1×100 mL), dried over magnesium sulfate, filtered, and concentrated in vacuo. The two batches of product were combined to afford 1-trityl-1H-imidazole-4-carboxylic acid (1.55 g, 95.1%.) as a white solid: LR-MS for $C_{23}H_{18}N_2O_2$ (M+H)$^+$ at m/z=355.

Step 3: Preparation of 1-trityl-1H-imidazole-4-carboxylic acid (4-{[6-amino-1-butyl-3-(2-fluoro-benzyl)-2,4-dioxo-1,2,3,4-tetrahydro-pyrimidin-5-ylcarbamoyl]-methyl}-phenyl)-amide

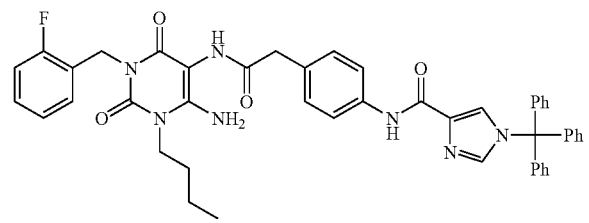

A solution of 1-trityl-1H-imidazole-4-carboxylic acid (67 mg, 0.19 mmol) in N,N-dimethylformamide (1.0 mL) at 25° C. was treated with 1-hydroxybenzotriazole hydrate (25.4 mg, 0.19 mmol) and O-benzotriazol-1-yl-N,N,N'N'-tetramethyluronium hexafluorophosphate (71 mg, 0.19 mmol). This solution was cooled to 0° C. and then was treated with N-[6-amino-1-butyl-3-(2-fluoro-benzyl)-2,4-dioxo-1,2,3,4-tetrahydro-pyrimidin-5-yl]-2-(4-amino-phenyl)-acetamide hydrochloride salt (81.5 mg, 0.17 mmol) and N,N-diisopropylethylamine (0.15 mL, 0.85 mmol). The reaction was stirred at 0° C. for 1 h and then at 25° C. for 4 h. At this time, the reaction was concentrated in vacuo. The residue was dissolved in ethyl acetate (100 mL) and was washed with a saturated aqueous sodium bicarbonate solution (1×25 mL). Some residual solids were then removed by filtration. The filtrate was washed with a saturated aqueous sodium chloride solution. The organics were dried over magnesium sulfate, filtered, and concentrated in vacuo to afford 1-trityl-1H-imidazole-4-carboxylic acid (4-{[6-amino-1-butyl-3-(2-fluoro-benzyl)-2,4-dioxo-1,2,3,4-tetrahydro-pyrimidin-5-ylcarbamoyl]-methyl}-phenyl)-amide (147 mg, quant.) as a pale yellow foam: LR-MS for $C_{23}H_{18}N_2O_2$ (M–H)$^+$ at m/z=353.

Step 4: Preparation of 1-trityl-1H-imidazole-4-carboxylic acid {4-[3-butyl-1-(2-fluoro-benzyl)-2,6-dioxo-2,3,6,7-tetrahydro-1H-purin-8-ylmethyl]-phenyl}-amide

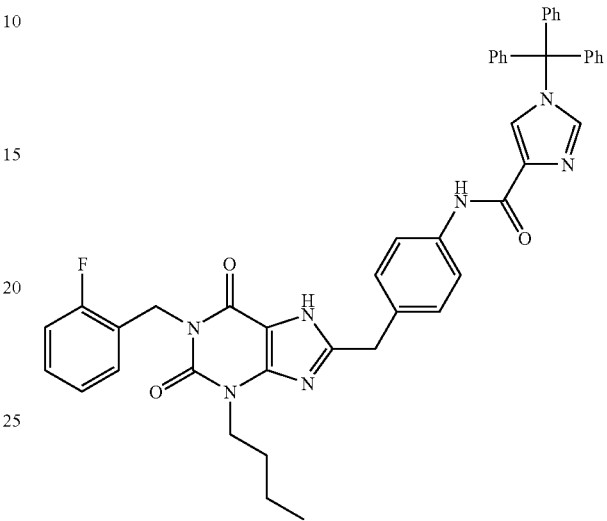

A solution of 1-trityl-1H-imidazole-4-carboxylic acid (4-{[6-amino-1-butyl-3-(2-fluoro-benzyl)-2,4-dioxo-1,2,3,4-tetrahydro-pyrimidin-5-ylcarbamoyl]-methyl}-phenyl)-amide (68.5 mg, 0.09 mmol) in methanol (2.0 mL) at 25° C. was treated with a 10% aqueous sodium hydroxide solution (1.06 mL, 0.26 mmol). The reaction was then warmed to 50° C. for 1 h. At this time, additional methanol (1.0 mL) was added. The reaction was continued at 50° C. for 2.5 h. At this time, the reaction was treated with a 3N aqueous hydrochloric acid solution (0.88 mL) and was stirred for 10 min. The resulting solid was collected by filtration, washed with water, and was dried in vacuo to afford 1-trityl-1H-imidazole-4-carboxylic acid {4-[3-butyl-1-(2-fluoro-benzyl)-2,6-dioxo-2,3,6,7-tetrahydro-1H-purin-8-ylmethyl]-phenyl}-amide (46.6 mg, 69.6%): EI-HRMS m/e calcd for $C_{46}H_{40}N_7O_3F$ (M$^+$) 757.3177, found 757.3160.

Step 5: Preparation of 1H-imidazole-4-carboxylic acid {4-[3-butyl-1-(2-fluoro-benzyl)-2,6-dioxo-2,3,6,7-tetrahydro-1H-purin-8-ylmethyl]-phenyl}-amide; compound with trifluoro-acetic acid A solution of 1-trityl-1H-imidazole-4-carboxylic acid {4-[3-butyl-1-(2-fluoro-benzyl)-2,6-dioxo-2,3,6,7-tetrahydro-1H-purin-8-ylmethyl]-phenyl}-amide (46 mg, 0.06 mmol) in dichloromethane (1.0 mL) at 25° C. was treated with trifluoroacetic acid (1.0 mL). The reaction was stirred at 25° C. for 30 min. At this time, the reaction was treated with triethylsilane (20 µL, 0.12 mmol) and then concentrated in vacuo. The resulting residue was purified by HPLC (20–95% acetonitrile/water (0.075% trifluoroacetic acid in both solvents) over 20 min). Fractions with the desired product were freeze dried to afford 1H-imidazole-4-carboxylic acid {4-[3-butyl-1-(2-fluoro-benzyl)-2,6-dioxo-2,3,6,7-tetrahydro-1H-purin-8-ylmethyl]-phenyl}-amide; compound with trifluoro-acetic acid (27.8 mg, 74%) as a white solid: EI-HRMS m/e calcd for $C_{27}H_{26}N_7O_3F$ (M$^+$) 515.2081, found 515.2083.

Example 68

N-{4-[3-Butyl-1-(2-fluorobenzyl)-2,6-dioxo-2,3,6,7-tetrahydro-1H-purin-8-ylmethyl]-phenyl}-3,4-dimethoxy-benzamide

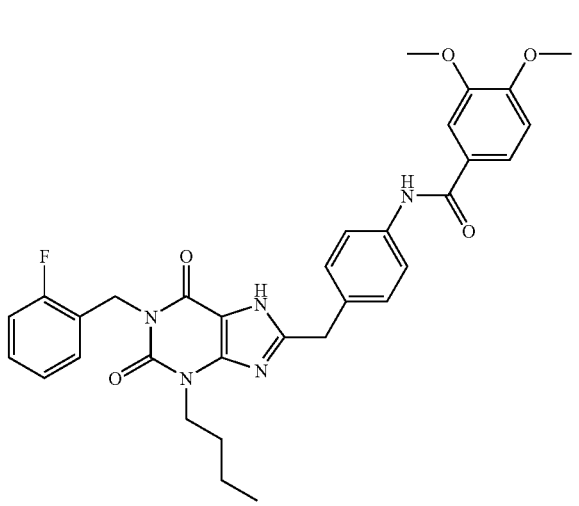

To a solution of 8-(4-amino-benzyl)-3-butyl-1-(2-fluorobenzyl)-3,7-dihydro-purine-2,6-dione (prepared as described in example 72) in pyridine (1 mL) was added 3,4-dimethoxy-benzoyl chloride (Aldrich) (13 mg, 0.06 mmol). The reaction was stirred at room temperature for 1 h and then concentrated under reduced pressure. The residue was purified by reverse phase HPLC to afford the product. LCMS, m/z(M+H)=586.33.

Example 69

3-Chloro-4-(propane-2-sulfonyl)-thiophene-2-carboxylic acid {4-[3-butyl-1-(2-fluorobenzyl)-2,6-dioxo-2,3,6,7-tetrahydro-1H-purin-8-ylmethyl]-phenyl}-amide

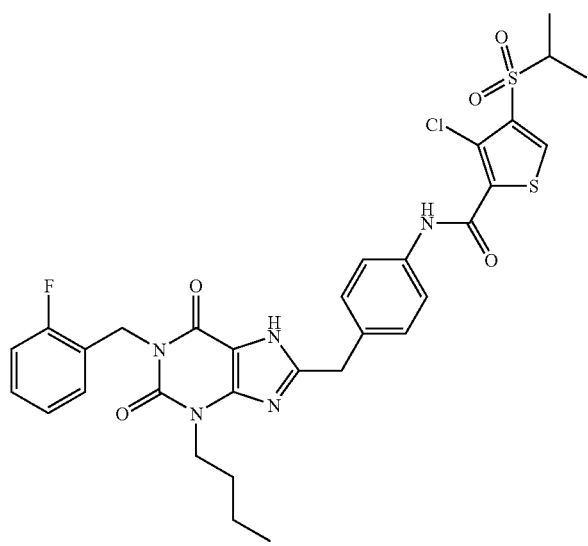

This compound was prepared by a method similar to that described in example 68 except that 3-chloro-4-(propane-2-sulfonyl)-thiophene-2-carbonyl chloride (Maybridge International) was used in place of 3,4-dimethoxy-benzoyl chloride. LCMS, m/z(M+H)=671.99.

Example 70

1-Methyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-amide

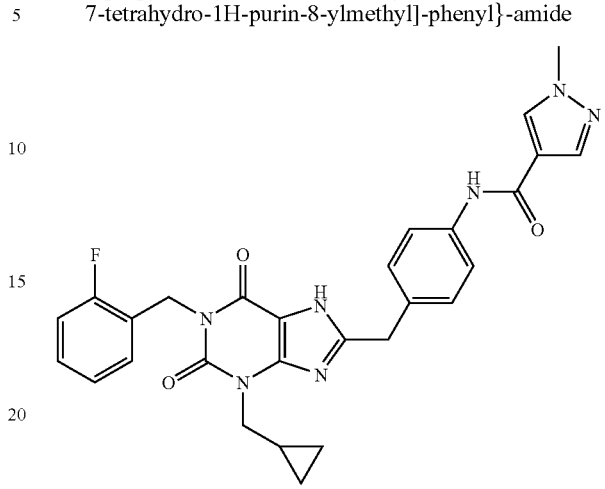

Step 1: Preparation of 1-methyl-1H-pyrazole-4-carboxylic acid ethyl ester

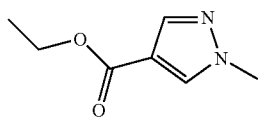

A mixture of sodium hydride (3.24 g, 12.84 mmol) in tetrahydrofuran (35 mL) cooled to 0° C. was treated with a solution of 1H-pyrazole-4-carboxylic acid ethyl ester (1.5 g, 10.7 mmol) in tetrahydrofuran (10 mL). The reaction was warmed to 25° C. and was stirred at 25° C. for 1 h. At this time, the reaction was treated with methyl iodide (1.0 mL, 16.05 mmol) and then was stirred at 25° C. for 18 h. The reaction was then cooled to 0° C. and was treated with a saturated aqueous ammonium chloride solution. The resulting mixture was diluted with ethyl acetate (150 mL). This solution was washed with water (1×50 mL) and a saturated aqueous sodium chloride solution (1×50 mL), dried over magnesium sulfate, filtered, and concentrated in vacuo to afford 1-methyl-1H-pyrazole-4-carboxylic acid ethyl ester (1.48 g, 89.7%) as a yellow oil: 1H NMR (DMSO-$d_6$, 300 MHz) δ8.27 (s, 1H), 7.80 (s, 1H), 4.18 (q, J=7.32 Hz, 2H), 3.84 (s, 3H), 1.24 (t, J=6.96 Hz, 3H).

Step 2: Preparation of 1-methyl-1H-pyrazole-4-carboxylic acid

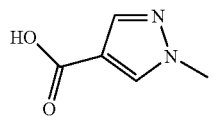

A solution of 1-methyl-1H-pyrazole-4-carboxylic acid ethyl ester (480 mg, 3.1 mmol) in ethanol cooled to 0° C. was treated with a 1N aqueous sodium hydroxide solution (9.3 mL, 9.3 mmol). The reaction was stirred at 25° C. for 18 h. At this time, the reaction was concentrated in vacuo and then acidified to pH=2 with a 1N aqueous hydrochloric acid solution. The product was extracted into ethyl acetate (2×50 mL). The organics were washed with a saturated aqueous sodium chloride solution (1×25 mL), dried over magnesium sulfate, filtered, and dried in vacuo to afford 1-methyl-1H-pyrazole-4-carboxylic acid (293 mg, 74.6%) as a white solid: EI-HRMS m/e calcd for $C_5H_6N_2O_2$ (M+) 126.0429, found 126.0429.

Step 3: Preparation of 1-methyl-1H-pyrazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-amide A solution of 8-(4-amino-benzyl)-3-cyclopropylmethyl-1-(2-fluoro-benzyl)-3,7-dihydro-purine-2,6-dione (50 mg, 0.12 mmol) in N,N-dimethylformamide at 25° C. was treated with a solution of 1-methyl-1H-pyrazole-4-carboxylic acid (15 mg, 0.12 mmol), O-benzotriazol-1-yl-N,N,N'N'-tetramethyluronium hexafluorophosphate (49.7 mg, 0.13 mmol), and N,N-diisopropylethylamine (62 µL, 0.36 mmol). The resulting solution was stirred at 25° C. for 18 h. At this time, the reaction was concentrated in vacuo. The residue was dissolved in chloroform and then was washed with a 1N aqueous hydrochloric acid solution (1×10 mL) and a saturated aqueous sodium chloride solution (1×10 mL). The organics were dried over magnesium sulfate, filtered, and concentrated in vacuo. Flash chromatography (Merck Silica gel 60, 230–400 760mesh, 5:95 methanol/dichloromethane) afforded 1-methyl-1H-pyrazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-amide (13.5 mg, 21.5%) as a tan solid: EI-HRMS m/e calcd for $C_{28}H_{26}N_7O_3$ (M+) 527.2081, found 527.2083.

Example 71

N-{4-[3-Cyclopropylmethyl-1-(2-fluorobenzyl)-2,6-dioxo-2,3,6,7-tetrahydro-1H-purin-8-ylmethyl]-phenyl}-2-dimethylamino-acetamide; compound with trifluoro-acetic acid

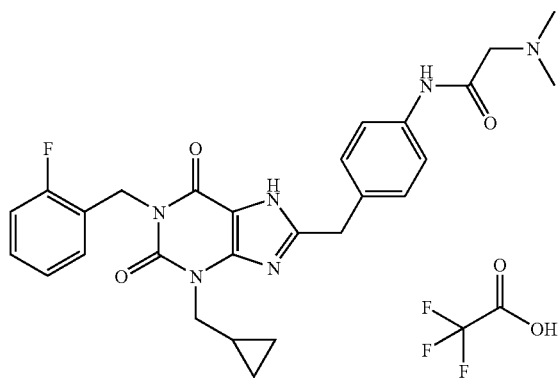

A solution of 8-(4-amino-benzyl)-3-cyclopropylmethyl-1-(2-fluoro-benzyl)-3,7-dihydro-purine-2,6-dione (45 mg, 0.11 mmol) in N,N-dimethylformamide (1.0 mL) at 25° C. was treated with dimethylamino-acetic acid (11 mg, 0.11 mmol), O-benzotriazol-1-yl-N,N,N'N'-tetramethyluronium hexafluorophosphate (45 mg, 0.12 mmol), and N,N-diisopropylethylamine (56 µL, 0.32 mmol). The resulting solution was stirred at 25° C. for 48 h. At this time, the reaction was concentrated in vacuo. The residue was dissolved in chloroform and then was washed with a saturated aqueous sodium chloride solution (1×10 mL). The organics were dried over magnesium sulfate, filtered, and concentrated in vacuo. The resulting residue was purified by HPLC (15–60% acetonitrile/water/0.075% trifluoroacetic acid over 30 min). Fractions with the desired product were combined and concentrated in vacuo. The resulting residue was diluted with dichloromethane (100 mL) and was washed with a saturated aqueous sodium bicarbonate solution (25 mL). The aqueous layer was re-extracted with dichloromethane (1×50 mL). The combined organics were dried over magnesium sulfate, filtered, and concentrated in vacuo. The resulting solid was dried in vacuo for 24 h to afford N-{4-[3-cyclopropylmethyl-1-(2-fluoro-benzyl)-2,6-dioxo-2,3,6,7-tetrahydro-1H-purin-8-ylmethyl]-phenyl}-2-dimethylamino-acetamide (24 mg, 44.3%) as an off-white solid: LR-MS for $C_{27}H_{29}FN_6O_3$ (M+H)+ at m/z=505.

Example 72

{4-[3-Butyl-1-(2-fluorobenzyl)-2,6-dioxo-2,3,6,7-tetrahydro-1H-purin-8-ylmethyl]-phenyl}-urea

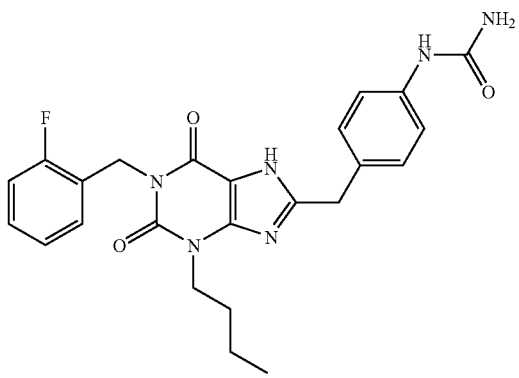

This compound was prepared according to the routes outlined in schemes 5, 6 and 11.

Step 1: Preparation of 1-butyl-3-(2-fluorobenzyl)-6-[2-(4-nitro-phenyl)-ethylamino]-1H-pyrimidine-2,4-dione.

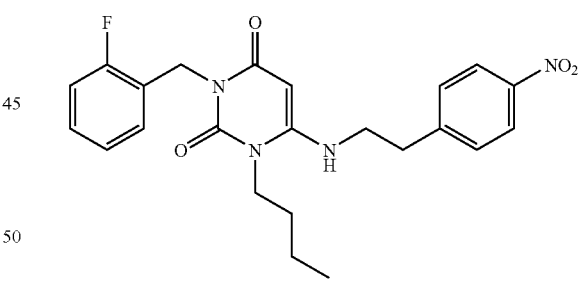

This compound was prepared from 1-butyl-6-chloro-3-(2-fluorobenzyl)-1H-pyrimidine-2,4-dione by a similar procedure as described in example 11 (method 2) except that 2-(4-nitro-phenyl)-ethylamine hydrochloride salt was used in place of N-[4-(2-amino-ethyl)-phenyl]-acetamide.

A mixture of 2-(4-nitro-phenyl)-ethylamine hydrochloride salt (Fluka) (7.85 g, 38.7 mmol), 1-butyl-6-chloro-3-(2-fluorobenzyl)-1H-pyrimidine-2,4-dione (8.0 g, 25.8 mmol) and triethylamine (10.7 mL, 77 mmol) in N-methyl-pyrrolidin-2-one (200 mL) was stirred at 75° C. for 16 hours. The reaction was then mixed with water and extracted with ethyl acetate (3×). The combined ethyl acetate layers were dried (magnesium sulfate) and concentrated. Column chromatography afforded 1-butyl-3-(2-fluorobenzyl)-6-[2-(4-nitro-phenyl)-ethylamino]-1H-pyrimidine-2,4-dione (4.7 g, 41 %) as a solid. ¹H NMR (CDCl₃, 200 MHz) δ$_H$ 0.84 (t, 3H), 1.11–1.50 (m, 4H), 3.10 (t, 2H), 3.48 (m, 2H), 3.70 (t, 2H), 436 (t, 1H), 4.94 (t, 1H), 5.20 (s, 2H), 6.95–7.10 (m, 2H), 7.17–7.30 (m, 2H), 7.39 (d, 2H), 8.20 (d, 2H).

Step 2: Preparation of 3-butyl-1-(2-fluorobenzyl)-8-(4-nitro-benzyl)-3,7-dihydro-purine-2,6-dione.

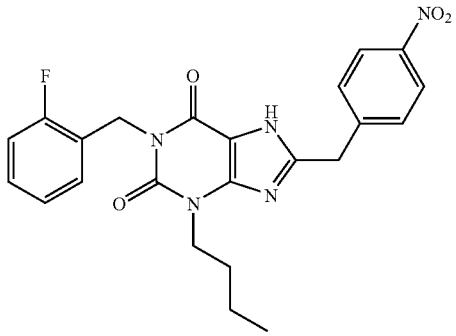

1-Butyl-3-(2-fluorobenzyl)-6-[2-(4-nitro-phenyl)-ethylamino]-1H-pyrimidine-2,4-dione (2.3 g, 5.2 mmol) was dissolved in ethanol (20 mL) and treated with isoamyl nitrite (Aldrich) (3.6 mL, 26 mmol). Concentrated aqueous hydrochloric acid (1 mL) was added to the reaction mixture. The reaction was stirred at 23° C. for 40 minutes. The ethanol was removed under reduced pressure and the residue washed with diethyl ether. The solid residue was then dissolved in n-butanol (15 mL), and the mixture refluxed for 30 minutes. After cooling to room temperature 1-butyl-3-(2-fluorobenzyl)-6-[2-(4-nitro-phenyl)-ethylamino]-1H-pyrimidine-2,4-dione separated as pale yellow crystals which were collected by filtration (1.91 g, 81%). LCMS, m/z(M+H)=452.24.

Step 3: Preparation of 8-(4-amino-benzyl)-3-butyl-1-(2-fluorobenzyl)-3,7-dihydro-purine-2,6-dione.

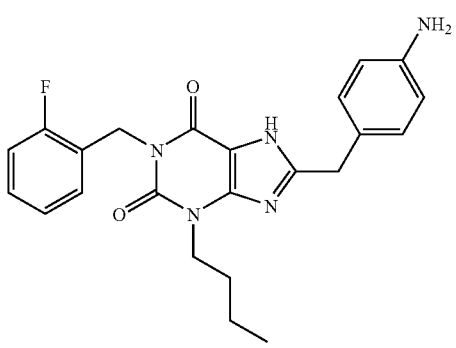

1-Butyl-3-(2-fluorobenzyl)-6-[2-(4-nitro-phenyl)-ethylamino]-1H-pyrimidine-2,4-dione (2.0 g, 4.46 mmol) was dissolved in methanol (100 mL) and treated with zinc dust (<10 μm, Aldrich; 2.91 g) followed by the addition of a solution of ammonium chloride (5.96 g, 112 mmol) in water (50 mL). The reaction mixture was stirred at room temperature for 3 h. The reaction mixture was then filtered through a pad of celite. The filtrate was concentrated to remove methanol and the residual aqueous solution was extracted with ethyl acetate (3×). The combined organic extracts were washed with brine, dried (sodium sulfate) and concentrated in vacuo to afford 8-(4-amino-benzyl)-3-butyl-1-(2-fluorobenzyl)-3,7-dihydro-purine-2,6-dione as a pale yellow solid (1.64 g, 87%). LCMS, m/z(M+H)=422.18.

Step 4: Preparation of {4-[3-Butyl-1-(2-fluorobenzyl)-2,6-dioxo-2,3,6,7-tetrahydro-1H-purin-8-ylmethyl]-phenyl}-urea.

8-(4-Amino-benzyl)-3-butyl-1-(2-fluorobenzyl)-3,7-dihydro-purine-2,6-dione (25 mg, 0.06 mmol) was dissolved in 95:5 dichloromethane/N,N-dimethylformamide (2 mL), and treated with trimethylsilyl isocyanate (Aldrich) (47 μl, 0.3 mmol). The reaction was stirred at room temperature for 18 h. The reaction was then concentrated under reduced pressure and the residue was purified by reverse phase HPLC to afford the desired product. LCMS, m/z(M+H)=464.98.

Example 73

1-{4-[3-Cyclopropylmethyl-1-(2-fluorobenzyl)-2,6-dioxo-2,3,6,7-tetrahydro-1H-purin-8-ylmethyl]-phenyl}-3-(2,6-dichloro-pyridin-4-yl)-urea

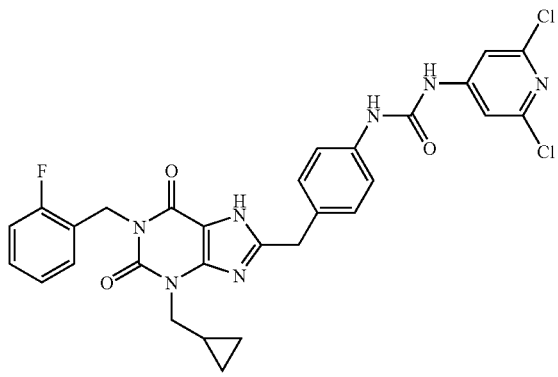

This compound was prepared by a method similar to that described in example 72 except that cyclopropylmethyl bromide (Lancaster) was used in place of 1-iodobutane and 2,6-dichloro-4-isocyanato-pyridine (Maybridge International) in the presence of diisopropylethylamine (1.3 equivalents) was used in place of trimethylsilyl isocyanate. LCMS, m/z(M+H)=608.08.

Example 74

1-{4-[3-Cyclopropylmethyl-1-(2-fluorobenzyl)-2,6-dioxo-2,3,6,7-tetrahydro-1H-purin-8-ylmethyl]-phenyl}-3-(3,5-dimethyl-1-phenyl-1H-pyrazol-4-yl)-urea

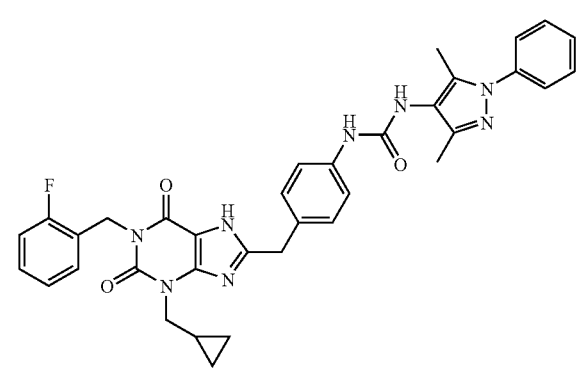

This compound was prepared by a method similar to that described in example 72 except that 4-isocyanato-3,5-dimethyl-1-phenyl-1H-pyrazole (Chembridge) was used in place of 2,6-dichloro-4-isocyanato-pyridine. LCMS, m/z (M+H)=633.22.

Example 75

8-[4-(4-tert-Butoxymethyl-2,5-dioxo-imidazolidin-1-yl)-benzyl]-3-cyclopropylmethyl-1-(2-fluorobenzyl)-3,7-dihydro-purine-2,6-dione

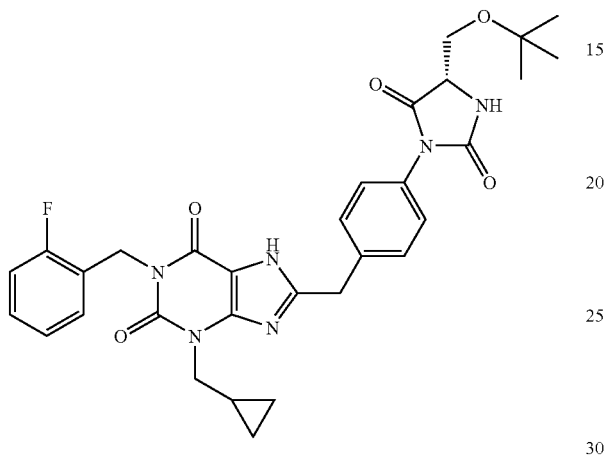

This compound was prepared by the method outlined in scheme 12. 8-(4-Amino-benzyl)-3-cyclopropylmethyl-1-(2-fluorobenzyl)-3,7-dihydro-purine-2,6-dione (100 mg, 0.24 mmol) was dissolved in N,N-dimethylformamide (5 mL), and treated with 2S-3-tert-butoxy-2-(9H-fluoren-9-yl-methoxycarbonylamino)-propionic acid (Bachem) (96 mg, 0.25 mmol), benzotriazol-1-yloxy-tris-(pyrrolidino)phosphonium hexafluorophosphate (AdvancedChemtech) (248 mg, 0.48 mmol) and diisopropylethylamine (131 µL, 0.75 mmol). The reaction was stirred at 23° C. for 3 h and then mixed with water and extracted with ethyl acetate (3×). The combined ethyl acetate layers were then dried (sodium sulfate) and concentrated in vacuo to dryness. The residue obtained was then dissolved in of 20% piperazine in dichloromethane (5 mL) and stirred for 1 h at room temperature. The reaction was mixed with water and extracted with ethyl acetate. The organic solution was dried (sodium sulfate) and concentrated. Chromatography using silica gel eluted with 10% methanol/dichloromethane afforded the pure α-amino amide intermediate, which was added to a solution of di-imidazol-1-yl-methanone (Aldrich) (40 mg, 0.24 mmol) and diisopropylethylamine (76 µL, 0.44 mmol) in dichloromethane (2 mL). The reaction was stirred at room temperature for 3 h, and was then concentrated under a stream of nitrogen gas. The dry mixture was purified by reverse phase HPLC to afford the product. LCMS, m/z(M+H)= 589.20.

[8-(4-Amino-benzyl)-3-cyclopropylmethyl-1-(2-fluorobenzyl)-3,7-dihydro-purine-2,6-dione was prepared by a method similar to that described in example 71 except that 6-chloro-1-cyclopropylmethyl-3-(2-fluorobenzyl)-1H-pyrimidine-2,4-dione was used in place of 1-butyl-6-chloro-3-(2-fluorobenzyl)-1H-pyrimidine-2,4-dione. 6-Chloro-1-cyclopropylmethyl-3-(2-fluorobenzyl)-1H-pyrimidine-2,4-dione was prepared by a method similar to that described in example 11 (method 2) except that cyclopropylmethyl bromide was used in place of butyl iodide.]

Example 76

3-Cyclopropylmethyl-1-(2-fluorobenzyl)-8-[4-(4-(S)-hydroxymethyl-2,5-dioxo-imidazolidin-1-yl)-benzyl]-3,7-dihydro-purine-2,6-dione

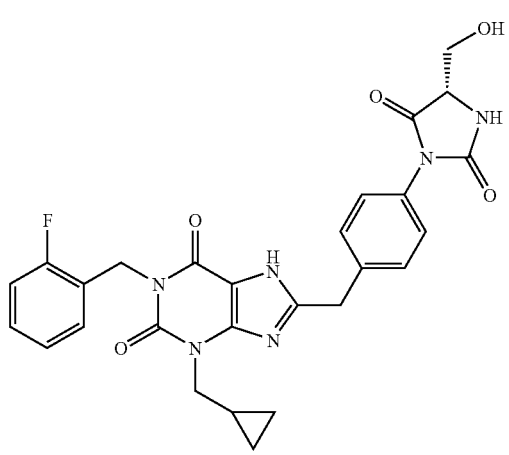

8-[4-(4-tert-Butoxymethyl-2,5-dioxo-imidazolidin-1-yl)-benzyl]-3-cyclopropylmethyl-1-(2-fluorobenzyl)-3,7-dihydro-purine-2,6-dione was treated with trifluoroacetic acid (2 mL). After stirring at room temperature for 2 h, the reaction was concentrated and the residue was purified by reverse phase HPLC. LCMS, m/z(M+H)=533.12.

Example 77

N-{3-Acetylamino-4-[3-butyl-1-(2-fluorobenzyl)-2,6-dioxo-2,3,6,7-tetrahydro-1H-8-ylmethyl]-phenyl}-acetamide

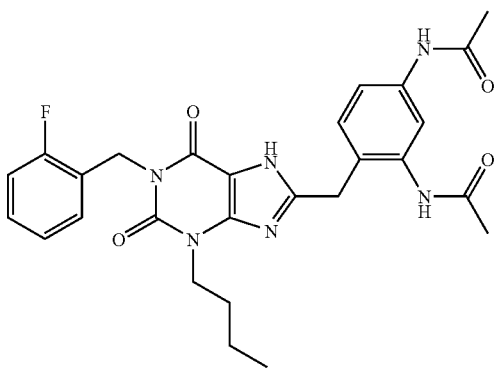

This compound was prepared by a method similar to that described in example 11 except that (2,4-bis-acetylamino-phenyl)-acetic acid was used in place of 4-acetylamino-phenylacetic acid. MS, m/z(M+H)=521.2307.

[(2,4-Bis-acetylamino-phenyl)-acetic acid was prepared from 2,4-dinitrophenylacetic acid by nitro group reduction with 10 equivalents of zinc dust (<10 μm particle size) and 15 equivalents of ammonium chloride in 2:1 methanol/water, followed by acetylation with acetic anhydride in 20:1 acetonitrile/water.]

Example 78

N-{5-Amino-2-[3-butyl-1-(2-fluorobenzyl)-2,6-dioxo-2,3,6,7-tetrahydro-1H-purin-8-ylmethyl]-phenyl}-acetamide

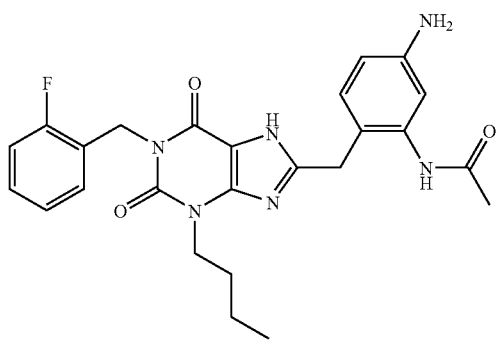

Prepared from N-{3-acetylamino-4-[3-butyl-1-(2-fluorobenzyl)-2,6-dioxo-2,3,6,7-tetrahydro-1H-purin-8-ylmethyl]-phenyl}-acetamide by refluxing with 20% aqueous potassium hydroxide. The product was purified by chromatography using silica eluted with 92:8 chloroform/methanol. MS, m/z(M+)=478.2132.

Example 79

6-Acetylamino-pyridine-2-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

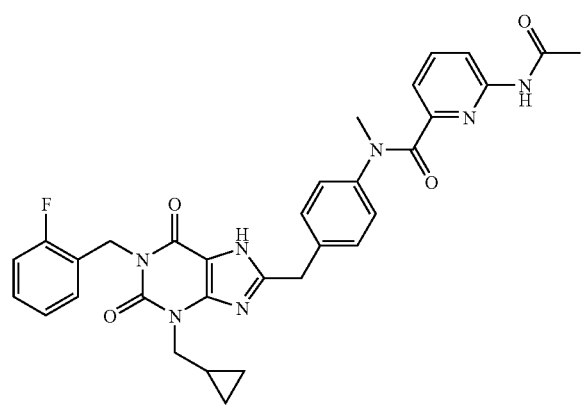

This compound was prepared according to the procedure outlined in scheme 13.

Step 1: Preparation of 3-cyclopropylmethyl-8-[4-(methylamino)-benzyl]-1-(2-fluorobenzyl)-3,7-dihydro-purine-2,6-dione.

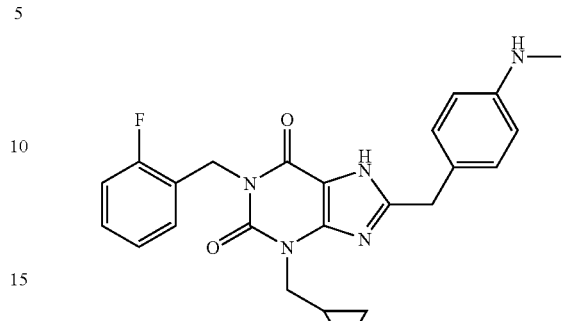

To a suspension of 10% palladium on carbon (0.50 g) in tetrahydrofuran (tetrahydrofuran) (500 mL) was added 3-cyclopropylmethyl-8-[4-aminobenzyl]-1-(2-fluorobenzyl)-3,7-dihydro-purine-2,6-dione (prepared as described in example 63) (2.10 g, 5.00 mmol) and 37% aqueous formaldehyde solution (237 μL, 8.5 mmol).

The mixture was shaken under an atmosphere of hydrogen at 1 atmosphere pressure and ambient temperature for 63 hours. The catalyst was removed by filtration through celite, washing the filter pad through with tetrahydrofuran and methanol. The combined filtrate was concentrated in vacuo and the residue purified by chromatography using silica eluted with 1:2 hexanes/ethyl acetate. Concentration of the appropriate fractions gave the product as a colorless solid (1.40 g, 65%). MS, m/z(M+H)=434.

Step 2: Preparation of 6-acetylamino-pyridine-2-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide.

N-Acetyl-6-amino-pyridine-2-carboxylic acid (12.4 mg, 0.069 mmol) was placed in a flask and dry dichloromethane (1 mL) was added. The resulting suspension was stirred in an ice-water bath and PPh₃ (18.5 mg, 0.071 mmol) was added followed by N-chlorosuccinimide (8.9 mg, 0.067 mmol). This mixture was stirred in the cooling bath for ½ h and then the cooling bath removed. After stirring at room temperature for 15 min, 3-cyclopropylmethyl-8-[4-(methylamino)-benzyl]-1-(2-fluorobenzyl)-3,7-dihydropurine-2,6-dione (57.7 mg, 0.131 mmol) was added. The reaction was then stirred at room temperature for 48 h. The solids were filtered off and washed with dichloromethane and the filtrate diluted with dichloromethane (20 mL) and washed once with saturated aqueous sodium bicarbonate, dried and concentrated to give 55.6 mg of a yellow foam. The product was purified by chromatography using silica gel eluted with 96:4 chloroform/methanol to give recovered starting material and the stated product (6.6 mg). MS, m/z(M+)=618.2237.

[N-Acetyl-6-amino-pyridine-2-carboxylic acid was prepared from 2-amino-6-methylpyridine by acetylation with acetic anhydride followed by oxidation with potassium permanganate.]

Example 80

[4-({4-[3-Cyclopropyl-1-(2-fluorobenzyl)-2,6-dioxo-2,3,6,7-tetrahydro-1H-purin-8-ylmethyl]-phenyl}-methyl-carbamoyl)-benzyl]-carbamic acid benzyl ester

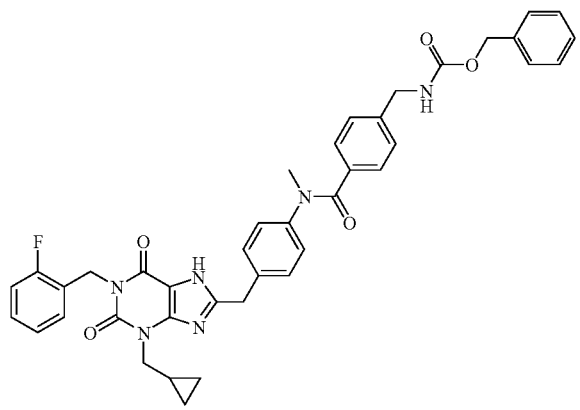

This compound was prepared by a method similar to that described in example 79 except that N-carbobenzyloxycarbonyl-4-aminomethylbenzoic acid was used in place of N-acetyl-6-amino-2-pyridine carboxylic acid, 0.62 equivalents of 3-cyclopropylmethyl-8-[4-(methylamino)-benzyl]-1-(2-fluorobenzyl)-3,7-dihydropurine-2,6-dione, and 0.68 equivalents of 4-dimethylaminopyridine added as the final reagent. The product was purified by chromatography using silica gel eluted with 95:5 chloroform/methanol followed by crystallization from acetonitrile. MS, observe m/z(M+H)= 701.3 and m/z(M–H)=699.4.

[N-Carbobenzyloxycarbonyl-4-aminomethylbenzoic acid was prepared from 4-aminomethylbenzoic acid (Aldrich) according to the general procedure of M. Bergmann et al. as reported in *Ber.* 1932, 65, 1192.]

Example 81

4-Aminomethyl-N-{4-[3-cyclopropylmethyl-1-(2-fluorobenzyl)-2,6-dioxo-2,3,6,7-tetrahydro-1H-purin-8-ylmethyl]-phenyl}-N-methyl-benzamide; compound with trifluoro-acetic acid

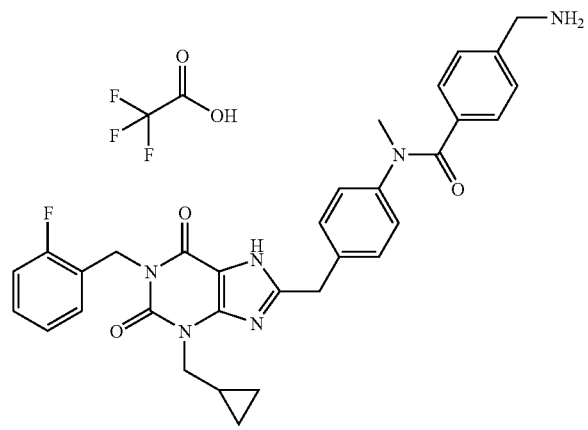

This compound was prepared by hydrogenolysis of [4-({4-[3-cyclopropyl-1-(2-fluorobenzyl)-2,6-dioxo-2,3,6,7-tetrahydro-1H-purin-8-ylmethyl]-phenyl}-methyl-carbamoyl)-benzyl]-carbamic acid benzyl ester using 10% palladium on carbon in absolute ethanol under 53 psi of hydrogen. Two products were isolated by reverse phase HPLC. The first product eluted was 4-aminomethyl-N-{4-[3-cyclopropylmethyl-1-(2-fluorobenzyl)-2,6-dioxo-2,3,6,7-tetrahydro-1H-purin-8-ylmethyl]phenyl}-N-methylbenzamide which was isolated as the trifluoroacetic acid salt. MS, m/z(M+H)=567.3.

Example 82

4-Aminomethyl-N-{4-[3-cyclopropylmethyl-1-(2-fluorobenzyl)-2,6-dioxo-2,3,6,7-tetrahydro-1H-purin-8-ylmethyl]phenyl-4-ethylaminomethyl-N-methylbenzamide; compound with trifluoro-acetic acid

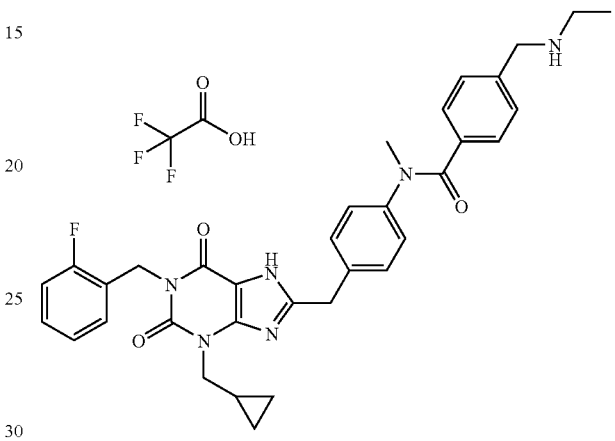

This compound was prepared as described in example 81. Two products were isolated by reverse phase HPLC. The second product eluted was 4-aminomethyl-N-{4-[3-cyclopropylmethyl-1-(2-fluorobenzyl)-2,6-dioxo-2,3,6,7-tetrahydro-1H-purin-8-ylmethyl]phenyl-4-ethylaminomethyl-N-methylbenzamide which was isolated as the trifluoroacetic acid salt. MS, m/z(M+H)=595.3.

Example 83

[({4-[3-Cyclopropylmethyl-1-(2-fluorobenzyl)-2,6-dioxo-2,3,6,7-tetrahydro-1H-purin-8-ylmethyl]phenyl}-methyl-carbamoyl)-phenyl-methyl]-carbamic acid benzyl ester

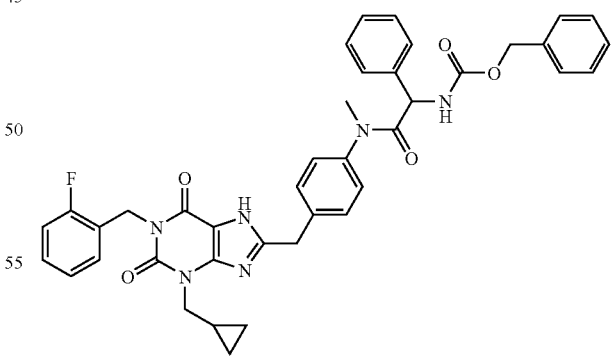

This compound was prepared by a method similar to that described in example 79 except that commercially available N-carbobenzyloxycarbonyl-D,L-phenylglycine was used in place of N-acetyl-6-amino-2-pyridine carboxylic. The reaction performed with only 0.67 equivalents of 3-cyclopropylmethyl-8-[4-(methylamino)-benzyl]-1-(2-fluorobenzyl)-3,7-dihydropurine-2,6-dione and with 0.74 equivalents of 4-dimethylaminopyridine added as the final reagent. The product was purified by chromatography using silica gel eluted with 97:3 chloroform/methanol. MS, m/z(M+H)=701.4.

Example 84

2-Amino-N-{4-[3-cyclopropylmethyl-1-(2-fluorobenzyl)-2,6-dioxo-2,3,6,7-tetrahydro-1H-purin-8-ylmethyl]-phenyl}-N-methyl-2-phenyl-acetamide

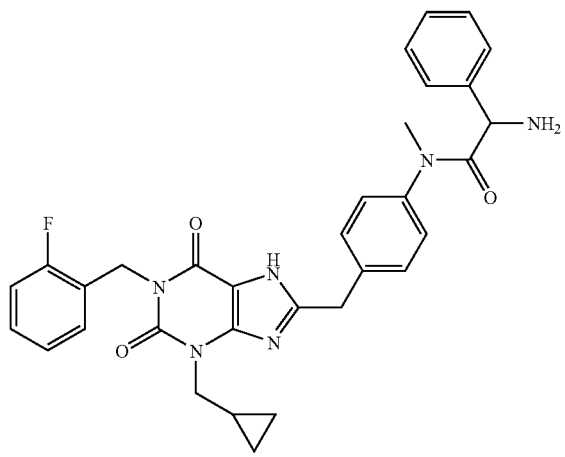

This compound was prepared by a method similar to that described in example 81 except that [({4-[3-cyclopropylmethyl-1-(2-fluorobenzyl)-2,6-dioxo-2,3,6,7-tetrahydro-1H-purin-8-ylmethyl]phenyl}-methyl-carbamoyl)-phenyl-methyl]-carbamic acid benzyl ester was used in place of [4-({4-[3-cyclopropyl-1-(2-fluorobenzyl)-2,6-dioxo-2,3,6,7-tetrahydro-1H-purin-8-ylmethyl]-phenyl}-methyl-carbamoyl)-benzyl]-carbamic acid benzyl ester. The product was purified by chromatography using silica gel eluted with 92:8 chloroform/methanol. MS, m/z(M+)=567.2496.

Example 85

N-{4-[3-cyclopropylmethyl-1-(2-fluorobenzyl)-2,6-dioxo-2,3,6,7-tetrahydro-1H-purin-8-ylmethyl]-phenyl}-5,N-dimethyl-nicotinamide

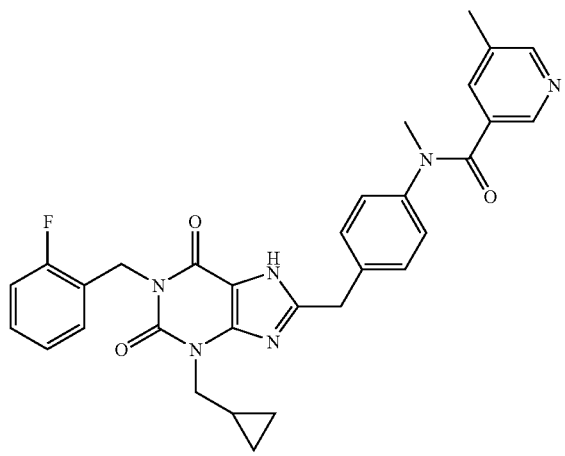

This compound was prepared by a method similar to that described in example 79 except that 5-methylnicotinic acid (Lancaster) was used in place of N-acetyl-6-amino-2-pyridine carboxylic acid and 2 equivalents of 3-cyclopropylmethyl-8-[4-(methylamino)-benzyl]-1-(2-fluorobenzyl)-3,7-dihydropurine-2,6-dione were used. The product was purified by chromatography using silica gel eluted with 96:4 chloroform/methanol. MS, m/z(M+)=553.2365.

Example 86

N-{4-[3-cyclopropylmethyl-1-(2-fluorobenzyl)-2,6-dioxo-2,3,6,7-tetrahydro-1H-purin-8-ylmethyl]-phenyl}-6,N-dimethyl-nicotinamide

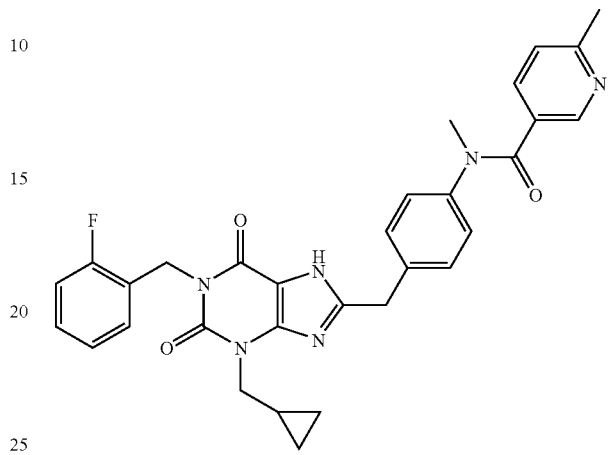

This compound was prepared by a method similar to that described in example 79 except that commercially available 6-methylnicotinic acid was used in place of N-acetyl-6-amino-2-pyridine carboxylic acid, the reaction was performed using 0.54 equivalents of 3-cyclopropylmethyl-8-[4-(methylamino)-benzyl]-1-(2-fluorobenzyl)-3,7-dihydropurine-2,6-dione and 1.2 equivalents of triethylamine were added as the final reagent to the reaction mixture. The product was purified by chromatography using silica gel eluted with 95:5 chloroform/methanol followed by crystallization from acetonitrile. MS, m/z(M+)=553.2365.

Example 87

N-{4-[3-Butyl-1-(2-fluorobenzyl)-2,6-dioxo-2,3,6,7-tetrahydro-1H-purin-8-ylmethyl]-phenyl}-6,N-dimethyl-nicotinamide

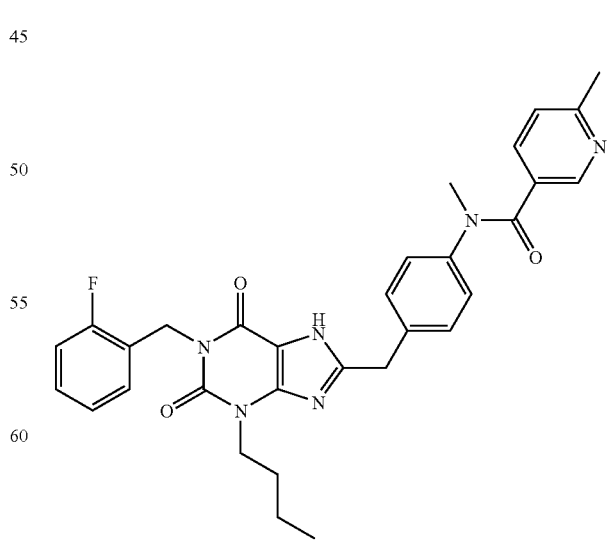

This compound was prepared by the methods outlined in schemes 4 and 13.

Step 1: Preparation of 8-(4-amino-benzyl)-3-butyl-1-(2-fluorobenzyl)-3,7-dihydro-purine-2,6-dione.

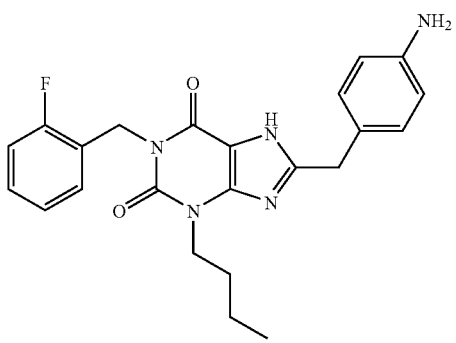

This compound was prepared by a method similar to that described in example 11 (method 1) except that [4-(2,2,2-trifluoro-acetylamino)-phenyl]-acetic acid (prepared by the method of K. D. Janda et al, as described in *J. Amer. Chem. Soc.* 1991, 113, 291) was used in place of (4-acetylamino-phenyl)-acetic acid. A mixture of products arising from mono-alkylation at the 1 position of the 1H-pyrimidine-2,4-dione and bis-alkylation at both the 1 position of the 1H-pyrimidine-2,4-dione and acetanilide nitrogen were obtained. When this mixture of compounds was directly subjected to the conditions used to effect cyclization to the xanthine the trifluoroacetyl groups were removed by hydrolysis. A 2:1 mixture of 8-(amino-benzyl)-3-butyl-1-(2-fluorobenzyl)-3,7-dihydro-purine-2,6-dione and 3-butyl-8-(4-butylamino-benzyl)-1-(2-fluorobenzyl)-3,7-dihydro-purine-2,6-dione was obtained which was separated by chromatography using silica gel eluted with 96:4 chloroform/methanol. MS, m/z(M+)=421.1914.

Step 2: Preparation of 3-butyl-8-[4-(methylamino)-benzyl]-1-(2-fluorobenzyl)-3,7-dihydropurine-2,6-dione.

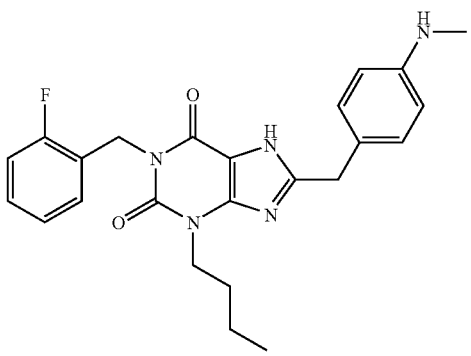

This compound was prepared by a method similar to that described in example 79 (step 1) except that 3-butyl-8-[4-aminobenzyl]-1-(2-fluorobenzyl)-3,7-dihydro-purine-2,6-dione was used in place of 3-cyclopropylmethyl-8-[4-aminobenzyl]-1-(2-fluorobenzyl)-3,7-dihydro-purine-2,6-dione. The mono-methyl product was separated from the bulk of the di-methyl byproduct by chromatography using silica gel eluted with 98:2 chloroform/methanol. This material was used without further purification.

Step 3: Preparation of N-{4-[3-butyl-1-(2-fluorobenzyl)-2,6-dioxo-2,3,6,7-tetrahydro-1H-purin-8-ylmethyl]-phenyl}-6,N-dimethyl-nicotinamide This compound was prepared by a method similar to that described in example 86 except that 3-butyl-8-[4-(methyl-amino)-benzyl]-1-(2-fluorobenzyl)-3,7-dihydro-purine-2,6-dione was used in place of 3-cyclopropylmethyl-8-[4-(methyl-amino)-benzyl]-1-(2-fluorobenzyl)-3,7-dihydro-purine-2,6-dione and excess triethylamine and a catalytic amount of 4-dimethylaminopyridine were added as the final reagents to the reaction mixture. The product was purified by chromatography using silica gel eluted with 4:1 ethyl acetate/hexanes. MS, m/z(M+)=553.3.

Example 88

N-{4-[3-Cyclobutylmethyl-1-(2-fluorobenzyl)-2,6-dioxo-2,3,6,7-tetrahydro-1H-purin-8-ylmethyl]-phenyl}-6,N-dimethyl-nicotinamide

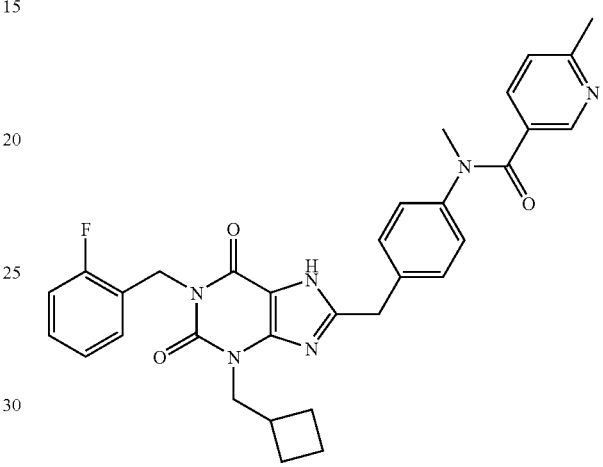

This compound was prepared by the methods outlined in schemes 4 and 13.

Step 1: Preparation of 8-(4-amino-benzyl)-3-cyclobutylmethyl-1-(2-fluorobenzyl)-3,7-dihydro-purine-2,6-dione

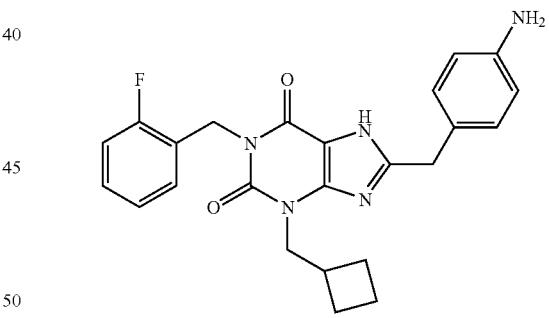

This compound was prepared by a method similar to that described in example 87 (step 1) except that cyclobutylmethyl bromide (Aldrich) was used in place of butyl bromide. A mixture of products arising from mono-alkylation at the 1 position of the 1H-pyrimidine-2,4-dione and bis-alkylation at both the 1 position of the 1H-pyrimidine-2,4-dione and acetanilide nitrogen were obtained. When this mixture of compounds was directly subjected to the conditions used to effect cyclization to the xanthine the trifluoroacetyl groups were removed by hydrolysis. A 4:1 mixture of 8-(4-amino-benzyl)-3-cyclobutylmethyl-1-(2-fluorobenzyl)-3,7-dihydro-purine-2,6-dione and 3-cyclobutylmethyl-8-[4-(cyclobutylmethyl-amino)-benzyl]-1-(2-fluorobenzyl)-3,7-dihydro-purine-2,6-dione was obtained which was separated by chromatography using silica gel eluted with 5:2 ethyl acetate/hexanes. MS, m/z(M+)=434.1990.

Step 2: Preparation of 3-cyclobutylmethyl-1-(2-fluorobenzyl)-8-(4-methylamino-benzyl)-3,7-dihydro-purine-2,6-dione

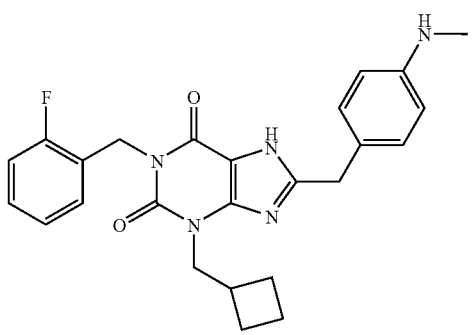

This compound was prepared by a method similar to that described in example 87 (step 2) except that 8-(4-amino-benzyl)-3-cyclobutylmethyl-1-(2-fluorobenzyl)-3,7-dihydro-purine-2,6-dione was used in place of 3-butyl-8-[4-aminobenzyl]-1-(2-fluorobenzyl)-3,7-dihydro-purine-2,6-dione. The mono-methyl product was separated from the bulk of the di-methyl byproduct by chromatography using silica gel eluted with 98:2 chloroform/methanol. This material was used without further purification. $^1$H NMR (DMSO-$d_6$) $\delta_H$ 1.70–1.91 (m, 6H), 2.61 (d, 3H), 2.73 (m, 1H), 3.86 (s, 2H), 4.01 (d, 2H), 5.09 (s, 2H), 5.49 (q, 1H ex), 6.45 (d, 2H), 7.01 (d, 2H), 6.95–7.29 (m, 4H), 13.33 (s, 1H ex).

Step 3: Preparation of N-{4-[3-cyclobutylmethyl-1-(2-fluorobenzyl)-2,6-dioxo-2,3,6,7-tetrahydro-1H-purin-8-ylmethyl]-phenyl}-6,N-dimethyl-nicotinamide This compound was prepared by a method similar to that described in example 86 except that 3-cyclobutylmethyl-1-(2-fluorobenzyl)-8-(4-methylamino-benzyl)-3,7-dihydro-purine-2,6-dione was used in place of 3-cyclopropylmethyl-8-[4-(methyl-amino)-benzyl]-1-(2-fluorobenzyl)-3,7-dihydro-purine-2,6-dione and excess triethylamine and a catalytic amount of 4-dimethylaminopyridine were added as the final reagents to the reaction mixture. The product was purified by chromatography using silica gel eluted with 96:4 chloroform/methanol. MS, m/z(M+)=567.2511.

Example 89

2-Acetamino-N-{4-[3-cyclopropylmethyl-1-(2-fluorobenzyl)-2,6-dioxo-2,3,6,7-tetrahydro-1H-purin-8-ylmethyl]-phenyl}-4,6,N-trimethyl-nicotinamide

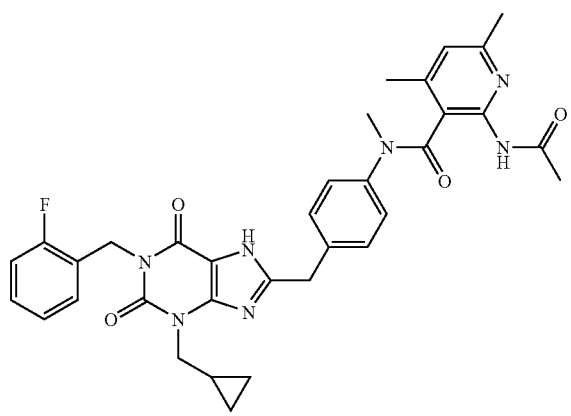

This compound was prepared by a method similar to that described in example 79 except that 2-acetylamino-4,6-dimethylnicotinic acid was used in place of N-acetyl-6-amino-2-pyridine carboxylic acid, the reaction was performed using 1 equivalent of 3-cyclopropylmethyl-8-[4-(methylamino)-benzyl]-1-(2-fluorobenzyl)-3,7-dihydropurine-2,6-dione and excess triethyl amine and a catalytic amount of 4-dimethylaminopyridine were added as the final reagents to the reaction mixture. The product was purified by chromatography using silica gel eluted with 93:7 chloroform/methanol. MS, m/z(M+)=624.4 and m/z(M−)= 622.5.

[2-Acetylamino-4,6-dimethylnicotinic acid was prepared from 2-amino-4,6-dimethyl-nicotinic acid; hydrochloride (Acros) by treatment with 2 equivalents of acetic anhydride and 24 equivalents of sodium carbonate in acetonitrile containing a small amount of water at 0° C. for 2 hours. The product was partitioned between ethyl acetate and water, the ethyl acetate extract washed with 0.1 M aqueous hydrochloric acid, brine, dried and concentrated in vacuo to a colorless solid which was used without further purification.]

Example 90

N-{4-[3-cyclopropylmethyl-1-(2-fluorobenzyl)-2,6-dioxo-2,3,6,7-tetrahydro-1H-purin-8-ylmethyl]-phenyl}-2,6-dimethoxy-N-methyl-nicotinamide

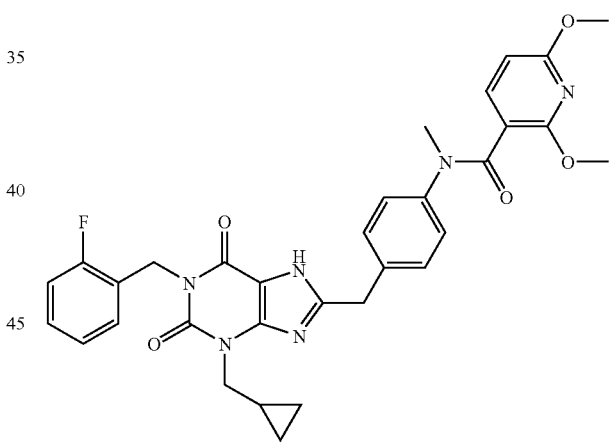

This compound was prepared by a method similar to that described in example 79 except that 2,6-dimethoxynicotinic acid (Aldrich) was used in place of N-acetyl-6-amino-2-pyridine carboxylic acid, the reaction was performed using 1 equivalent of 3-cyclopropylmethyl-8-[4-(methylamino)-benzyl]-1-(2-fluorobenzyl)-3,7-dihydropurine-2,6-dione and excess triethylamine and a catalytic amount of 4-dimethylaminopyridine were added as the final reagents to the reaction mixture. The product was purified by chromatography using silica gel eluted with 9:1 ethyl acetate/hexanes followed by crystallization from acetonitrile. MS, m/z(M+)= 599.2417.

Example 91

N-{4-[3-cyclopropylmethyl-1-(2-fluorobenzyl)-2,6-dioxo-2,3,6,7-tetrahydro-1H-purin-8-ylmethyl]-phenyl}-N-methyl-2-pyridin-3-yl-acetamide

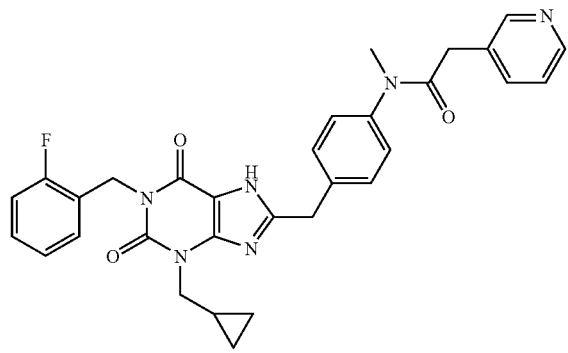

This compound was prepared by a method similar to that described in example 79 except that commercially available 3-pyridylacetic acid was used in place of N-acetyl-6-amino-2-pyridine carboxylic acid, the reaction was performed using 0.69 equivalents of 3-cyclopropylmethyl-8-[4-(methylamino)-benzyl]-1-(2-fluorobenzyl)-3,7-dihydropurine-2,6-dione and 0.78 equivalents of triethylamine was added as the final reagent to the reaction mixture. The product was purified by chromatography using silica gel eluted with 93:7 chloroform/methanol followed by crystallization from acetonitrile. MS, m/z(M+)=553.2364.

Example 92

6-Cyano-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide

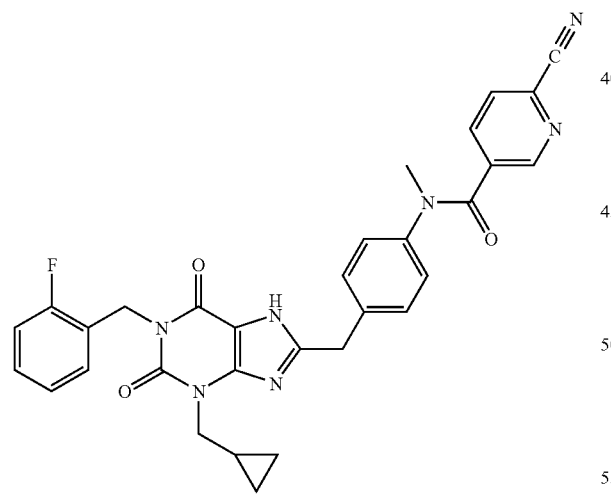

This compound was prepared by a method similar to that described in example 79 except that 6-cyanonicotinic acid (Lancaster) was used in place of N-acetyl-6-amino-2-pyridine carboxylic acid, the reaction was performed using 0.66 equivalents of 3-cyclopropylmethyl-8-[4-(methylamino)-benzyl]-1-(2-fluorobenzyl)-3,7-dihydropurine-2,6-dione and 0.68 equivalents of 4-dimethylaminopyridine was added as the final reagent to the reaction mixture. The product was purified by chromatography using silica gel eluted with 5:95 hexanes/ethyl acetate followed by crystallization from acetonitrile. MS, m/z(M+)=564.2161.

Example 93

2-Amino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide

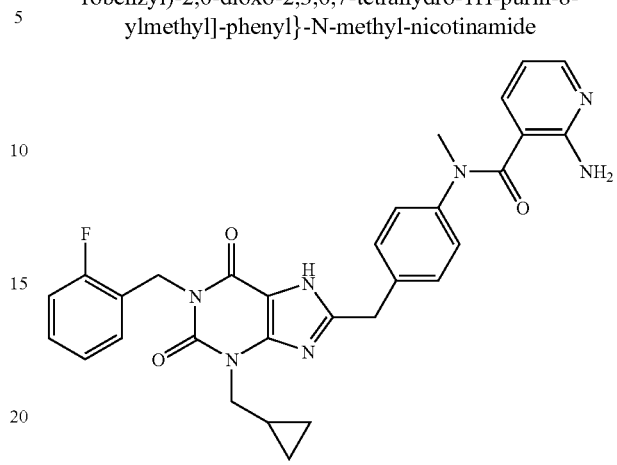

This compound was prepared by a method similar to that described example 79 except that 2-acetylamino-nicotinic acid was used in place of N-acetyl-6-amino-pyridine-2-carboxylic acid. None of the expected 2-acetylamino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide was obtained. The reaction mixture was purified by chromatography using silica eluted with 9:1 dichloromethane/methanol to give the stated product as a pale yellow solid following lyophilization from acetonitrile/water (4%). MS, m/z(M+H)=554.23 17.

[2-Acetylamino-nicotinic acid was prepared according to the procedure of A.

Stempel and L. H. Sternbach as described in U.S. Pat. No. 3,415,835.]

Example 94

6-Amino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide

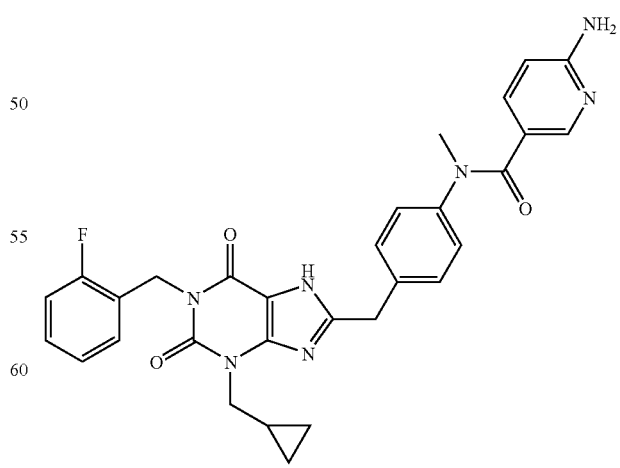

This compound was prepared by a method similar to that described in example 79 except that 6-tert-butoxycarbonylamino-nicotinic acid was used in place of N-acetyl-6-amino-2-pyridine carboxylic acid. After applying the standard work-up procedure the Boc-derivative was purified by chromatography using silica eluted with 98:2 ethyl acetate/methanol (95%). The Boc-derivative was heated to reflux in 4M hydrogen chloride in p-dioxane for 3 hrs under argon. The reaction mixture was then cooled to ambient temperature and concentrated to dryness in vacuo. The residue was neutralized with 0.1 M aqueous sodium hydroxide and extracted with ethyl acetate. The organic extracts were dried (sodium sulfate) and concentrated in vacuo. Purification by chromatography using silica eluted with 97:3 dichloromethane/methanol gave the product as a colorless solid (53%). MS, m/z(M+H)=554.2313.

[6-Tert-butoxycarbonylamino-nicotinic acid was prepared from 6-aminonicotinic acid (Acros) in 3 steps by (i) methyl ester formation with hydrogen chloride dissolved in methanol (66%), (ii) Boc-protection of the primary amine with Boc-anhydride and sodium hexamethyldisilazide according to the general procedure of T. A. Kelly et al. as described in *Tetrahedron Lett.* 1994, 35(48), 9003 (72%), and (iii) saponification of the methyl ester with 3M aqueous lithium hydroxide in tetrahydrofuran (86%).]

Example 95

N-{4-[3-Cyclopropylmethyl-1-(2-fluorobenzyl)-2,6-dioxo-2,3,6,7-tetrahydro-1H-purin-8-ylmethyl]-phenyl}-2,N-dimethyl-nicotinamide

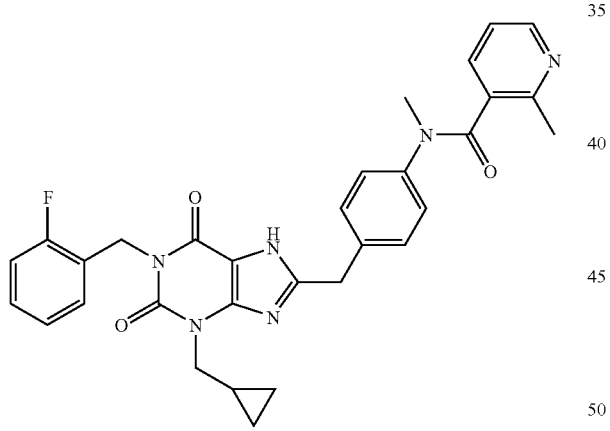

This compound was prepared by a method similar to that described in example 79 except that 2-methylnicotinic acid (Aldrich) was used in place of N-acetyl-6-amino-2-pyridine carboxylic acid, N-bromosuccinimide was used in place of N-chlorosuccinimide, the reaction was performed using 0.66 equivalents of 3-cyclopropylmethyl-8-[4-(methylamino)-benzyl]-1-(2-fluorobenzyl)-3,7-dihydropurine-2,6-dione and 1 equivalent of triethylamine was added as the final reagent to the reaction mixture. Purification was performed by chromatography using silica eluted with 95:5 ethyl acetate/methanol to give the product as a light brown solid (34%). MS, M+H)=553.2361.

Example 96

Pyrimidine-5-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

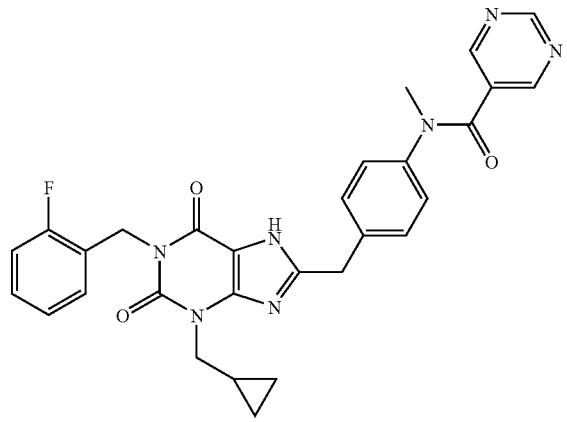

This compound was prepared by a method similar to that described in example 79 except that pyrimidine-5-carboxylic acid was used in place of N-acetyl-6-amino-2-pyridine carboxylic acid, the reaction was performed using 0.75 equivalents of 3-cyclopropylmethyl-8-[4-(methylamino)-benzyl]-1-(2-fluorobenzyl)-3,7-dihydropurine-2,6-dione and 1.5 equivalent of 4-dimethylaminopyridine was added as the final reagent to the reaction mixture. Purification was performed by chromatography using silica eluted with 94:6 ethyl acetate/methanol followed by trituration with hot acetonitrile to give the product as a colorless solid (72%). MS, m/z(M+H)=540.2161.

[Pyrimidine-5-carboxylic acid was prepared in 2 step from 5-bromopyrimidine (Aldrich) by (i) ethyl ester formation using bis(triphenylphosphine)palladium dichloride, triethylamine and carbon monoxide in absolute ethanol at 60 psi pressure and 85° C. for 17 hrs {similar procedure described for formation of the methyl ester by J. R. Young et al., *Bioorg. Med. Chem. Lett.* 2000, 10(15), 1723}, and (ii) saponification of the ethyl ester with 2 M aqueous lithium hydroxide in tetrahydrofuran.]

Example 97

N-{4-[3-Cyclopropylmethyl-1-(2-fluorobenzyl)-2,6-dioxo-2,3,6,7-tetrahydro-1H-purin-8-ylmethyl]-phenyl}-N-methyl-nicotinamide

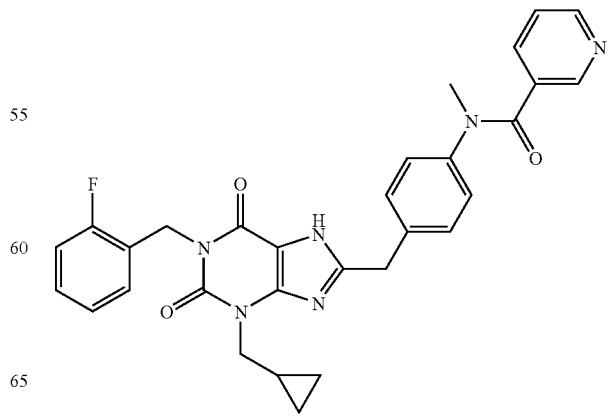

This compound was prepared by a method similar to that described in example 95 except that nicotinic acid (Aldrich) was used in place of 2-methylnicotinic acid. Purification by chromatography using silica eluted with 97:3 ethyl acetate/methanol gave the product as a light brown solid (79%). MS, m/z(M+H)=539.2199.

Example 98

6-Acetylamino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide

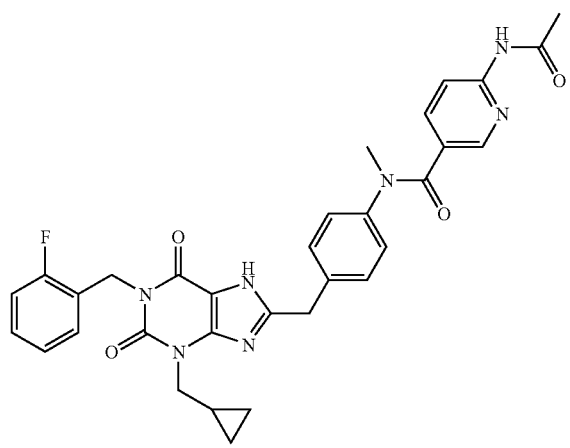

This compound was prepared by a method similar to that described in example 95 except that 6-acetylamino-nicotinic acid was used in place of 2-methylnicotinic acid and the reaction was performed using 1.2 equivalents of xanthine with 1.5 equivalents of triethylamine and a catalytic amount of 4-dimethylaminopyridine added as the final reagents to the reaction mixture. Purification by chromatography using silica eluted with 97:3 ethyl acetate/methanol gave the product as a colorless solid (70%). MS, m/z(M+H)=596.2423.

Example 99

Pyrazine-2-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

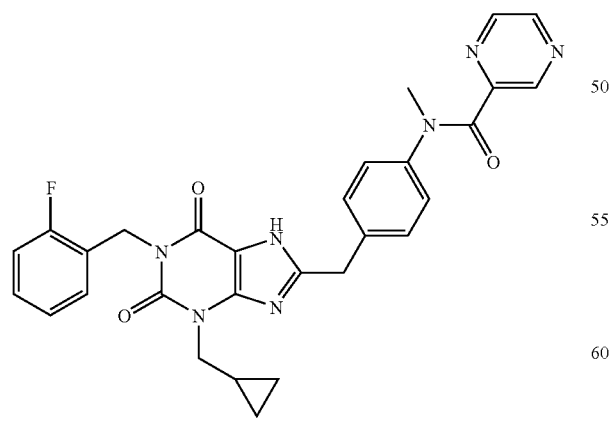

This compound was prepared by a method similar to that described in example 95 except that pyrazine-2-carboxylic acid (Aldrich) was used in place of 2-methylnicotinic acid and the reaction was performed using 1.2 equivalents of xanthine with 1.5 equivalents of triethylamine and a catalytic amount of 4-dimethylaminopyridine added as the final reagents to the reaction mixture. Purification by chromatography using silica eluted with 97:3 ethyl acetate/methanol gave the product as a colorless solid (83%). MS, m/z(M+Na)=562.1980.

Example 100

N-{4-[3-Cyclopropylmethyl-1-(2-fluorobenzyl)-2,6-dioxo-2,3,6,7-tetrahydro-1H-purin-8-ylmethyl]-phenyl}-6-hydroxy-N-methyl-nicotinamide

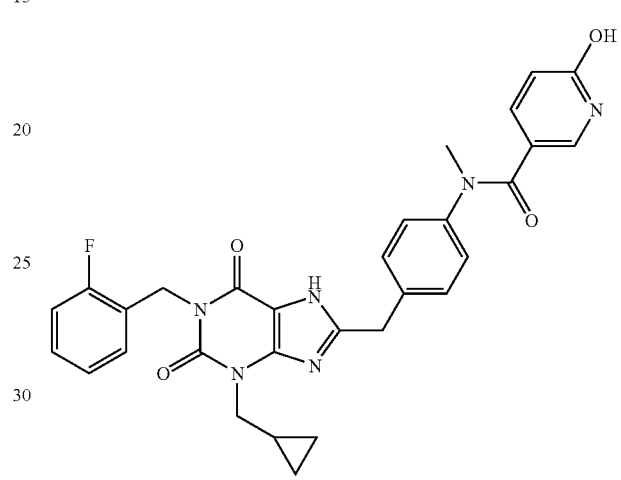

This compound was prepared by a method similar to that described in example 95 except that 6-hydroxynicotinic acid (Aldrich) was used in place of 2-methylnicotinic acid and N-bromosuccinimide was used in place of N-chlorosuccinimide. Purification by chromatography using silica eluted with 9:1 chloroform/methanol gave the product as a light green solid (23%). MS, m/z(M+H)=555.2155.

Example 101

N-{4-[3-Cyclopropylmethyl-1-(2-fluorobenzyl)-2,6-dioxo-2,3,6,7-tetrahydro-1H-purin-8-ylmethyl]-phenyl}-2-hydroxy-N-methyl-nicotinamide

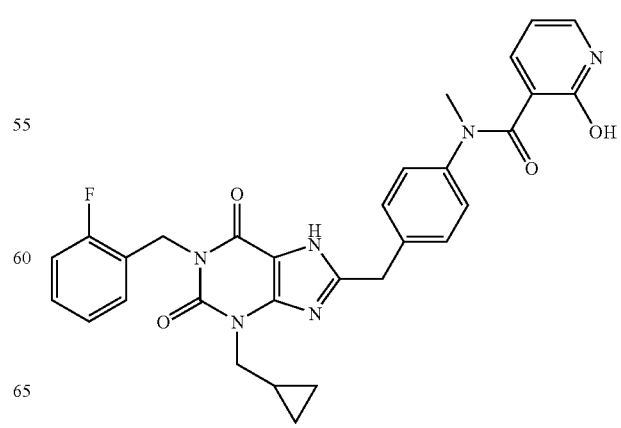

This compound was prepared by a method similar to that described in example 95 except that 2-hydroxynicotinic acid (Aldrich) was used in place of 2-methylnicotinic acid, N-bromosuccinimide was used in place of N-chlorosuccinimide and the reaction was performed using 0.67 equivalents of xanthine with 1 equivalent of triethylamine added as the final reagent to the reaction mixture. Purification by chromatography using silica eluted with 9:1 chloroform/methanol gave the product as an off white solid (51 %).

MS, m/z(M+H)=555.2158.

Example 102

1,3,5-Trimethyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

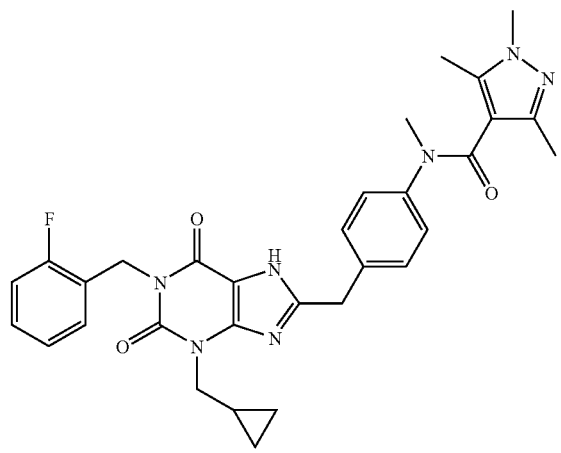

A mixture of 1,3,5-trimethyl-1H-pyrazole-4-carboxylic acid (71 mg, 0.46 mmol) in dichloromethane (2.5 mL) at 0° C. was treated with triphenylphosphine (145 mg, 0.55 mmol) and N-chlorosuccinimide (74 mg, 0.55 mmol). This mixture was stirred at 0° C. for 30 min and then was warmed to 25° C. for 10 min. At this time, the reaction was treated with a solution of 3-cyclopropylmethyl-1-(2-fluoro-benzyl)-8-(4-methylamino-benzyl)-3,7-dihydro-purine-2,6-dione (400 mg, 0.92 mmol) in dichloromethane (2.5 mL). The reaction was stirred at 25° C. for 24 h. At this time, the reaction was diluted with dichloromethane (50 mL) and then was washed with a saturated aqueous sodium bicarbonate solution (1×50 mL). The aqueous layer was re-extracted with dichloromethane (2×50 mL). The combined organics were dried over magnesium sulfate, filtered, and concentrated in vacuo. Flash chromatography (Merck Silica gel 60, 230–400 mesh, 3:97 methanol/dichloromethane) afforded impure product. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (50 mL) and was washed with a saturated aqueous sodium bicarbonate solution (50 mL). The water layer was re-extracted with dichloromethane (2×50 mL). The organic layers were combined and dried with magnesium sulfate, filtered and concentrated under reduced pressure. The resulting solid was dried in vacuo for 24 h to afford 1,3,5-trimethyl-1H-pyrazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (169 mg, 65%) as a white solid: (ES)$^+$-HRMS m/e calcd for $C_{31}H_{32}N_7O_3F$ (M+H)$^+$ 570.2623, found 570.2619.

Example 103

N-{4-[3-Cyclopropylmethyl-1-(2-fluorobenzyl)-2,6-dioxo-2,3,6,7-tetrahydro-1H-purin-8-ylmethyl]-phenyl}-N-methyl-2-oxo-2-(1,3,5-trimethyl-1H-pyrazol-4-yl)-acetamide

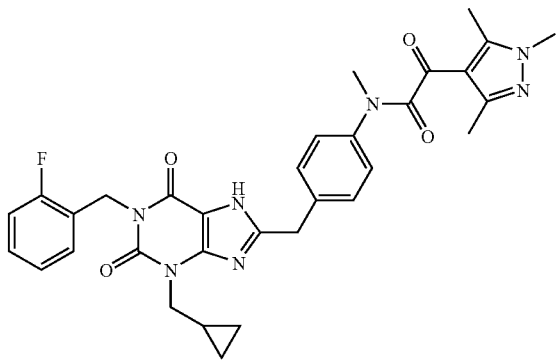

Step 1: Preparation of oxo-(1,3,5-trimethyl-1H-pyrazol-4-yl)-acetic acid

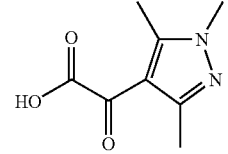

1,3,5-Trimethyl-1H-pyrazole (630 mg, 5.71 mmol) cooled to 0° C. was treated with oxalyl chloride (7.0 mL). The reaction was then warmed to 25° C. and then heated to reflux for 4 h. At this time, the reaction was cooled to 25° C. and was stirred at 25° C. for 24 h. At this time, the excess oxalyl chloride was removed by distillation. The resulting residue was cooled to 0° C. and treated with ice/water (15 mL). The mixture was slowly warmed to 25° C. over 4 h. At this time, the resulting solids were collected by filtration, washed with water, and dried in vacuo to afford oxo-(1,3,5-trimethyl-1H-pyrazol-4-yl)-acetic acid (700 mg, 70%) as brown solid: LR-MS for $C_8H_{10}N_2O_3$ (M–H)$^+$ at m/z=181.

Step 2: Preparation of N-{4-[3-cyclopropylmethyl-1-(2-fluoro-benzyl)-2,6-dioxo-2,3,6,7-tetrahydro-1H-purin-8-ylmethyl]-phenyl}-N-methyl-2-oxo-2-(1,3,5-trimethyl-1H-pyrazol-4-yl)-acetamide A mixture of oxo-(1,3,5-trimethyl-1H-pyrazol-4-yl)-acetic acid (134 mg, 0.87 mmol) in dichloromethane (4.0 mL) at 25° C. was treated with triphenylphosphine (145 mg, 0.55 mmol). The reaction was cooled to 0° C. and was treated with N-chlorosuccinimide (74 mg, 0.55 mmol). This mixture was stirred at 0° C. for 30 min and then was warmed to 25° C. for 20 min. At this time, the reaction was treated with 3-cyclopropylmethyl-1-(2-fluoro-benzyl)-8-(4-methylamino-benzyl)-3,7-dihydro-purine-2,6-dione (290 mg, 0.69 mmol) and triethylamine (0.23 mL, 1.67 mmol). The reaction was stirred at 25° C. for 24 h. At this time, the reaction was diluted with dichloromethane and then was washed with a 1N aqueous hydrochloric acid solution (2×50 mL) followed by a saturated aqueous sodium bicarbonate solution (2×50 mL). The organics were dried over magnesium sulfate, filtered, and concentrated in vacuo. Flash chromatography (Merck Silica gel 60, 230–400 mesh, 2:98 methanol/dichloromethane) afforded impure product. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (50 mL) and was washed with a saturated aqueous sodium bicarbonate solution (50 mL). The organics were dried over magnesium sulfate, filtered, and concentrated in vacuo. The resulting solid was dried in vacuo for 24 h to afford N-{4-[3-cyclopropylmethyl-1-(2-fluoro-benzyl)-2,6-dioxo-2,3,6,7-tetrahydro-1H-purin-8-ylmethyl]-phenyl}-N-methyl-2-oxo-2-(1,3,5-trimethyl-1H-pyrazol-4-yl)-acetamide (183 mg, 45.8%) as a white solid: (ES)$^+$-HRMS m/e calcd for $C_{32}H_{32}N_7O_4F$ (M+H)$^+$ 598.2573, found 598.2578.

Example 104

3-Chloro-1,5-dimethyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

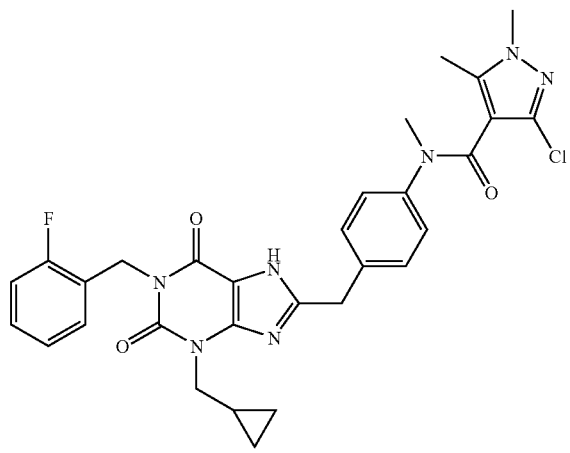

A mixture of 5-chloro-1,3-dimethyl-1H-pyrazole-4-carboxylic acid (40 mg, 0.231 mmol) in dichloromethane (2.0 mL) at 25° C. was treated with triphenylphosphine (72 mg, 0.28 mmol). The reaction was cooled to 0° C. and then was treated with N-chlorosuccinimide (37 mg, 0.28 mmol). This mixture was stirred at 0° C. for 5 min and then was warmed to 25° C. for 15 min. At this time, the reaction was treated with 3-cyclopropylmethyl-1-(2-fluoro-benzyl)-8-(4-methylamino-benzyl)-3,7-dihydro-purine-2,6-dione (100 mg, 0.23 mmol) and triethylamine (0.04 mL, 0.28 mmol). This mixture was stirred at 25° C. for 24 h. At this time, the reaction was diluted with dichloromethane (50 mL) and then was washed with a 1N aqueous hydrochloric acid solution (1×50 mL) and a saturated aqueous sodium bicarbonate solution (1×50 mL). The organics were dried over magnesium sulfate, filtered, and concentrated in vacuo. Flash chromatography (Merck Silica gel 60, 230–400 mesh, 1:99 methanol/dichloromethane) afforded 5-chloro-1,3-dimethyl-1H-pyrazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (54 mg, 48%) as a white solid: LR-MS for $C_{30}H_{29}ClFN_7O_3$ (M+H)$^+$ at m/z=590.

Example 105

2,4-Dimethyl-thiazole-5-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

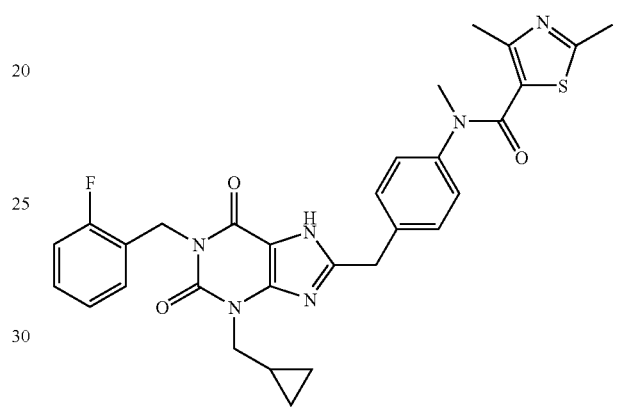

A mixture of 2,4-dimethyl-thiazole-5-carboxylic acid (18.1 mg, 0.11 mmol) in dichloromethane (3.0 mL) at 25° C. was treated with triphenylphosphine (33 mg, 0.13 mmol). The reaction was cooled to 0° C. and was treated with N-chlorosuccinimide (19.9 mg, 0.15 mmol). This mixture was stirred at 0° C. for 20 min and then was warmed to 25° C. for 20 min. At this time, the reaction was treated with N-chlorosuccinimide (5.0 mg, 0.04 mmol) and 3-cyclopropylmethyl-1-(2-fluoro-benzyl)-8-(4-methylamino-benzyl)-3,7-dihydro-purine-2,6-dione (100 mg, 0.23 mmol) and was stirred at 25° C. for 2 d. At this time, the reaction was diluted with dichloromethane (100 mL) and then was washed with a saturated aqueous sodium bicarbonate solution (1×20 mL). The organics were dried over magnesium sulfate, filtered, and concentrated in vacuo. Flash chromatography (Merck Silica gel 60, 230–400 mesh, 5:95 methanol/dichloromethane) afforded impure product. The resulting residue was purified by HPLC (15–60% acetonitrile/water (0.075% trifluoroacetic acid in both solvents) over 40 min). Fractions with the desired product were combined and concentrated in vacuo. The resulting residue was diluted with chloroform (100 mL) and was washed with a saturated aqueous sodium bicarbonate solution (25 mL). The aqueous layer was re-extracted with chloroform (1×50 mL). The combined organics were dried over magnesium sulfate, filtered, and concentrated in vacuo. The resulting solid was dried in vacuo for 24 h to afford 2,4-dimethyl-thiazole-5-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (30.2 mg, 45.8%) as a white solid: EI-HRMS m/e calcd for $C_{30}H_{29}N_6O_3FS$ (M+H)$^+$ 573.2079, found 573.2083.

Example 106

2-Amino-4-methyl-thiazole-5-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

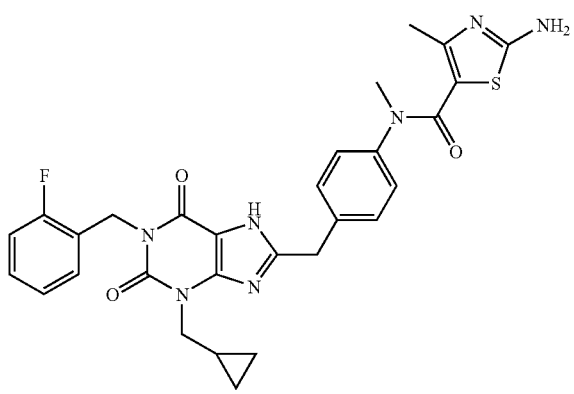

Step 1: Preparation of 4-methyl-2-(trityl-amino)-thiazole-5-carboxylic acid ethyl ester.

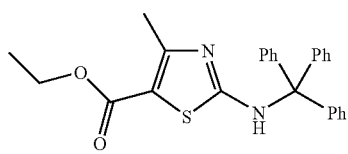

A mixture of 2-amino-4-methyl-thiazole-5-carboxylic acid ethyl ester (1.0 g, 5.4 mmol) in N,N-dimethylformamide at 25° C. was treated with triethylamine (1.89 mL, 13.5 mmol) and triphenylmethylchloride (1.66 g, 5.94 mmol). The reaction was stirred at 2° C. for 2 days. At this time, the reaction was concentrated in vauco. The residue was dissolved in dichloromethane (100 mL) and was washed with a 1N aqueous hydrochloric acid solution (1×20 mL), a saturated aqueous sodium bicarbonate solution (1×20 mL), and a saturated aqueous sodium chloride solution (1×20 mL). The organics were dried over magnesium sulfate, filtered, and concentrated in vacuo to afford 4-methyl-2-(trityl-amino)-thiazole-5-carboxylic acid ethyl ester (2.3 g, quant.). The product was used without further purification: LR-MS for $C_{26}H_{24}N_2O_2S$ (M–H)$^+$ at m/z=427.

Step 2: Preparation of 4-methyl-2-(trityl-amino)-thiazole-5-carboxylic acid.

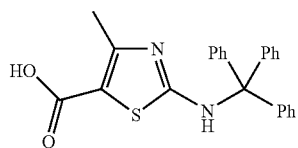

A mixture of 4-methyl-2-(trityl-amino)-thiazole-5-carboxylic acid ethyl ester (500 mg, 1.17 mmol) in ethanol (10 mL) at 25° C. was treated with a 1N aqueous sodium hydroxide solution (3.51 mL, 3.51 mmol). The resulting mixture was heated to 50° C. for 18 h. At this time, the reaction was treated with an additional amount of a 1N aqueous sodium hydroxide solution (3.6 mL, 3.6 mmol). This mixture was heated at 50° C. for an additional 8 days. At this time, the reaction was diluted with water (100 mL), acidified to pH=5, and treated with ethyl acetate. The resulting white solid was collected by filtration and dried in vacuo. The filtrate was extracted with ethyl acetate. The organics were dried over magnesium sulfate, filtered, and concentrated in vacuo to afford 4-methyl-2-(trityl-amino)-thiazole-5-carboxylic acid (55.7 mg, 11.9%) as a white solid: $^1$H NMR (DMSO-d$_6$, 300 MHz) δ9.09 (broad s, 1H), 7.22 (m, 15 H), 2.22 (s, 3H).

Step 3: Preparation of 4-methyl-2-(trityl-amino)-thiazole-5-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide

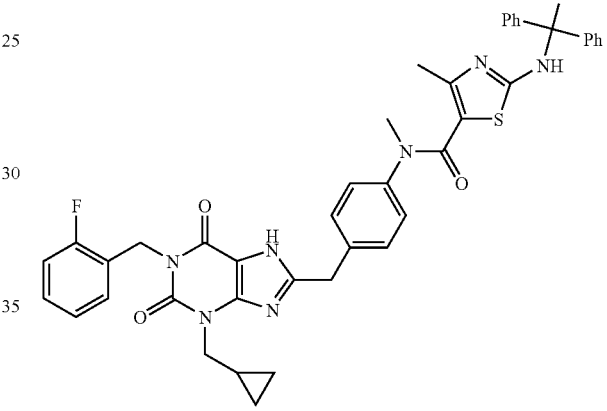

A mixture of 4-methyl-2-(trityl-amino)-thiazole-5-carboxylic acid (46 mg, 0.11 mmol) in dichloromethane (1.0 mL) at 25° C. was treated with triphenylphosphine (36 mg, 0.14 mmol). The reaction was cooled to 0° C. and was treated with N-chlorosuccinimide (18 mg, 0.14 mmol). This mixture was stirred at 0° C. for 30 min and then was warmed to 25° C. for 20 min. At this time, the reaction was treated with 3-cyclopropylmethyl-1-(2-fluoro-benzyl)-8-(4-methylamino-benzyl)-3,7-dihydro-purine-2,6-dione (100 mg, 0.23 mmol) and dichloromethane (2.5 mL). The reaction was stirred at 25° C. for 18 h. At this time, the reaction was treated with another portion of triphenylphosphine (36 mg, 0.14 mmol) and N-chlorosuccinimide (18 mg, 0.14 mmol). The reaction was stirred at 25° C. for 1 h. At this time, the reaction was diluted with dichloromethane (100 mL) and then washed with a saturated aqueous sodium bicarbonate solution (1×25 mL). The organics were dried over magnesium sulfate, filtered, and concentrated in vacuo. Flash chromatography (Merck Silica gel 60, 230–400 mesh, 80:20 ethyl acetate/petroleum ether) afforded 4-methyl-2-(tritylamino)-thiazole-5-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (75.1 mg, 80.0%). The product was used without further purification or characterization.

Step 4: Preparation of 2-amino-4-methyl-thiazole-5-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide.

A solution of 4-methyl-2-(trityl-amino)-thiazole-5-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (74.0 mg, 0.09 mmol) in dichloromethane (1.0 mL) at 25° C. was treated with trifluoroacetic acid (1.0 mL). The reaction was stirred at 25° C. for 1 h. At this time, the reaction was treated with triethylsilane (16 μL, 0.10 mmol). The reaction was concentrated in vacuo. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (100 mL) and was washed with a saturated aqueous sodium bicarbonate solution (25 mL). The aqueous layer was re-extracted with dichloromethane (1×50 mL). The combined organics were dried over magnesium sulfate, filtered, and concentrated in vacuo. The resulting solid was dried in vacuo for 24 h to afford 2-amino-4-methyl-thiazole-5-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (3.0 mg, 5.8%) as a white solid: (ES)$^+$-HRMS m/e calcd for $C_{29}H_{28}N_7O_3SF$ (M+H)$^+$ 574.2031, found 574.2035.

Example 107

1,3-Dimethyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

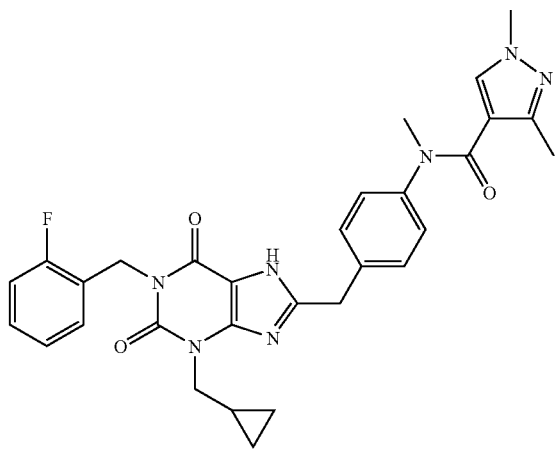

A mixture of 5-chloro-1,3-dimethyl-1H-pyrazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (81.5 mg, 0.14 mmol) (prepared as described in example 104), 10% palladium on carbon (313 mg), and sodium acetate (28.3 mg, 0.35 mmol) in dichloromethane (25 mL) and methanol (25 mL) was hydrogenated at 50 psi on a Parr apparatus for 8 days. At this time, the reaction was filtered through a pad of celite and washed with a 90/10 dichloromethane/methanol solution (100 mL). The filtrated was concentrated in vacuo. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (100 mL) and was washed with a saturated aqueous sodium bicarbonate solution (25 mL). The organics were dried over magnesium sulfate, filtered, and concentrated in vacuo. The resulting solid was dried in vacuo for 24 h to afford 1,3-dimethyl-1H-pyrazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (7.0 mg, 9.1%) as a white solid: $^1$H NMR (DMSO-$d_6$, 300 MHz) δ13.122 (broad s, 1H), 6.79 (m, 9H), 6.33 (s, 1H), 4.76 (s, 2H), 3.70 (s, 2H), 3.47 (d, J=6.96 Hz, 2H), 3.11 (s, 3H), 2.87 (s, 3H), 1.75 (s, 3H), 0.85 (broad s, 1H), 0.026 (m, 4H).

Example 108

4-Methyl-[1,2,3]thiadiazole-5-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

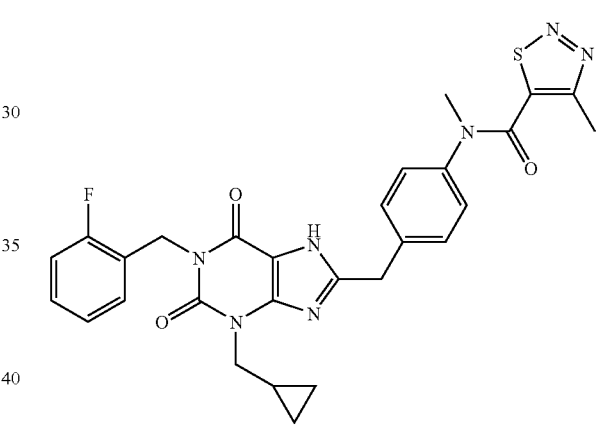

A mixture of 4-methyl-[1,2,3]thiadiazole-5-carboxylic acid (12 mg, 0.08 mmol) in dichloromethane (2.0 mL) cooled to 0° C. was treated with triphenylphosphine (27 mg, 0.10 mmol), and N-chlorosuccinimide (14 mg, 0.10 mmol). This mixture was stirred at 0° C. for 30 min and at 25° C. for 10 min. At this time, the reaction was treated with 3-cyclopropylmethyl-1-(2-fluoro-benzyl)-8-(4-methylamino-benzyl)-3,7-dihydro-purine-2,6-dione (75 mg, 0.17 mmol). The reaction was then stirred at 25° C. for 18 h. At this time, the reaction was diluted with dichloromethane. The organics were washed with a saturated aqueous sodium bicarbonate solution. This solution was extracted with a 90/10 dichloromethane/methanol solution. The organics were dried over magnesium sulfate, filtered, and concentrated in vacuo. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (100 mL) and was washed with a saturated aqueous sodium bicarbonate solution (25 mL). The aqueous layer was re-extracted with dichloromethane (1×50 mL). The combined organics were dried over magnesium sulfate, filtered, and concentrated in vacuo. The resulting solid was dried in vacuo for 24 h to afford 4-methyl-[1,2,3]thiadiazole-5-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (7.0 mg, 14.5%) as a white solid: $^1$H NMR (DMSO-$d_6$, 300 MHz) δ13.14 (broad s, 1H), 6.92–6.67 (m, 8H), 4.75 (s, 2H), 3.70 (s, 2H), 3.47 (d, J=7.32 Hz, 2H), 2.99 (s, 3H), 2.26 (s, 3H), 0.82 (m, 1H), 0.03 (m, 4H).

Example 109

3-Methyl-isoxazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

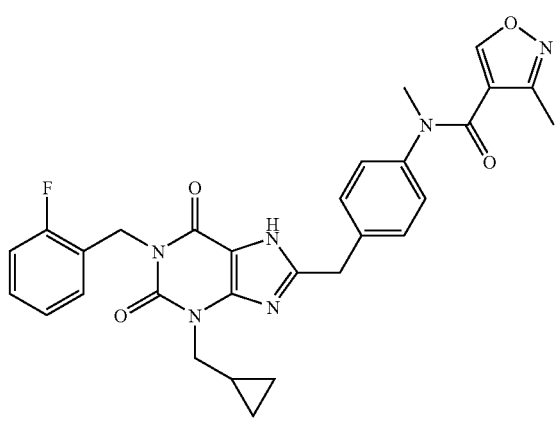

A mixture of 3-methyl-isoxazole-4-carboxylic acid (7.3 mg, 0.057 mmol) in dichloromethane (1.0 mL) cooled to 0° C. was treated with triphenylphosphine (17 mg, 0.063 mmol), and N-chlorosuccinimide (10 mg, 0.074 mmol). This mixture was stirred at 0° C. for 15 min and at 25° C. for 20 min. At this time, the reaction was treated with 3-cyclopropylmethyl-1-(2-fluoro-benzyl)-8-(4-methylamino-benzyl)-3,7-dihydro-purine-2,6-dione (50 mg, 0.11 mmol). The reaction was then stirred at 25° C. for 18 h. At this time, the reaction was diluted with dichloromethane (50 mL) and was washed with a saturated aqueous sodium bicarbonate solution (1×10 mL). The organics were dried over magnesium sulfate, filtered, and concentrated in vacuo. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (100 mL) and was washed with a saturated aqueous sodium bicarbonate solution (25 mL). The aqueous layer was re-extracted with dichloromethane (1×50 mL). The combined organics were dried over magnesium sulfate, filtered, and concentrated in vacuo. The resulting solid was dried in vacuo for 24 h to afford 3-methyl-isoxazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (6.8 mg, 21.8%) as an off-white solid: EI-HRMS m/e calcd for $C_{29}H_{27}N_6O_4$ (M$^+$) 542.2078, found 542.2077.

Example 110

3,5-Dimethyl-isoxazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

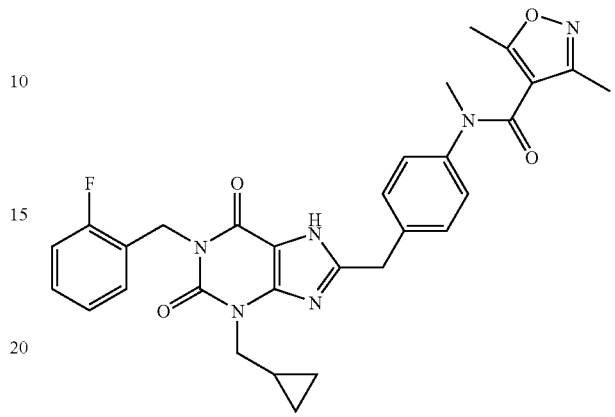

A mixture of 3,5-dimethyl-isoxazole-4-carboxylic acid (8.1 mg, 0.057 mmol) in dichloromethane (1.5 mL) cooled to 0° C. was treated with triphenylphosphine (17 mg, 0.063 mmol), and N-chlorosuccinimide (10 mg, 0.074 mmol). This mixture was stirred at 0° C. for 15 min and at 25° C. for 20 min. At this time, the reaction was treated with 3-cyclopropylmethyl-1-(2-fluoro-benzyl)-8-(4-methylamino-benzyl)-3,7-dihydro-purine-2,6-dione (50 mg, 0.11 mmol). The reaction was then stirred at 25° C. for 18 h. At this time, the reaction was diluted with dichloromethane (50 mL) and was washed with a saturated aqueous sodium bicarbonate solution (1×10 mL). The organics were dried over magnesium sulfate, filtered, and concentrated in vacuo. Flash chromatography (Merck Silica gel 60, 230–400 mesh, 2:98 methanol/dichloromethane) afforded 3,5-dimethyl-isoxazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (7.4 mg, 23.2%) as an off-white solid: EI-HRMS m/e calcd for $C_{30}H_{29}N_6O_4F$ (M$^+$) 556.2234, found 556.2229.

Example 111

[1,2,3]Thiadiazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

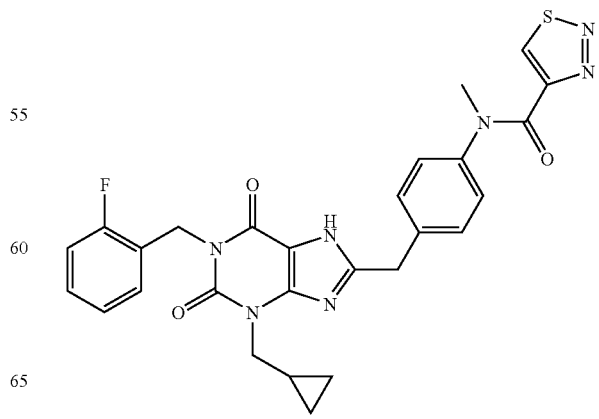

A mixture of [1,2,3]thiadiazole-4-carboxylic acid (29 mg, 0.30 mmol) in dichloromethane (6 mL) at 25° C. was treated with triphenylphosphine-polystyrene 100–200 mesh (372 mg, 0.46 mmol). This mixture was cooled to 0° C. and then treated with N-chlorosuccinimide (49 mg, 0.37 mmol). This mixture was stirred at 0° C. for 15 min and at 25° C. for 15 min. At this time, the reaction was treated with 3-cyclopropylmethyl-1-(2-fluoro-benzyl)-8-(4-methylamino-benzyl)-3,7-dihydro-purine-2,6-dione (55 mg, 0.12mmol) and triethylamine (96 µL, 0.69 mmol). The reaction was then stirred at 25° C. for 3 days. At this time, the reaction was filtered to remove solids and rinsed with dichloromethane. The filtrate was washed with a saturated aqueous sodium bicarbonate solution and a saturated aqueous sodium chloride solution. The organics were dried over magnesium sulfate, filtered, and concentrated in vacuo. Flash chromatography (Merck Silica gel 60, 230–400 mesh, 1:99 methanol/dichloromethane) afforded [1,2,3]thiadiazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (17 mg, 24.7%): LR-MS for $C_{27}H_{24}FN_7O_3S$ (M+H)$^+$ at m/z=546.

Example 112

1-Methyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

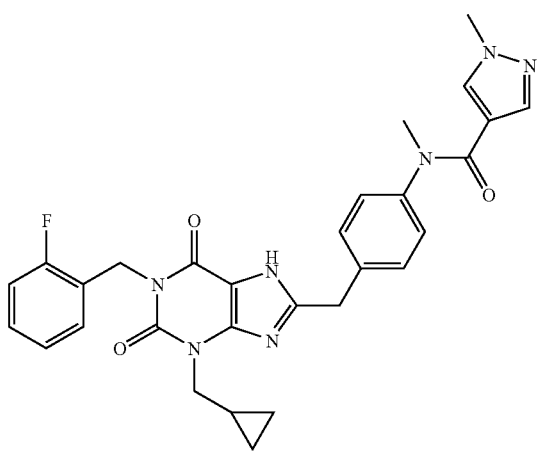

Step 1: Preparation of 1-methyl-1H-pyrazole-4-carboxylic acid ethyl ester

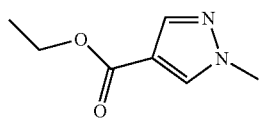

A mixture of sodium hydride (216 mg, 8.57 mmol) in tetrahydrofuran (10 mL) cooled to 0° C. was treated with a solution of 1H-pyrazole-4-carboxylic acid ethyl ester (1.0 g, 7.14 mmol) in tetrahydrofuran (10 mL). The reaction was warmed to 25° C. and was stirred at 25° C. for 45 min. At this time, the reaction was treated with methyl iodide (0.67 mL, 10.71 mmol). The reaction was then stirred at 25° C. for 18 h. At this time, the reaction was cooled to 0° C. and was quenched by the dropwise addition of a saturated aqueous ammonium chloride solution. This mixture was diluted with ethyl acetate (150 mL). The organics were washed with water (1×50 mL) and a saturated aqueous sodium chloride solution (1×50 mL), dried over magnesium sulfate, filtered, and concentrated in vacuo. Flash chromatography (Merck Silica gel 60, 230–400 mesh, 40:60 ethyl acetate/petroleum ether) afforded 1-methyl-1H-pyrazole-4-carboxylic acid ethyl ester (897 mg, 81.5%) as a clear oil: $^1$H NMR (DMSO-$d_6$, 300 MHz) δ8.27 (s, 1H), 7.80 (s, 1H), 4.18 (q, J=7.32 Hz, 2H), 3.85 (s, 3H), 1.24 (t, J =7.32 Hz, 3H).

Step 2: Preparation of 1-methyl-1H-pyrazole-4-carboxylic acid

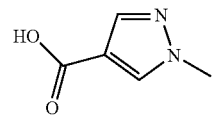

A solution of 1-methyl-1H-pyrazole-4-carboxylic acid ethyl ester (300 mg, 1.95 mmol) in ethanol cooled to 0° C. was treated with a 1N aqueous sodium hydroxide solution. The reaction was then warmed to 25° C. and was stirred at 25° C. for 18 h. At this time, the reaction was concentrated in vacuo and acidified to pH=2 with a 1N aqueous hydrochloric acid solution. This solution was extracted with ethyl acetate (3×50 mL). The organics were washed with a saturated aqueous sodium chloride solution, dried over magnesium sulfate, filtered, and dried in vacuo to afford 1-methyl-1H-pyrazole-4-carboxylic acid (193 mg, 78.5%) as a white solid: LR-MS for $C_5H_6N_2O_2$ (M–H)$^+$ at m/z=125.

Step 3: Preparation of 1-methyl-1H-pyrazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide A mixture of 1-methyl-1H-pyrazole-4-carboxylic acid (22 mg, 0.17 mmol) in dichloromethane (2.0 mL) at 25° C. was treated with triphenylphosphine (54 mg, 0.21 mmol). This mixture was cooled to 0° C. and then treated with N-chlorosuccinimide (28 mg, 0.21 mmol). This mixture was stirred at 0° C. for 30 min and then was warmed to 25° C. At this time, the reaction was treated with 3-cyclopropylmethyl-1-(2-fluoro-benzyl)-8-(4-methylamino-benzyl)-3,7-dihydro-purine-2,6-dione (150 mg, 0.34 mmol). The reaction was then stirred at 25° C. for 2 days. At this time, the reaction was diluted with dichloromethane and then was washed with a saturated aqueous sodium bicarbonate solution. The organics were dried over magnesium sulfate, filtered, and concentrated in vacuo. Flash chromatography (Merck Silica gel 60, 230–400 mesh, 3:97 methanol/dichloromethane) afforded 1-methyl-1H-pyrazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (87 mg, 92.8%) as an off-white solid: LR-MS for $C_{29}H_{28}FN_7O_3$ (M+H)$^+$ at m/z=542.

Example 113

4-Acetylamino-2-methyl-thiophene-3-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

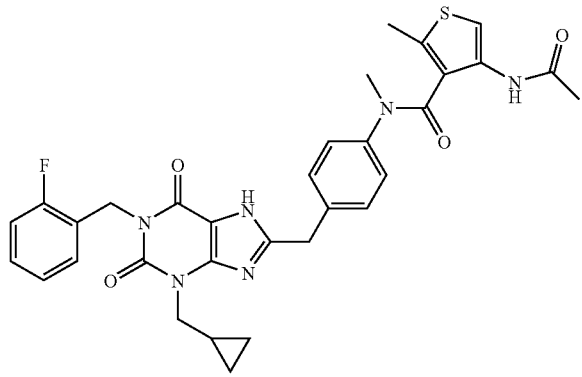

Step 1: Preparation of 4-acetylamino-2-methyl-thiophene-3-carboxylic acid

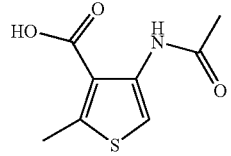

A mixture of 4-acetylamino-2-methyl-thiophene-3-carboxylic acid methyl ester (250 mg, 1.17 mmol) in methanol (4.0 mL) at 25° C. was treated with a 1N aqueous sodium hydroxide solution (3.5 mL, 3.51 mmol). The reaction was stirred at 25° C. for 28 h. At this time, the reaction was concentrated in vacuo, diluted with water (15 mL), and then acidified to pH=2 by the addition of a 1N aqueous hydrochloric acid solution. The resulting slurry was cooled to 0° C. The solid was collected by filtration, washed with water, and the dried in vacuo to afford 4-acetylamino-2-methyl-thiophene-3-carboxylic acid (212 mg, 90.9%) as a tan solid: LR-MS for $C_8H_9NO_3$ $(M-H)^+$ at m/z=198.

Step 2: Preparation of 4-acetylamino-2-methyl-thiophene-3-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide A mixture of 4-acetylamino-2-methyl-thiophene-3-carboxylic acid (45 mg, 0.17 mmol) in dichloromethane (3 mL) at 25° C. was treated with triphenylphosphine (71 mg, 0.22 mmol). This mixture was cooled to 0° C. and then was treated with N-chlorosuccinimide (36 mg, 0.22 mmol). This mixture was stirred at 0° C. for 15 min and then was warmed to 25° C. for 15 min. At this time, the reaction was treated with 3-cyclopropylmethyl-1-(2-fluoro-benzyl)-8-(4-methylamino-benzyl)-3,7-dihydro-purine-2,6-dione (75 mg, 0.17 mmol). This solution was then cooled to 0° C. and was treated with triethylamine (38 μL, 0.22 mmol). The reaction was warmed to 25° C. and was stirred at 25° C. for 18 h. At this time, the reaction was diluted with dichloromethane (100 mL) and was washed with a saturated aqueous sodium bicarbonate solution (1×50 mL). The organics were dried over magnesium sulfate, filtered, and concentrated in vacuo. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (100 mL) and was washed with a saturated aqueous sodium bicarbonate solution (1×25 mL). The aqueous layer was re-extracted with dichloromethane (1×50 mL). The combined organics were dried over magnesium sulfate, filtered, and concentrated in vacuo. The resulting solid was dried in vacuo for 24 h to afford 4-acetylamino-2-methyl-thiophene-3-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (27.8 mg, 26.1%): EI-HRMS m/e calcd for $C_{32}H_{31}N_6O_4SF$ $(M+Na)^+$ 637.2004, found 637.2018.

Example 114

5-Methyl-isoxazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide

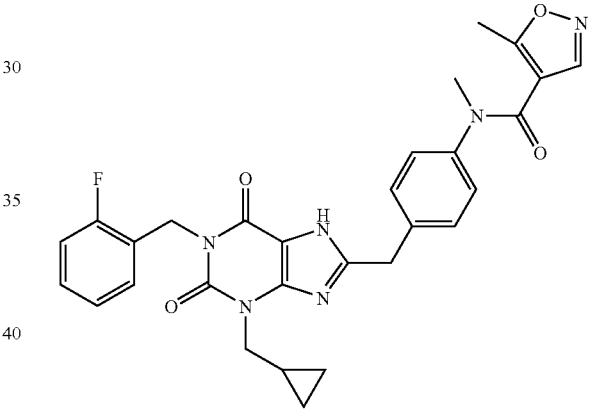

A mixture of 5-methyl-isoxazole-4-carboxylic acid (7.3 mg, 0.05 mmol) in dichloromethane (1.0 mL) at 25° C. was treated with triphenylphosphine (17 mg, 0.06 mmol). This mixture was cooled to 0° C. and then was reacted with N-chlorosuccinimide (10 mg, 0.07 mmol). This mixture was stirred at 0° C. for 15 min and then was warmed to 25° C. for 20 min. At this time, the reaction was treated with 3-cyclopropylmethyl-1-(2-fluoro-benzyl)-8-(4-methylamino-benzyl)-3,7-dihydro-purine-2,6-dione (50 mg, 0.11 mmol). The reaction was stirred at 25° C. for 18 h. At this time, the reaction was diluted with dichloromethane (50 mL) and then was washed with a saturated aqueous sodium bicarbonate solution (1×10 mL). The organics were dried over magnesium sulfate, filtered, and concentrated in vacuo. Flash chromatography (Merck Silica gel 60, 230–400 mesh, 3:97 methanol/dichloromethane) afforded impure product. The resulting residue was purified by HPLC (15–60% acetonitrile/water (0.075% trifluoroacetic acid in both solvents) over 40 min). Fractions with the desired product were combined and concentrated in vacuo. The resulting residue was diluted with dichloromethane (100 mL) and was washed with a saturated aqueous sodium bicarbonate solution (25 mL). The aqueous layer was re-extracted with dichloromethane (1×50 mL). The combined organics were dried over magnesium sulfate, filtered, and concentrated in vacuo. The resulting solid was dried in vacuo for 24 h to afford 5-methyl-isoxazole-4-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (7.6 mg, 24.4%) as an off-white solid: EI-HRMS m/e calcd for $C_{29}H_{27}N_6O_4F$ (M+) 542.2078, found 542.2083.

Example 115

Thiophene-2,3-dicarboxylic acid 3-amide 2-({4-[3-cyclopropylmethyl-1-(2-fluorobenzyl)-2,6-dioxo-2,3,6,7-tetrahydro-1H-purin-8-ylmethyl]-phenyl}-methyl-amide)

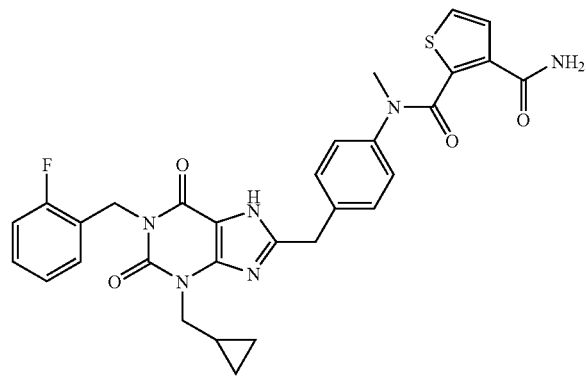

Step 1: Preparation of 3-carbamoyl-thiophene-2-carboxylic acid.

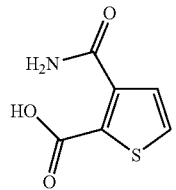

A solution of 3-carbamoyl-thiophene-2-carboxylic acid methyl ester (125 mg, 0.67 mmol) in methanol (2.0 mL) at 25° C. was treated with a 1N aqueous sodium hydroxide solution (2.0 mL, 2.02 mmol). The reaction was stirred at 25° C. for 18 h. At this time, the reaction was concentrated in vacuo. The residue was diluted with water (10 mL) and then acidified to pH=2 with a 1N aqueous hydrochloric acid solution. The resulting slurry was cooled to 0° C. The solids were collected by filtration, washed with water, and dried in vacuo to afford 3-carbamoyl-thiophene-2-carboxylic acid (102 mg, 88.3%) as an off-white solid: LR-MS for $C_6H_5NO_3S$ (M−H)+ at m/z=170.

Step 2: Preparation of thiophene-2,3-dicarboxylic acid 3-amide 2-({4-[3-cyclopropylmethyl-1-(2-fluoro-benzyl)-2,6-dioxo-2,3,6,7-tetrahydro-1H-purin-8-ylmethyl]-phenyl}-methyl-amide)

A mixture of 3-carbamoyl-thiophene-2-carboxylic acid (38 mg, 0.22 mmol) in dichloromethane (3.0 mL) at 25° C. was treated with triphenylphosphine (71 mg, 0.27 mmol). This mixture was cooled to 0° C. and then was treated with N-chlorosuccinimide (36 mg, 0.27 mmol). This mixture was stirred at 0° C. for 15 min and then was warmed to 25° C. for 15 min. At this time, the reaction was treated with 3-cyclopropylmethyl-1-(2-fluoro-benzyl)-8-(4-methylamino-benzyl)-3,7-dihydro-purine-2,6-dione (75 mg, 0.17 mmol). The reaction was cooled to 0° C. and then treated with triethylamine (38 µL, 0.27 mmol). The reaction was stirred at 25° C. for 18 h. At this time, the reaction was diluted with dichloromethane (100 mL) and then was washed with a saturated aqueous sodium bicarbonate solution (1×25 mL). The organics were dried over magnesium sulfate, filtered, and concentrated in vacuo. Flash chromatography (Merck Silica gel 60, 230–400 mesh, 1:99 methanol/dichloromethane) afforded thiophene-2,3-dicarboxylic acid 3-amide 2-({4-[3-cyclopropylmethyl-1-(2-fluoro-benzyl)-2,6-dioxo-2,3,6,7-tetrahydro-1H-purin-8-ylmethyl]-phenyl}-methyl-amide) (37 mg, 36.5%) as a white solid: EI-HRMS m/e calcd for $C_{30}H_{27}N_6O_4SF$ (M+Na)+ 609.1691, found 609.1698.

Example 116

4-Amino-1-methyl-1H-pyrazole-3-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide

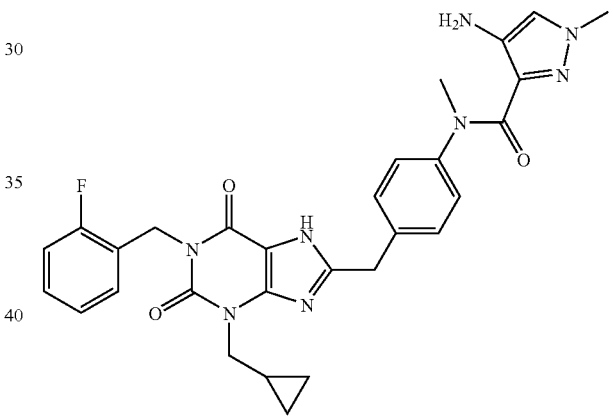

Step 1: Preparation of 4-nitro-1H-pyrazole-3-carboxylic acid methyl ester

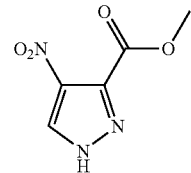

A mixture of 4-nitro-1H-pyrazole-3-carboxylic acid (2.0 g, 12.7 mmol) in dichloromethane at 25° C. was treated with 1-(3-dimethylaminopropyl)-3-ethylcarbodiimide hydrochloride (2.68 g, 14.0 mmol), methanol (8.2 mL), and 4-dimethylaminopyridine (155 mg, 1.27 mmol). The reaction was stirred at 25° C. for 18 h. At this time, the reaction was diluted with dichloromethane and was washed with a 1N aqueous hydrochloric acid solution (1×50 mL). The organics were dried over magnesium sulfate, filtered, and concentrated in vacuo. Flash chromatography (Merck Silica gel 60, 230–400 mesh, 45:55 ethyl acetate/petroleum ether)

afforded 4-nitro-1H-pyrazole-3-carboxylic acid methyl ester (1.06 g, 48.8%) as a white solid: LR-MS for $C_5H_5N_3O_4$ (M–H)$^+$ at m/z=170.

Step 2: Preparation of 1-methyl-4-nitro-1H-pyrazole-3-carboxylic acid methyl ester

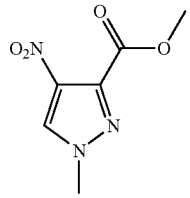

A mixture of sodium hydride (167 mg, 6.96 mmol) in tetrahydrofuran (15 mL) cooled to 0° C. was treated with a solution of 4-nitro-1H-pyrazole-3-carboxylic acid methyl ester (1.0 g, 5.8 mmol) in tetrahydrofuran (10 mL). This mixture was stirred at 0° C. for 1 h. It was then treated with methyl iodide (0.54 mL, 8.7 mmol). The reaction was stirred at 25° C. for 18 h. At this time, the reaction was cooled to 0° C. and was then quenched with a saturated aqueous ammonium chloride solution and diluted with ethyl acetate (200 mL). This solution was washed with water (1×100 mL) and a saturated aqueous sodium chloride solution (1×100 mL). The organics were dried over magnesium sulfate, filtered, and concentrated in vacuo. The resulting solid was slurried in 40% ethyl acetate/petroleum ether and cooled in the freezer for 15 min. At this time, the solids were collected by filtration to afford 1-methyl-4-nitro-1H-pyrazole-3-carboxylic acid methyl ester (889 mg, 82.8%) as a white solid: $^1$H NMR (DMSO-d$_6$, 300 MHz) δ8.93 (s, 1H), 3.92 (s, 3H), 3.86 (s, 3H).

Step 3: Preparation of 4-amino-1-methyl-1H-pyrazole-3-carboxylic acid methyl ester

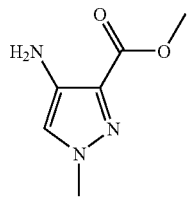

A mixture of 1-methyl-4-nitro-1H-pyrazole-3-carboxylic acid methyl ester (500 mg, 2.7 mmol) and 10% palladium on carbon (50 mg) in methanol (25 mL) was subjected to 60 psi pressure of hydrogen gas in a Parr apparatus for 24 h. At this time, the reaction mixture was filtered through a pad of celite and washed with methanol. The filtrate was concentrated in vacuo to afford 4-amino-1-methyl-1H-pyrazole-3-carboxylic acid methyl ester (402 mg, 96%) as an off-white solid: $^1$H NMR (DMSO-d$_6$, 300 MHz) δ7.10 (s, 1H), 4.65 (broad s, 2H), 3.73 (s, 3H), 3.72 (s, 3H).

Step 4: Preparation of 1-methyl-4-(trityl-amino)-1H-pyrazole-3-carboxylic acid methyl ester

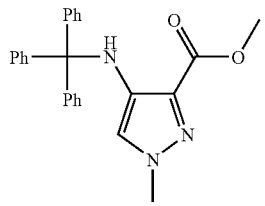

A solution of 4-amino-1-methyl-1H-pyrazole-3-carboxylic acid methyl ester (160 mg, 1.03 mmol) in N,N-dimethylformamide (1.0 mL) at 25° C. was treated with triethylamine (0.35 mL, 2.6 mmol) and triphenylmethylchloride (316 mg, 1.13 mmol). Additional N,N-dimethylformamide (2.0 mL) was added to the reaction to aid stirring. The reaction was stirred at 25° C. for 18 h. At this time, the reaction was concentrated in vacuo. The residue was dissolved in dichloromethane (50 mL) and then was washed with a 1N aqueous hydrochloric acid solution (1×10 mL), a saturated aqueous sodium bicarbonate solution (1×10 mL), and a saturated aqueous sodium chloride solution (1×10 mL). The organics were dried over magnesium sulfate, filtered, and concentrated in vacuo to afford 1-methyl-4-(trityl-amino)-1H-pyrazole-3-carboxylic acid methyl ester (373 mg, 91.1%) as an off-white solid: $^1$H NMR (DMSO-d$_6$, 300 MHz) δ7.25 (m, 16H), 3.74 (s, 3H), 3.53 (s, 3H).

Step 5: Preparation of 1-methyl-4-(trityl-amino)-1H-pyrazole-3-carboxylic acid

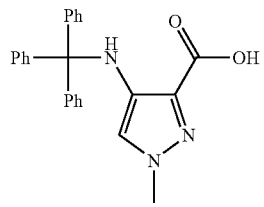

A solution of 1-methyl-4-(trityl-amino)-1H-pyrazole-3-carboxylic acid methyl ester (70 mg, 0.18 mmol) in methanol (2.0 mL) cooled to 0° C. was treated with a 1N aqueous sodium hydroxide solution (0.7 mL, 0.70 mmol). The reaction was stirred at 25° C. for 18 h. At this time, the reaction was treated with another portion of a 1N aqueous sodium hydroxide solution (0.7 mL, 0.70 mmol). The reaction was stirred for 24 h. At this time, the reaction was warmed to 50° C. for 5 days. At this time, the reaction was concentrated in vacuo. The residue was dissolved into dichloromethane and methanol and then brought to pH=4 by the addition of a 1N aqueous hydrochloric acid solution. The resulting mixture was concentrated in vacuo. The solids were slurried in cold water, collected by filtration, washed with water, and dried in vacuo to afford 1-methyl-4-(trityl-amino)-1H-pyrazole-3-carboxylic acid (60 mg, 88.9%) as an off-white solid: EI-HRMS m/e calcd for $C_{24}H_{21}N_3O_2$ (M+Na)$^+$ 406.1526, found 406.1526.

Step 6: Preparation of 4-amino-1-methyl-1H-pyrazole-3-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide A mixture of 1-methyl-4-(trityl-amino)-1H-pyrazole-3-carboxylic acid (44 mg, 0.46 mmol) in dichloromethane (1.0 mL) at 25° C. was treated with triphenylphosphine (40 mg, 0.30 mmol). This mixture was cooled to 0° C. and then treated with N-chlorosuccinimide (20 mg, 0.30 mmol). This mixture was stirred at 0° C. for 15 min and then was warmed to 25° C. for 15 min. At this time, the reaction was treated with 3-cyclopropylmethyl-1-(2-fluoro-benzyl)-8-(4-methylamino-benzyl)-3,7-dihydro-purine-2,6-dione (100 mg, 0.23 mmol). The reaction was stirred at 25° C. for 4 days. At this time, the reaction was diluted with dichloromethane and then was washed with a saturated aqueous sodium bicarbonate solution (1×25 mL). The organics were dried over magnesium sulfate, filtered, and concentrated in vacuo.

Flash chromatography (Merck Silica gel 60, 230–400 mesh, 2:98 methanol/dichloromethane) afforded 4-amino-1-methyl-1H-pyrazole-3-carboxylic acid {4-[3-cyclopropylmethyl-1-(2-fluoro-benzyl)-2,6-dioxo-2,3,6,7-tetrahydro-1H-purin-8-ylmethyl]-phenyl}-methyl-amide (17 mg, 13.3%): $^1$H NMR (DMSO-$d_6$, 300 MHz) δ13.11 (broad s, 1H), 7.29 (broad s, 1H), 6.73 (m, 9H), 4.71 (s, 2H), 4.15 (broad s, 2H), 3.65 (s, 2H), 3.45 (d, J=6.59 Hz, 2H), 3.12 (s, 3H), 3.04 (s, 3H), 0.45 (m, 1H), 0.03 (m, 4H).

Example 117

1,3,5-Trimethyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-ethyl-amide

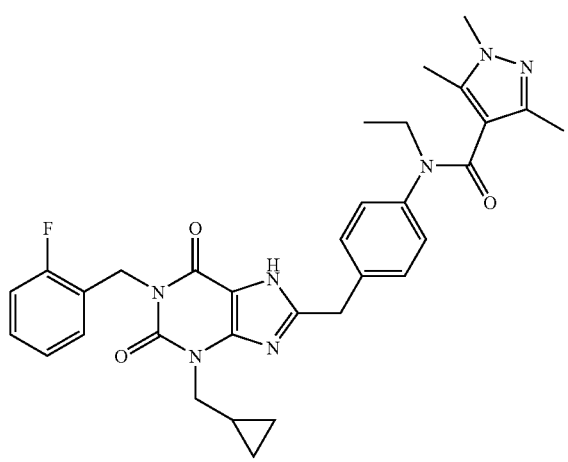

This compound was prepared by the method outlined in scheme 13.

Step 1: Preparation of 3-cyclopropylmethyl-8-[4-(ethylamino)-benzyl]-1-(2-fluorobenzyl)-3,7-dihydro-purine-2,6-dione

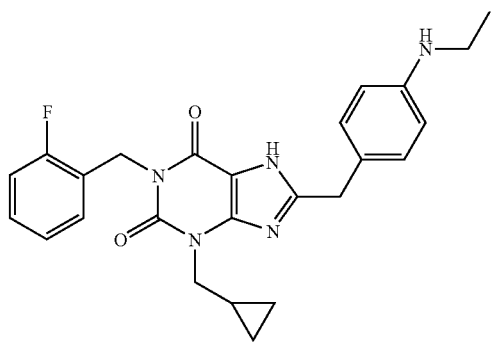

To a suspension of 10% palladium on carbon (0.10 g) in tetrahydrofuran (50 mL) was added 3-cyclopropylmethyl-8-[4-aminobenzyl]-1-(2-fluorobenzyl)-3,7-dihydro-purine-2,6-dione (prepared as described in example 64, step 1) (0.21 g, 0.50 mmol) and acetaldehyde (72.6 μL, 1.3 mmol). The mixture was shaken under an atmosphere of hydrogen at 1 atmosphere pressure and ambient temperature for 3 days. The catalyst was removed by filtration through celite, washing the filter pad through with tetrahydrofuran and methanol. The combined filtrate was concentrated in vacuo and the residue purified by chromatography using silica eluted with 1:1 hexanes/ethyl acetate. Concentration of the appropriate fractions gave the product as a colorless solid (0.14 g, 62%). MS, m/z(M+H)=553.

Step 2: Preparation of 1,3,5-trimethyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-ethyl-amide.

A suspension of triphenylphosphine (59.3 mg, 0.226 mmol) and 1,3,5-trimethyl-1H-pyrazole-4-carboxylic acid (SALOR) (26.8 mg, 0.174 mmol) in dichloromethane was cooled to 0° C. and N-chlorosuccinimide added. The mixture was stirred at 0° C. for 0.5 h then ambient temperature for an additional 0.5 h. 3-Cyclopropylmethyl-8-[4-(ethylamino)-benzyl]-1-(2-fluorobenzyl)-3,7-dihydro-purine-2,6-dione (93.4 mg, 0.209 mmol) was added followed by triethylamine (30.2 mg, 0.226 mmol) and 4-dimethylaminopyridine (a few crystals). The reaction was left to stir at ambient temperature overnight before washing with 1M aqueous hydrochloric acid, saturated aqueous sodium bicarbonate, drying the organic extract (sodium sulfate) and concentrating in vacuo. Purification by chromatography using silica eluted with 5:9 methanol/dichloromethane gave the product as a colorless solid (83.5 mg, 69%). MS, m/z(M+H)=584.2787.

Example 118

N-Butyl-N-{4-[3-butyl-1-(2-fluorobenzyl)-2,6-dioxo-2,3,6,7-tetrahydro-1H-purin-8-ylmethyl]-phenyl}-6-methyl-nicotinamide

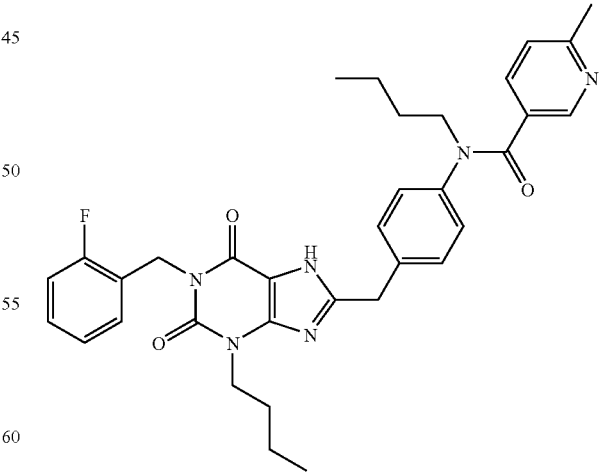

This compound was prepared by the methods outlined in schemes 4 and 13.

Step 1: Preparation of 3-butyl-8-(4-butylamino-benzyl)-1-(2-fluorobenzyl)-3,7-dihydro-purine-2,6-dione.

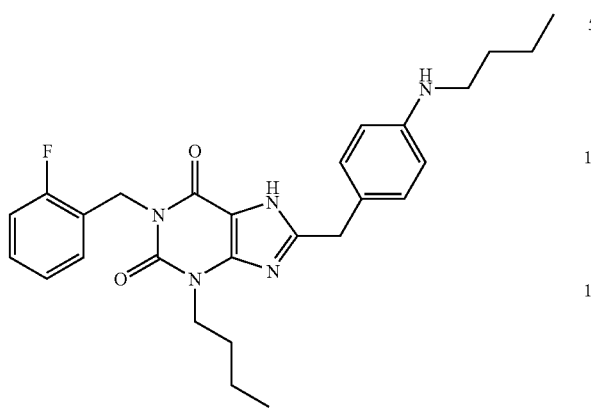

This compound was isolated as a byproduct in example 87 (step 1). A 2:1 mixture of 8-(amino-benzyl)-3-butyl-1-(2-fluorobenzyl)-3,7-dihydro-purine-2,6-dione and 3-butyl-8-(4-butylamino-benzyl)-1-(2-fluorobenzyl)-3,7-dihydro-purine-2,6-dione was obtained which was separated by chromatography using silica gel eluted with 96:4 chloroform/methanol. MS, m/z(M+H)=478.2.

Step 2: Preparation of N-butyl-N-{4-[3-butyl-1-(2-fluorobenzyl)-2,6-dioxo-2,3,6,7-tetrahydro-1H-purin-8-ylmethyl]-phenyl}-6-methyl-nicotinamide.

This compound was prepared by a method similar to that described in example 86 except that 3-butyl-8-(4-butylamino-benzyl)-1-(2-fluorobenzyl)-3,7-dihydro-purine-2,6-dione was used in place of 3-cyclopropylmethyl-8-[4-(methyl-amino)-benzyl]-1-(2-fluorobenzyl)-3,7-dihydro-purine-2,6-dione and excess triethylamine and a catalytic amount of 4-dimethylaminopyridine were added as the final reagents to the reaction mixture. The product was purified by chromatography using silica gel eluted with 96:4 chloroform/methanol. MS, m/z(M+)=597.2990.

Example 119

N-{4-[3-Cyclopropylmethyl-1-(2-fluorobenzyl)-2,6-dioxo-2,3,6,7-tetrahydro-1H-purin-8-ylmethyl]-phenyl}-N-isopropyl-6-methyl-nicotinamide

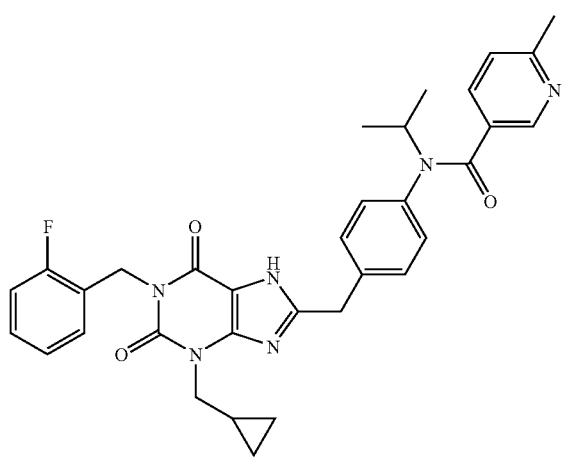

This compound was prepared by the method outlined in scheme 13.

Step 1: Preparation of 3-cyclopropylmethyl-8-[4-((1-methyl)-ethyl-amino)-benzyl]-1-(2-fluorobenzyl)-3,7-dihydro-purine-2,6-dione.

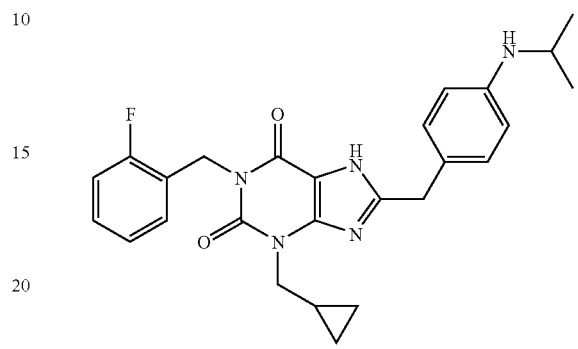

To a solution of 3-cyclopropylmethyl-8-[4-aminobenzyl]-1-(2-fluorobenzyl)-3,7-dihydro-purine-2,6-dione (0.21 g, 0.50 mmol) in tetrahydrofuran (tetrahydrofuran) (5 mL) was added acetone (36.7 μL, 5.0 mmol) and sodium cyanoborohydride (Aldrich, catalog number 15,615-9) (94.3 mg, 1.5 mmol). Stirred vigorously at ambient temperature and glacial acetic acid (J. T. Baker, catalog number 9508-5) (50 μL, 0.87 mmol) added. After 3 h additional glacial acetic acid (50 μL, 0.87 mmol) was added and the mixture stirred at ambient temperature for an additional 1 h. The reaction mixture was diluted with dichloromethane and washed with 1M aqueous sodium hydroxide (2×), brine, dried (sodium sulfate) and concentrated in vacuo. The residue was purified by chromatography using silica eluted with 1:2 hexanes/ethyl acetate. Concentration of the appropriate fractions gave the product as a colorless solid (0.055 g, 23%). $^1$H NMR, $\delta_H$(DMSO-d6, 300 MHz) 13.29 (br s, 1H), 7.30–6.85 (m, 6H), 6.40 (d, J=8.8 Hz, 2H), 5.16 (d, J=8.4 Hz, 1H), 5.04 (s, 2H), 3.78 (s, 2H), 3.42 (sept, J=6.4 Hz, 1H), 1.25–1.10 (m, 1H), 1.01 (d, J=6.2 Hz, 6H) and 0.45–0.30 (m, 4H)

Step 2: Preparation of N-{4-[3-Cyclopropylmethyl-1-(2-fluorobenzyl)-2,6-dioxo-2,3,6,7-tetrahydro-1H-purin-8-ylmethyl]-phenyl}-N-isopropyl-6-methyl-nicotinamide.

This compound was prepared by a method similar to that described in example 86 except that 3-cyclopropylmethyl-8-[4-((1-methyl)-ethyl-amino)-benzyl]-1-(2-fluorobenzyl)-3,7-dihydro-purine-2,6-dione was used in place of 3-cyclopropylmethyl-8-[4-(methyl-amino)-benzyl]-1-(2-fluorobenzyl)-3,7-dihydro-purine-2,6-dione. 1.5 Equivalents of triethylamine and a catalytic amount of 4-dimethylaminopyridine were added to the reaction mixture following addition of the aniline and the reaction was allowed to proceed for 96 h at ambient temperature before applying the standard work-up procedure. Following purification by chromatography using silica eluted with 4:96 methanol/dichloromethane the product was obtained as a colorless solid (14%). MS, m/z(M+H)=581.2673.

Example 120

N-{4-[3-Cyclopropylmethyl-1-(2-fluorobenzyl)-2,6-dioxo-2,3,6,7-tetrahydro-1H-purin-8-ylmethyl]-phenyl}-N-isopropyl-2-pyridin-3-yl-acetamide

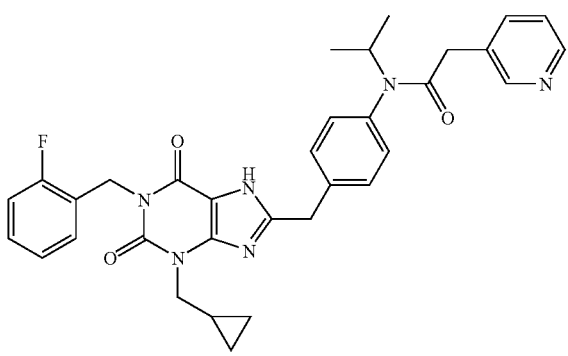

This compound was prepared by a method similar to that described in example 91 except that 3-cyclopropylmethyl-8-[4-((1-methyl)-ethyl-amino)-benzyl]-1-(2-fluorobenzyl)-3,7-dihydro-purine-2,6-dione was used in place of 3-cyclopropylmethyl-8-[4-(methyl-amino)-benzyl]-1-(2-fluorobenzyl)-3,7-dihydro-purine-2,6-dione. Triethylamine was omitted and 1.5 equivalents of 4-dimethylaminopyridine was added to the reaction mixture following addition of the aniline. The reaction was allowed to proceed for 24 hrs at ambient temperature before applying the standard work-up procedure. The product was purified by chromatography using silica eluted with 6:94 methanol/dichloromethane the product was further purified using a Chromatotron equipped with a 2 mm silica plate eluted with 9:1 2-propanol/dichloromethane. Following lyophilization from acetonitrile/water the product was obtained as a colorless solid (8%). MS, m/z(M+H)=581.2666.

Example 121

N-Cyclobutylmethyl-N-{4-[3-cyclobutylmethyl-1-(2-fluorobenzyl)-2,6-dioxo-2,3,6,7-tetrahydro-1H-purin-8-ylmethyl]-phenyl}-6-methyl-nicotinamide

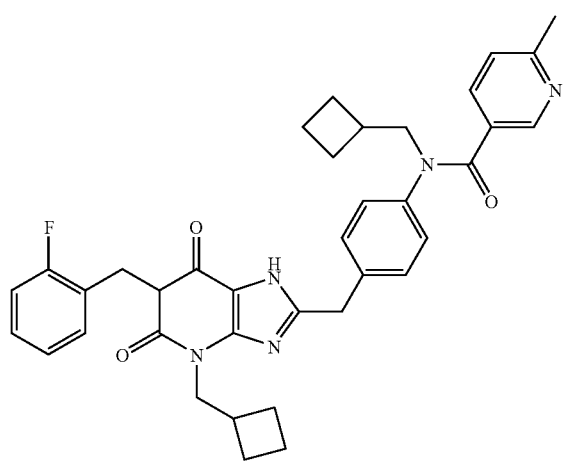

This compound was prepared by the methods outlined in schemes 4 and 13.

Step 1: Preparation of 3-cyclobutylmethyl-8-[4-(cyclobutyl-methyl-amino)-benzyl]-1-(2-fluorobenzyl)-3,7-dihydro-purine-2,6-dione

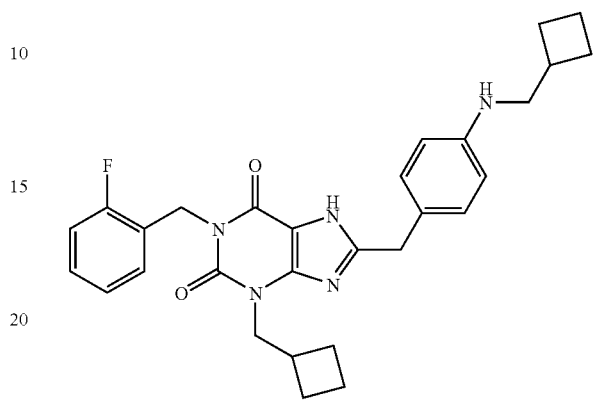

This compound was isolated as a byproduct from example 88 (step 1). A 4:1 mixture of 8-(4-amino-benzyl)-3-cyclobutylmethyl-1-(2-fluorobenzyl)-3,7-dihydro-purine-2,6-dione and 3-cyclobutylmethyl-8-[4-(cyclobutylmethyl-amino)-benzyl]-1-(2-fluorobenzyl)-3,7-dihydro-purine-2,6-dione was obtained. 3-Cyclobutylmethyl-8-[4-(cyclobutylmethyl-amino)-benzyl]-1-(2-fluorobenzyl)-3,7-dihydro-purine-2,6-dione was isolated by chromatography using silica gel eluted with 5:2 ethyl acetate/hexanes. MS, m/z(M+H)=502.2.

Step 2: Preparation of N-cyclobutylmethyl-N-{4-[3-cyclobutylmethyl-1-(2-fluorobenzyl)-2,6-dioxo-2,3,6,7-tetrahydro-1H-purin-8-ylmethyl]-phenyl}-6-methyl-nicotinamide This compound was prepared by a method similar to that described in example 86 except that 3-cyclobutylmethyl-8-[4-(cyclobutylmethyl-amino)-benzyl]-1-(2-fluorobenzyl)-3,7-dihydro-purine-2,6-dione was used in place of 3-cyclopropylmethyl-8-[4-(methyl-amino)-benzyl]-1-(2-fluorobenzyl)-3,7-dihydro-purine-2,6-dione and excess triethylamine and a catalytic amount of 4-dimethylaminopyridine were added as the final reagents to the reaction mixture. The product was purified by chromatography using silica gel eluted with 7:3 ethyl acetate/hexanes. MS, m/z (M+)=621.2981.

The therapeutically effective amount of a compound in accordance with this invention can vary within wide limits and may be determined by a manner known in the art. Such dosage will be adjusted to the individual requirements in each particular case including the specific compound or compounds being administered, the route of administration, the condition being treated, as well as the patient being treated. In general, in the case of parenteral administration to adult humans weighing approximately 70 Kg, a daily dosage of about 10 mg to about 10,000 mg, preferably from about 200 mg to about 1,000 mg should be appropriate, although the upper limit may be exceeded when indicated. The daily dosage can be administered as a single dose or in divided doses, or for parental administration, it may be given as continuous infusion. The examples below are exemplary, but not limitative of, the invention.

Example A

Tablet Formulation

| Item | Ingredients | Mg/Tablet | | | | | |
|---|---|---|---|---|---|---|---|
| 1 | Compound A * | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

* Compound A represents a compound of the invention.

Manufacturing Procedure:
Mix Items 1, 2 and 3 in a suitable mixer for 15 minutes.
Granulate the powder mix from Step 1 with 20% Povidone K30 Solution (Item 4).
Dry the granulation from Step 2 at 50° C.
Pass the granulation from Step 3 through a suitable milling equipment.
Add the Item 5 to the milled granulation Step 4 and mix for 3 minutes.
Compress the granulation from Step 5 on a suitable press.

Example B

Capsule Formulation

| Item | Ingredients | mg/Capsule | | | | |
|---|---|---|---|---|---|---|
| 1 | Compound A * | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

* Compound A represents a compound of the invention.

Manufacturing Procedure:
Mix Items 1, 2 and 3 in a suitable mixer for 15 minutes.
Add Items 4 & 5 and mix for 3 minutes.
Fill into a suitable capsule.

Example C

Injection Solution/Emulsion Preparation

| Item | Ingredient | mg/mL |
|---|---|---|
| 1 | Compound A * | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

* Compound A represents a compound of the invention.

Manufacturing Procedure:
Dissolve item 1 in item 2.
Add items 3, 4 and 5 to item 6 and mix until dispersed, then homogenize.
Add the solution from step 1 to the mixture from step 2 and homogenize until the dispersion is translucent.
Sterile filter through a 0.2 μm filter and fill into vials.

Example D

Injection Solution/Emulsion Preparation

| Item | Ingredient | mg/mL |
|---|---|---|
| 1 | Compound A * | 1 mg |
| 2 | Glycofurol | 10–50 mg |
| 3 | Lecithin | 20–50 mg |
| 4 | Soy Oil | 1–5mg |
| 5 | Glycerol | 8–12 mg |
| 6 | Water | q.s. 1 mL |

* Compound A represents a compound of the invention.

Manufacturing Procedure:
Dissolve item 1 in item 2.
Add item 3, 4 and 5 to item 6 and mix until dispersed, then homogenize.
Add the solution from step 1 to the mixture from step 2 and homogenize until the dispersion is translucent.
Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:
1. A compound of formula

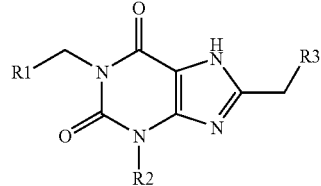

wherein
$R^1$ is selected from the group consisting of
lower alkenyl,
lower alkynyl,
lower alkenyl substituted by halogen,
phenyl and
phenyl substituted by one or two substituents independently selected from the group consisting of halogen, hydroxy, lower alkoxy, nitro, amino and a 5- or 6-membered aromatic heterocyclic ring having 1, 2, 3 or 4 nitrogen atoms, the heterocyclic ring attached to the phenyl by a ring carbon atom;
$R^2$ is selected from the group consisting of
unsubstituted lower alkyl,
lower alkyl substituted by lower alkoxy or hydroxy,
lower alkenyl,
phenyl,
—$(CH_2)_n$-unsubstituted lower cycloalkyl and
—$(CH_2)_n$-lower cycloalkyl substituted by at least one substitutent selected from the group consisting of carboxy, lower alkyl, carboxy-lower alkyl and lower alkyl substituted by hydroxy, —$(CH_2)_n$—$C(O)R^b$, wherein $R^b$ is selected from the group consisting of hydroxyl, lower alkoxy, —$NHR^c$, wherein $R^c$ is selected from the group consisting of hydrogen, benzyl, lower alkyl and —$NHR^d$ and wherein $R^d$ is selected from the group consisting of hydrogen and carboxy-lower alkyl;

—$(CH_2)_n$-unsubstituted aromatic five-member heterocyclic ring with one oxygen or sulfur, —$(CH_2)_n$-aromatic five-member heterocyclic ring with one oxygen or sulfur, the ring substituted by a carboxylic acid moiety, —$(CH_2)_n$-unsubstituted aromatic five-member heterocyclic ring with 1, 2 or 3 nitrogen atoms, —$(CH_2)_n$-non-aromatic five or six member heterocyclic ring with at least one oxygen atom and no or two nitrogen atoms, the non-aromatic heterocyclic ring having no substituents or having one ring carbon in the form of a carbonyl, and wherein $R^3$ is

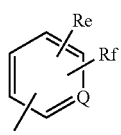

wherein Q is N or CH, with the proviso that
when Q is N, $R^e$ is —NH—C(O)—$CH_3$ and $R^f$ is H,
when Q is CH, $R^e$ is —$NR^g$—C(O)—$R^h$ or

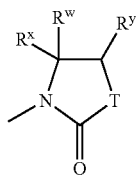

and
$R^f$ is selected from the group consisting of H, —$NH_2$ and —NH—C(O)—$CH_3$, $R^g$ is selected from the group consisting of H, lower alkyl and —$(CH_2)_n$-unsubstituted lower cycloalkyl, $R^h$ is selected from the group consisting of —$(CH_2)_n$—5- or 6-member aromatic heterocyclic ring having one, two or three hetero atoms independently selected from the group consisting of N, O and S, the aromatic heterocyclic ring being unsubstituted or having at least one substituent independently selected from the group consisting of lower alkyl, lower alkoxy, hydroxy, halogen, —$NH_2$, —NH—C(O)-lower alkyl, —CN, —C(O)—$NH_2$ and $SO_2$-lower alkyl, lower alkyl, lower alkyl substituted by at least one substituent independently selected from the group consisting of halogen, phenyl and —$(CH_2)_n NR^i R^i$, wherein $R^i$ is independently selected from the group consisting of H, lower alkyl and benzyloxycarbonyl, —$NHR^j$, wherein $R^j$ is selected from the group consisting of a 5- or 6-membered aromatic heterocyclic ring having one, two or three heteroatoms independently selected from the group consisting of N, O and S, the heterocyclic ring being substituted by at least one substituent selected from the group consisting of halogen, lower alkyl and phenyl, —C(O)—$R^k$, wherein $R^k$ is a 5- or 6-member aromatic heterocyclic ring having one, two or three hetero atoms independently selected from the group consisting of N, O and S, the aromatic heterocyclic ring being unsubstituted or substituted by at least one lower alkyl, phenyl, phenyl substituted by at least one substitutent independently selected from the group consisting of lower alkyl, lower alkoxy, —$(CH_2)_m$—$NHR^1$, wherein $R^1$ is selected from the group consisting of H, lower alkyl and benzyloxycarbonyl, and wherein T is NH or $CH_2$, with the proviso that when T is NH, $R^w$ and $R^x$ are, taken together with the carbon to which they are attached, to form —C(O)— and $R^y$ is selected from the group consisting of H and —$(CH_2)OR^z$, wherein $R^z$ is selected from the group consisting of hydrogen and lower alkyl, and when T is $CH_2$, $R^w$ and $R^x$ are both hydrogen or are, taken together with the carbon to which they are attached, to form —C(O)—; and n is 0, 1 or 2, m is 0 or 1, or a pharmaceutically acceptable salt or prodrug thereof.

2. The compound of claim 1, wherein $R^1$ is selected from the group consisting of lower alkenyl, lower alkenyl substituted by halogen and lower alkynyl.

3. The compound of claim 2, wherein the compound is selected from the group consisting of N-{4-[1-allyl-3-(2-methoxy-ethyl)-2,6-dioxo-2,3,6,7-tetrahydro-1H-purin-8-ylmethyl]-phenyl}-acetamide, N-{4-[3-butyl-1-(3-methyl-but-2-enyl)-2,6-dioxo-2,3,6,7-tetrahydro-1H-purin-8-ylmethyl]-phenyl}-acetamide, N-[4-(1-but-2-enyl-3-butyl-2,6-dioxo-2,3,6,7-tetrahydro-1H-purin-8-ylmethyl)-phenyl]-acetamide, N-[4-(1-allyl-3-butyl-2,6-dioxo-2,3,6,7-tetrahydro-1H-purin-8-ylmethyl)-phenyl]-acetamide, N-{4-[1-(3-bromo-allyl)-3-butyl-2,6-dioxo-2,3,6,7-tetrahydro-1H-purin-8-ylmethyl]-phenyl}-acetamide, and N-[4-(3-butyl-2,6-dioxo-1-prop-2-ynyl-2,3,6,7-tetrahydro-1H-purin-8-ylmethyl)-phenyl]-acetamide.

4. The compound of claim 1 wherein $R^1$ is unusbstituted phenyl or phenyl substituted by at least one substitutent selected from the group consisting of halogen, amino, lower alkoxy, hydroxy, nitro and a 5- or 6-membered heterocyclic ring having 1, 2, 3 or 4 nitrogen atoms, the heterocyclic ring attached by a ring carbon atom to the phenyl.

5. The compound of claim 4, wherein $R^1$ is selected from the group consisting of

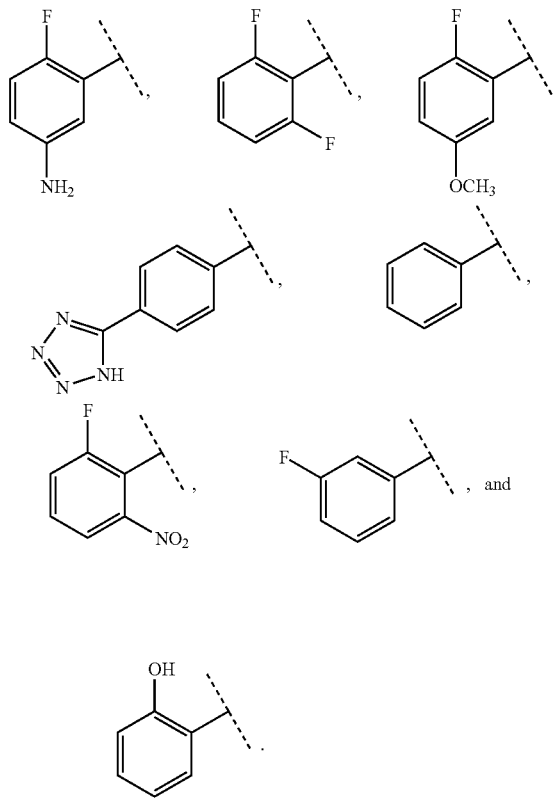

6. The compound of claim 5 wherein the compound is selected from the group consisting of
N-[4-(1-benzyl-3-methoxymethyl-2,6-dioxo-2,3,6,7-tetrahydro-1H-purin-8-ylmethyl)-phenyl]-acetamide,
N-[4-(1-benzyl-3-methyl-2,6-dioxo-2,3,6,7-tetrahydro-1H-purin-8-ylmethyl)-phenyl]-acetamide,
N-[3-(1-benzyl-3-furan-3-ylmethyl-2,6-dioxo-2,3,6,7-tetrahydro-1H-purin-8-ylmethyl)-phenyl]-acetamide,
N-(4-{3-butyl-1-[4-(1-methyl-1H-tetrazol-5-yl)-benzyl]-2,6-dioxo-2,3,6,7-tetrahydro-1H-purin-8-ylmethyl}-phenyl)-acetamide,
N-[4-(1-benzyl-3-butyl-2,6-dioxo-2,3,6,7-tetrahydro-1H-purin-8-ylmethyl)-phenyl]-acetamide,
N-{4-[3-butyl-1-(2,6-difluoro-benzyl)-2,6-dioxo-2,3,6,7-tetrahydro-1H-purin-8-ylmethyl]-phenyl}-acetamide,
N-[5-(1-benzyl-3-butyl-2,6-dioxo-2,3,6,7-tetrahydro-1H-purin-8-ylmethyl)-pyridin-2-yl]-acetamide,
N-{4-[3-butyl-1-(3-fluoro-benzyl)-2,6-dioxo-2,3,6,7-tetrahydro-1H-purin-8-ylmethyl]-phenyl}-acetamide,
5-[8-(4-acetylamino-benzyl)-1-benzyl-2,6-dioxo-1,2,6,7-tetrahydro-purin-3-ylmethyl]-furan-2-carboxylic acid; compound with trifluoro-acetic acid,
N-[4-(1-benzyl-2,6-dioxo-3-thiophen-2-ylmethyl-2,3,6,7-tetrahydro-1H-purin-8-ylmethyl)-phenyl]-acetamide,
N-[6-(1-benzyl-3-butyl-2,6-dioxo-2,3,6,7-tetrahydro-1H-purin-8-ylmethyl)-pyridin-3-yl]-acetamide,
N-[4-(1-benzyl-3-furan-3-ylmethyl-2,6-dioxo-2,3,6,7-tetrahydro-1H-purin-8-ylmethyl)-phenyl]-acetamide,
1-benzyl-3-butyl-8-[4-(2,5-dioxo-pyrrolidin-1-yl)-benzyl]-3,7-dihydro-purine-2,6-dione,
N-{4-[1-(5-amino-2-fluorobenzyl)-3-butyl-2,6-dioxo-2,3,6,7-tetrahydro-1H-purin-8-ylmethyl]-phenyl}-acetamide; compound with trifluoro-acetic acid,
N-{4-[3-butyl-1-(2-hydroxy-benzyl)-2,6-dioxo-2,3,6,7-tetrahydro-1H-purin-8-ylmethyl]-phenyl}-acetamide, and
1-benzyl-3-butyl-8-[4-(2-oxo-pyrrolidin-1-yl)-benzyl]-3,7-dihydro-purine-2,6-dione.

7. The compound of claim 1 with the formula

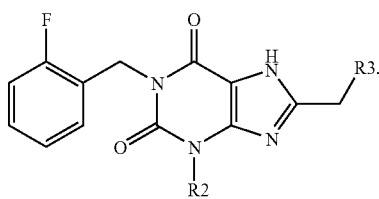

Ia

8. The compound of claim 7 wherein $R^2$ is selected from the group consisting of
-phenyl;
—$(CH_2)_n$-unsubstituted aromatic 5-member heterocyclic ring with one heteroatom selected from O or S,
—$(CH_2)_n$-aromatic 5-member heterocyclic ring with one heteroatom selected from the group consisting of O and S, the 5-member heterocyclic ring being substituted by a carboxylic acid,
—$(CH_2)_n$-unsubstituted aromatic heterocyclic ring having 1, 2 or 3 N-atoms, and
—$(CH_2)_n$-non-aromatic heterocyclic ring with at least one oxygen atom and no or two nitrogen atoms, the non-aromatic heterocyclic ring having no substituents or having one ring carbon in the form of a carbonyl.

9. The compound of claim 8 wherein the compound is selected from the group consisting of
N-{4-[1-(2-fluorobenzyl)-2,6-dioxo-3-(1H-[1,2,4]triazol-3-ylmethyl)-2,3,6,7-tetrahydro-1H-purin-8-ylmethyl]-phenyl}-acetamide; compound with trifluoro-acetic acid,
N-{4-[1-(2-fluorobenzyl)-2,6-dioxo-3-(tetrahydro-pyran-2-ylmethyl)-2,3,6,7-tetrahydro-1H-purin-8-ylmethyl]-phenyl}-acetamide,
N-(4-{1-(2-fluorobenzyl)-2,6-dioxo-3-[2-(5-oxo-4,5-dihydro-[1,3,4]oxadiazol-2-yl)-ethyl]-2,3,6,7-tetrahydro-1H-purin-8-ylmethyl}-phenyl)-acetamide,
N-(4-{1-(2-fluorobenzyl)-2,6-dioxo-3-[3-(5-oxo-4,5-dihydro-[1,3,4]oxadiazol-2-yl)-propyl]-2,3,6,7-tetrahydro-1H-purin-8-ylmethyl}-phenyl)-acetamide,
N-{4-[1-(2-fluorobenzyl)-3-phenyl-2,6-dioxo-2,3,6,7-tetrahydro-1H-purin-8-ylmethyl]-phenyl}-acetamide,
N-{4-[1-(2-fluorobenzyl)-3-furan-3-ylmethyl-2,6-dioxo-2,3,6,7-tetrahydro-1H-purin-8-ylmethyl]-phenyl}-acetamide,
N-{4-[1-(2-fluorobenzyl)-3-(tetrahydrofuran-2-ylmethyl)-2,6-dioxo-2,3,6,7-tetrahydro-1H-purin-8-ylmethyl]-phenyl}-acetamide and
N-{4-[1-(2-fluorobenzyl)-2,6-dioxo-3-thiophen-2-ylmethyl-2,3,6,7-tetrahydro-1H-purin-8-ylmethyl]-phenyl}-acetamide.

10. The compound of claim 7 wherein $R^2$ is selected from the group consisting of lower alkyl, lower alkyl substituted by lower alkoxy or hydroxy, and lower alkenyl.

11. The compound of claim 10 wherein $R^2$ is unsubstituted lower alkyl or lower alkenyl.

12. The compound of claim 11 wherein the compound is selected from the group consisting of
- N-{4-[1-(2-fluorobenzyl)-3-hexyl-2,6-dioxo-2,3,6,7-tetrahydro-1H-purin-8-ylmethyl]-phenyl}-acetamide,
- N-{3-acetylamino-4-[3-butyl-1-(2-fluorobenzyl)-2,6-dioxo-2,3,6,7-tetrahydro-1H-purin-8-ylmethyl]-phenyl}-acetamide,
- 3-chloro-4-(propane-2-sulfonyl)-thiophene-2-carboxylic acid {4-[3-butyl-1-(2-fluorobenzyl)-2,6-dioxo-2,3,6,7-tetrahydro-1H-purin-8-ylmethyl]-phenyl}-amide
- N-{5-amino-2-[3-butyl-1-(2-fluorobenzyl)-2,6-dioxo-2,3,6,7-tetrahydro-1H-purin-8-ylmethyl]-phenyl}-acetamide,
- N-{6-[3-butyl-1-(2-fluorobenzyl)-2,6-dioxo-2,3,6,7-tetrahydro-1H-purin-8-ylmethyl]-pyridin-3-yl}-acetamide,
- N-{4-[1-(2-fluorobenzyl)-3-(3,3-dimethylbutyl)-2,6-dioxo-2,3,6,7-tetrahydro-1H-purin-8-ylmethyl]-phenyl}-acetamide,
- N-{5-[3-butyl-1-(2-fluorobenzyl)-2,6-dioxo-2,3,6,7-tetrahydro-1H-purin-8-ylmethyl]-pyridin-2-yl}-acetamide,
- N-{4-[3-butyl-1-(2-fluorobenzyl)-2,6-dioxo-2,3,6,7-tetrahydro-1H-purin-8-ylmethyl]-phenyl}-3,4-dimethoxy-benzamide,
- N-{4-[1-(2-fluorobenzyl)-3-(3-methylbutyl)-2,6-dioxo-2,3,6,7-tetrahydro-1H-purin-8-ylmethyl]-phenyl}-acetamide,
- N-{4-[1-(2-fluorobenzyl)-3-butyl-2,6-dioxo-2,3,6,7-tetrahydro-1H-purin-8-ylmethyl]-phenyl}-acetamide,
- N-{4-[1-(2-fluorobenzyl)-3-butyl-2,6-dioxo-2,3,6,7-tetrahydro-1H-purin-8-ylmethyl]-phenyl}-2,2,2-trifluoro-acetamide,
- N-{4-[1-(2-fluorobenzyl)-3-isobutyl-2,6-dioxo-2,3,6,7-tetrahydro-1H-purin-8-ylmethyl]-phenyl}-acetamide,
- {4-[3-butyl-1-(2-fluorobenzyl)-2,6-dioxo-2,3,6,7-tetrahydro-1H-purin-8-ylmethyl]-phenyl}-urea,
- 1H-imidazole-4-carboxylic acid {4-[3-butyl-1-(2-fluorobenzyl)-2,6-dioxo-2,3,6,7-tetrahydro-1H-purin-8-ylmethyl]-phenyl}-amide; compound with trifluoro-acetic acid,
- 1H-[1,2,4]triazole-3-carboxylic acid {4-[3-butyl-1-(2-fluorobenzyl)-2,6-dioxo-2,3,6,7-tetrahydro-1H-purin-8-ylmethyl]-phenyl}-amide; compound with trifluoro-acetic acid,
- N-{4-[1-(2-fluorobenzyl)-3-propyl-2,6-dioxo-2,3,6,7-tetrahydro-1H-purin-8-ylmethyl]-phenyl}-acetamide,
- N-{4-[3-butyl-1-(2-fluorobenzyl)-2,6-dioxo-2,3,6,7-tetrahydro-1H-purin-8-ylmethyl]-phenyl}-6,N-dimethyl-nicotinamide,
- N-butyl-N-{4-[3-butyl-1-(2-fluorobenzyl)-2,6-dioxo-2,3,6,7-tetrahydro-1H-purin-8-ylmethyl]-phenyl}-6-methyl-nicotinamide and
- N-{4-[1-(2-fluorobenzyl)-3-(3-methyl-but-2-enyl)-2,6-dioxo-2,3,6,7-tetrahydro-1H-purin-8-ylmethyl]-phenyl}-acetamide.

13. The compound of claim 10 wherein $R^2$ is a lower alkyl substituted by hydroxy or lower alkoxy.

14. The compound of claim 13 wherein the compound is selected from the group consisting of
- N-{4-[1-(2-fluorobenzyl)-3-(2-hydroxymethyl-butyl)-2,6-dioxo-2,3,6,7-tetrahydro-1H-purin-8-ylmethyl]-phenyl}-acetamide,
- N-{4-[1-(2-fluorobenzyl)-3-(4-hydroxy-propyl)-2,6-dioxo-2,3,6,7-tetrahydro-1H-purin-8-ylmethyl]-phenyl}-acetamide, and
- N-{4-[1-(2-fluorobenzyl)-3-(4-hydroxy-butyl)-2,6-dioxo-2,3,6,7-tetrahydro-1H-purin-8-ylmethyl]-phenyl}-acetamide.

15. The compound of formula Ia in accordance with claim 7 wherein $R^2$ is $-(CH_2)_n-C(O)R^b$, wherein $R^b$ is selected from the group consisting of hydroxyl, lower alkoxy, and $-NHR^c$, wherein $R^c$ is selected from the group consisting of hydrogen, benzyl, lower alkyl and $-NHR^d$ and wherein $R^d$ is hydrogen or carboxy-lower alkyl.

16. The compound of formula Ia in accordance with claim 15 wherein the compound is selected from the group consisting of
- N-{4-[1-(2-fluorobenzyl)-3-(2-hydrazinocarbonyl-ethyl)-2,6-dioxo-2,3,6,7-tetrahydro-1H-purin-8-ylmethyl]-phenyl}-acetamide,
- 3-[8-(4-acetylamino-benzyl)-1-(2-fluorobenzyl)-2,6-dioxo-1,2,6,7-tetrahydro-purin-3-yl]-propionic acid methyl ester,
- 4-[8-(4-acetylamino-benzyl)-1-(2-fluorobenzyl)-2,6-dioxo-1,2,6,7-tetrahydro-purin-3-yl]-N-butyl-butyramide,
- 4-[8-(4-acetylamino-benzyl)-1-(2-fluorobenzyl)-2,6-dioxo-1,2,6,7-tetrahydro-purin-3-yl]-butyric acid methyl ester,
- 4-[8-(4-acetylamino-benzyl)-1-(2-fluorobenzyl)-2,6-dioxo-1,2,6,7-tetrahydro-purin-3-yl]-butyramide,
- 4-[8-(4-acetylamino-benzyl)-1-(2-fluorobenzyl)-2,6-dioxo-1,2,6,7-tetrahydro-purin-3-yl]-N-benzyl-butyramide,
- 4-[8-(4-acetylamino-benzyl)-1-(2-fluorobenzyl)-2,6-dioxo-1,2,6,7-tetrahydro-purin-3-yl]-propionic acid,
- 4-[8-(4-acetylamino-benzyl)-1-(2-fluorobenzyl)-2,6-dioxo-1,2,6,7-tetrahydro-purin-3-yl]-N-benzyl-butyramide, and
- 4-[8-(4-acetylamino-benzyl)-1-(2-fluorobenzyl)-2,6-dioxo-1,2,6,7-tetrahydro-purin-3-yl]-butyric acid.

17. The compound of formula Ia in accordance with claim 7 wherein $R^2$ is substituted cycloalkyl-methyl.

18. The compound of formula Ia in accordance with claim 17 wherein the compound is selected from the group consisting of
- 2-[8-(4-acetylamino-benzyl)-1-(2-fluorobenzyl)-2,6-dioxo-1,2,6,7-tetrahydro-purin-3-ylmethyl]-cyclopropanecarboxylic acid,
- N-{4-[1-(2-fluorobenzyl)-3-(2-methyl-cyclopropylmethyl)-2,6-dioxo-2,3,6,7-tetrahydro-1H-purin-8-ylmethyl]-phenyl}-acetamide,
- N-{4-[3-(2,2-bis-hydroxymethyl-cyclopropylmethyl)-1-(2-fluorobenzyl)-2,6-dioxo-2,3,6,7-tetrahydro-1H-purin-8-ylmethyl]-phenyl}-acetamide,
- N-{4-[1-(2-fluorobenzyl)-3-(2-hydroxymethyl-cyclopropylmethyl)-2,6-dioxo-2,3,6,7-tetrahydro-1H-purin-8-ylmethyl]-phenyl}-acetamide and
- 2-[8-(4-acetylamino-benzyl)-1-(2-fluorobenzyl)-2,6-dioxo-1,2,6,7-tetrahydro-purin-3-ylmethyl]-cyclopropanecarboxylic acid methyl ester.

19. The compound of claim 7 wherein $R^2$ is unsubstituted cycloalkyl.

20. The compound of claim 19, wherein $R^2$ is cyclopentyl.

21. The compound of claim 20, wherein the compound is N-{4-[3-cyclopentylmethyl-1-(2-fluorobenzyl)-2,6-dioxo-2,3,6,7-tetrahydro-1H-purin-8-ylmethyl]-phenyl}-acetamide.

22. The compound of claim 19, wherein $R^2$ is cyclobutyl.

23. The compound of claim 22 wherein the compound is selected from the group consisting of N-{4-[3-cyclobutylmethyl-1-(2-fluorobenzyl)-2,6-dioxo-2,3,6,7-tetrahydro-1H-purin-8-ylmethyl]-phenyl}-6,N-dimethyl-nicotinamide, N-cyclobutylmethyl-N-{4-[3-cyclobutylmethyl-1-(2-fluorobenzyl)-2,6-dioxo-2,3,6,7-tetrahydro-1H-purin-8-ylmethyl]-phenyl}-6-methyl-nicotinamide and N-{4-[3-cyclobutylmethyl-1-(2-fluorobenzyl)-2,6-dioxo-2,3,6,7-tetrahydro-1H-purin-8-ylmethyl]-phenyl}-acetamide.

24. The compound of claim 19 of formula

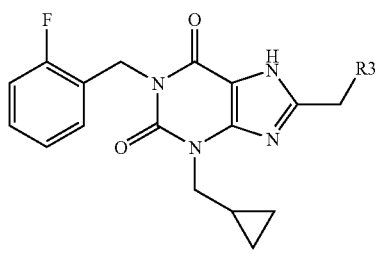

Ib wherein R³ is

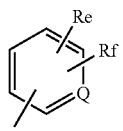

wherein Q is N or CH, with the proviso that
when Q is N, R$^e$ is —NH—C(O)—CH$_3$ and R$^f$ is H,
when Q is CH, R$^e$ is —NR$^g$—C(O)—R$^h$ or

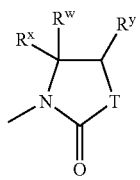

and
R$^f$ is selected from the group consisting of H, —NH$_2$ and —NH—C(O)—CH$_3$, R$^g$ is selected from the group consisting of H, lower alkyl and —(CH$_2$)$_n$-unsubstituted lower cycloalkyl, R$^h$ is selected from the group consisting of
—(CH$_2$)$_n$-5- or 6-member aromatic heterocyclic ring having one, two or three hetero atoms independently selected from the group consisting of N, O and S, the aromatic heterocyclic ring being unsubstituted or having at least one substituent independently selected from the group consisting of lower alkyl, lower alkoxy, hydroxy, halogen, —NH$_2$, —NH—C(O)-lower alkyl, —CN, —C(O)—NH$_2$ and —SO$_2$-lower alkyl,
lower alkyl,
lower alkyl substituted by at least one substituent independently selected from the group consisting of halogen, phenyl and —(CH$_2$)$_n$NHR$^i$R$^i$, wherein R$^i$ is independently selected from the group consisting of H, lower alkyl and benzyloxycarbonyl, —NHR$^j$, wherein R$^j$ is selected from the group consisting of a 5- or 6-membered aromatic heterocyclic ring having one, two or three heteroatoms independently selected from the group consisting of N, O and S, the heterocyclic ring being substituted at least one substituent selected from the group consisting of halogen, lower alkyl and phenyl, —C(O)—R$^k$, wherein R$^k$ is a 5- or 6-member aromatic heterocyclic ring having one, two or three hetero atoms independently selected from the group consisting of N, O and S, the aromatic heterocyclic ring being unsubstituted or substituted by at least one lower alkyl, unsubstituted phenyl, phenyl substituted by a substituent independently selected from the group consisting of lower alkyl, lower alkoxy, —(CH$_2$)$_m$—NHR$^1$, wherein R$^1$ is selected from the group consisting of H, lower alkyl and benzyloxycarbonyl, and wherein T is NH or CH$_2$, with the proviso that
when T is NH, R$^w$ and R$^x$ are, taken together with the carbon to which they are attached, form —C(O)— and R$^y$ is —(CH$_2$)OR$^z$ wherein R$^z$ is selected from the group consisting of hydrogen and lower alkyl, and when T is CH$_2$, R$^w$ and R$^x$ are both hydrogen or are, taken together with the carbon to which they are attached, form —C(O)—; and n is 0, 1 or 2;
m is 0 or 1;
or a pharmaceutically acceptable salt or prodrug thereof.

25. The compound of claim 24 having the formula

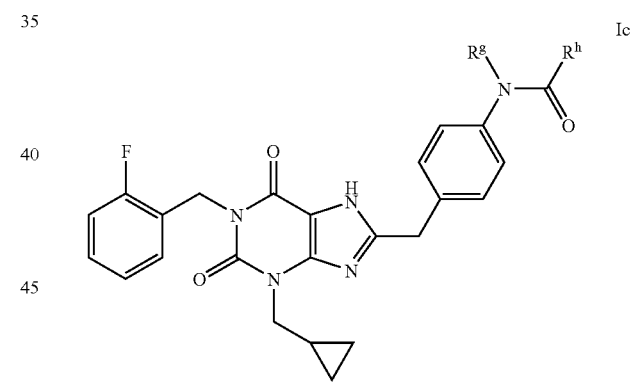

Ic wherein
R$^g$ is selected from the group consisting of H, lower alkyl and —(CH$_2$)$_n$-unsubstituted lower cycloalkyl; and R$^h$ is selected from the group consisting of
a —(CH$_2$)$_n$-5- or 6-member aromatic heterocyclic ring having one, two or three hetero atoms independently selected from the group consisting of N, O and S, the aromatic heterocyclic ring being unsubstituted or having at least one substituent independently selected from the group consisting of lower alkyl, lower alkoxy, hydroxy, halogen, —NH$_2$, —NH—C(O)-lower alkyl, —CN, —C(O)—NH$_2$ and —SO$_2$-lower alkyl,
lower alkyl,
lower alkyl substituted by at least one substituent independently selected from the group consisting of halogen, phenyl and —(CH$_2$)$_n$NHR$^i$R$^i$, wherein R$^i$ is independently selected from the group consisting of H, lower alkyl, lower alkyl substituted by halogen and carbonyloxybenzyl, —NHR$^j$, wherein R$^j$ is selected from the group consisting of a 5- or 6-membered aromatic heterocyclic ring having one, two or three heteroatoms independently selected from the group consisting of N, O and S, the heterocyclic ring being substituted at least one substituent selected from the group consisting of halogen, lower alkyl and phenyl, —C(O)—R$^k$, wherein R$^k$ is a 5- or 6-member aromatic heterocyclic ring having one, two or three hetero atoms independently selected from the group consisting of N, O and S, the aromatic heterocyclic ring being unsubstituted or substituted by at least one lower alkyl, phenyl, substituted phenyl substituted by a substitutent independently selected from the group consisting of lower alkyl, lower alkoxy, —(CH$_2$)$_m$—NHR$^1$, wherein R$^1$ is selected from the group consisting of H, lower alkyl and benzyloxycarbonyl; and n is 0, 1 or 2;

m is 0 or 1;

or a pharmaceutically acceptable salt or prodrug thereof.

26. The compound of formula Ic of claim 25 wherein R$^g$ is lower alkyl.

27. The compound of claim 26 with the formula

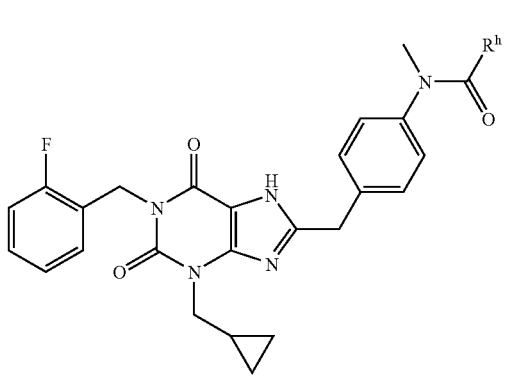

Id wherein R$^h$ is selected from the group consisting of
—(CH$_2$)$_n$-5- or 6-member aromatic heterocyclic ring having one, two or three hetero atoms independently selected from the group consisting of N, O and S, the aromatic heterocyclic ring being unsubstituted or having at least one substituent independently selected from the group consisting of
lower alkyl,
lower alkoxy,
hydroxy,
halogen,
—NH$_2$,
—NH—C(O)-lower alkyl,
—CN,
—C(O)—NH$_2$ and
—SO$_2$-lower alkyl,
lower alkyl,
lower alkyl substituted by at least one substituent independently selected from the group consisting of
halogen,
phenyl and —(CH$_2$)$_m$NR$^i$R$^i$, wherein R$^i$ is independently selected from the group consisting of
H,
lower alkyl and
benzyloxycarbonyl, —NHR$^j$, wherein R$^j$ is selected from the group consisting of a —(CH$_2$)n-5- or 6-membered aromatic heterocyclic ring having one, two or three heteroatoms independently selected from the group consisting of N, O and S, the heterocyclic ring being substituted at least one substituent selected from the group consisting of
halogen,
lower alkyl and
phenyl, —C(O)—R$^k$, wherein R$^k$ is a —(CH$_2$)$_n$-5- or 6-member aromatic heterocyclic ring having one, two or three hetero atoms independently selected from the group consisting of N, O and S, the aromatic heterocyclic ring being unsubstituted or substituted by at least one lower alkyl, phenyl, the phenyl optionally substituted by a substituent independently selected from the group consisting of
lower alkyl,
lower alkoxy,
—(CH$_2$)$_m$-NH R$^1$, wherein R$^1$ is selected from the group consisting of
H,
lower alkyl and
benzyloxycarbonyl; and m is 0 or 1;

n is 0, 1 or 2;

or a pharmaceutically acceptable salt or prodrug thereof.

28. The compound of claim 27 wherein R$^h$ is a —(CH$_2$)$_n$-5- or 6-membered aromatic heterocyclic ring with 1, 2 or 3 heteroatoms independently selected from the group consisting of N, O and S, the aromatic heterocyclic ring being unsubstituted or having at least one substitutent selected from the group consisting of
lower alkyl,
lower alkoxy,
hydroxy,
halogen,
amino,
—NH—C(O)-lower alkyl,
—CN,
—C(O)—NH$_2$ and
—SO$_2$-lower alkyl.

29. The compound of claim 28 wherein R$^h$ is an unsubstituted —(CH$_2$)$_n$-5- or 6-membered unsubstituted aromatic heterocyclic ring having 1, 2 or 3 heteroatoms independently selected from the group consisting of N, O and S.

30. The compound of claim 29 wherein the compound is selected from the group consisting of
N-pyrimidine-5-carboxylic acid N-{4-[3-cyclopropylmethyl-1-(2-fluorobenzyl)-2,6-dioxo-2,3,6,7-tetrahydro-1H-purin-8-ylmethyl]-phenyl}-N-methyl-amide,
N-{4-[3-cyclopropylmethyl-1-(2-fluorobenzyl)-2,6-dioxo-2,3,6,7-tetrahydro-1H-purin-8-ylmethyl]-phenyl}-N-methyl-2-pyridin-3-yl-acetamide,
N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide,
N-pyrazine-2-carboxylic acid N-{4-[3-cyclopropylmethyl-1-(2-fluorobenzyl)-2,6-dioxo-2,3,6,7-tetrahydro-1H-purin-8-ylmethyl]-phenyl}-N-methyl-amide and

[1,2,3]thiadiazole-4-carboxylic acid N-{4-[3-cyclopropylmethyl-1-(2-fluorobenzyl)-2,6-dioxo-2,3,6,7-tetrahydro-1H-purin-8-ylmethyl]-phenyl}-N-methyl-amide.

31. The compound of claim 27, wherein $R^h$ is a —(CH$_2$)$_n$-5- or 6-membered aromatic heterocyclic ring having 1, 2 or 3 heteroatoms independently selected from the group consisting of N, O and S, the aromatic heterocyclic ring being substituted by lower alkyl.

32. The compound of claim 1, wherein the compound is selected from the group consisting of
- 1,3,5-trimethyl-1H-pyrazole-4-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide,
- 4-amino-1-methyl-1H-pyrazole-3-carboxylic acid-N-{4-[3-cyclopropylmethyl-1-(2-fluoro-benzyl)-2,6-dioxo-2,3,6,7-tetrahydro-1H-purin-8-ylmethyl]-phenyl}-N-methyl-amide,
- 2,4-dimethyl-thiazole-5-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide,
- 3-methyl-isoxazole-4-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide,
- 2,4-dimethyl-thiazole-5-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide,
- 3,5-dimethyl-isoxazole-4-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide,
- N-{4-[3-cyclopropylmethyl-1-(2-fluorobenzyl)-2,6-dioxo-2,3,6,7-tetrahydro-1H-purin-8-ylmethyl]-phenyl}-5,N-dimethyl-nicotinamide,
- 1-methyl-1H-pyrazole-4-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide,
- N-{4-[3-cyclopropylmethyl-1-(2-fluorobenzyl)-2,6-dioxo-2,3,6,7-tetrahydro-1H-purin-8-ylmethyl]-phenyl}-6,N-dimethyl-nicotinamide,
- 5-methyl-isoxazole-4-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide and
- 4-methyl-[1,2,3]thiadiazole-5-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide.

33. The compound of claim 28 wherein the 5- or 6-membered aromatic heterocyclic ring is substituted by halogen and lower alkyl.

34. The compound of claim 33 wherein the compound is selected from the group consisting of
- 3-chloro-1,5-dimethyl-1H-pyrazole-4-carboxylic acid-N-{4-[3-cyclopropyl-methyl-1-(2-fluorobenzyl)-2,6-dioxo-2,3,6,7-tetrahydro-1H-purin-8-ylmethyl]-phenyl}-N-methyl-amide.

35. The compound of claim 28 wherein the 5- or 6-membered aromatic heterocyclic ring is substituted by hydroxy.

36. The compound of claim 35 wherein the compound is selected from the group consisting of
- N-{4-[3-cyclopropylmethyl-1-(2-fluorobenzyl)-2,6-dioxo-2,3,6,7-tetrahydro-1H-purin-8-ylmethyl]-phenyl}-6-hydroxy-N-methyl-nicotinamide and
- N-{4-[3-cyclopropylmethyl-1-(2-fluorobenzyl)-2,6-dioxo-2,3,6,7-tetrahydro-1H-purin-8-ylmethyl]-phenyl}-2-hydroxy-N-methyl-nicotinamide.

37. The compound of claim 28 wherein the 5- or 6-membered aromatic heterocyclic ring is substituted by amino.

38. The compound of claim 37 wherein the compound is selected from the group consisting of
- 2-amino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide and
- 6-amino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide.

39. The compound of claim 28 wherein the 5- or 6-membered aromatic heterocyclic ring is substituted by amino and alkyl.

40. The compound of claim 39 wherein the compound is selected from the group consisting of
- 2-amino-4-methyl-thiazole-5-carboxylic acid-N-{4-[3-cyclopropylmethyl-1-(2-fluorobenzyl)-2,6-dioxo-2,3,6,7-tetrahydro-1H-purin-8-ylmethyl]-phenyl}-N-methyl-amide and
- 4-amino-1-methyl-1H-pyrazole-3-carboxylic acid-N-{4-[3-cyclopropylmethyl-1-(2-fluoro-benzyl)-2,6-dioxo-2,3,6,7-tetrahydro-1H-purin-8-ylmethyl]-phenyl}-N-methyl-amide.

41. The compound of claim 28 wherein the 5- or 6-membered aromatic heterocyclic ring is substituted by lower alkoxy.

42. The compound of claim 41 wherein the compound is N-{4-[3-cyclopropylmethyl-1-(2-fluorobenzyl)-2,6-dioxo-2,3,6,7-tetrahydro-1H-purin-8-ylmethyl]-phenyl}-2,6-dimethoxy-N-methyl-nicotinamide.

43. The compound of claim 28 wherein the 5- or 6-membered aromatic heterocyclic ring is substituted by —CN.

44. The compound of claim 43 wherein the compound is 6-cyano-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide.

45. The compound of claim 28 wherein the 5- or 6-membered heteroaromatic ring is substituted by —NH—C(O)-lower alkyl.

46. The compound of claim 45 wherein the compound is selected from the group consisting of
- 6-acetylamino-N-{4-[3-cyclopropylmethyl-1-(2-fluorobenzyl)-2,6-dioxo-2,3,6,7-tetrahydro-1H-purin-8-ylmethyl]-phenyl}-N-methyl-nicotinamide,
- 6-acetylamino-pyridine-2-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide and
- 4-acetylamino-2-methyl-thiophene-3-carboxylic acid {4-[3-cyclopropylmethyl-1-(2-fluorobenzyl)-2,6-dioxo-2,3,6,7-tetrahydro-1H-purin-8-ylmethyl]-phenyl}-methyl-amide.

47. The compound of claim 28 wherein the 5- or 6-membered heteroaromatic ring is substituted by lower alkyl and —NH—C(O)-lower alkyl.

48. The compound of claim 47 wherein the compound is 2-acetamino-N-{4-[3-cyclopropylmethyl-1-(2-fluorobenzyl)-2,6-dioxo-2,3,6,7-tetrahydro-1H-purin-8-ylmethyl]-phenyl}-4,6,N-trimethyl-nicotinamide.

49. The compound of claim 28 wherein the 5- or 6-membered heteroaromatic ring is substituted by —C(O)—NH$_2$.

50. The compound of claim 49 wherein the compound is selected from the group consisting of thiophene-2,3-dicarboxylic acid 3-amide 2-(N-{4-[3-cyclopropylmethyl-1-(2-fluorobenzyl)-2,6-dioxo-2,3,6,7-tetrahydro-1H-purin-8-ylmethyl]-phenyl}-N-methyl-amide).

51. The compound of claim 27 wherein $R^h$ is —C(O)—$R^k$, wherein $R^k$ is a 5- or 6-member aromatic heterocyclic ring having one, two or three hetero atoms independently selected from the group consisting of N, O and S, the aromatic heterocyclic ring being unsubstituted or substituted by at least one lower alkyl.

52. The compound of claim 51 wherein the compound is N-{4-[3-cyclopropylmethyl-1-(2-fluorobenzyl)-2,6-dioxo-2,3,6,7-tetrahydro-1H-purin-8-ylmethyl]-phenyl}-N-methyl-2-oxo-2-(1,3,5-trimethyl-1H-pyrazol-4-yl)-acetamide.

53. The compound of claim 27 wherein $R^h$ is phenyl, the phenyl optionally substituted by a substituent independently selected from the group consisting of
lower alkyl,
lower alkoxy,
—(CH$_2$)$_n$—NHR$^1$, wherein R$^1$ is selected from the group consisting of
H,
lower alkyl and
benzyloxycarbonyl.

54. The compound of claim 53 wherein the compound is selected from the group consisting of

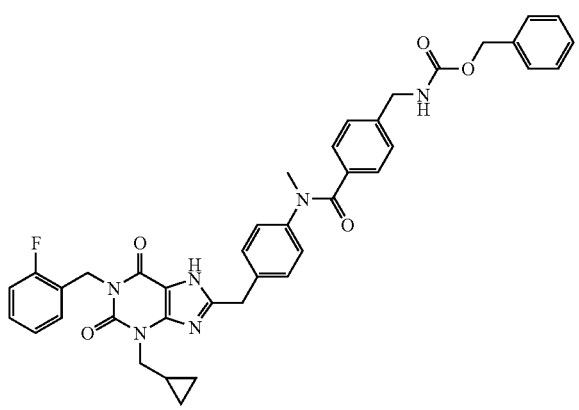

and

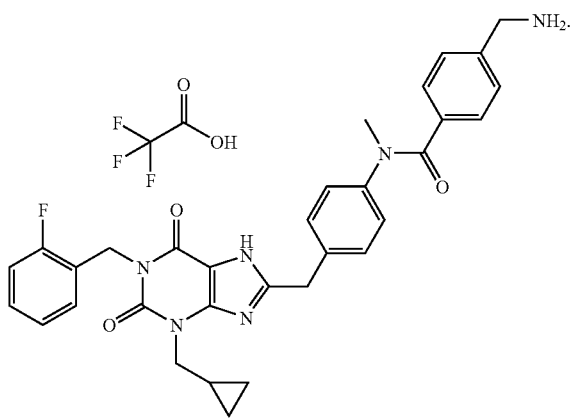

55. The compound of claim 1 wherein $R^h$ is lower alkyl substituted by —(CH$_2$)$_n$—NHR$^j$ wherein R$^j$ is independently selected from the group consisting of H, lower alkyl and benzyloxycarbonyl.

56. The compound of claim 1 wherein the compound is selected from the group consisting of
2-amino-N-{4-[3-cyclopropylmethyl-1-(2-fluorobenzyl)-2,6-dioxo-2,3,6,7-tetrahydro-1H-purin-8-ylmethyl]-phenyl}-N-methyl-2-phenyl-acetamide and

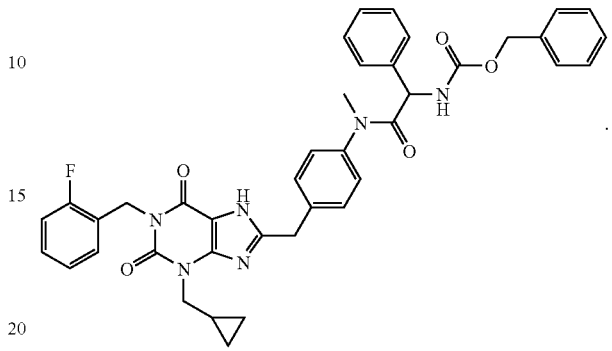

57. The compound of claim 26 wherein $R^g$ is ethyl.

58. The compound of claim 57 wherein the compound is 1,3,5-Trimethyl-1H-pyrazole-4-carboxylic acid-N-{4-[3-cyclopropyl-methyl-1-(2-fluorobenzyl)-2,6-dioxo-2,3,6,7-tetrahydro-1H-purin-8-ylmethyl]-phenyl}-N-ethyl-amide.

59. The compound of claim 26 wherein $R^g$ is isopropyl.

60. The compound of claim 59 wherein the compound is selected from the group consisting of
N-{4-[3-cyclopropylmethyl-1-(2-fluorobenzyl)-2,6-dioxo-2,3,6,7-tetrahydro-1H-purin-8-ylmethyl]-phenyl}-N-isopropyl-6-methyl-nicotinamide and
N-{4-[3-cyclopropylmethyl-1-(2-fluorobenzyl)-2,6-dioxo-2,3,6,7-tetrahydro-1H-purin-8-ylmethyl]-phenyl}-N-isopropyl-2-pyridin-3-yl-acetamide.

61. The compound in accordance with claim 25, wherein the compound is N-{4-[3-cyclopropylmethyl-1-(2-fluorobenzyl)-2,6-dioxo-2,3,6,7-tetrahydro-1H-purin-8-ylmethyl]-phenyl}-N-isopropyl-6-methyl-nicotinamide.

62. The compound in accordance with claim 25, wherein the compound is N-{4-[3-cyclopropylmethyl-1-(2-fluorobenzyl)-2,6-dioxo-2,3,6,7-tetrahydro-1H-purin-8-ylmethyl]-phenyl}-N-isopropyl-2-pyridin-3-yl-acetamide.

63. The compound of claim 25 wherein $R^g$ is H and $R_h$ is lower alkyl substituted by halogen.

64. The compound of claim 63 wherein the compound is N-{4-[3-cyclopentylmethyl-1-(2-fluorobenzyl)-2,6-dioxo-2,3,6,7-tetrahydro-1H-purin-8-ylmethyl]-phenyl}-2,2,2-trifluoroacetamide.

65. The compound of claim 25 wherein $R^g$ is H and $R^h$ is a —(CH$_2$)$_n$-5- or 6-membered aromatic heterocyclic ring having 1, 2 or 3 heteroatoms independently selected from the group consisting of N, O and S, the aromatic heterocyclic ring being substituted by lower alkyl.

66. The compound of claim 65 wherein the compound is 1-methyl-1H-pyrazole-4-carboxylic acid {4-[3-cyclopropylmethyl-1-(2-fluorobenzyl)-2,6-dioxo-2,3,6,7-tetrahydro-1H-purin-8-ylmethyl]-phenyl}-amide.

67. The compound of claim 25 wherein $R^g$ is H and $R^h$ is —NHR$^j$, wherein R$^j$ is selected from the group consisting of a 5- or 6-membered aromatic heterocyclic ring having one, two or three heteroatoms independently selected from the group consisting of N, O and S, the heterocyclic ring being substituted by at least one substituent selected from the group consisting of halogen, lower alkyl and phenyl.

68. The compound of claim 67 wherein the compound is selected from the group consisting of
   1-{4-[3-cyclopropylmethyl-1-(2-fluorobenzyl)-2,6-dioxo-2,3,6,7-tetrahydro-1H-purin-8-ylmethyl]-phenyl}-3-(2,6-dichloro-pyridin-4-yl)-urea and
   1-{4-[3-cyclopropylmethyl-1-(2-fluorobenzyl)-2,6-dioxo-2,3,6,7-tetrahydro-1H-purin-8-ylmethyl]-phenyl}-3-(3,5-dimethyl-1-phenyl-1H-pyrazol-4-yl)-urea.

69. The compound of claim 25 wherein $R^g$ is H and $R^h$ is a —$(CH_2)_n$-5- or 6-member aromatic heterocyclic ring having one, two or there hetero atoms independently selected from the group consisting of N, O and S, the aromatic heterocyclic ring being unsubstituted or substituted —NH—C(O)-lower alkyl.

70. The compound of claim 1 wherein the compound is N-{4-[3-cyclopropylmethyl-1-(2-fluorobenzyl)-2,6-dioxo-2,3,6,7-tetrahydro-1H-purin-8-ylmethyl]-phenyl}-acetamide.

71. The compound of claim 25 wherein $R^g$ is H and $R^h$ is lower alkyl substituted by at least one substituent independently selected from the group consisting of
   halogen,
   phenyl and
   —$(CH_2)_n NR^i R^i$, wherein $R^i$ is independently selected from the group consisting of
      H,
      lower alkyl, and
      benzyloxycarbonyl.

72. The compound of claim 71 wherein the compound is N-{4-[3-cyclopropylmethyl-1-(2-fluorobenzyl)-2,6-dioxo-2,3,6,7-tetrahydro-1H-purin-8-ylmethyl]-phenyl}-2-dimethylamino-acetamide; compound with trifluoro-acetic acid.

73. The compound of claim 24 wherein $R^3$ is

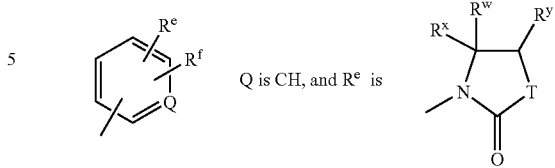

and $R^f$ is selected from the group consisting of H, —$NH_2$ and —NH—C(O)—$CH_3$
   wherein T is NH or $CH_2$, and
   when T is NH, $R^w$ and $R^x$ are, taken together with the carbon to which they are attached, to form —C(O)— and $R^y$ is —$(CH_2)OR^z$ wherein $R^z$ is selected from the group consisting of hydrogen and lower alkyl.

74. The compound of claim 1 wherein the compound is selected from the group consisting of
   8-[4-(4-tert-butoxymethyl-2,5-dioxo-imidazolidin-1-yl)-benzyl]-3-cyclopropylmethyl-1-(2-fluorobenzyl)-3,7-dihydro-purine-2,6-dione and
   1-{4-[3-cyclopropylmethyl-1-(2-fluorobenzyl)-2,6-dioxo-2,3,6,7-tetrahydro-1H-purin-8-ylmethyl]-phenyl}-3-(2,6-dichloro-pyridin-4-yl)-urea.

75. A pharmaceutical composition comprising a compound of formula I according to claim 1 or a pharmaceutically acceptable salt or prodrug thereof, and a pharmaceutically acceptable excipient.

76. A method of treatment for type 2 diabetes comprising administering a therapeutically effective amount of a compound of formula I according to claim 1, or a pharmaceutically acceptable salt or prodrug thereof, to a patient in need of such treatment.

* * * * *